(12) United States Patent
Betancort et al.

(10) Patent No.: US 11,466,158 B2
(45) Date of Patent: Oct. 11, 2022

(54) PHTHALOCYANINE DYE COMPOUNDS, CONJUGATES AND METHODS OF USE THEREOF

(71) Applicant: Rakuten Medical, Inc., San Diego, CA (US)

(72) Inventors: Juan Betancort, San Diego, CA (US); Lew Makings, Encinitas, CA (US); Torsten Wiemann, Encinitas, CA (US)

(73) Assignee: RAKUTEN MEDICAL, INC., San Diego, CA (US)

(*) Notice: Subject to any disclaimer, the term of this patent is extended or adjusted under 35 U.S.C. 154(b) by 0 days.

(21) Appl. No.: 17/482,239

(22) Filed: Sep. 22, 2021

(65) Prior Publication Data

US 2022/0010140 A1 Jan. 13, 2022

Related U.S. Application Data

(63) Continuation of application No. PCT/US2021/026705, filed on Apr. 9, 2021.

(60) Provisional application No. 63/008,502, filed on Apr. 10, 2020, provisional application No. 63/008,476, filed on Apr. 10, 2020.

(51) Int. Cl.
*C09B 47/30* (2006.01)
*C09B 47/32* (2006.01)

(52) U.S. Cl.
CPC .............. *C09B 47/30* (2013.01); *C09B 47/32* (2013.01)

(58) Field of Classification Search
CPC .................. C09B 47/30; C09B 47/32
See application file for complete search history.

(56) References Cited

U.S. PATENT DOCUMENTS

| | | | |
|---|---|---|---|
| 3,710,795 | A | 1/1973 | Higuchi et al. |
| 5,585,089 | A | 12/1996 | Queen et al. |
| 6,060,598 | A | 5/2000 | Devlin et al. |
| 10,295,719 | B2 | 5/2019 | Rose et al. |
| 10,416,366 | B2 | 9/2019 | Rose et al. |
| 10,527,771 | B2 | 1/2020 | Rose et al. |
| 2004/0171827 | A1 | 9/2004 | Peng et al. |
| 2018/0239074 | A1 | 8/2018 | Rose et al. |

FOREIGN PATENT DOCUMENTS

| | | |
|---|---|---|
| CN | 1583762 A | 2/2005 |
| CN | 103539799 A | 1/2014 |
| JP | 2018528268 A | 9/2018 |
| JP | 2020017910 A | 1/2020 |
| WO | WO-2015042325 A1 | 3/2015 |
| WO | WO-2018080952 A1 | 5/2018 |
| WO | WO-2018167104 A1 | 9/2018 |
| WO | WO-2019008386 A1 | 1/2019 |
| WO | WO-2021157655 A1 | 8/2021 |
| WO | WO-2021207691 A1 | 10/2021 |

OTHER PUBLICATIONS

Al-Lazikani et al. Standard conformations for the canonical structures of immunoglobulins. J Mol Biol. 273(4):927-48 (1997).
Honegger et al. Yet another numbering scheme for immunoglobulin variable domains: an automatic modeling and analysis tool. J Mol Biol 309(3):657-70 (2001).
Kabat et al. Sequences of proteins of immunological interest. NIH Publ. No. 91-3242 1:647-669 (1991).
Lefranc et al. IMGT unique numbering for immunoglobulin and T cell receptor variable domains and Ig superfamily V-like domains. Dev Comp Immunol 27(1):55-77 (2003).
Lofblom et al. Affibody molecules: engineered proteins for therapeutic, diagnostic and biotechnological applications. FEBS Letters 584(12):2670-2680 (2010).
MacCallum et al. Antibody-antigen interactions: contact analysis and binding site topography. J Mol Biol. 262(5):732-745 (1996).
Martin et al. Modeling antibody hypervariable loops: a combined algorithm. PNAS USA 86(23):9268-9272 (1989).
PCT/US2021/026705 International Search Report and Written Opinion dated Jul. 16, 2021.
Steiner et al. Efficient Selection of DARPins with Sub-nanomolar Affinities using SRP Phage Display. J. Mol. Biol. 382:1211-1227 (2008).
Tamaskovic et al. Chapter 5: Designed Ankyrin Repeat Proteins (DARPins): from research to therapy. Methods in Enzymology 503:101-134 (2012).
Zheng et al., A silicon(IV) phthalocyanine-folate conjugate as an efficient photosensitizer. Chem. Lett. 43:1701-1703 (2014).
Bandera et al., Synthesis of water soluble axially disubstituted silicon (IV) phthalocyanines with alkyne & azide functionality. Dyes and Pigments 125:72-79 (2016).
Sato et al., Photoinduced ligand release from a silicon phthalocyanine dye conjugated with monoclonal antibodies: a mechanism of cancer cell cytotoxicity after near-infrared photoimmunotherapy. ACS Cent Sci. 4(11):1559-1569 (2018).
SciFinder Report SiPc [SilylPropylamine]2 (Aug. 25, 2021).
SciFinder report SiPc [SilylPropylamine]2_2021-08-25_113435 (2021).
SciFinder Report SiPc [SilylPropylamine]2_Propylsulfonate _2021-08-25_161057 (2021).
SciFinder SiPc [SilylPropylamine]2_Propylsulfonate. (Available at scifinder.cas.org/scifinder/view/scifinder/scifinderexplore.jsf (downloaded 2022).

(Continued)

*Primary Examiner* — Noble E Jarrell
(74) *Attorney, Agent, or Firm* — Wilson Sonsini Goodrich & Rosati

(57) ABSTRACT

Disclosed herein are phthalocyanine dyes, and conjugates thereof, useful as fluorescent reporters for bioassays, for optical imaging and as therapeutic conjugates as the photosensitizing agents in light-based therapies including photoimmuno therapy (PIT). Certain phthalocyanine dyes disclosed herein are water soluble, and possess photophysical and photochemical profiles useful for use in imaging or therapy.

29 Claims, 6 Drawing Sheets

Specification includes a Sequence Listing.

(56) References Cited

OTHER PUBLICATIONS

SiPc_[SilylPropylamine]_Propylsulfonate_22021-08-25_120124 (2021).

Takahashi et al. Axially Substituted Silicon Phthalocyanine Payloads for Antibody-Drug Conjugates. Synlett 32(11):1098-1103 (2021).

Zheng et al., A silicon(IV) phthalocyanine-folate conjugate as an efficient photosensitizer. Chem. Lett. 43:1701-1703 (2014).

SEQUENCE LISTING

```
<160> NUMBER OF SEQ ID NOS: 6

<210> SEQ ID NO 1
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Thr Met His Trp Val Arg Gln Ala Pro Gly Lys Gly Leu Glu Trp Val
            35                  40                  45

Thr Phe Ile Ser Tyr Asp Gly Asn Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220
```

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 2
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

```
Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
        180                 185                 190

Tyr Ala Cys Glu Val Thr His Gln Gly Leu Ser Ser Pro Val Thr Lys
    195                 200                 205

Ser Phe Asn Arg Gly Glu Cys
    210                 215

<210> SEQ ID NO 3
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Cys Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr
225

<210> SEQ ID NO 4
<211> LENGTH: 214
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 4

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 5
<211> LENGTH: 151
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 5

Gln Val Lys Leu Glu Glu Ser Gly Gly Gly Ser Val Gln Thr Gly Gly
1               5                   10                  15

Ser Leu Arg Leu Thr Cys Ala Ala Ser Gly Arg Thr Ser Arg Ser Tyr
            20                  25                  30

Gly Met Gly Trp Phe Arg Gln Ala Pro Gly Lys Glu Arg Glu Phe Val
        35                  40                  45

Ser Gly Ile Ser Trp Arg Gly Asp Ser Thr Gly Tyr Ala Asp Ser Val
50                  55                  60

Lys Gly Arg Phe Thr Ile Ser Arg Asp Asn Ala Lys Asn Thr Val Asp
65                  70                  75                  80

Leu Gln Met Asn Ser Leu Lys Pro Glu Asp Thr Ala Ile Tyr Tyr Cys
                85                  90                  95

Ala Ala Ala Ala Gly Ser Ala Trp Tyr Gly Thr Leu Tyr Glu Tyr Asp
            100                 105                 110

```
Tyr Trp Gly Gln Gly Thr Gln Val Thr Val Ser Ser Cys Ser Gly Ser
        115                 120                 125
Ser Glu Gln Lys Leu Ile Ser Glu Glu Asp Leu Ala Ser His His His
    130                 135                 140
His His His His His His His
145                 150

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Tyr His Trp Tyr Gly Tyr Thr Pro Gln Asn Val Ile Gly Gly Gly Lys
1               5                   10                  15
```

PHTHALOCYANINE DYE COMPOUNDS, CONJUGATES AND METHODS OF USE THEREOF

CROSS-REFERENCE TO RELATED APPLICATIONS

This application is a continuation of International PCT Application No. PCT/US2021/026705, filed Apr. 9, 2021, which claims the benefit of U.S. Provisional Patent Application No. 63/008,476, filed on Apr. 10, 2020, and U.S. Provisional Patent Application No. 63/008,502, filed on Apr. 10, 2020, all of which are herein incorporated by reference in their entirety.

FIELD OF THE INVENTION

Provided herein are phthalocyanine dye compounds and conjugates with phthalocyanine dye compounds that find use in therapeutics and diagnostic applications such as reporters for bioassays, for optical imaging and as photosensitizing agents in light-based therapies including photoimmunotherapy. Also provided herein are methods for preparing the phthalocyanine dye compounds and compositions and kits comprising the phthalocyanine dye compounds provided herein. Also provided herein are methods for preparing phthalocyanine dye conjugates and methods of treatment using the phthalocyanine dye conjugates.

BACKGROUND OF THE INVENTION

Phthalocyanine (Pc) dye compounds are currently used as fluorescent reporter groups in bioassays, as fluorescent markers for optical imaging and as photosensitizers in light based therapies such as photodynamic therapy (PDT), photothermal therapy (PTT) and photoimmunotherapy (PIT). Pcs are particularly attractive in light based therapies given the stability and high extinction coefficients in the near infrared radiation of certain phthalocyanine dyes. Improved phthalocyanine dyes are needed to improve the effectiveness, cost and availability of biological assays, optical imaging and therapies dependent on these dyes. Provided herein are such compounds, compositions and methods that meet such needs.

SUMMARY OF THE INVENTION

In one aspect, provided herein are phthalocyanine dye compounds that may be used as an unconjugated fluorescent dye, or when conjugated to a molecule may be used in biological assays, diagnostics and light-based therapies. In another aspect, provided herein are phthalocyanine dye compounds and conjugates thereof for use in biological assays, diagnostics and light-based therapies. In one embodiment, provided herein are phthalocyanine dye compounds of Formula (0) comprising an unsubstituted phthalocyanine scaffold containing a core metal or metalloid atom, which are coordinated to two axial ligands, the first ligand comprising at least one water soluble group and the second ligand comprising at least one reactive group. The phthalocyanine dye compounds provided herein do not exist as regioisomers. Because the core phthalocyanine structure is unsubstituted, synthesis of the compounds herein does not create regioisomers, and the manufacturing of the present compounds is thus efficient, cost effective and improves the effectiveness of isolation and/or separation procedures.

In one aspect, provided herein are conjugates comprising a phthalocyanine dye covalently linked to a targeting molecule, wherein the phthalocyanine dye comprises Formula (0) for use in the conjugates, pharmaceutical compositions and methods herein, and where the Formula (0) compound comprises a metal or metalloid atom, such as a silicon atom, coordinated by (a) an unsubstituted phthalocyanine, (b) a first axial silicon-containing ligand having a conjugatable group; and (c) a second axial silicon-containing ligand having a water-solubilizing group that is not a conjugatable group. In some embodiments of Formula (0) the axial silicon-containing ligand having a conjugatable group further comprises a water-solubilizing group. In some embodiments, the chemical structures of the first and second axial ligands are different from one another.

In one aspect, provided herein are phthalocyanine dye compounds having the Formula (X):

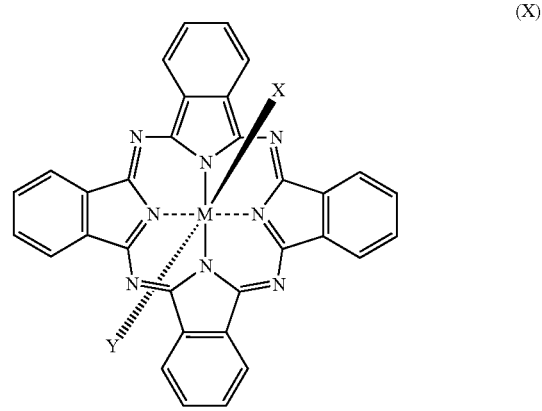

or a salt, stereoisomer, or tautomer thereof, wherein:

M is a metal or metalloid;

X is

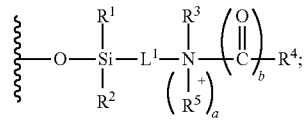

Y is

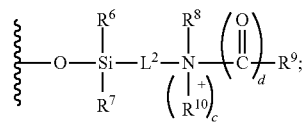

$R^1$ and $R^2$ are each independently optionally substituted alkyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl;

R³, R⁴ or R⁵ are selected from substituent group (a) or substituent group (b) wherein,
(a) R³ is hydrogen, -L³-H, -L³-A, or -L³-Z;
R⁴ is -L⁴-H, —(NH)$_m$-L⁴-A, —(NH)$_m$-L⁴-Z, —(O)$_m$-L⁴-A or —(O)$_m$-L⁴-Z;
R⁵ is -L⁵-H or -L⁵-A; and
(b) R³ is -L³-H, or -L³-A;
R⁴ is -L⁴-H, —(NH)$_m$-L⁴-A, or —(O)$_m$-L⁴-A; wherein R³ and R⁴ are connected with a bond to form a heterocyclyl substituted with -L⁴-A; and
R⁵ is -L⁵-H or -L⁵-A;
provided at least one of R³, R⁴ and R⁵ is a group containing A;
A is a reactive group capable of forming a covalent bond with a thiol, hydroxyl, carboxyl or amino group of a second moiety, or a protected form thereof or a reacted form thereof;
R⁶ and R⁷ are each independently optionally substituted alkyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl or optionally substituted heteroaralkyl;
R⁸, R⁹ or R¹⁰ are selected from substituent group (a) or substituent group (b) wherein,
(a) R⁸ is hydrogen, -L⁸-H or -L⁸-Z;
R⁹ is -L⁹-H, —(NH)$_n$-L⁹-Z or —(O)$_{n\text{-}L}$⁹-Z;
R¹⁰ is -L¹⁰-Z; and
(b) R⁸ and R⁹ are connected with a bond to form a heterocyclyl substituted with -L⁹-Z and R¹⁰ is -L¹⁰-H or -L¹⁰-Z;
provided at least one of R⁸, R⁹ and R¹⁰ is a group containing Z;
Z is a water soluble group optionally substituted with A or L'-A;
L¹ and L² are each independently optionally substituted alkylene, optionally substituted heteroalkylene, optionally substituted alkenylene, optionally substituted heteroalkenylene, optionally substituted cycloalkyl, or optionally substituted heterocyclyl;
L³, L⁴, L⁵, L⁸, L⁹ and L¹⁰ are each independently optionally substituted alkylene, optionally substituted heteroalkylene, optionally substituted alkenylene, optionally substituted heteroalkenylene, optionally substituted cycloalkylene, optionally substituted heterocyclene, optionally substituted arylene, optionally substituted aralkylene, optionally substituted heteroaralkylene, or optionally substituted heteroarylene, where the carbon atom of the alkylene, heteroalkylene, alkenylene, heteroalkenylene, cycloalkylene, heterocyclene, arylene, aralkylene, heteroaralkylene, or optionally substituted heteroarylene is further optionally substituted with Z and each nitrogen atom of the heteroalkylene or heteroalkenylene is optionally substituted with one or two L'-Z;
L' is each independently optionally substituted alkylene, optionally substituted heteroalkylene, optionally substituted alkenylene, optionally substituted heteroalkenylene, optionally substituted cycloalkylene, optionally substituted heterocyclene, optionally substituted arylene, optionally substituted aralkylene, optionally substituted heteroaralkylene, or optionally substituted heteroarylene;
a is 0 or 1;
b is 0 or 1;
c is 0 or 1;
d is 0 or 1;
m is 0 or 1;
n is 0 or 1;
provided that if b is 1, then a is 0;
if d is 1, then c is 0;
if m is 1, b is 1; and
if n is 1, c is 1.

In yet another aspect, provided herein is a compound of Formula (0) comprising a silicon atom coordinated by (a) an unsubstituted phthalocyanine, (b) an axial silicon-containing ligand having a conjugatable group; and (c) an axial silicon-containing ligand having a water-solubilizing group that is not a conjugatable group.

The conjugates provided herein include one or more targeting molecule(s), such as where wherein the targeting molecule(s) is a polypeptide or other molecule that binds to the surface of a cell. In some embodiments, the one or more targeting molecule(s) of the conjugate is an antibody or an antigen-binding antibody fragment. In some embodiments, the one or more targeting molecule(s) is an antigen-binding antibody fragment such as a Fab, single VH domain, multiple VH domain, a single chain variable fragment (scFv), a multivalent scFv, a bispecific scFv, and/or an scFv-CH3 dimer. In some embodiments, the one or more targeting molecule(s) is an antibody or an antigen-binding antibody fragment that binds to at least one of CD25. CEA, CTLA-4, EGFR/HER1, FAP, HER2, MUC-1, PD-1, PD-L1, and/or PSMA. In some embodiments, the targeting molecule is an antibody or an antigen-binding antibody fragment that binds to CD25, such as an antibody or antigen-binding fragment that binds CD25 but does not block interleukin-2 (IL-2) signaling of the IL-2 receptor. In some embodiments, the targeting molecule is an antibody or an antigen-binding antibody fragment that binds to CEA. In some embodiments, the targeting molecule is an antibody or an antigen-binding antibody fragment that binds to CTLA-4. In some embodiments, the targeting molecule is an antibody or an antigen-binding antibody fragment that binds to EGFR/HER1. In some embodiments, the targeting molecule is an antibody or an antigen-binding antibody fragment that binds to HER2. In some embodiments, the targeting molecule is an antibody or an antigen-binding antibody fragment that binds to MUC-1. In some embodiments, the targeting molecule is an antibody or an antigen-binding antibody fragment that binds to PD-1. In some embodiments, the targeting molecule is an antibody or an antigen-binding antibody fragment that binds to PD-L1. In some embodiments, the targeting molecule is an antibody or an antigen-binding antibody fragment that binds to PSMA.

In some embodiments, the conjugates provided herein include a targeting molecule that is an antibody or an antigen-binding antibody fragment of 3F8, 8H9, AB122, ab75705, Abagovomab, Abciximab, Abituzumab, Abrezekimab, Abrilumab, Actoxumab, Adalimumab, Adecatumumab, ADG116, ADU-1604, Aducanumab, Afasevikumab, Afelimomab, Afutuzumab, AGEN1181, AGEN1884, AGX-115, AK104, AK105, Alacizumab pegol, Alemtuzumab, Alirocumab, Altumomab pentetate, Amatuximab, AMG 404, AMP-224, AMP-514, Anatumomab mafenatox, Andecaliximab, Anetumab ravtansine, Anifrolumab, Anrukinzumab, anti-CD133, Apolizumab, Aprutumab ixadotin, Arcitumomab, arcitumomab Fab fragment, Ascrinvacumab, Aselizumab, Atezolizumab, Atidortoxumab, Atinumab, Atlizumab (Tocilizumab), ATOR-1015, Atorolimumab, Avelumab, Azintuxizumab vedotin, B72.3, Bapineuzumab, Basiliximab, Bavituximab, BCD-100, BCD-135, BCD-145, BCD-217, Bectumomab, Begelomab, Belantamab mafodotin, Belimumab, Bemarituzumab, Benralizumab, Berlimatoxumab, Bermekimab, Bersanlimab, Bertilimumab, Besilesomab, Bevacizumab, Bezlotoxumab, BGB-A333, BI 754091, Biciromab, Bimagrumab, Bimekizumab, Birtamimab, Bivatuzumab, Bivatuzumab mertansine, BL-8040, Bleselumab, Blinatumomab, Blontuvetmab, Blosozumab, BMS-936559, BMS-986218, Bococizumab, Brazikumab, Brentuximab vedotin, Briakinumab, Brodalumab, Brolucizumab, Brontictuzumab, Burosumab, Cabiralizumab, Camidanlumab tesirine, Camrelizumab, Canakinumab, Cantuzumab mertansine, Cantuzumab ravtansine, Caplacizumab, Capromab, Capromab pendetide, Carlumab, Carotuximab, Catumaxomab, cBR96-doxorubicin, CBT-502, CC-90002, CDC-022, Cedelizumab, Cemiplimab, Cergutuzumab amunaleukin, Certolizumab pegol, Cetrelimab, Cetuximab, Cibisatamab, Cirmtuzumab, Citatuzumab bogatox, Cixutumumab, Clazakizumab, Clenoliximab, Clivatuzumab tetraxetan, CMAB302, Codrituzumab, Cofetuzumab pelidotin, Coltuximab ravtansine, Conatumumab, Concizumab, Cosfroviximab, Cosibelimab, CP-870,893, CR6261, Crenezumab, Crizanlizumab, Crotedumab, CS1001, CS1003, Cusatuzumab, CX-188, Dacetuzumab, Daclizumab, Dalotuzumab, Dapirolizumab pegol, Daratumumab, Dectrekumab, Demcizumab, Denintuzumab mafodotin, Denosumab, Depatuxizumab mafodotin, Derlotuximab biotin, Detumomab, Dezamizumab, Dinutuximab, Diridavumab, Domagrozumab, Dorlimomab aritox, Dostarlimab, Drozitumab, DS-8201, Duligotumab, Duligotuzumab, Dupilumab, Durvalumab, Dusigitumab, Duvortuxizumab, Ecromeximab, Eculizumab, Edobacomab, Edrecolomab, Efalizumab, Eftilagimod alpha, Efungumab, Eldelumab, Elezanumab, Elgemtumab, Elotuzumab, Elsilimomab, Emactuzumab, Emapalumab, Emibetuzumab, Emicizumab, Enapotamab vedotin, Enavatuzumab, Enfortumab vedotin, Enlimomab pegol, Enoblituzumab, Enokizumab, Enoticumab, Ensituximab, Epitumomab cituxetan, Epratuzumab, Eptinezumab, Erenumab, Erlizumab, Ertumaxomab, Etaracizumab, Etigilimab, Etrolizumab, Evinacumab, Evolocumab, Exbivirumab, F3, F520, Fanolesomab, Faralimomab, Faricimab, Farletuzumab, Fasinumab, FAZ053, FBTA05, Felvizumab, Fezakinumab, Fibatuzumab, Ficlatuzumab, Figitumumab, Firivumab, Flanvotumab, Fletikumab, Flotetuzumab, Fontolizumab, Foralumab, Foravirumab, Fremanezumab, Fresolimumab, Frovocimab, Frunevetmab, Fulranumab, Futuximab, Galcanezumab, Galiximab, Gancotamab, Ganitumab, Gantenerumab, Gatipotuzumab, Gavilimomab, GB221, Gedivumab, Gemtuzumab ozogamicin, genolimzumab, Gevokizumab, Gilvetmab, Gimsilumab, Girentuximab, Glembatumumab vedotin, GLS-010, Golimumab, Gomiliximab, Gosuranemab, Guselkumab, HD201, Hervycta, HLX02, HLX10, HLX20, HLX22, HX008, HX009, Ianalumab, Ibalizumab, IBI308, Ibritumomabtiuxetan, Icrucumab, Idarucizumab, Ieramilimab, Ifabotuzumab, Igovomab, Iladatuzumab vedotin, IMAB362, Imalumab, Imaprelimab, Imciromab, Imgatuzumab, INBRX-105, Inclacumab, Indatuximab ravtansine, Indusatumab vedotin, Inebilizumab, Infliximab, Inolimomab, Inotuzumab ozogamicin, Intetumumab, Iomab-B, IPH2101, Ipilimumab, Iratumumab, Isatuximab, Iscalimab, Istiratumab, Itolizumab, Ixekizumab, JTX-4014, Keliximab, KN035, KN046, Labetuzumab, Lacnotuzumab, Ladiratuzumab vedotin, Lambrolizumab (Pembrolizumab), Lampalizumab, Lanadelumab, Landogrozumab, Laprituximab emtansine, Larcaviximab, LDP, Lebrikizumab, Lemalesomab, Lendalizumab, Lenvervimab, Lenzilumab, Lerdelimumab, Leronlimab, Lesofavumab, Letolizumab, Lexatumumab, Libivirumab, Lifastuzumab vedotin, Ligelizumab, Lilotomab satetraxetan, Lintuzumab, Lirilumab, Lodelcizumab, Lokivetmab, Loncastuximab tesirine, Lorvotuzumab mertansine, Losatuxizumab vedotin, Lucatumumab, Lulizumab pegol, Lumiliximab, Lumretumab, Lupartumab, Lupartumab amadotin, Lutikizumab, LY3300054, LY3415244, LZM009, mAb114, Mapatumumab, Margetuximab, Marstacimab, Maslimomab, Matuzumab, Mavrilimumab, MCLA-145, MED16469, MED16383, Mepolizumab, Metelimumab, MGA012, MGD013, MGD019, Milatuzumab, Minretumomab, Mirikizumab, Mirvetuximab soravtansine, Mitumomab, MK-1308, MK-4166, MNRP1685A, Modotuximab, Mogamulizumab, Monalizumab, Morolimumab, Mosunetuzumab, Motavizumab, Moxetumomab pasudotox, MOXR0916, MSB2311, Muromonab-CD3, Nacolomabtafenatox, Namilumab, Naptumomabestafenatox, Naratuximabemtansine, Namatumab, Natalizumab, Navicixizumab, Navivumab, Naxitamab, Nebacumab, Necitumumab, Nemolizumab, NEOD001, Nerelimomab, Nesvacumab, Netakimab, Nimotuzumab, Nirsevimab, Nivolumab, NM-01, Nofetumomab merpentan, Obiltoxaximab, Obinutuzumab, OC125 monoclonal antibody, Ocaratuzumab, Ocrelizumab, Odulimomab, Ofatumumab, Olaratumab, Oleclumab, Olendalizumab, Olokizumab, Omalizumab, Omburtamab, OMS721, Onartuzumab, Ontuxizumab, Onvatilimab, Opicinumab, Oportuzumab monatox, Oregovomab, Orticumab, Otelixizumab, Otilimab, Otlertuzumab, Oxelumab, Ozanezumab, Ozoralizumab, Pagibaximab, Palivizumab, Pamrevlumab, Panitumumab, Pankomab, Panobacumab, Parsatuzumab, Pascolizumab, Pasotuxizumab, Pateclizumab, Patritumab, PDR001, Pembrolizumab, Pemtumomab, Perakizumab, Pertuzumab, Pexelizumab, PF-05280014, PF-06801591, Pidilizumab, Pinatuzumab vedotin, Pintumomab, Placulumab, Plozalizumab, Pogalizumab, Polatuzumab vedotin, Ponezumab, Porgaviximab, Prasinezumab, Prezalizumab, Prezalumab, Priliximab, Pritoxaximab, Pritumumab, PRO 140, Quilizumab, Racotumomab, Radretumab, Rafivirumab, Ralpancizumab, Ramucirumab, Ranevetmab, Ranibizumab, Ravagalimab, Ravulizumab, Raxibacumab, Refanezumab, Regavirumab, REGN2810, REGN3504, REGN4659, REGN-EB3, Relatlimab, Remtolumab, Reslizumab, rHIgM12B7, Rilotumumab, Rinucumab, Risankizumab, Rituximab, Rituximab, Rivabazumab pegol, Rmab, RO7121661, Robatumumab, Roledumab, Romilkimab, Romosozumab, Rontalizumab, Rosmantuzumab, Rovalpituzumab tesirine, Rovelizumab, Rozanolixizumab, Ruplizumab, SA237, Sacituzumab, Sacituzumab govitecan, Samalizumab, Samrotamab vedotin, Sarilumab, Satralizumab, Satumomab pendetide, SB3, SCT-110A, SEA-CD40, Secukinumab, Selicrelumab, Seribantumab, Setoxaximab, Setrusumab, Sevirumab, SG001, SGN-CD19A, SHP647, SHR-1316, SIBP-01, Sibrotuzumab, Sifalimumab, Siltuximab, Simtuzumab, Sintilimab, Siplizumab, Sirtratumab vedotin, Sirukumab, Sofituzumab vedotin, Solanezumab, Solitomab, Sonepcizumab, Sontuzumab, Spartalizumab, Stamulumab, STI-3031, Sulesomab, Suptavumab, Sutimlimab, Suvizumab, Suvratoxumab, Sym021, Tabalumab, Tacatuzumab tetraxetan, Tadocizumab, Talacotuzumab, Talizumab, Tamtuvetmab, Tanezumab, Taplitumomab paptox, Tarextumab, Tavolimab, Tefibazumab, Telimomab aritox, Telisotuzumab, Telisotuzumab vedotin, Tenatumomab, Teneliximab, Teplizumab, Tepoditamab, Teprotumumab, Tesidolumab, Tetulomab, Tezepelumab, TG-1501, TGN1412, Tibulizumab, Ticilimumab, Tigatuzumab, Tildrakizumab, Timigutuzumab, Timolumab, Tiragolumab, Tiragotumab, Tislelizumab, Tisotumab vedotin, TNX-650, Tocilizumab, Tocilizumab, Tomuzotuximab, Toralizumab, Toripalimab, Tosatoxumab, Tositumomab, Tositumomab, Tovetumab, Tralokinumab, Trastuzumab, Trastuzumab deruxtecan, Trastuzumab-anns, trastuzumab-dkst, Trastuzumab emtansine, TRBS07, Tregalizumab, Tremelimumab, Trevogrumab, TRX385, TRX518, TSR-042, Tucotuzumab celmoleukin, Tuvirumab, TX05, Ublituximab, Ulocuplumab, Urelumab, Urtoxazumab, Ustekinumab, Utomilumab, Vadastuximab talirine, Vanalimab, Vandortuzumab vedotin, Vantictumab, Vanucizumab, Vapaliximab, Varisacumab, Varlilumab, Vatelizumab, Vedolizumab, Veltuzumab, Vepalimomab, Vesencumab, Visilizumab, Vobarilizumab, Vociximab, Vonlerolizumab, Vopratelimab, Vorsetuzumabmafodotin, Votumumab, Vunakizumab, Xentuzumab, XmAb20717, XmAb22841, XMAB-5574, Zalutumumab, Zanolimumab, Zatuximab, Zenocutuzumab, Ziralimumab, ZKAB001, Zolbetuximab, Zolimomab aritox, or an antigen-binding fragment thereof.

In some embodiments, the conjugates provided herein include a targeting molecule that is Alacizumab pegol, Cetuximab, Depatuxizumab mafodotin, Futuximab, Icrucumab, Imgatuzumab. Laprituximab emtansine, Matuzumab, Modotuximab, Necitumumab, Nimotuzumab, Panitumumab, Ramucirumab, Tomuzotuximab, Zalutumumab, or an antigen-binding fragment thereof.

In some embodiments, the conjugates provided herein include a targeting molecule that is an anti-CD25 antibody such as Basiliximab (SIMULECT), Camidanlumab tesirine, daclizumab (Zinbryta; Zenapax), Inolimomab, RA8, STI-003, Xenopax or an antigen-binding fragment thereof.

In some embodiments, the conjugates provided herein include a targeting molecule that is an anti-PD-L1 antibody such as atezolizumab (MPDL3280A, Tecentriq), avelumab (Bavencio), durvalumab (MEDI4736, Imfinzi), LDP, NM-01, STI-3031, KN035, LY3300054, M7824 (MSB0011359C), BMS-936559, MSB2311, BCD-135, BGB-A333, CBT-502, cosibelimab (CK-301), CS1001, FAZ053. MDX-1105, SHR-1316, TG-1501, ZKAB001, INBRX-105, MCLA-145, KN046, LY3415244, REGN3504, HLX20, and antigen-binding fragments of any thereof.

In some embodiments, the conjugates provided herein include a targeting molecule that is an anti-PD-1 antibody selected from the group consisting of pembrolizumab (MK-3475, Keytruda), nivolumab (Opdivo), cemiplimab (Libtayo), toripalimab (JS001), HX008, SG001, GLS-010, dostarlimab (TSR-042), tislelizumab (BGB-A317), cetrelimab (JNJ-63723283), pidilizumab (CT-011), genolimzumab (APL-501, GB226), BCD-100, cemiplimab (REGN2810), F520, sintilimab (1B1308), GLS-010, CS1003, LZM009, camrelizumab (SHR-1210), SCT-110A, MGA012, AK105, PF-06801591, AMP-224, AB122, AMG 404, BI 754091, HLX10, JTX-4014, MED10680, Sym021, MGD019, MGD013, AK104, XmAb20717, RO7121661, CX-188, spartalizumab and, antigen-binding fragments of any thereof.

In some embodiments, the conjugates provided herein include a targeting molecule that is ipilimumab (Yervoy®), tremelimumab (ticilimumab), AGEN1181, AGEN1884, ADU-1064, BCD-145, BCD-217, or an antigen-binding fragment of any thereof.

In some embodiments, the conjugates provided herein include a targeting molecule that is CDC-022 (HERtiCAD), CMAB302 (Cipterbin), DS-8201, Gancotamab, GB221, HD201, Hervycta, HLX02, HLX22, Margetuximab. Pertuzumab (Perjeta), PF-05280014 (Trazimera), SB3, SIBP-01, Timigutuzumab, Trastuzumab (Herceptin), trastuzumab deruxtecan (ENHERTU), Trastuzumab emtansine (Kadcyla), trastuzumab-anns (Kanjinti), trastuzumab-dkst (Ogivri), TX05, or an antigen-binding fragment thereof.

In some embodiments, the conjugates provided herein include a targeting molecule that includes the antibody or an antigen-binding antibody fragment of cetuximab, basiliximab, daclizumab, F3, trastuzumab, panitumumab, or antigen-binding fragment thereof. In some embodiments, the conjugates provided herein include a targeting molecule that is a peptide or small molecule that binds to EGFR, HER2, CD25, PD-1, PD-L1, MUC1, PSMA, FAP, or CTLA-4. In some embodiments, the conjugates provided herein include a targeting molecule that binds to a viral particle or a viral capsid protein or a portion thereof.

In some aspects, the conjugates of a targeting molecule and a phthalocyanine dye of Formula (X). Formula (0), Formula (I) or Formula (II) have a dye to targeting molecule ratio of about 5:1, 4:1, 3:1, 2:1 or 1:1. In some embodiments, the conjugates have a dye to targeting molecule ratio between about 1:1 to 5:1, 1.5:1 to 4:1, 1.5:1 to 3.5:1, 1.5:1 to 3:1 or about 2:1 to 3:1.

In some aspects, the phthalocyanine dye of the conjugates such as the compounds of Formula (X), Formula (0), Formula (I) or Formula (II) have a maximum absorption at a wavelength between about 600 nm to 800 nm, about 620 nm to 720 nm, about 640 to 700 nm, or about 640 to 680 nm.

Among the conjugates provided herein are conjugates of a targeting molecule (also referred to interchangeably as a targeting moiety) and a phthalocyanine dye is selected from Compound 1, 5, 12, 13, 14, 16, 17, 18 or 19 of Table A.

Among the conjugates provided herein are conjugates of a targeting molecule (also referred to interchangeably as a targeting moiety) and a phthalocyanine dye is selected from Table A.

Also provided herein are pharmaceutical compositions of a conjugate and a pharmaceutically acceptable excipient. The conjugates provided herein and the pharmaceutical compositions find use in methods of treatment. In some embodiments, the methods include a method of treating a subject having a disease or condition by administering to a subject a conjugate or pharmaceutical composition of a conjugate described herein, after administering the conjugate, illuminating a target region of the subject at a wavelength of at or about 600 nm to at or about 850 nm at a dose of or of about 10 J/cm$^2$ to a dose of or of about 200 J/cm$^2$ or at a dose from at or about 10 J/cm fiber length to at or about 100 J/cm fiber length, thereby treating the disease or condition in the subject. In some embodiments of the method, the wavelength is at least about 600 nm, 610 nm, 620 nm, 630, nm, 640 nm, 650 nm, 660 nm, 670 nm, 680, nm, 690 nm or 700 nm. In some embodiments of the method, the wavelength is between 660 nm and 680 nm. In some embodiments of the method, the wavelength is at or about 670±50 nm, or at or about 670±40 nm or at or about 670±20 nm, or at or about 670±10 nm. In some embodiments of the method, the wavelength is less than 690 nm or less than 680 nm.

In certain aspects, the methods of treatment herein include treatment of where the target region is a tumor cell, a mass of tumor cells, a solid tumor, in the vicinity of a solid tumor, a metastasis, a metastasized tumor cell, in the vicinity of a metastasis or a pre-cancerous lesion.

In some embodiments of the methods, the illumination is performed at least 5 minutes after administration of the conjugate. In some embodiments of the methods, the illumination is performed at about 1 hour, 5 hours, 10 hours, 15 hours, 20 hours, 21 hours, 22 hours, 23 hours, 24 hours, 25 hours, 26 hours, 27 hours, 28 hours, 29 hours, 30 hours, 36 hours, 40 hours, 48 hours, 72 hours, or 96 hours after administration of the conjugate. In some embodiments of the methods, the illumination is performed 24+/−4 h after administration of the conjugate.

The methods provided herein include those where the disease or condition for treatment is a cancer. In some aspects, the cancer is selected from the group consisting of colon cancer, colorectal cancer, pancreatic cancer, breast cancer, skin cancer, lung cancer, non-small cell lung carcinoma, renal cell carcinoma, thyroid cancer, prostate cancer, head and neck cancer, gastrointestinal cancer, stomach cancer, cancer of the small intestine, spindle cell neoplasm, hepatic carcinoma, liver cancer, cholangiocarcinoma, cancer of peripheral nerve, brain cancer, cancer of skeletal muscle, cancer of smooth muscle, bone cancer, cancer of adipose tissue, cervical cancer, uterine cancer, cancer of genitals, lymphoma, and multiple myeloma. In some aspects of the methods of treatment herein, the steps of administering the conjugate and illuminating are repeated.

Also provided herein are methods of imaging a cell or tissue having a target molecule that include administering to a subject a conjugate or the pharmaceutical composition of a conjugate described herein, after administering the conjugate, illuminating a target region of the subject at a wavelength of at or about 600 nm to at or about 850 nm, thereby providing an image of the presence of the target molecule on the cell or tissue.

Also provided herein are systems for treating a subject having a disease or condition that include a conjugate or pharmaceutical composition of a conjugate described herein, a laser capable of emitting light at a wavelength of between 600 nm to about 800 nm, such as 670±20 nm, an optic fiber operably connected to the laser for transmitting the light to a target region of the subject; and a light diffusing device comprising a non-circular core fiber. In some embodiments, the non-circular core fiber has a "top hat" core irradiance distribution. In some embodiments, the light diffusing device is a cylindrical diffuser or a frontal diffuser.

In yet certain embodiments, provided herein is a kit comprising a compound Formula (X), Formula (0), Formula (I) or Formula (II), and instructions for use. In yet certain embodiments, the kit further comprises additional reagents.

DETAILED DESCRIPTION OF THE INVENTION

A. Phthalocyanine Dye Compounds

Figure 1:
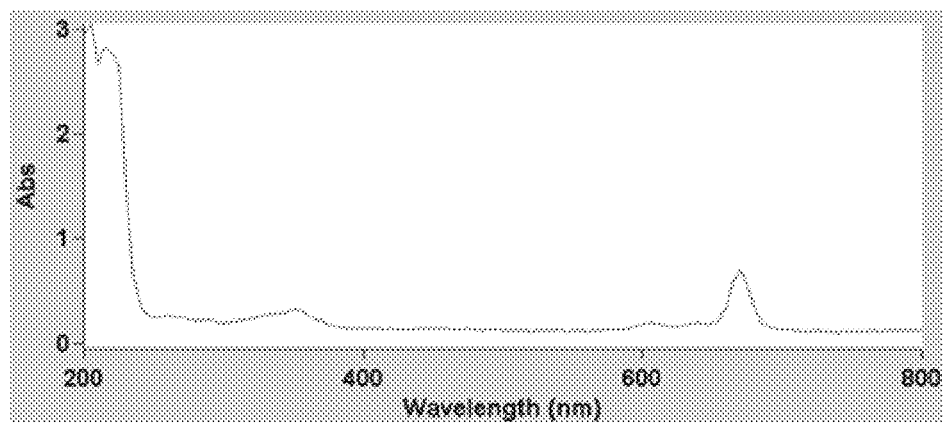
FIG. 1 provides the UV-Vis spectra of Chemical Synthesis Example 1.

Phthalocyanines are a group of photosensitizer compounds having the phthalocyanine ring system. Phthalocyanines are azaporphyrins that contain four benzoindole groups connected by nitrogen bridges in a 16-membered ring of alternating carbon and nitrogen atoms (i.e., $C_{32}H_{18}N_8$) which form stable chelates with a metal or metalloid cation. In these compounds, the ring center is occupied by a metal ion (either a diamagnetic or a paramagnetic ion) that may, depending on the ion, carry zero, one or two ligands. In addition, the ring periphery may be either unsubstituted or substituted.

In some embodiments, phthalocyanines strongly absorb red or near IR radiation with absorption peaks falling between about 600 nm and 810 nm, which, in some cases, allow deep penetration of tissue by the light. Phthalocyanines are generally photostable. This photostability is typically advantageous in pigments and dyes and in many of the other applications of phthalocyanines.

In some embodiments, the phthalocyanine dye is water soluble and contains a luminescent fluorophore moiety having at least one aqueous-solubilizing moiety. In some embodiments, the aqueous solubilizing moiety contains silicon. In some embodiments, the phthalocyanine dye has a core atom such as Si, Ge, Sn, Al, or Zn. In some embodiments, the phthalocyanine dye contains a linker that has a reactive group, which is able to form a bond between the linker and another molecule, i.e., to form a conjugate. In some embodiments, the phthalocyanine dye can be tailored to fluoresce at a particular wavelength.

In some embodiments, the phthalocyanine dye contains a linker, i.e., is a linker-phthalocyanine dye moiety (L-D). In some embodiments, the linker contains a reactive group. In one aspect, provided herein are phthalocyanine dye compounds having the Formula (X):

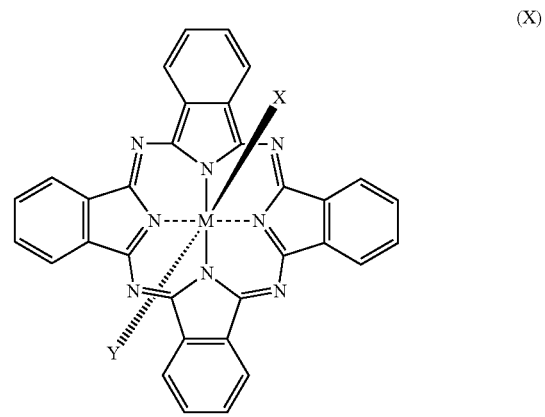

(X)

or a salt, stereoisomer, or tautomer thereof, wherein:

M is a metal or metalloid;

X is a

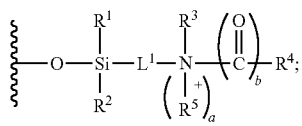

Y is

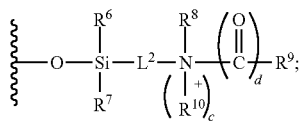

R$^1$ and R$^2$ are each independently optionally substituted alkyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl;

R$^3$, R$^4$ or R$^5$ are selected from substituent group (a) or substituent group (b) wherein, (a) R$^3$ is hydrogen, -L$^3$-H, -L$^3$-A, or -L$^3$-Z;

R$^4$ is -L$^4$-H, —(NH)$_m$-L$^4$-A, —(NH)$_m$-L$^4$-Z, —(O)$_m$-L$^4$-A or —(O)$_m$-L$^3$-Z;

R$^5$ is -L$^5$-H or -L$^3$-A; and (b) R$^3$ is -L$^3$-H, or -L$^3$-A;

R$^4$ is -L$^4$-H, —(NH)$_m$-L$^4$-A, or —(O)$_m$-L$^4$-A; wherein R$^3$ and R$^4$ are connected with a bond to form a heterocyclyl substituted with -L$^4$-A; and R$^5$ is -L$^5$-H or -L$^5$-A;

provided at least one of R$^3$, R$^4$ and R$^5$ is a group containing A;

A is a reactive group capable of forming a covalent bond with a thiol, hydroxyl, carboxyl or amino group of a second moiety, or a protected form thereof or a reacted form thereof;

R$^6$ and R$^7$ are each independently optionally substituted alkyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl or optionally substituted heteroaralkyl;

R$^8$, R$^9$ or R$^{10}$ are selected from substituent group (a) or substituent group (b) wherein, (a) R$^8$ is hydrogen, -L$^8$-H or -L$^8$-Z;

R$^9$ is -L$^9$-H, —(NH)$_n$-L$^9$-Z or —(O)$_n$-L$^9$-Z;

R$^{10}$ is -L$^{10}$-Z; and (b) R$^8$ and R$^9$ are connected with a bond to form a heterocyclyl substituted with -L$^9$-Z and R$^{10}$ is -L$^{10}$-H or -L$^{10}$-Z;

provided at least one of R$^8$, R$^9$ and R$^{10}$ is a group containing Z;

Z is a water soluble group optionally substituted with A or L'-A;

L$^1$ and L$^2$ are each independently optionally substituted alkylene, optionally substituted heteroalkylene, optionally substituted alkenylene, optionally substituted heteroalkenylene, optionally substituted cycloalkyl, or optionally substituted heterocyclyl;

L$^3$, L$^4$, L$^5$, L$^8$, L$^9$ and L$^{10}$ are each independently optionally substituted alkylene, optionally substituted heteroalkylene, optionally substituted alkenylene, optionally substituted heteroalkenylene, optionally substituted cycloalkylene, optionally substituted heterocyclene, optionally substituted arylene, optionally substituted aralkylene, optionally substituted heteroaralkylene, or optionally substituted heteroarylene, where the carbon atom of the alkylene, heteroalkylene, alkenylene, heteroalkenylene, cycloalkylene, heterocyclene, arylene, aralkylene, heteroaralkylene, or optionally substituted heteroarylene is further optionally substituted with Z and each nitrogen atom of the heteroalkylene or heteroalkenylene is optionally substituted with one or two L'-Z;

L' is each independently optionally substituted alkylene, optionally substituted heteroalkylene, optionally substituted alkenylene, optionally substituted heteroalkenylene, optionally substituted cycloalkylene, optionally substituted heterocyclene, optionally substituted arylene, optionally substituted aralkylene, optionally substituted heteroaralkylene, or optionally substituted heteroarylene;

a is 0 or 1;
b is 0 or 1;
c is 0 or 1;
d is 0 or 1;
m is 0 or 1;
n is 0 or 1;
provided that if b is 1, then a is 0;
if d is 1, then c is 0;
if m is 1, b is 1; and
if n is 1, c is 1.

In some embodiments, the phthalocyanine dye contains a linker, i.e., is a linker-phthalocyanine dye moiety (L-D). In some embodiments, the linker contains a reactive group. In some embodiments the phthalocyanine dye is of Formula (I):

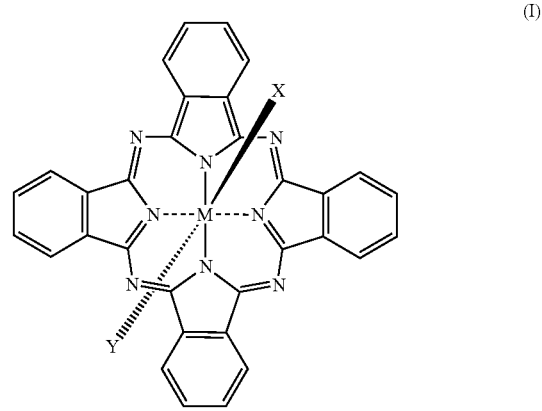

or a salt, stereoisomer, or tautomer thereof, wherein,

M is a metal or metalloid;

X is

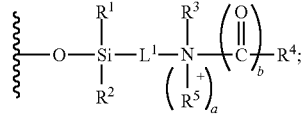

Y is

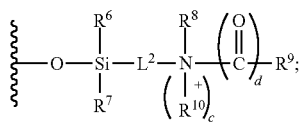

R$^1$ and R$^2$ are each independently optionally substituted alkyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl;

R$^3$, R$^4$ or R$^5$ are selected from substituent group (a) or substituent group (b) wherein, (a) R$^3$ is hydrogen, -L$^3$-H, -L$^3$-A, or -L$^3$-Z;

R$^4$ is -L$^4$-H, —(NH)$_m$-L$^4$-A, —(NH)$_m$-L$^4$-Z, —(O)$_m$-L$^4$-A or —(O)$_m$-L$^4$-Z;

R$^5$ is -L$^5$-H or -L$^5$-A; and (b) R$^3$ is -L$^3$-H, or -L$^3$-A;

R$^4$ is -L$^4$-H, —(NH)$_m$-L$^4$-A, or —(O)$_m$-L$^4$-A; wherein R$^3$ and R$^4$ are connected with a bond to form a heterocyclyl substituted with -L$^5$-A; and R$^5$ is -L$^5$-H or -L$^5$-A;

provided at least one of R$^3$, R$^4$ and R$^5$ is a group containing A;

A is a reactive group capable of forming a covalent bond with a thiol, hydroxyl, carboxyl or amino group of a second moiety, or a protected form thereof or a reacted form thereof;

R$^6$ and R$^7$ are each independently optionally substituted alkyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl or optionally substituted heteroaralkyl;

R$^8$, R$^9$ or R$^{10}$ are selected from substituent group (a) or substituent group (b) wherein, (a) R$^8$ is hydrogen, -L$^8$-H or -L$^8$-Z;

R$^9$ is -L$^9$-H, —(NH)$_n$-L$^9$-Z or —(O)$_n$-L$^9$-Z;

R$^{10}$ is -L$^{10}$-Z; and (b) R$^8$ and R$^9$ are connected with a bond to form a heterocyclyl substituted with -L$^9$-Z and R$^{10}$ is -L$^{10}$-H or -L$^{10}$-Z;

provided at least one of R$^8$, R$^9$ and R$^{10}$ is a group containing Z;

Z is a water soluble group optionally substituted with A or L'-A;

L$^1$ and L$^2$ are each independently optionally substituted alkylene, optionally substituted heteroalkylene, optionally substituted alkenylene, optionally substituted heteroalkenylene, optionally substituted cycloalkyl, or optionally substituted heterocyclyl;

L$^3$, L$^4$, L$^5$, L$^8$, L$^9$ and L$^{10}$ are each independently optionally substituted alkylene, optionally substituted heteroalkylene, optionally substituted alkenylene, optionally substituted heteroalkenylene, optionally substituted cycloalkylene, optionally substituted heterocyclene, optionally substituted arylene, optionally substituted aralkylene, optionally substituted heteroaralkylene, or optionally substituted heteroarylene, where the carbon atom of the alkylene, heteroalkylene, alkenylene, heteroalkenylene, cycloalkylene, heterocyclene, arylene, aralkylene, heteroaralkylene, or optionally substituted heteroarylene is further optionally substituted with Z and each nitrogen atom of the heteroalkylene or heteroalkenylene is optionally substituted with one or two L'-Z;

L' is each independently optionally substituted alklene, optionally substituted heteroalkylene, optionally substituted alkenylene, optionally substituted heteroalkenylene, optionally substituted cycloalkylene, optionally substituted heterocyclene, optionally substituted arylene, optionally substituted aralkylene, optionally substituted heteroaralkylene, or optionally substituted heteroarylene;

a is 00 or 1;

b is 0 or 1;

c is 0 or 1;

d is 0 or 1;

m is 0 or 1;

n is 0 or 1;

provided that if b is 1, then a is 0;

if d is 1, then c is 0;

if m is 1, b is 1; and if n is 1, c is 1; and provided that when R$^6$ and R$^7$ are both methyl, and L$^2$ is propylene, c is 1 and d is 0, then L$^8$, L$^9$ and L$^{10}$ are each not propylene.

In certain embodiments, provided herein are compounds of Formula (I) with the proviso that when R$^6$ and R$^7$ are both methyl, and L$^2$ is propylene, c is 1 and d is 0; then L$^8$, L$^9$ and L$^{10}$ are each not propylene.

In certain embodiments, provided herein are compounds of Formula (I) with the proviso that when R$^6$ and R$^7$ are both methyl, and L$^2$ is propylene, then c is 0 and d is 1.

In certain embodiments, provided herein are compounds of Formula (I) with the proviso that when R$^6$ and R$^7$ are both methyl, L$^2$ is propylene, c is 1 and d is 0 and L$^8$, L$^9$ and L$^{10}$ are each propylene, then Z is not —SO$_3$—.

In certain embodiments, the alkyl, cycloalkyl, cycloalkylalkyl, heterocyclyl, heterocyclyalkyl, aryl, aralkyl, heteroaryl, heteroaralkyl of R$^1$, R$^2$, R$^6$ and R$^7$ is optionally substituted with halo, haloalkyl, hydroxyl, alkoxy, haloalkoxy, amino or cyano.

In certain embodiments, a carbon atom of the alkylene, heteroalkylene, alkenylene or heteroalkenylene of L$^1$ and L$^2$ is each independently and optionally substituted with halo, oxo, haloalkyl, hydroxyl, alkoxy, haloalkoxy, amino or cyano.

In certain embodiments, provided herein are compounds of Formula (I):

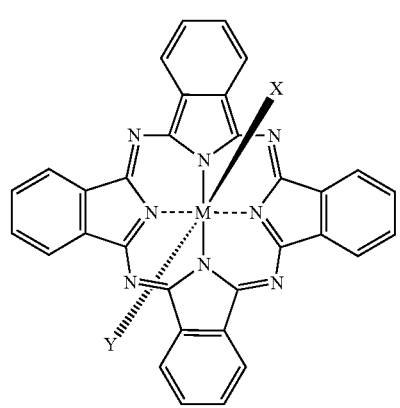

(I)

wherein,
M is a metal or metalloid;
X is

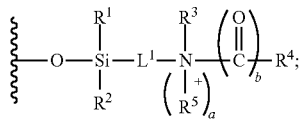

Y is

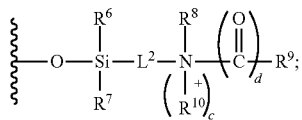

R$^1$ and R$^2$ are each independently optionally substituted alkyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl or optionally substituted heteroaralkyl;

R$^3$, R$^4$ or R$^5$ are selected from (a) and (b) wherein,
(a) R$^3$ is hydrogen, -L$^3$-H, -L$^3$-A, or -L$^3$-Z;
R$^4$ is -L$^4$-H, —(NH)$_m$-L$^4$-A, —(NH)$_m$-L$^4$-Z, —(O)$_m$-L$^4$-A or —(O)$_m$-L$^4$-Z;
R$^5$ is -L$^5$-H or -L$^5$-A; and
(b) R$^3$ and R$^4$ are connected with a bond to form a heterocyclyl substituted with -L$^4$-A and R$^5$ is -L$^5$-H or -L$^5$-A;
provided at least one of R$^3$, R$^4$ and R$^5$ is a group containing A;
A is a reactive group capable of forming a covalent bond with a second moiety, or a protected form thereof or a reacted form thereof;
R$^6$ and R$^7$ are each methyl;
R$^8$ is -L$^8$-Z;
R$^9$ is -L$^9$-Z;
R$^{10}$ is -L$^{10}$-Z; and
Z is a water soluble group optionally substituted with A, or L'-A;
L$^1$ is selected from optionally substituted alkylene, optionally substituted heteroalkylene, optionally substituted alkenylene, or optionally substituted heteroalkenylene;
L$^2$ is propylene;
L$^3$, L$^4$, L$^5$ are each independently selected from optionally substituted alkylene, optionally substituted heteroalkylene, optionally substituted alkenylene, optionally substituted heteroalkenylene, optionally substituted cycloalkylene, optionally substituted heterocyclene, optionally substituted arylene, or optionally substituted heteroarylene where the carbon atom of the alkylene, heteroalkylene, alkenylene, heteroalkenylene, cycloalkylene, heterocyclene or arylene is optionally substituted with a Z, and each nitrogen atom of the heteroalkylene or heteroalkenylene is optionally substituted with one or two L'-Z;
L' is each independently optionally substituted alkylene, optionally substituted heteroalkylene, optionally substituted alkenylene, optionally substituted heteroalkenylene, optionally substituted cycloalkylene, optionally substituted heterocyclene, optionally substituted arylene, or optionally substituted heteroarylene;

L$^8$, L$^9$ and L$^{10}$ are each propylene; a is 0 or 1; b is 0 or 1; c is 0 or 1; d is 0 or 1;
m is 0 or 1; n is 0 or 1;
provided that if b is 1, then a is 0;
if d is 1, then c is 0;
if m is 1, then b is 1; and
if n is 1, then c is 1.

In certain embodiments, a carbon atom of the alkylene, heteroalkylene, alkenylene, heteroalkenylene, cycloalkylene, heterocyclene or arylene of L$^3$, L$^4$, L$^5$, L$^8$, L$^9$ and L$^{10}$ is optionally substituted with halo, oxo, haloalkyl, hydroxyl, alkoxy, haloalkoxy, amino, cyano or Z and a nitrogen atom of the heteroalkylene or heteroalkenylene is optionally substituted with one or two L'-Z; L' is each independently alkylene, heteroalkylene, alkenylene, heteroalkenylene, cycloalkylene, heterocyclene, arylene or heteroarylene where a carbon atom of the alkylene, heteroalkylene, alkenylene, heteroalkenylene, cycloalkylene, heterocyclene, arylene or heteroarylene is optionally substituted with halo, oxo, haloalkyl, hydroxyl, alkoxy, haloalkoxy, amino or cyano.

In certain embodiments, L$^3$, L$^4$, L$^5$, L$^8$, L$^9$ and L$^{10}$ are each independently optionally substituted alkylene, optionally substituted heteroalkylene, optionally substituted alkenylene or optionally substituted heteroalkenylene, where each nitrogen atom of the heteroalkylene or heteroalkenylene is further optionally substituted with one or two L'-Z and L' is independently optionally substituted alkylene, optionally substituted heteroalkylene, optionally substituted alkenylene or optionally substituted heteroalkenylene.

In certain embodiments, L$^1$ and L$^2$, are each independently optionally substituted C$_{1-10}$alkylene, optionally substituted heteroC$_{1-10}$alkylene, optionally substituted C$_{2-10}$alkenylene or hetero C$_{2-10}$alkenylene. In yet certain embodiments, L$^1$ and L$^2$, are each independently C$_{2-4}$alkylene, heteroC$_{2-4}$alkylene, optionally substituted C$_{2-4}$alkenylene or optionally substituted hetero C$_{2-4}$alkenylene. In yet certain embodiments, L$^1$ and L$^2$ are each optionally substituted C$_{2-4}$alkylene.

In certain embodiments, the reactive group A is each independently —C(O)OR$^{11}$, —NR$^{12}$R$^{13}$, —NHC(O)R$^{14}$, —C(O)R$^{15}$, —OR$^{16}$, —SR$^{16}$, —OS(O)$_2$R$^{17}$, —OP(OR$^{18}$)(NR$^{19}$R$^{20}$), —N═C═O; —N═C═S, —S—C≡N, —SO$_2$—F, —SO$_2$—Cl, —SO$_2$—Br, —S—SR$^{21}$ or 5- or 6-membered dioxo-substituted heterocyclyl;

each R$^{11}$ is independently hydrogen, alkyl, haloalkyl, alkenyl, heterocyclyl, aryl or heteroaryl, where the heterocyclyl, aryl or heteroaryl is optionally substituted with one to five groups each independently selected from halo, —SO$_3$— and —SO$_2$F;
each R$^{12}$ is independently hydrogen or alkyl or haloalkyl;
each R$^{13}$ is independently aryl or heteroaryl where the aryl or heteroaryl is optionally substituted with one to five groups each independently selected from halo, —SO$_3$— and —SO$_2$F; or optionally R$^{12}$ and R$^{13}$, together with the nitrogen to which they are attached, form a cyclic imide;
each R$^{14}$ is independently haloalkyl;
each R$^{15}$ is independently aryl optionally substituted with one to five groups each independently halo, heterocyclyl, —SO$_3$— or —SO$_2$F;
each R$^{16}$ is independently aryl optionally substituted with one to five groups each independently halo or heterocylyl;

each $R^{17}$ is independently optionally substituted alkyl, optionally substituted haloalkyl, optionally substituted alkenyl, optionally substituted cycloalkyl, optionally substituted heterocyclyl, optionally substituted aryl or optionally substituted heteroaryl, wherein the heterocyclyl, aryl or heteroaryl is optionally substituted with one to five groups each independently selected from halo, —$SO_3$—, —$SO_2F$ and —$C(O)OR^c$;

each $R^c$ is independently optionally substituted alkyl, optionally substituted haloalkyl, optionally substituted cycloalkyl or optionally substituted aryl;

$R^{18}$, $R^{19}$ and $R^{20}$ are each independently optionally substituted alkyl or optionally substituted haloalkyl; and $R^{21}$ is a heteroaryl.

In certain embodiments, the reactive group A is selected from the group consisting of:

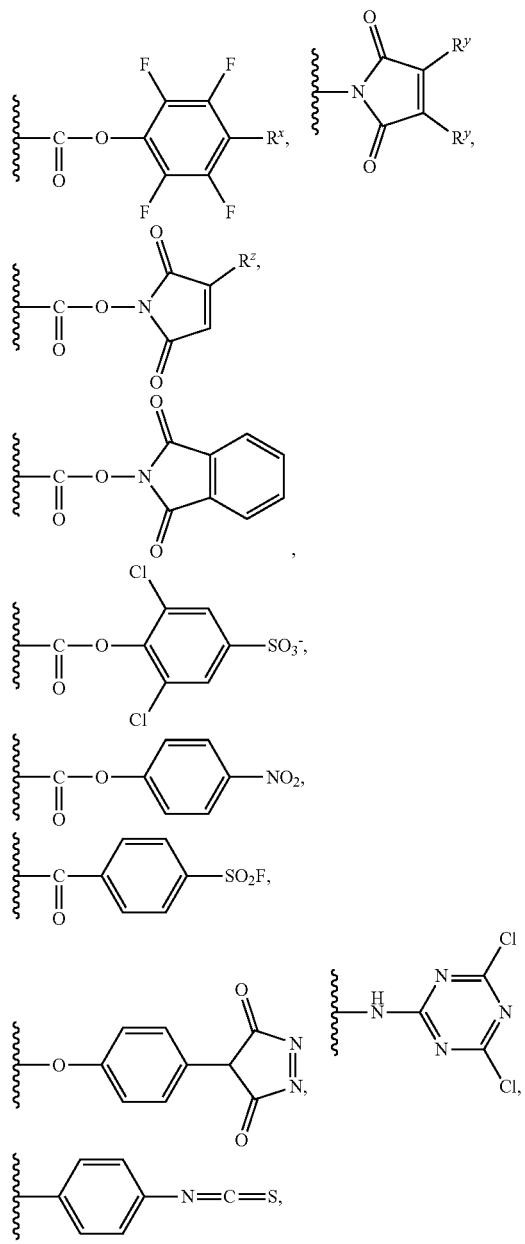

—$NHC(O)R^{14}$, —COOH and —$OSO_2R^{17}$ where each $R^x$ and $R^y$ are independently hydrogen or halo, and $R^z$ is hydrogen or —$SO_3$—;

$R^{14}$ is optionally substituted haloalkyl or optionally substituted aralkyl; and $R^{17}$ is each $R^{17}$ is independently optionally substituted alkyl, optionally substituted haloalkyl, optionally substituted alkenyl, optionally substituted cycloalkyl, optionally substituted heterocyclyl, optionally substituted aryl or optionally substituted heteroaryl, wherein the heterocyclyl, aryl or heteroaryl is optionally substituted with one to five groups each independently selected from halo, —$SO_3$—, —$SO_2F$ and —$C(O)OR^c$; and each $R^c$ is independently optionally substituted alkyl, optionally substituted haloalkyl, optionally substituted cycloalkyl or optionally substituted aryl.

In yet certain embodiments, the reactive group A or the conjugatable group A' is selected from the group consisting of:

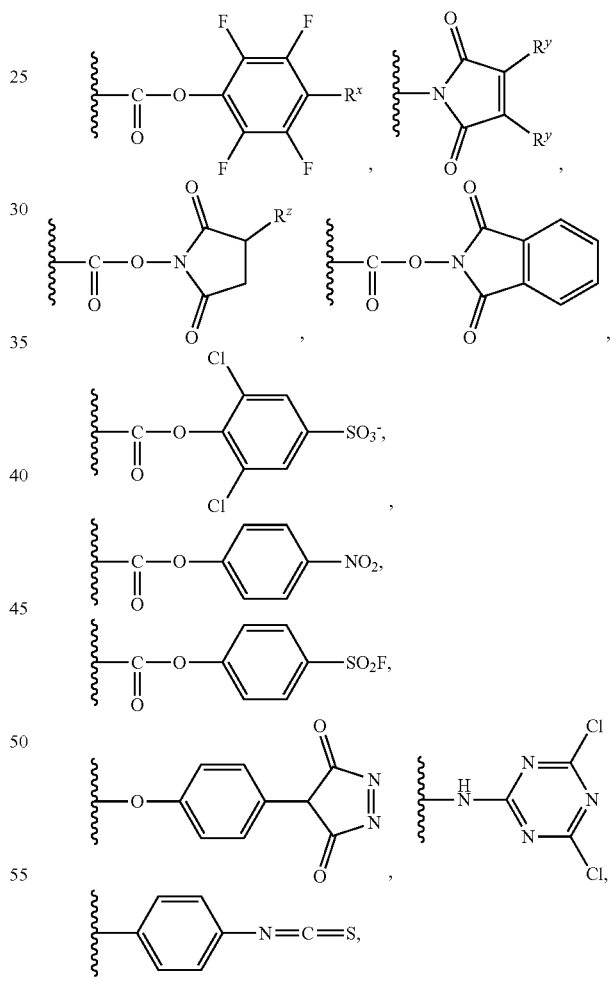

—$NHC(O)R^{14}$, and —$OSO_2R^{17}$ where each $R^x$ and $R^y$ are independently hydrogen or halo, and $R^z$ is hydrogen or —$SO_3$—;

each $R^{14}$ is independently haloalkyl or alkyl substituted aralkyl; and each $R^{17}$ is independently optionally substituted alkyl, optionally substituted haloalkyl, optionally substituted alkenyl, optionally substituted cycloalkyl, optionally substituted heterocyclyl, optionally substituted aryl or optionally substituted heteroaryl, wherein the heterocyclyl, aryl or heteroaryl is optionally substituted with one to five groups each independently selected from halo, —SO$_3$—, —SO$_2$F and —C(O)OR$^c$; and each R$^c$ is independently optionally substituted alkyl, optionally substituted haloalkyl, optionally substituted cycloalkyl or optionally substituted aryl.

In yet certain embodiments, the reactive group A is

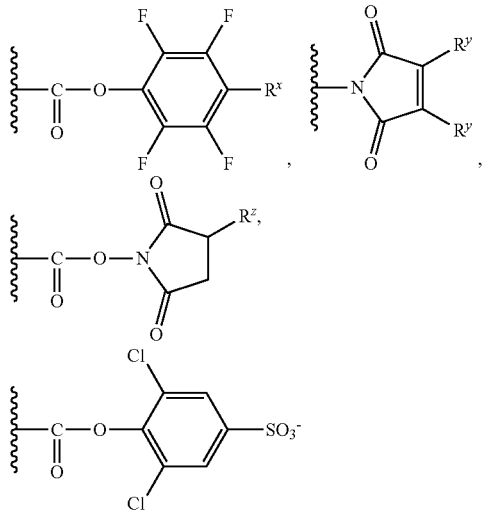

or COOH where each R$^x$ and R$^y$ are independently hydrogen or halo, and R$^z$ is hydrogen or —SO$_3$—.

In certain embodiments, reactive group is each independently —C(O)OR$^{11}$ or —NR$^{12}$R$^{13}$; R$^{11}$ is each independently hydrogen, alkyl, haloalkyl, alkenyl, heterocyclyl, aryl or heteroaryl, wherein the heterocyclyl, aryl or heteroaryl is optionally substituted;

R$^{12}$ is each independently hydrogen or alkyl and R$^{13}$ is aryl or heteroaryl optionally substituted with one to give groups each independently selected from halo, —SO$_3$— and —SO$_2$F; or R$^{12}$ and R$^{13}$, together with the nitrogen to which they are attached, form heterocylyl;

In certain embodiments, the water soluble group Z is
—C(O)OH,
—(CH$_2$)$_q$(OCH$_2$CH$_2$)$_v$(CH$_2$)$_q$C(O)OH,
—(CH$_2$CH$_2$O)$_v$(CH$_2$)$_p$C(O)OH,
—(CH$_2$)$_q$(OCH$_2$CH$_2$)$_v$OR$^{22}$,
—(CH$_2$CH$_2$O)$_v$(CH$_2$)$_p$OR$^{22}$,
—(CH$_2$)$_q$(OCH$_2$CH$_2$)$_v$SR$^{22}$,
—(CH$_2$CH$_2$O)$_v$(CH$_2$)$_p$SR$^{22}$,
—O(CH$_2$)$_v$N[(CH$_2$CH$_2$O)$_n$CH$_2$CH$_2$OR$^{22}$]$_t$,
—(CH$_2$)$_q$(OCH$_2$CH$_2$)$_v$N[(CH$_2$CH$_2$O)$_w$CH$_2$CH$_2$OR$^{22}$]$_t$,
—CH$_2$CH$_2$O)$_m$(CH$_2$)$_p$N[(CH$_2$CH$_2$O)$_w$CH$_2$CH$_2$OR$^{22}$]$_t$,
—NH$_2$,
—(CH$_2$)$_q$N[(CH$_2$CH$_2$O)$_v$CH$_2$CH$_2$OR$^{22}$]$_t$,
—(CH$_2$)$_q$NR$^b$[(CH$_2$CH$_2$O)$_w$CH$_2$CH$_2$OR$^{22}$]$_u$,
—(CH$_2$)$_q$N[(CH$_2$)$_p$(OCH$_2$CH$_2$)$_v$OR$^{22}$]$_t$,
—(CH$_2$)$_q$N[(CH$_2$)$_p$SO$_3$H]$_t$,
—(CH$_2$)$_q$NR$^b$[(CH$_2$)$_p$SO$_3$H]$_u$,
—(CH$_2$)$_q$NR$^b$(CH$_2$)$_p$CH(SO$_3$H)$_2$,
—(CH$_2$)$_q$N[(CH$_2$)$_p$S(O)$_u$OH]$_t$,
—(CH$_2$)$_q$N[(CH$_2$)$_p$OSO$_3$H]$_t$,
—(CH$_2$)$_q$(OCH$_2$CH$_2$)$_v$(CH$_2$)$_q$SO$_3$H,
—(CH$_2$)$_q$(OCH$_2$CH$_2$)$_v$(CH$_2$)$_q$S(O)$_u$OH,
—(CH$_2$)$_q$(OCH$_2$CH$_2$)$_v$(CH$_2$)$_q$OSO$_3$H,
—SO$_3$H,
—CH(SO$_3$H)$_2$,
—OSO$_3$H,
—S(O)$_u$OH,
—PO$_3$H,
—CH(PO$_3$H)$_2$,
—(CH$_2$)$_q$N[(CH$_2$)$_p$PO$_3$—]$_t$,
—(CH$_2$)$_q$(OCH$_2$CH$_2$)$_v$(CH$_2$)$_q$PO$_3$H,
—(CH$_2$)$_q$N[(CH$_2$)$_p$OPO$_3$H]$_t$,
—OPO$_3$H,
—(CH$_2$)$_q$(OCH$_2$CH$_2$)$_q$(CH$_2$)$_q$P(O)(OH)$_2$,
—(CH$_2$)$_q$N[(CH$_2$)$_p$P(O)(OH)$_2$]$_t$,
—P(O)(OH)$_2$, glutamate, aspartate, histidine, 1,3-beta-glucan or 1,4-beta-glucan;

each R$^{22}$ is independently alkyl, haloalkyl, cycloalkyl or aryl;

each R$^b$ is independently hydrogen, alkyl optionally substituted with —CO$_2$H, heteroalkylene optionally substituted with —CO$_2$H, haloalkyl or cycloalkyl;

each v, w and p are independently an integer from 1 to 10;
each q is independently an integer from 0 to 10;
t is 2 or 3; and
u is 1 or 2.

In certain embodiments, the water soluble group Z is selected from
—(CH$_2$)$_q$(OCH$_2$CH$_2$)$_v$OR$^{22}$,
—(CH$_2$)$_q$O(CH$_2$)$_v$N[(CH$_2$CH$_2$O)$_w$CH$_2$CH$_2$OR$^{22}$]$_t$,
—(CH$_2$)$_q$N[(CH$_2$)$_p$(OCH$_2$CH$_2$)$_v$OR$^{22}$]$_t$,
—(CH$_2$)$_q$N[(CH$_2$)$_p$SO$_3$H]$_t$,
—(CH$_2$)$_q$NR$^p$[(CH$_2$)$_p$SO$_3$H]$_u$,
—(CH$_2$)$_q$NR$^b$[(CH$_2$)$_p$CH(SO$_3$H)$_2$]$_u$,
—SO$_3$H,
—CH(SO$_3$H)$_2$,
—PO$_3$H,
—(CH$_2$)$_q$N[(CH$_2$)$_p$PO$_3$H]$_t$,
—(CH$_2$)$_q$NR$^b$[(CH$_2$)$_p$PO$_3$H]$_u$, or
—(CH$_2$)$_q$NR$^p$(CH$_2$)$_p$CH(PO$_3$H)$_2$, each R$^{22}$ is independently alkyl, haloalkyl, cycloalkyl or aryl;

each R$^b$ is independently hydrogen, alkyl, haloalkyl or cycloalkyl;

each v, w and p are independently an integer from 1 to 10;
each q is independently an integer from 0 to 10;
t is 2 or 3; and
u is 1 or 2.

In certain embodiments, the water soluble group Z is
—(CH$_2$)$_q$(OCH$_2$CH$_2$)$_v$OR$^{22}$,
—(CH$_2$CH$_2$O)$_v$(CH$_2$)$_p$OR$^{22}$,
—(CH$_2$)$_q$(OCH$_2$CH$_2$)$_v$SR$^{22}$,
—(CH$_2$CH$_2$O)$_v$(CH$_2$)$_p$SR$^{22}$,
—(CH$_2$)$_q$O(CH$_2$)$_v$N[(CH$_2$CH$_2$O)$_w$CH$_2$CH$_2$OR$^{22}$]$_t$,
—(CH$_2$)$_q$(OCH$_2$CH$_2$)$_v$N[(CH$_2$CH$_2$O)$_w$CH$_2$CH$_2$OR$^{22}$]$_t$,
—(CH$_2$CH$_2$O)$_m$(CH$_2$)$_p$N[(CH$_2$CH$_2$O)$_w$CH$_2$CH$_2$OR$^{22}$]$_t$,
—NH$_2$,
—(CH$_2$)$_q$N[(CH$_2$CH$_2$O)$_v$CH$_2$CH$_2$OR$^{22}$]$_t$,
—(CH$_2$)$_q$NR$^b$[(CH$_2$CH$_2$O)$_w$CH$_2$CH$_2$OR$^{22}$]$_u$,
—(CH$_2$)$_q$N[(CH$_2$)$_p$(OCH$_2$CH$_2$)$_v$OR$^{22}$]$_t$,
—(CH$_2$)$_q$N[(CH$_2$)$_p$SO$_3$—]$_t$,
—(CH$_2$)$_q$NR$^b$[(CH$_2$)$_p$SO$_3$—]$_u$,
—(CH$_2$)$_q$NR$^b$[(CH$_2$)$_p$CH(SO$_3$—)$_2$]$_u$,
—(CH$_2$)$_q$N[(CH$_2$)$_p$S(O)$_u$OH]$_t$,
—(CH$_2$)$_q$N[(CH$_2$)$_p$OSO$_3$$^{2-}$]$_t$,
—(CH$_2$)$_q$(OCH$_2$CH$_2$)$_v$(CH$_2$)$_q$SO$_3$—, —$(CH_2)_q(OCH_2CH_2)_v(CH_2)_qS(O)_uOH$,
—$(CH_2)_q(OCH_2CH_2)_v(CH_2)_qOSO_3^{2-}$,
—$CH(SO_3—)_2$,
—$SO_3—$,
—$OSO_3^{2-}$,
—$S(O)_uOH$,
—$PO_3^{2-}$,
—$CH(PO_3^{2-})_2$,
—$(CH_2)_qN[(CH_2)_pPO_3—]_t$,
—$(CH_2)_q(OCH_2CH_2)_v(CH_2)_qPO_3—$,
—$(CH_2)_qN[(CH_2)_pOPO_3]_t$,
—$OPO_3—$,
—$(CH_2)_q(OCH_2CH_2)_v(CH_2)_qP(O)(OH)_2$,
—$(CH_2)_qN[(CH_2)_pP(O)(OH)_2]_t$,
—$P(O)(OH)_2$,
glutamate, aspartate, histidine, 1,3-beta-glucan or 1,4-beta-glucan;
each $R^{22}$ is independently alkyl, haloalkyl, cycloalkyl or aryl;
each $R^b$ is independently hydrogen, alkyl, haloalkyl or cycloalkyl;
each v, w and p are independently an integer from 1 to 10;
each q is independently an integer from 0 to 10;
t is 2 or 3; and
u is 1 or 2.
In yet certain embodiments, the water soluble group Z is
—$(CH_2)_q(OCH_2CH_2)_vOR^{22}$,
—$(CH_2)_qO(CH_2)_vN[(CH_2CH_2O)_wCH_2CH_2OR^{22}]_t$,
—$(CH_2)_qN[(CH_2)_p(OCH_2CH_2)_vOR^{22}]_t$,
—$(CH_2)_qN[(CH_2)_pSO_3—]_t$,
—$(CH_2)_qNR^b[(CH_2)_pSO_3—]_u$,
—$(CH_2)_qNR^b[(CH_2)_pCH(SO_3—)_2]_u$,
—$SO_3—$,
—$CH(SO_3—)_2$,
—$PO_3^{2-}$,
—$(CH_2)_qN[(CH_2)_pPO_3—]_t$,
—$(CH_2)_qNR^b[(CH_2)_pPO_3—]_u$ or
—$(CH_2)_qNR^b(CH_2)_pCH(PO_3—)_2$;
each $R^{22}$ is independently alkyl, haloalkyl, cycloalkyl or aryl;
each $R^b$ is independently hydrogen, alkyl, haloalkyl or cycloalkyl;
each v, w and p are independently an integer from 1 to 10;
each q is independently an integer from 0 to 10;
t is 2 or 3; and
u is 1 or 2.
In yet certain embodiments, the water soluble group Z is
—$(CH_2)_q(OCH_2CH_2)_vOR^{22}$,
—$(CH_2)_qO(CH_2)_vN[(CH_2CH_2O)_wCH_2CH_2OR^{22}]_t$,
—$(CH_2)_qN[(CH_2)_pSO_3—]_t$,
—$(CH_2)_qNR^b[(CH_2)_pSO_3—]_u$,
—$(CH_2)_qNR^b[(CH_2)_pCH(SO_3)_2]_u$,
—$(CH_2)_qCH[(CH_2)_pN[(CH_2)(SO_3—)_2]_t$,
—$SO_3$,
—$PO_3^{2-}$ or
—$(CH_2)_qN[(CH_2)_pPO_3—]_t$;
each $R^{22}$ is independently alkyl, haloalkyl, cycloalkyl or aryl;
each $R^b$ is independently hydrogen, alkyl, haloalkyl or cycloalkyl;
each v, w and p are independently an integer from 1 to 10;
each q is independently an integer from 0 to 10;
t is 2 or 3; and
u is 1 or 2.
In certain embodiments, a and c are 0 and b and d are 1. In certain embodiments, a and c are 1 and b and d are 0. In yet certain embodiments, c is 0 and d is 1.

In certain embodiments, X is:

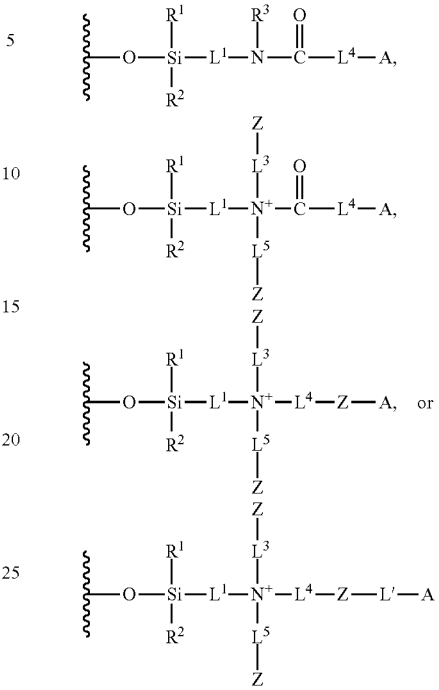

wherein $R^1$, $R^2$, $R^3$, $L^1$, $L^3$, $L^4$, $L^5$, Z and A are as described for Formula (I).

In certain embodiments, L is optionally substituted alkylene or optionally substituted alkenylene. In certain embodiments, $L^4$ is optionally substituted alkylene.

In certain embodiments, Y is:

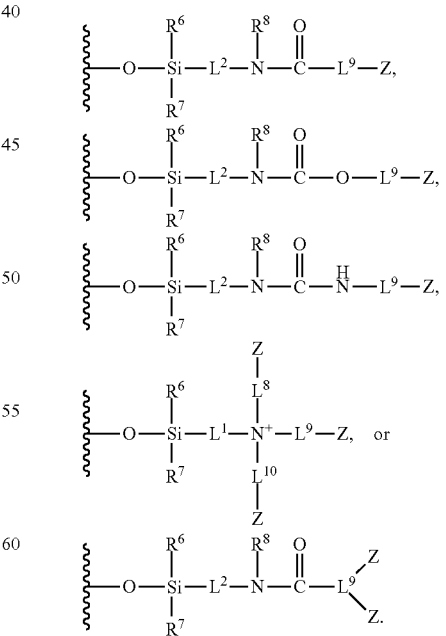

In certain embodiments, M is Si, Ge, Sn or Al. In yet certain embodiments, M is Si or Ge.

In certain embodiments, provided herein are compounds of Formula (X) or Formula (I) selected from the group consisting of:
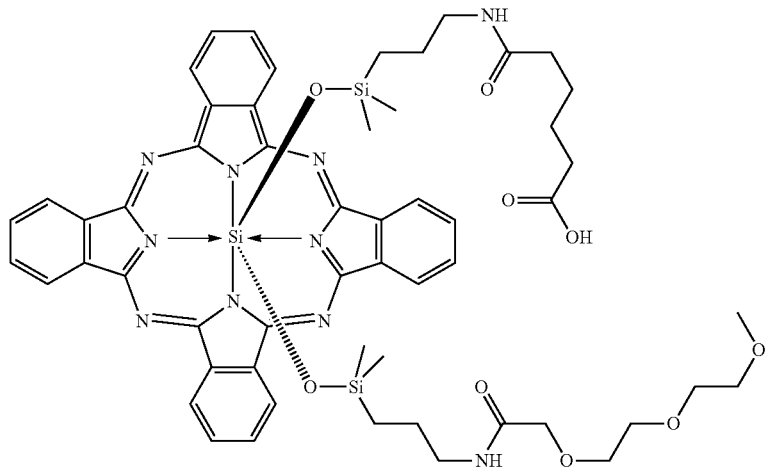
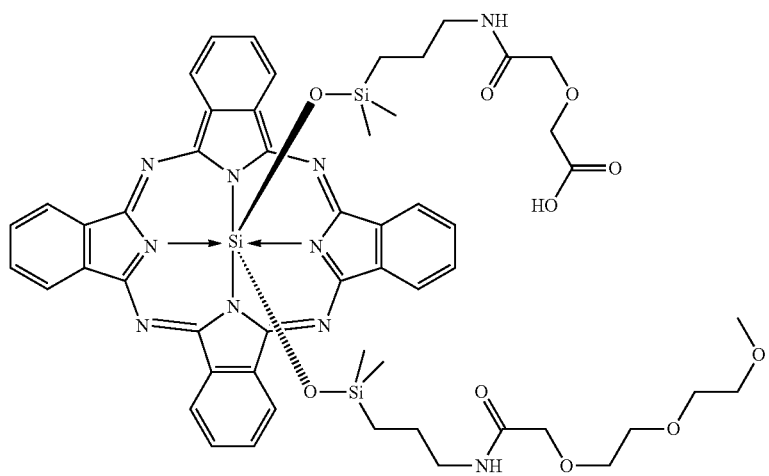
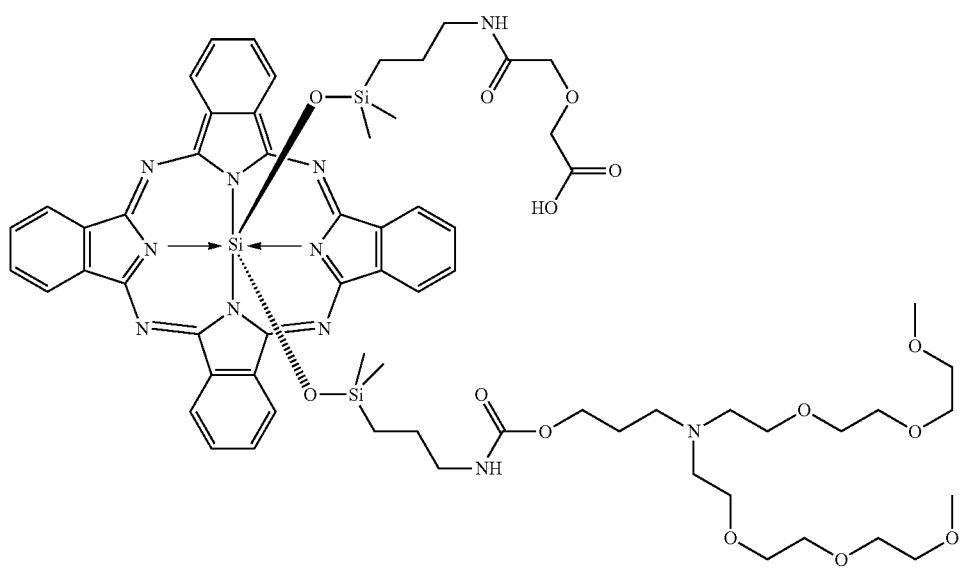

-continued
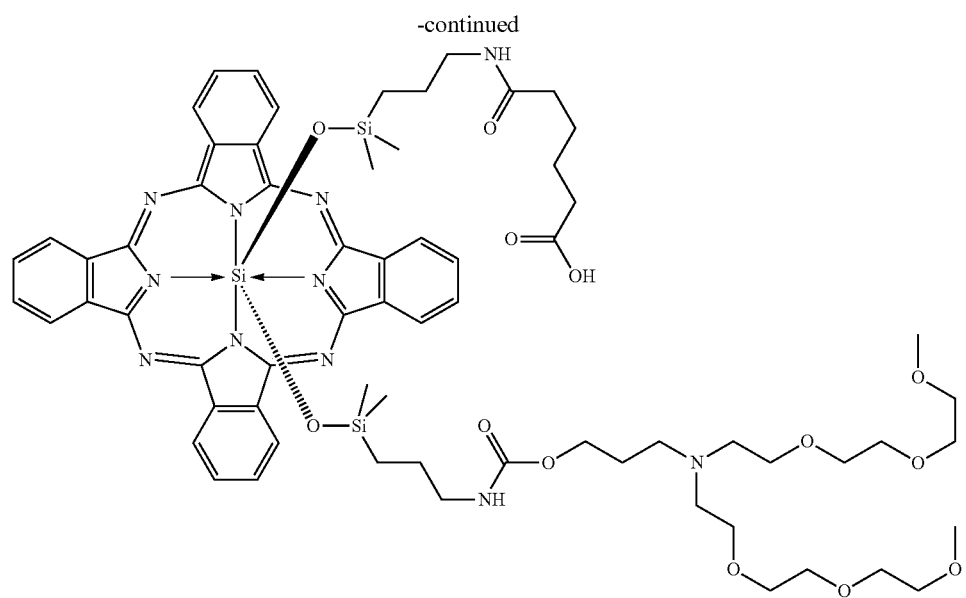
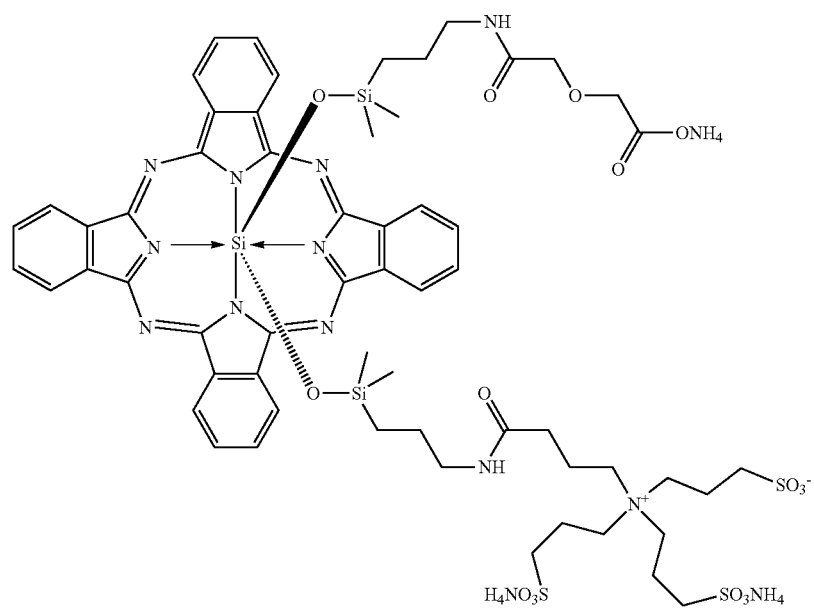

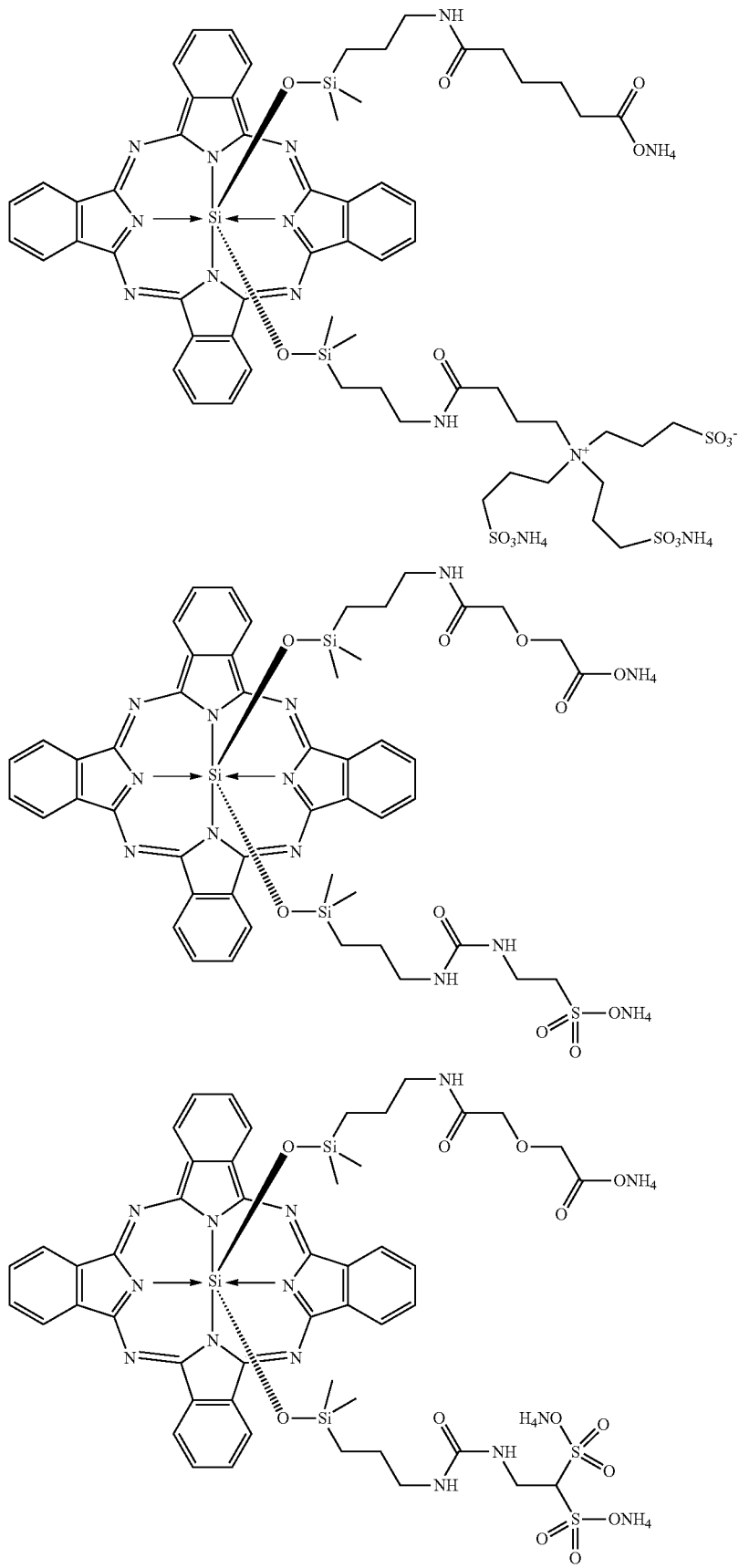

-continued
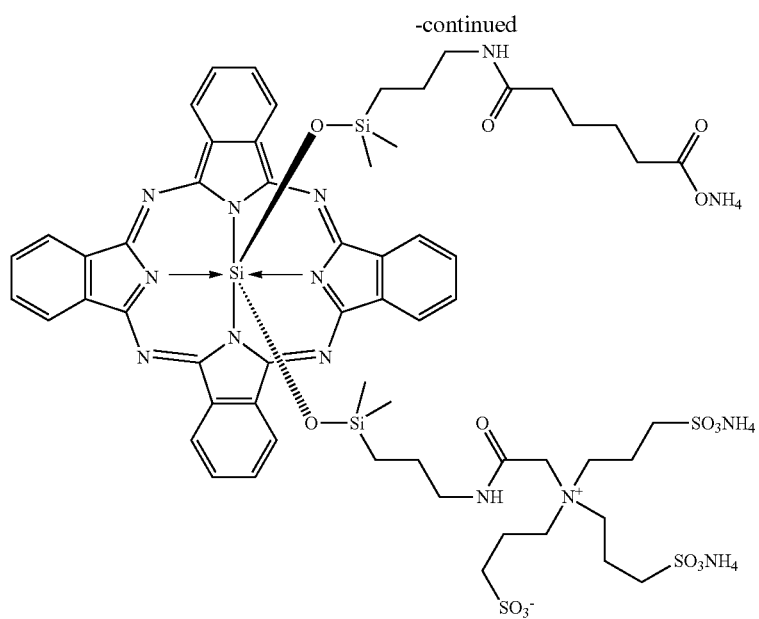
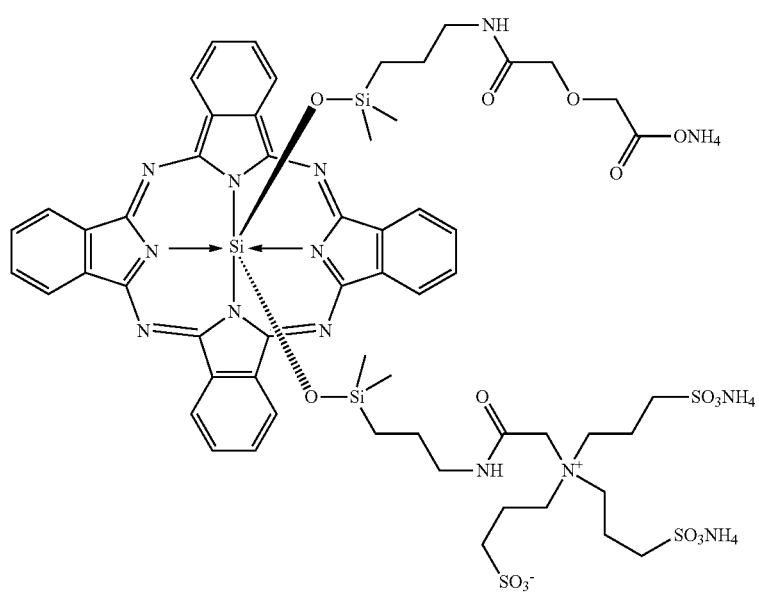

-continued
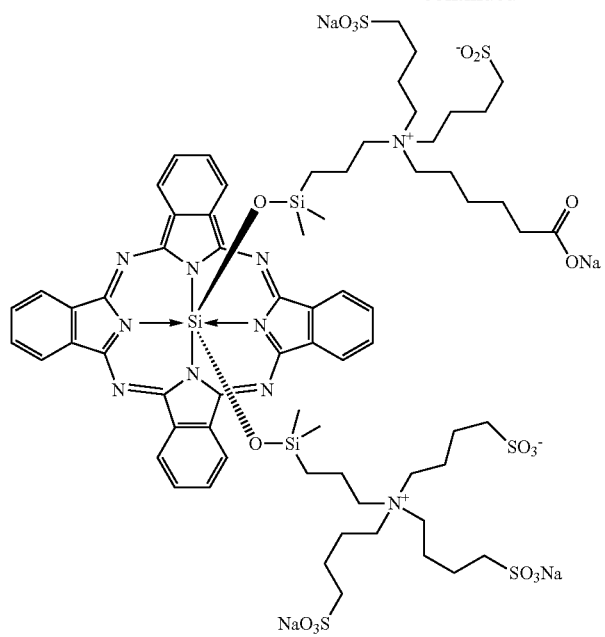
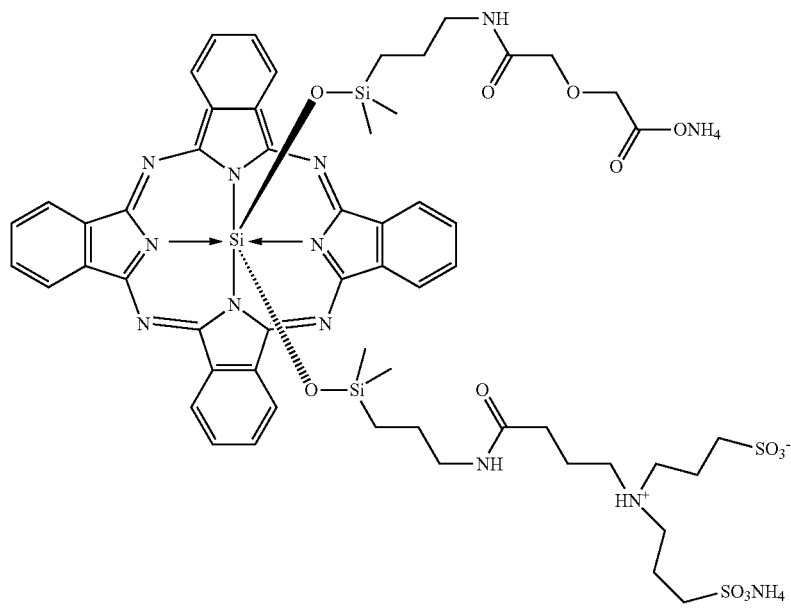

-continued
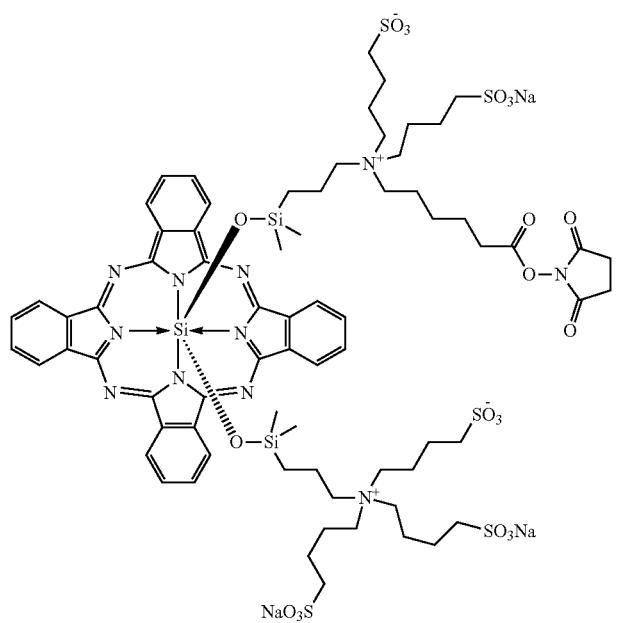
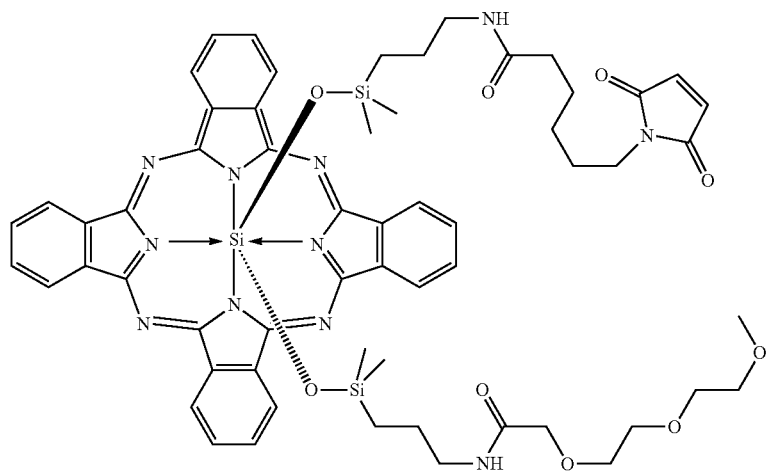
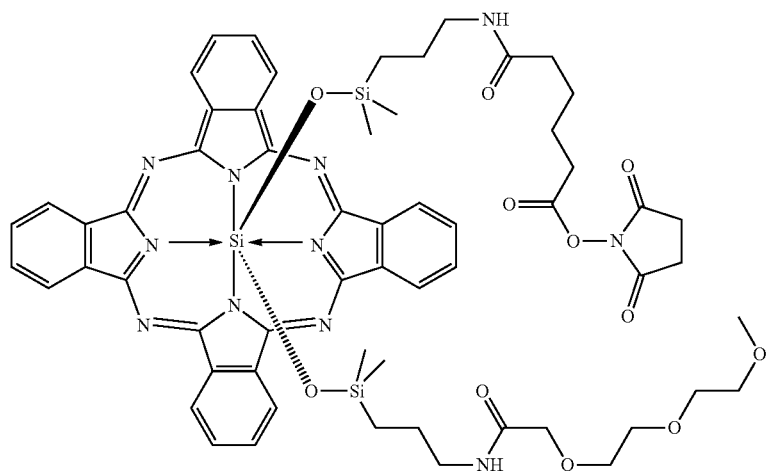

-continued
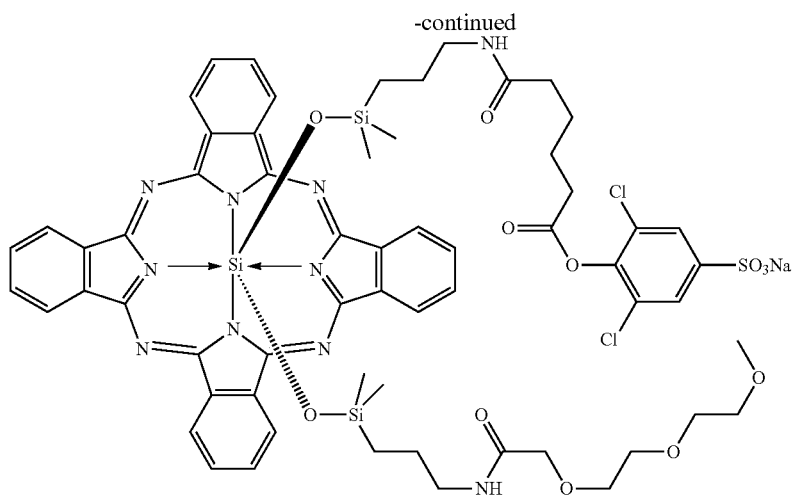
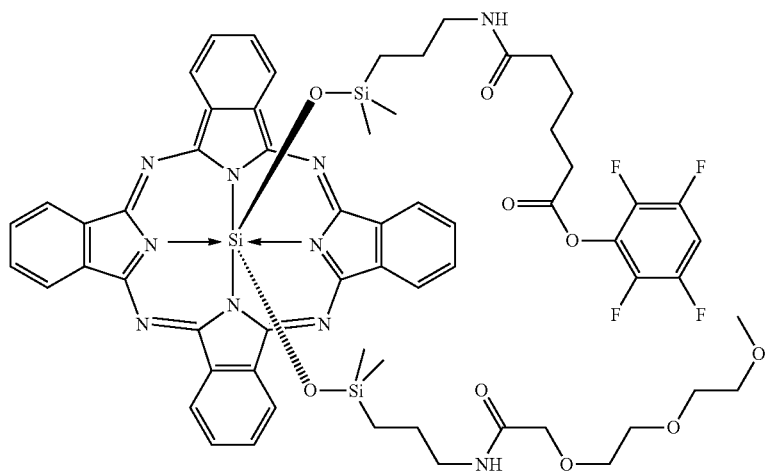
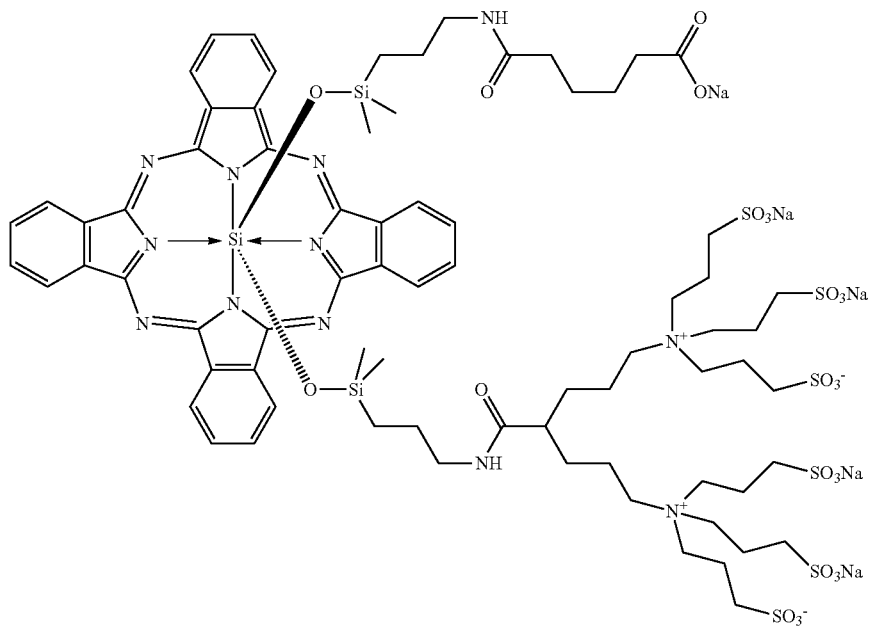

-continued
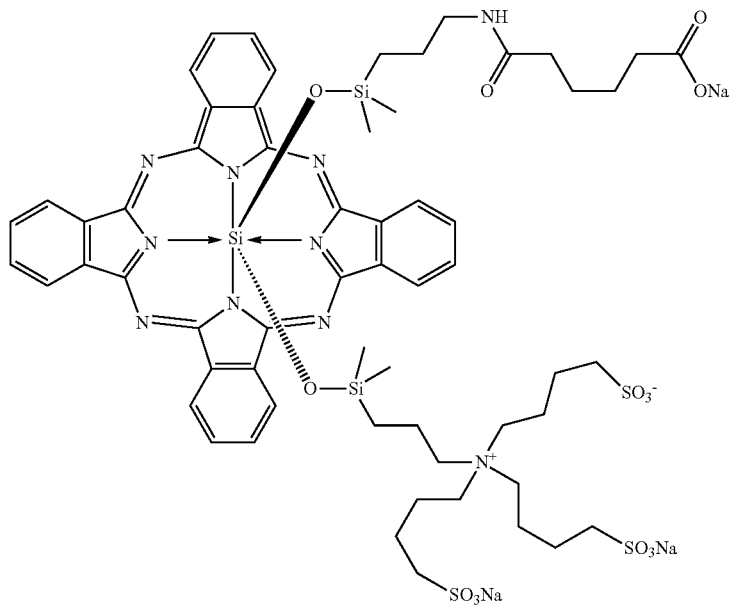
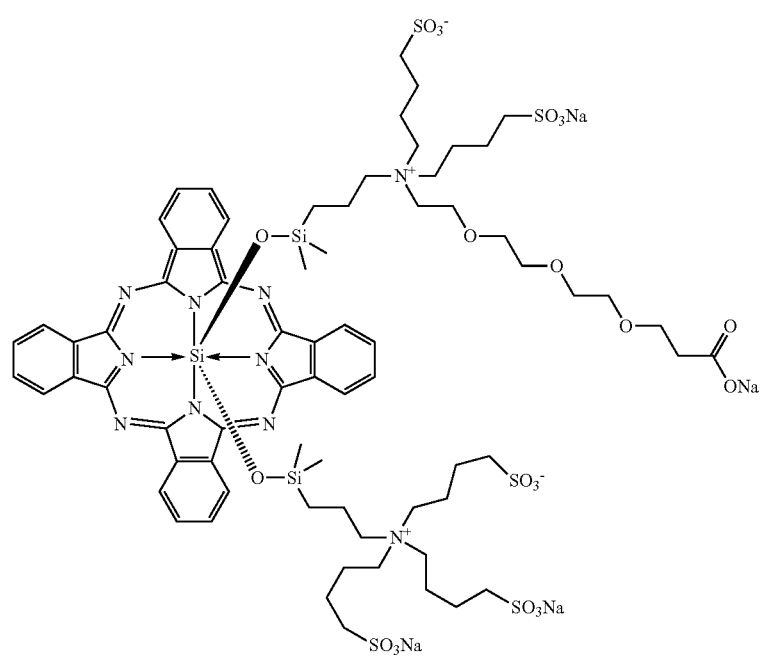

-continued
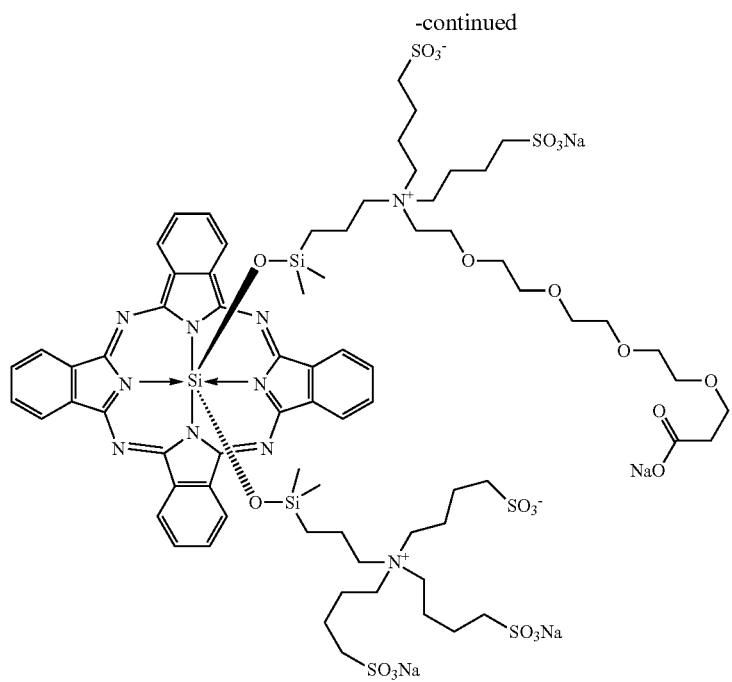
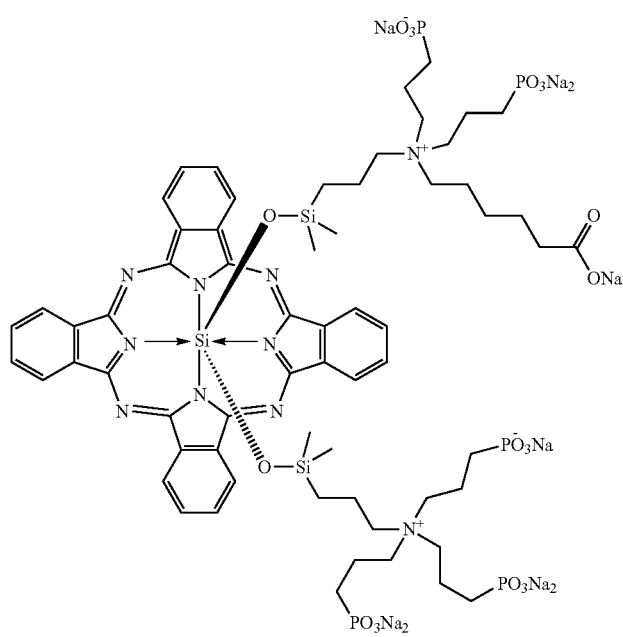

-continued
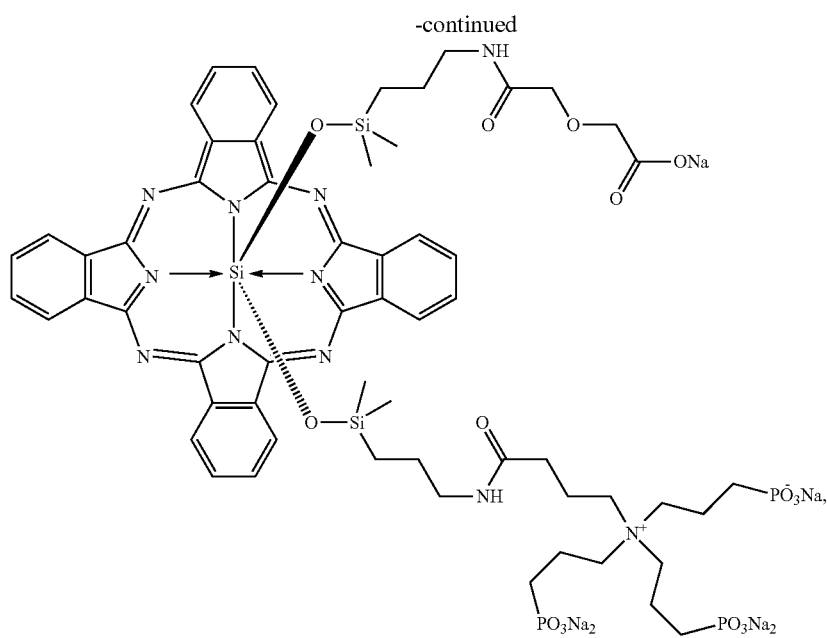
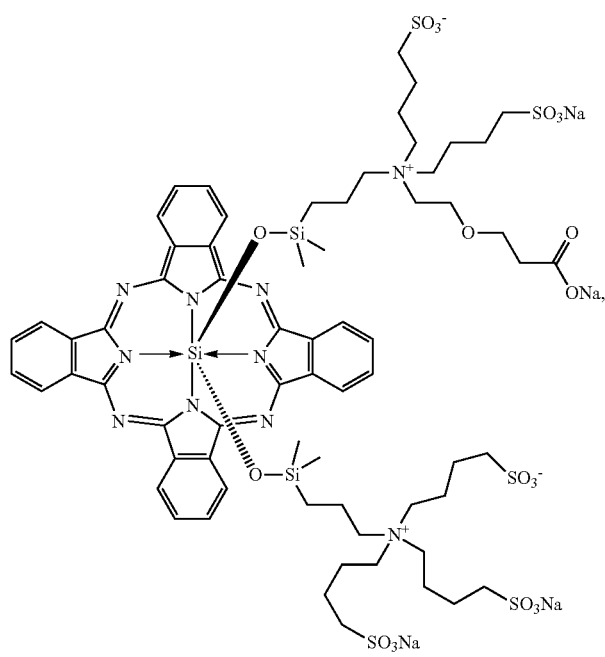

-continued
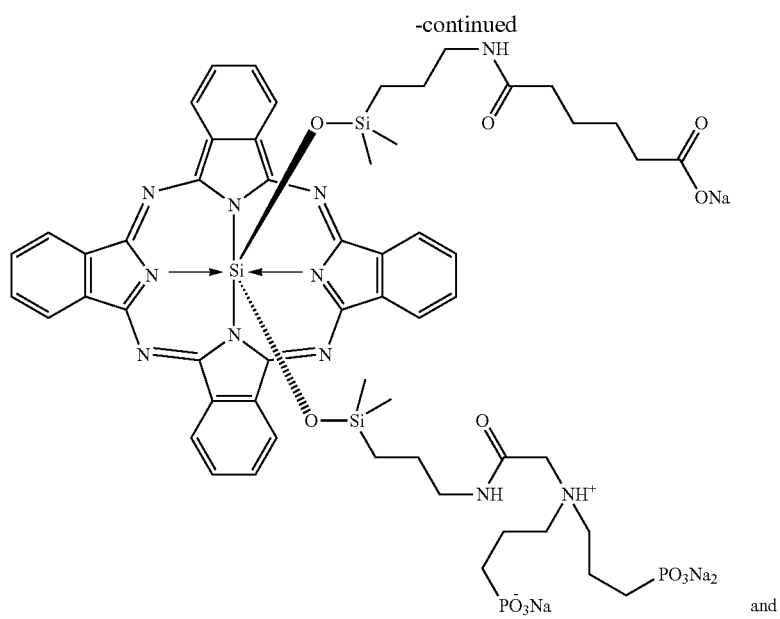
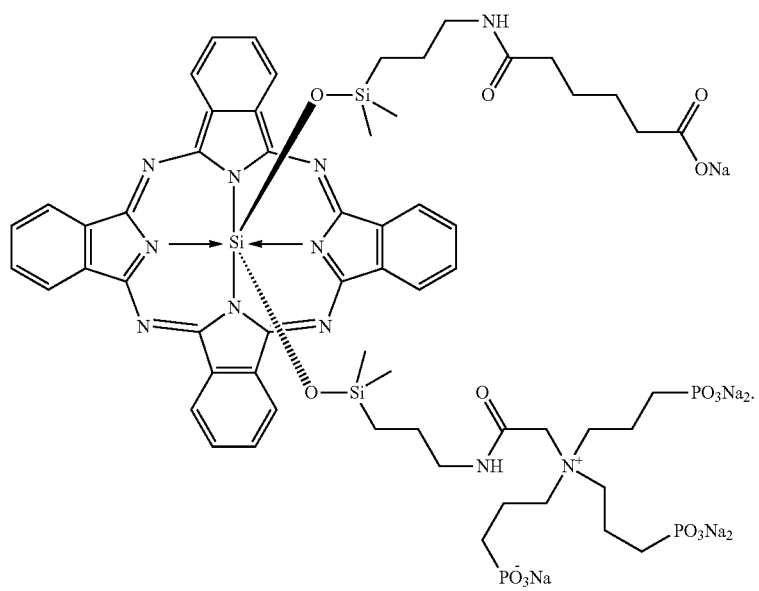
and

In yet certain embodiments, the compound of Formula (X) or Formula (I) is selected from the group consisting of:
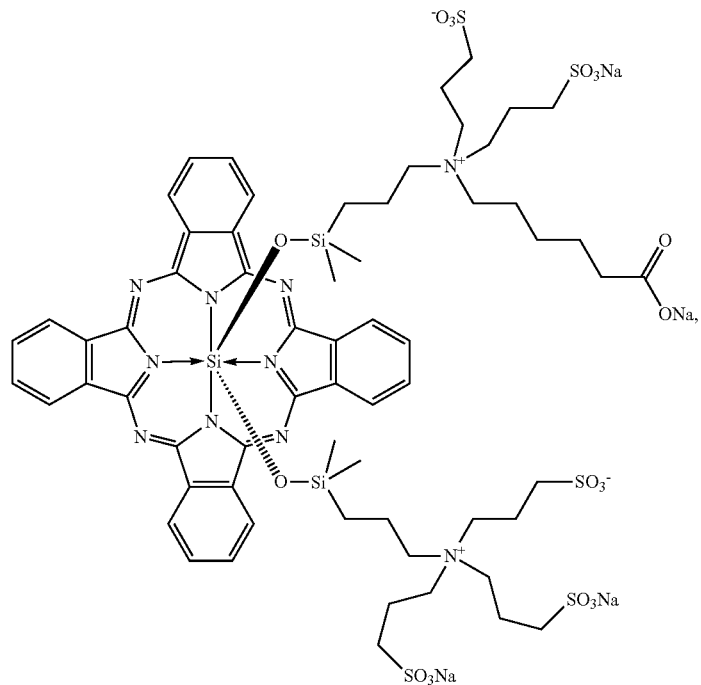
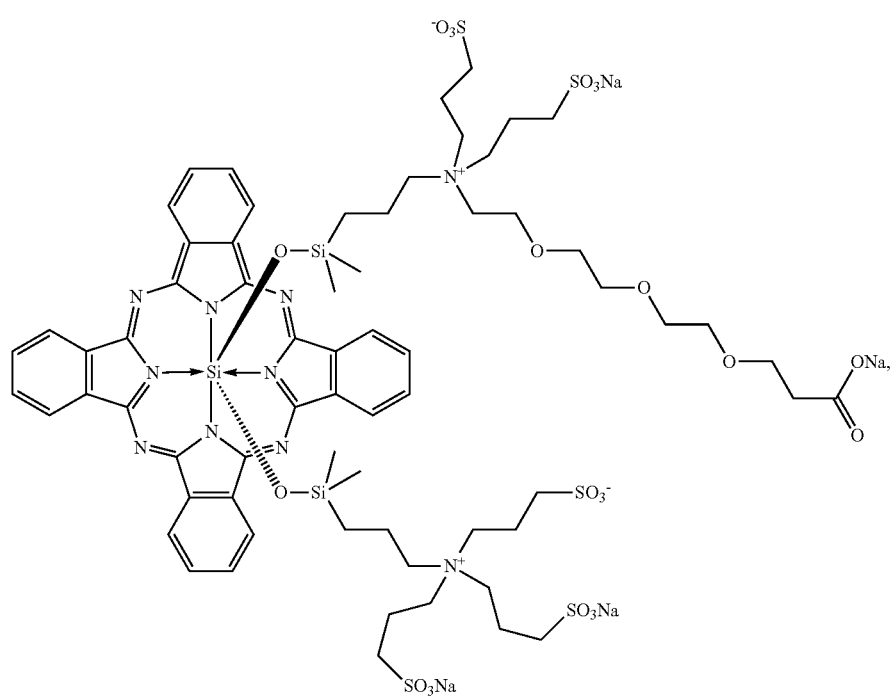

-continued
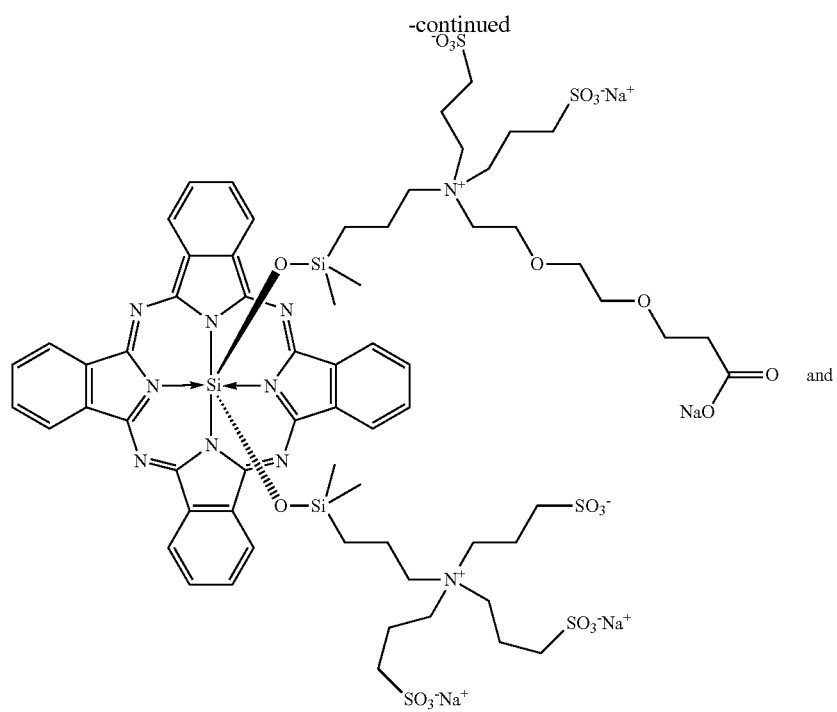
and
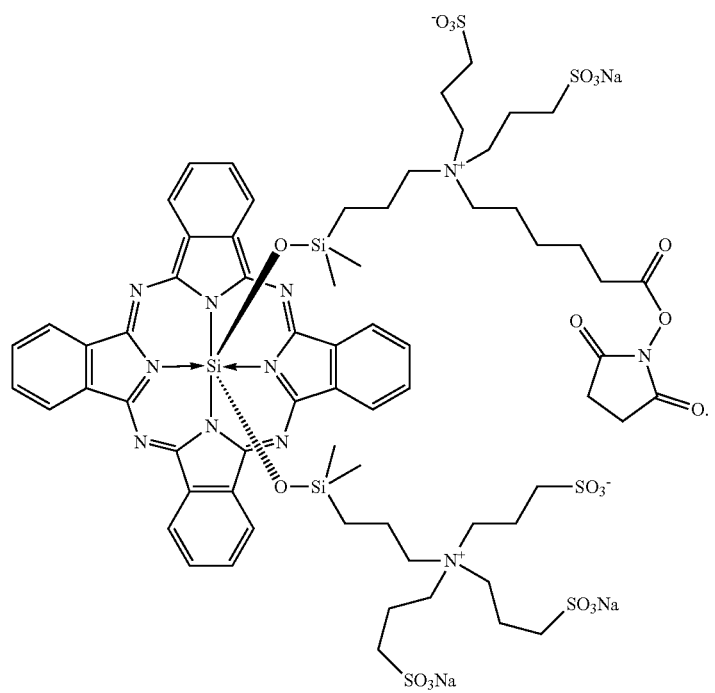

In certain embodiments, the reactive group is capable of forming a covalent bond In certain embodiments, provided herein are compound selected from Table 1.

TABLE 1

| Ex. No. | Structure Name |
|---|---|
| 1 | 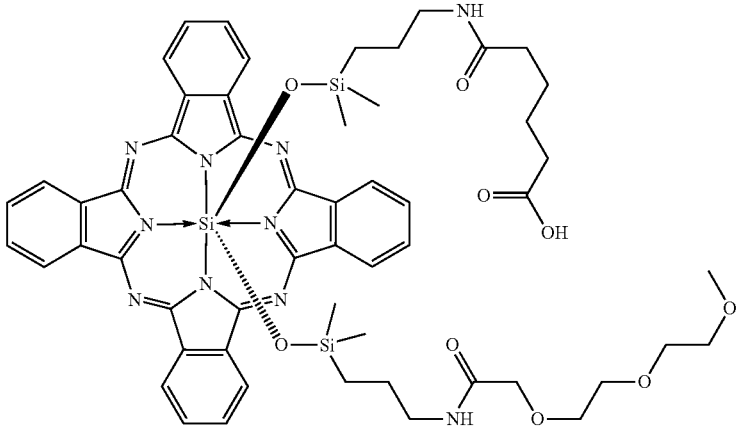<br>6-((3-(dimethyl((19-((15-methyl-10-oxo-2,5,8-trioxa-11-aza-15-silahexadecan-15-yl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)silyl)propyl)amino)-6-oxohexanoic acid |
| 2 | 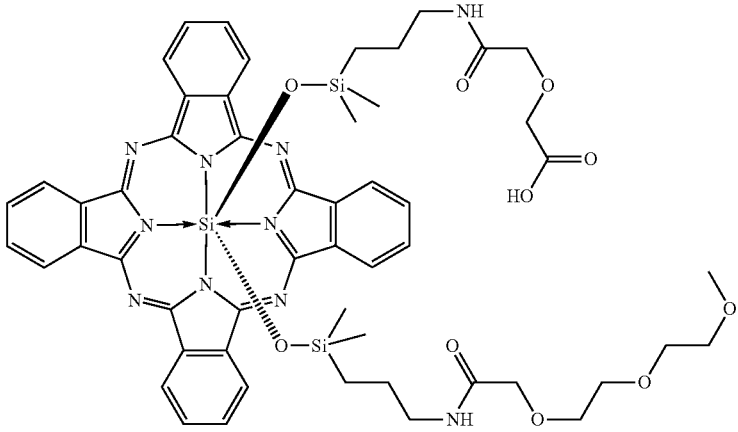<br>2-(2-((3-(dimethyl((19-((15-methyl-10-oxo-2,5,8-trioxa-11-aza-15-silahexadecan-15-yl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)silyl)propyl)amino)-2-oxoethoxy)acetic acid |

TABLE 1-continued

| Ex. No. | Structure Name |
|---|---|
| 3 | 2-(2-((3-(((19-(((11-(2-(2-(2-methoxyethoxy)ethoxy)ethyl)-21-methyl-16-oxo-2,5,8,15-tetraoxa-11,17-diaza-21-siladocosan-21-yl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)dimethylsilyl)propyl)amino)-2-oxoethoxy)acetic acid |
| 4 | 6-((3-(((19-(((11-(2-(2-(2-methoxyethoxy)ethoxy)ethyl)-21-methyl-16-oxo-2,5,8,15-tetraoxa-11,17-diaza-21-siladocosan-21-yl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)dimethylsilyl)propyl)amino)-6-oxohexanoic acid |

TABLE 1-continued

| Ex. No. | Structure Name |
|---|---|
| 5 | 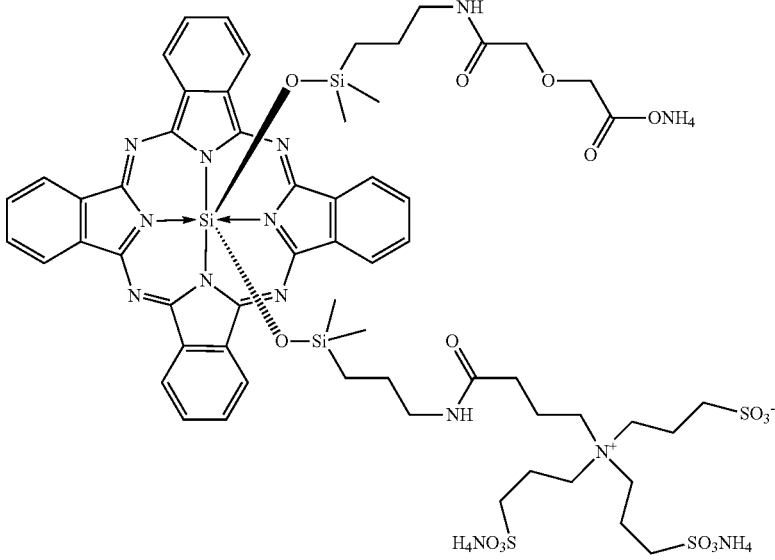<br>Ammonium 3-((4-((3-(((19-(((3-(2-(carboxymethoxy)acetamido)propyl)dimethylsilyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)dimethylsilyl)propyl)amino)-4-oxobutyl)bis(3-sulfopropyl)ammonio)propane-1-sulfonae |
| 6 | 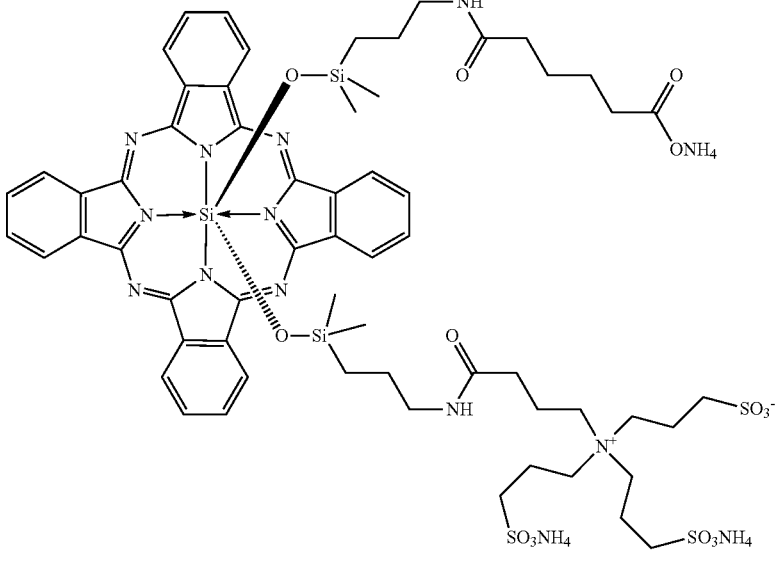<br>3-((4-((3-(((19-(((3-(6-(($\lambda^5$-azaneyl)oxy)-6-oxohexanamido)propyl)dimethylsilyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)dimethylsilyl)propyl)amino)-4-oxobutyl)bis(3-((($\lambda^5$-azaneyl)oxy)sulfonyl)propyl)ammonio)propane-1-sulfonate |

TABLE 1-continued

| Ex. No. | Structure Name |
|---|---|
| 7 | Ammonium 2-(2-((3-(((19-(((dimethyl(3-(3-(2-sulfonatoethyl)ureido)propyl)silyl)oxy)-19H-6,11-(azeno)-17,21-(azeno[1]episoindoloazeno)benzo[7,8][1,3,5,10]tetraaza[2]silacycloundecino[4,3-a:11,1-a']diisoindol-19-yl)oxy)dimethylsilyl)propyl)amino)-2-oxoethoxy)acetate |
| 8 | Ammonium 2-(2-((3-(((19-(((3-(3-(2,2-disulfonatoethyl)ureido)propyl)dimethylsilyl)oxy)-19H-6,11-(azeno)-17,21-(azeno[1]episoindoloazeno)benzo[7,8][1,3,5,10]tetraaza[2]silacycloundecino[4,3-a:11,1-a']diisoindol-19-yl)oxy)dimethylsilyl)propyl)amino)-2-oxoethoxy)acetate |

TABLE 1-continued

| Ex. No. | Structure Name |
|---|---|
| 9 | 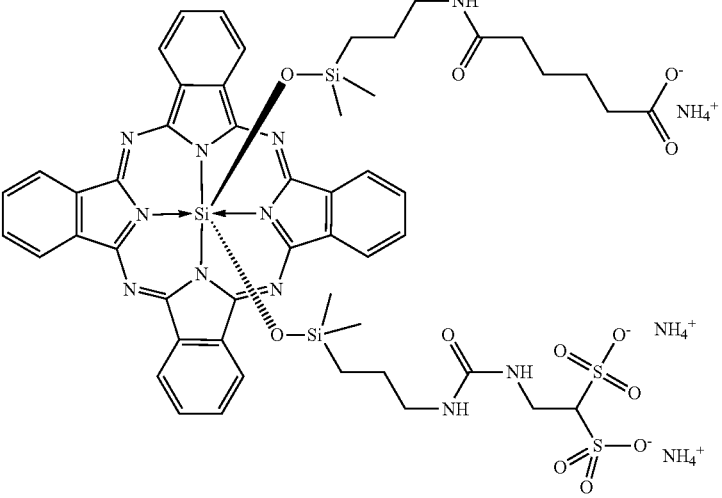<br>Ammonium 6-((3-(((19-(((3-(3-(2,2-disulfonatoethyl)ureido)propyl)dimethylsilyl)oxy)-19H-6,11-(azeno)-17,21-(azeno[1]episoindoloazeno)benzo[7,8][1,3,5,10]tetraaza[2]silacycloundecino[4,3-a:11,1-a']diisoindol-19-yl)oxy)dimethylsilyl)propyl)amino)-6-oxohexanoate |
| 10 | 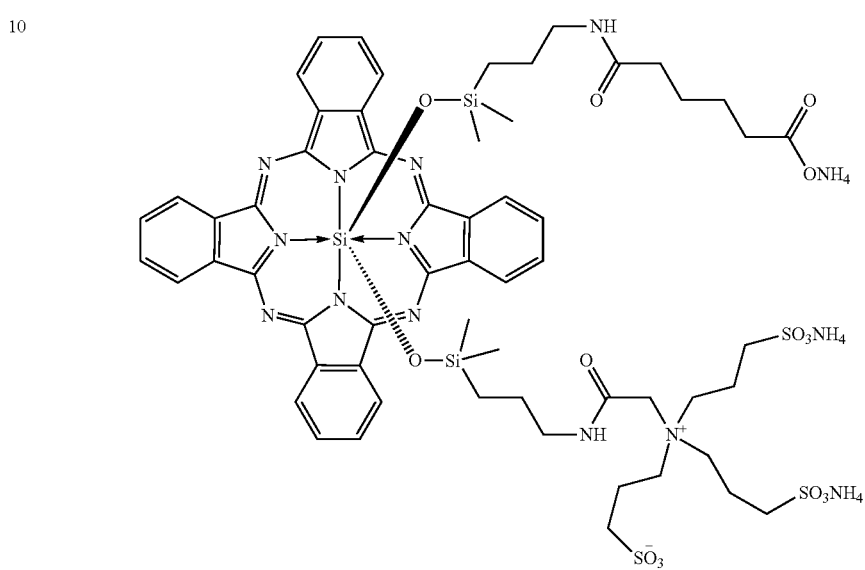<br>3-((2-((3-(((19-(((3-(6-(($\lambda^5$-azaneyl)oxy)-6-oxohexanamido)propyl)dimethylsilyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)dimethylsilyl)propyl)amino)-2-oxoethyl)bis(3-((($\lambda^5$-azaneyl)oxy)sulfonyl)propyl)ammonio)propane-1-sulfonate |

TABLE 1-continued

| Ex. No. | Structure Name |
|---|---|
| 11 | 3-((2-((3-(((19-(((3-(2-(2-((λ⁵-azaneyl)oxy)-2-oxoethoxy)acetamido)propyl)dimethylsilyl)oxy)-19H-6,11-(azeno)-17,21-(azeno[3]episoindoloazeno)benzo[7,8][1,3,5,10]tetraaza[2]silacycloundecino[4,3-a:11,1-a']diisodinol-19-yl)oxy)dimethylsilyl)propyl)amino)-2-oxoethyl)bis(3-(((λ⁵-azaneyl)oxy)sulfonyl)propyl)ammonio)propan-1-sulfonate |
| 12 | 3-((6-((λ⁵-azaneyl)oxy)-6-oxohexyl)(3-(((λ5-azaneyl)oxy)sulfonyl)propyl)(3-(((19-(((3-(bis(3-(((λ5-azaneyl)oxy)sulfonyl)propyl)(3-sulfonatopropyl)ammonio)propyl)dimethylsilyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)dimethylsilyl)propyl)ammonio)propane-1-sulfonate |

| Ex. No. | Structure Name |
|---|---|
| 13 | 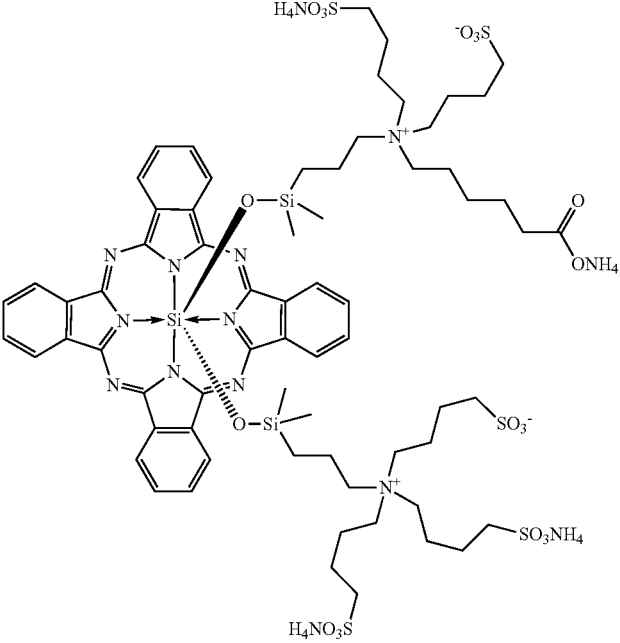 4-(((6-(((λ5-azaneyl)oxy)-6-oxohexyl)(4-(((λ5-azaneyl)oxy)sulfonyl)butyl)(3-(((19-(((3-(bis(4-(((λ5-azaneyl)oxy)sulfonyl)butyl)(4-sulfonatobutyl)ammonio)propyl)dimethylsilyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)dimethylsilyl)propyl)ammonio)butane-1-sulfonate |
| 14 | 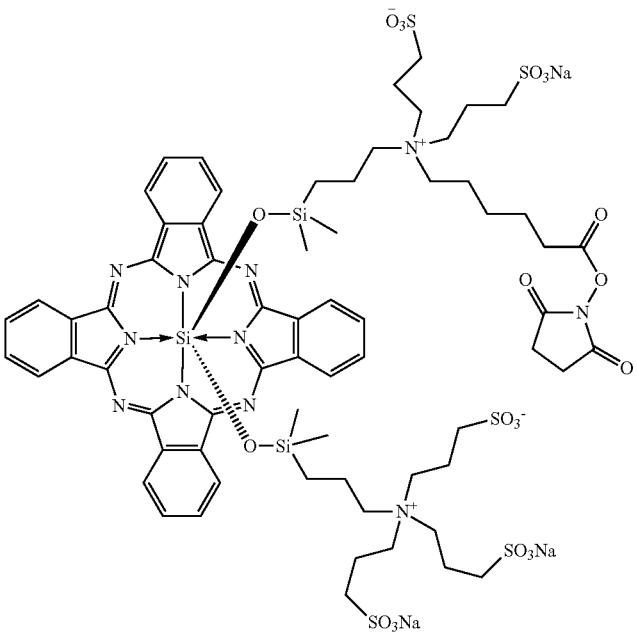 Sodium 3,3',3''-((3-(((19-(((3-((6-((2,5-dioxopyrrolidin-1-yl)oxy)-6-oxohexyl)bis(3-sulfonatopropyl)ammonio)propyl)dimethylsilyl)oxy)-19H-6,11-(azeno)-17,21-(azeno[1]episoindoloazeno)benzo[7,8][1,3,5,10]tetraaza[2]silacycloundecino[4,3-a:11,1-a']diisoindol-19-yl)oxy)dimethylsilyl)propyl)ammonio)tris(propane-1-sulfonate) |

TABLE 1-continued

| Ex. No. | Structure Name |
|---|---|
| 15 | 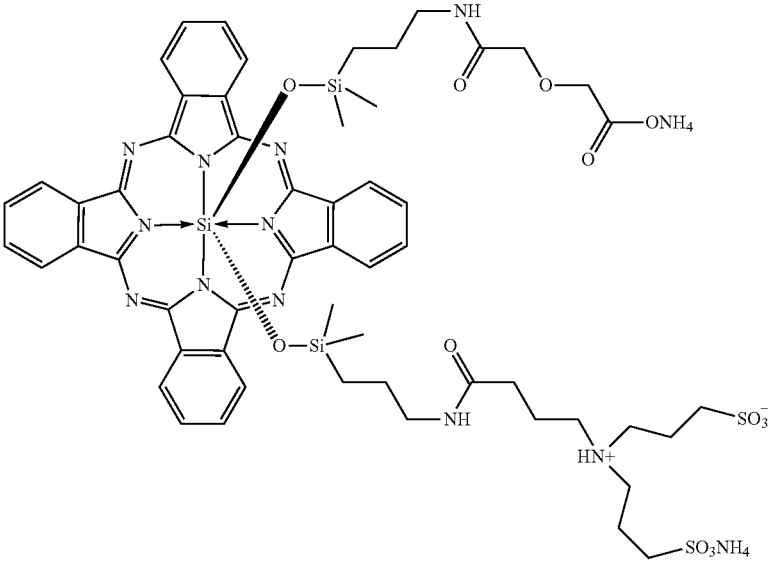<br>Ammonium 2-(2-((3-(((19-(((3-(4-(bis(3-sulfonatopropyl)ammonio)butanamido)propyl)dimethylsilyl)oxy)-19H-6,11-(azeno)-17,21-(azeno[1]episoindoloazeno)benzo[7,8][1,3,5,10]tetraaza[2]silacycloundecino[4,3-a:11,1-a']diisoindol-19-yl)oxy)dimethylsilyl)propyl)amino)-2-oxoethoxy)acetate |
| 16 | 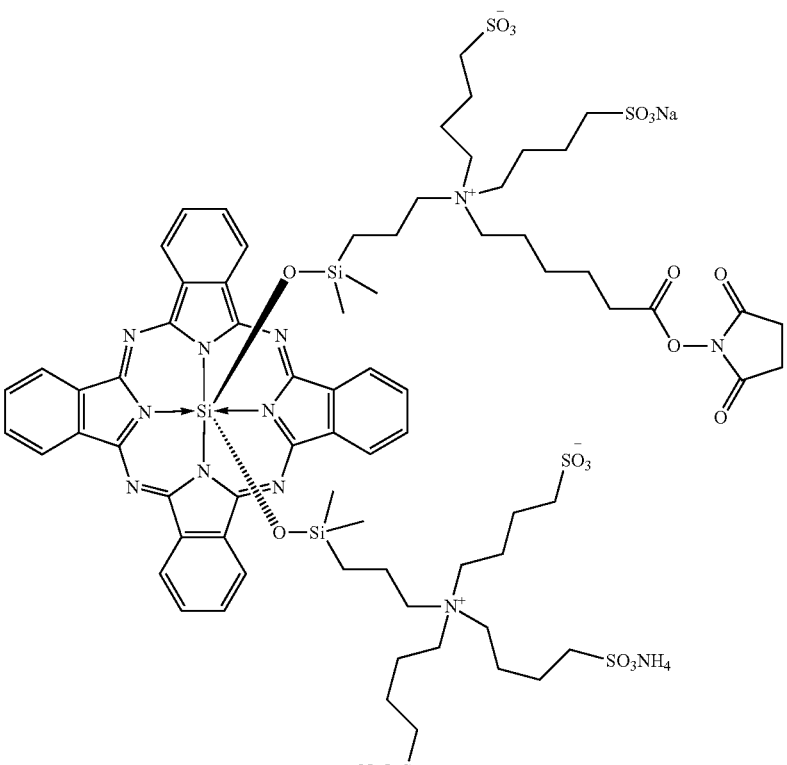<br>Sodium 4,4',4''-((3-(((19-(((3-((6-((2,5-dioxopyrrolidin-1-yl)oxy)-6-oxohexyl)bis(4-sulfonatobutyl)ammonio)propyl)dimethylsilyl)oxy)-19H-6,11-(azeno)-17,21-(azeno[1]episoindoloazeno)benzo[7,8][1,3,5,10]tetraaza[2]silacycloundecino[4,3-a:11,1-a']diisoindol-19-yl)oxy)dimethylsilyl)propyl)ammonio)tris(butane-1-sulfonate) |

TABLE 1-continued

| Ex. No. | Structure Name |
|---|---|
| 17 | Sodium 2-((19-(((dimethyl(3-(tris(4-sulfonatobutyl)ammonio)propyl)silyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)-2-methyl-6,6-bis(4-sulfonatobutyl)-9,12,15-trioxa-6-aza-2-silaoctadecan-6-ium-18-oate |
| 18 | Sodium 2-((19-(((dimethyl(3-(tris(4-sulfonatobutyl)ammonio)propyl)silyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)-2-methyl-6,6-bis(4-sulfonatobutyl)-9,12-dioxa-6-aza-2-silapentadecan-6-ium-15-oate |

TABLE 1-continued

| Ex. No. | Structure Name |
|---|---|
| 19 | Sodium 2-((19-((dimethyl(3-(tris(3-sulfonatopropyl)ammonio)propyl)silyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)-2-methyl-6,6-bis(3-sulfonatopropyl)-9,12,15-trioxa-6-aza-2-silaoctadecan-6-ium-18-oate |
| 20 | Sodium 6-((3-(((19-((dimethyl(3-(5-(tris(3-sulfonatopropyl)ammonio)-2-(3-(tris(3-sulfonatopropyl)ammonio)propyl)pentanamido)propyl)silyl)oxy)-19H-6,11-(azeno)-17,21-(azeno[1]episoindoloazeno)benzo[7,8][1,3,5,10]tetraaza[2]silacycloundecino[4,3-a:11,1-a']diisoindol-19-yl)oxy)dimethylsilyl)propyl)amino)-6-oxohexanoate) |

TABLE 1-continued

| Ex. No. | Structure Name |
|---|---|
| 21 | 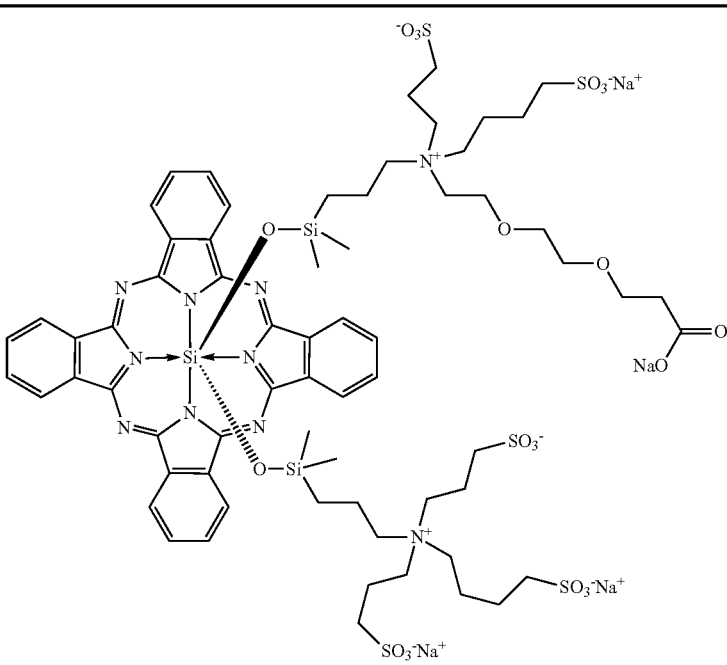<br>Sodium 2-((19-((dimethyl(3-(tris(3-sulfonatopropyl)ammonio)propyl)silyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)-2-methyl-6,6-bis(3-sulfonatopropyl)-9,12-dioxa-6-aza-2-silapentadecan-6-ium-15-oate |
| 22 | 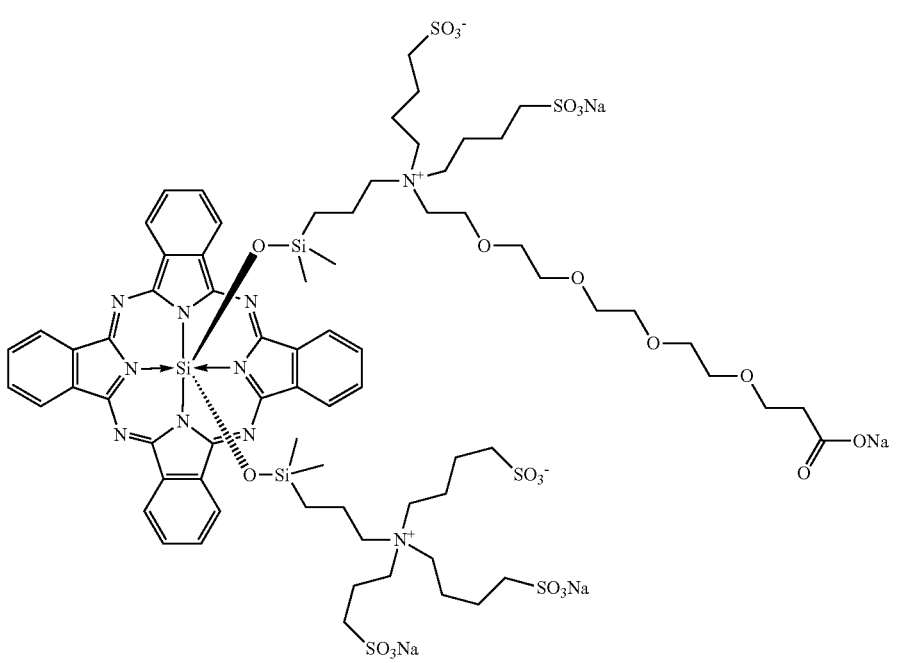<br>Sodium 2-((19-((dimethyl(3-(tris(4-sulfonatobutyl)ammonio)propyl)silyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)-2-methyl-6,6-bis(4-sulfonatobutyl)-9,12,15,18-tetraoxa-6-aza-2-silahenicosan-6-ium-21-oate |

TABLE 1-continued

| Ex. No. | Structure Name |
|---|---|
| 23 | 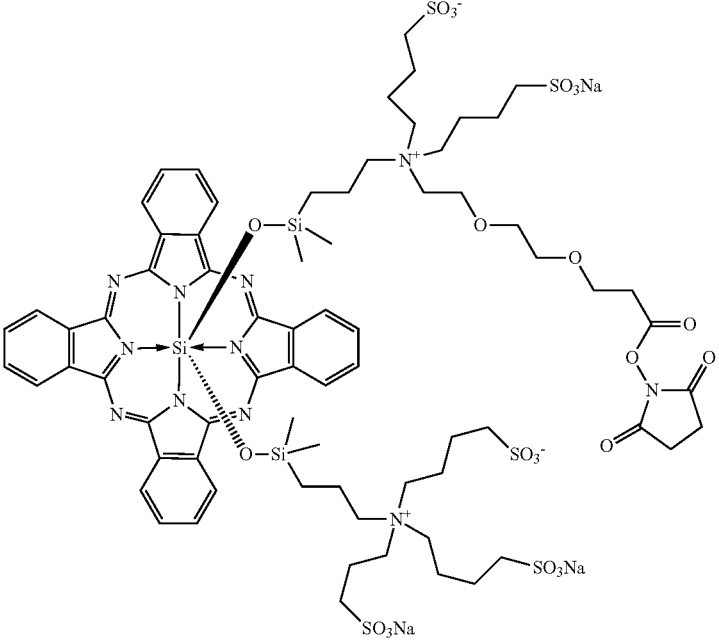  Sodium 4,4',4''-((3-(((19-((15-((2,5-dioxopyrrolidin-1-yl)oxy)-2-methyl-15-oxo-6,6-bis(4-sulfonatobutyl)-9,12-dioxa-6-aza-2-silapentadecan-6-ium-2-yl)oxy)-19H-6,11-(azeno)-17,21-(azeno[1]episoindoloazeno)benzo[7,8][1,3,5,10]tetraaza[2]silacycloundecino[4,3-a:11,1-a']diisoindol-19-yl)oxy)dimethylsilyl)propyl)ammonio)tris(butane-1-sulfonate) |
| 24 | 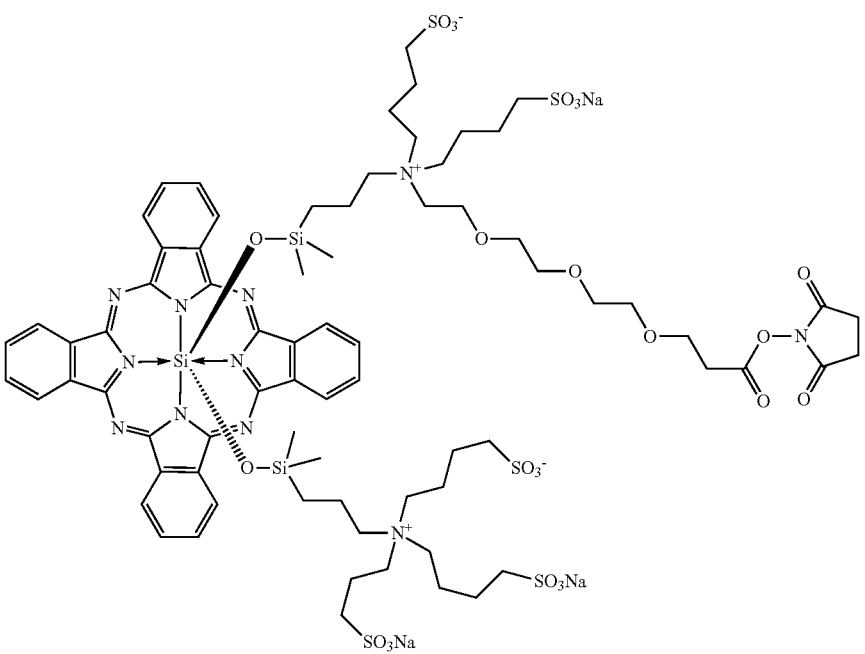  Sodium 4,4',4''-((3-(((19-((18-((2,5-dioxopyrrolidin-1-yl)oxy)-2-methyl-18-oxo-6,6-bis(4-sulfonatobutyl)-9,12,15-trioxa-6-aza-2-silaoctadecan-6-ium-2-yl)oxy)-19H-6,11-(azeno)-17,21-(azeno[1]episoindoloazeno)benzo[7,8][1,3,5,10]tetraaza[2]silacycloundecino[4,3-a:11,1-a']diisoindol-19-yl)oxy)dimethylsilyl)propyl)ammonio)tris(butane-1-sulfonate) |

TABLE 1-continued

| Ex. No. | Structure Name |
|---|---|
| 25 | 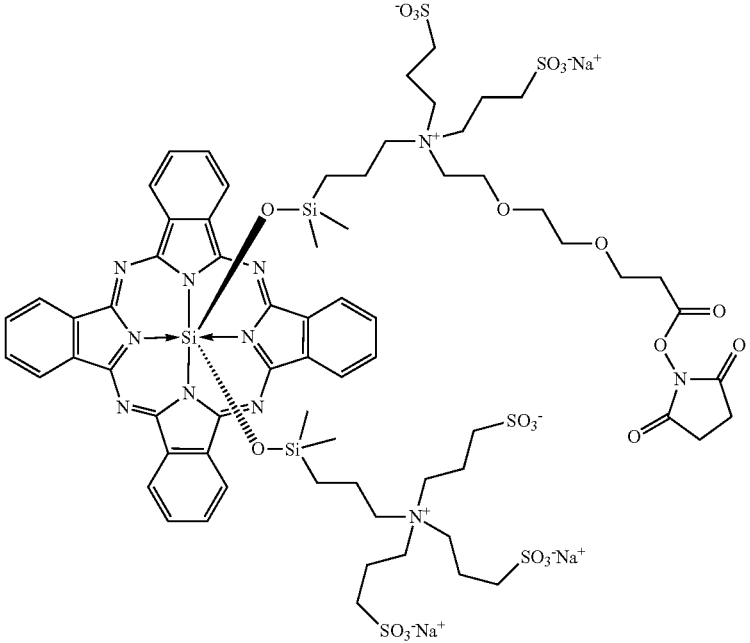

Sodium 3,3',3"-(3-(((19-((15-((2,5-dioxopyrrolidin-1-yl)oxy)-2-methyl-15-oxo-6,6-bis(3-sulfonatopropyl)-9,12-dioxa-6-aza-2-silapentadecan-6-ium-2-yl)oxy)-19H-6,11-(azeno)-17,21-(azeno[1]episoindoloazeno)benzo[7,8][1,3,5,10]tetraaza[2]silacycloundecino[4,3-a:11,1-a']diisoindol-19-yl)oxy)dimethylsilyl)propyl)ammonio)tris(propane-1-sulfonate) |
| 26 | 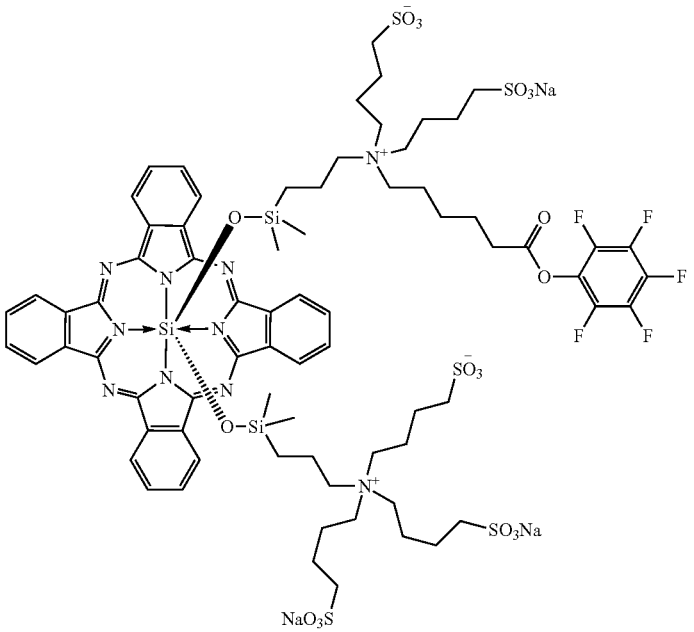

Sodium 4,4',4"-((3-(((19-((dimethyl(3-((6-oxo-6-(perfluorophenoxy)hexyl)bis(4-sulfonatobutyl)ammonio)propyl)silyl)oxy)-19H-6,11-(azeno)-17,21-(azeno[1]episoindoloazeno)benzo[7,8][1,3,5,10]tetraaza[2]silacycloundecino[4,3-a:11,1-a']diisoindol-19-yl)oxy)dimethylsilyl)propyl)ammonio)tris(butane-1-sulfonate) |

TABLE 1-continued

| Ex. No. | Structure Name |
|---|---|
| 27 | Sodium 4,4',4''-((3-(((19-(((3-((6-((2-(2,5-dioxo-2,5-dihydro-1H-pyrrol-1-yl)ethyl)amino)-6-oxohexyl)bis(4-sulfonatobutyl)ammonio)propyl)dimethylsilyl)oxy)-19H-6,11-(azeno)-17,21-(azeno[1]episoindoloazeno)benzo[7,8][1,3,5,10]tetraaza[2]silacycloundecino[4,3-a:11,1-a']diisoindol-19-yl)oxy)dimethylsilyl)propyl)ammonio)tris(butane-1-sulfonate) |

In yet certain embodiments, provided herein are compounds selected from Table 2A

TABLE 2A

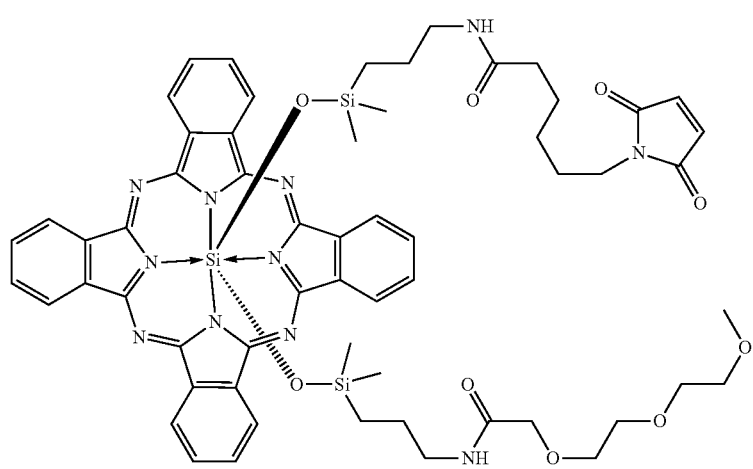

TABLE 2A-continued
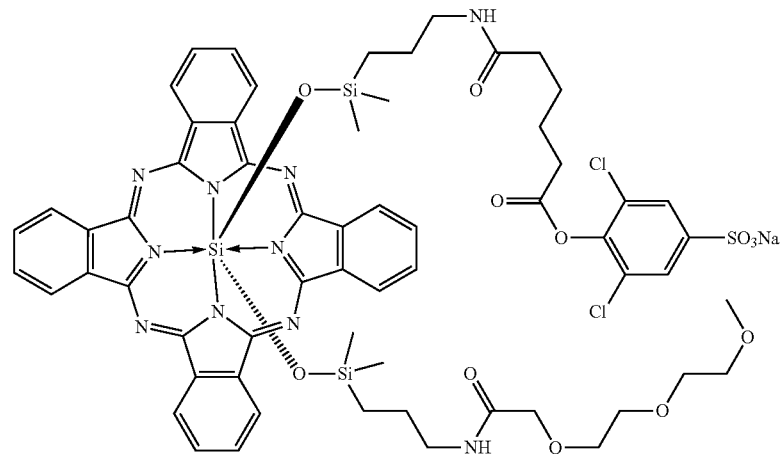
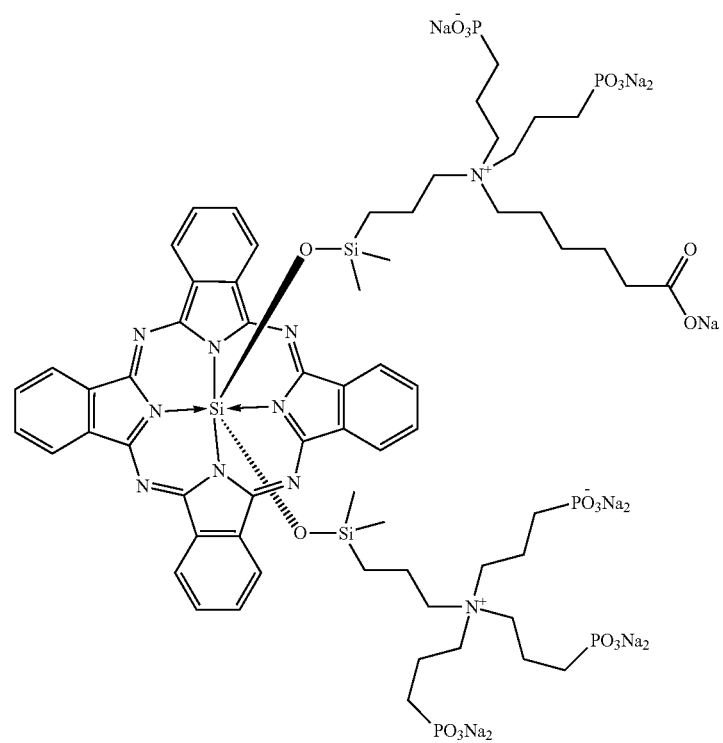

TABLE 2A-continued
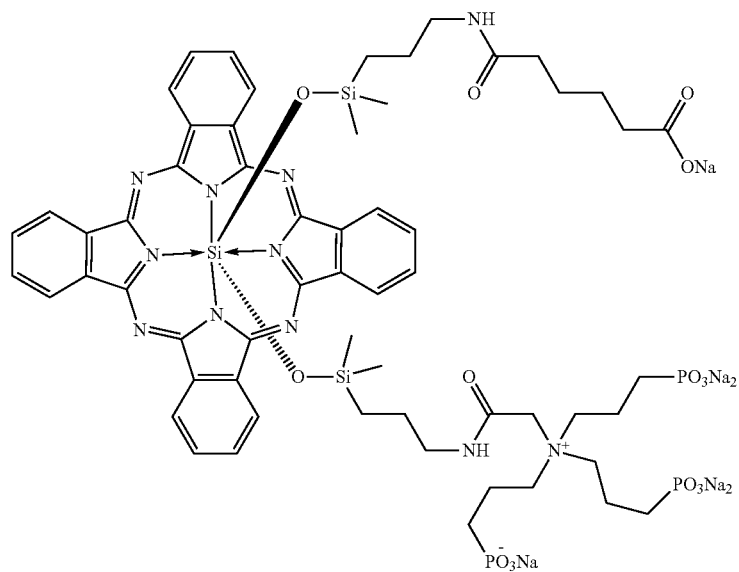
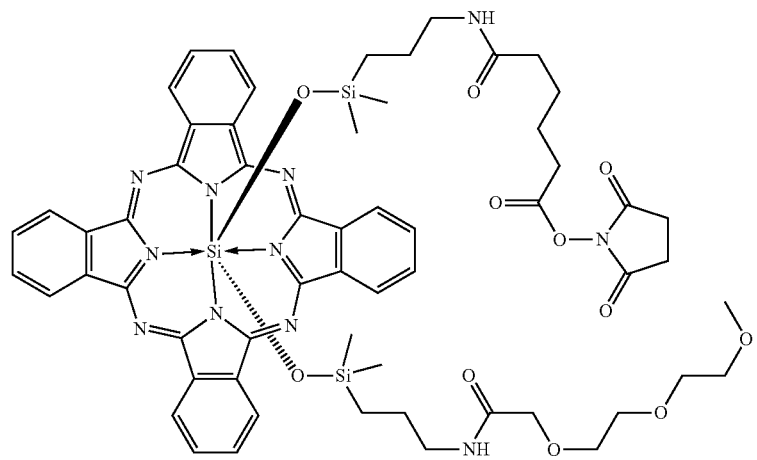
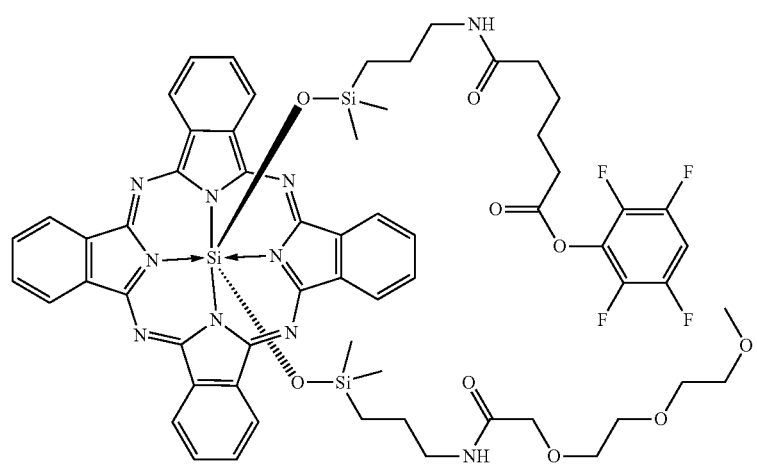

TABLE 2A-continued
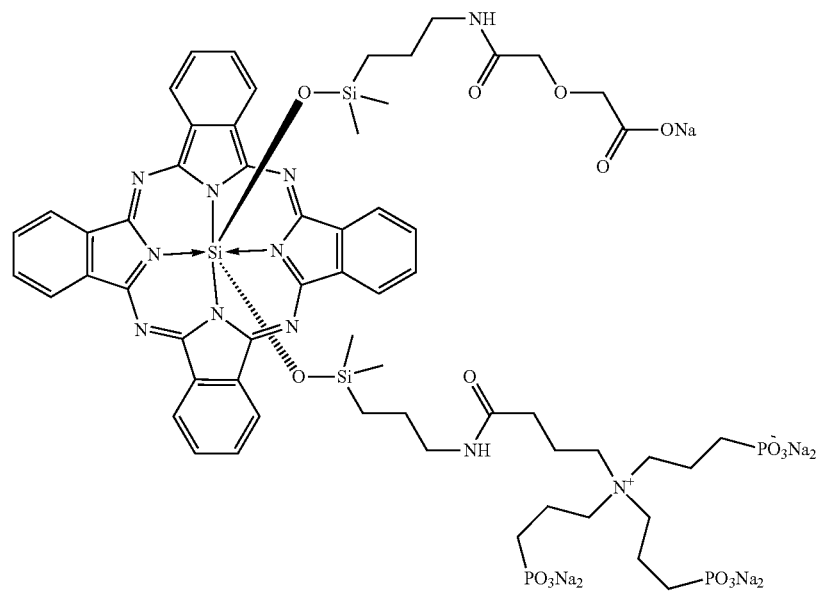
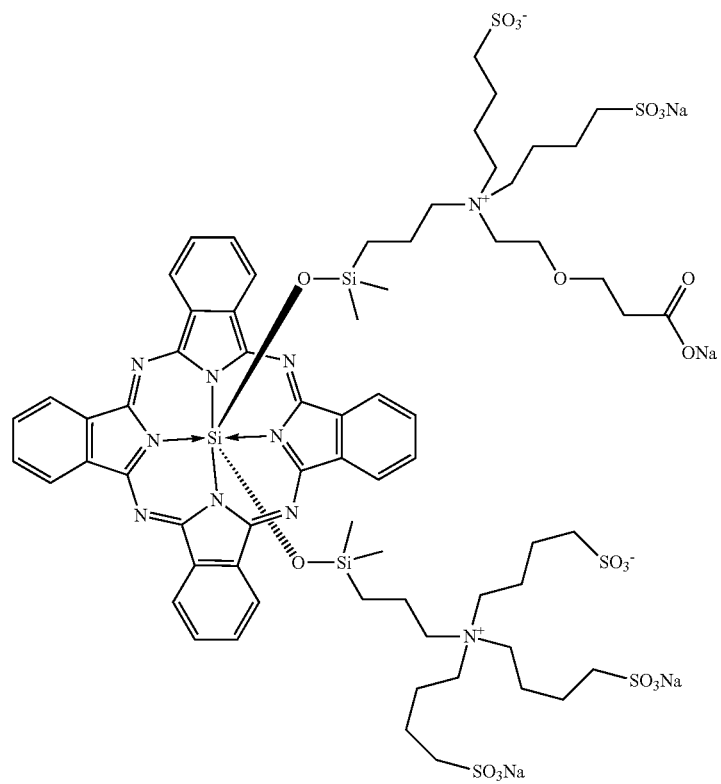

TABLE 2A-continued
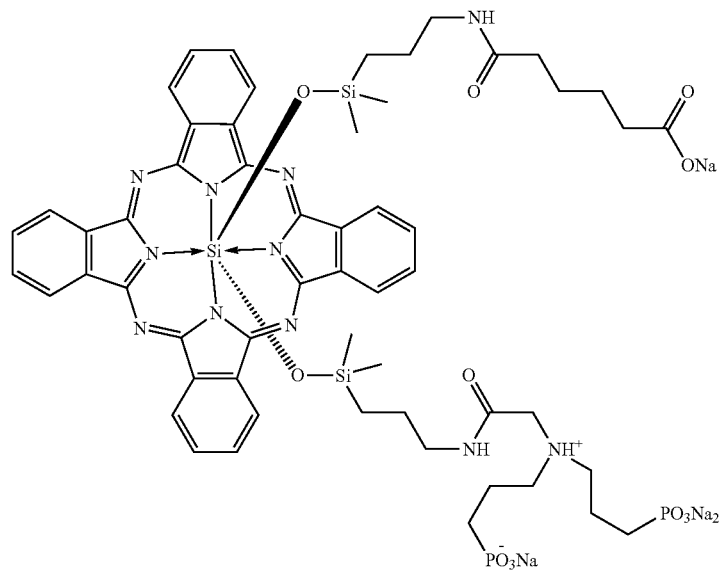
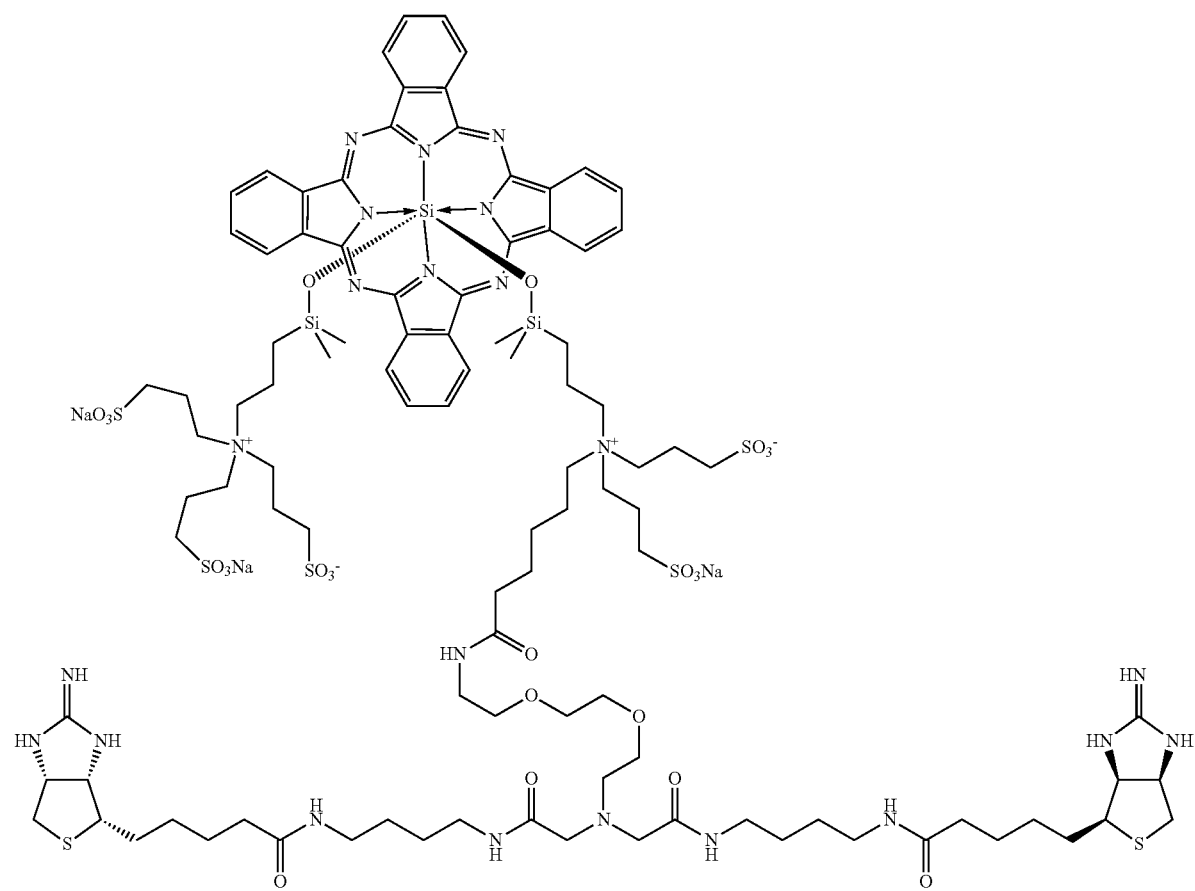

TABLE 2A-continued
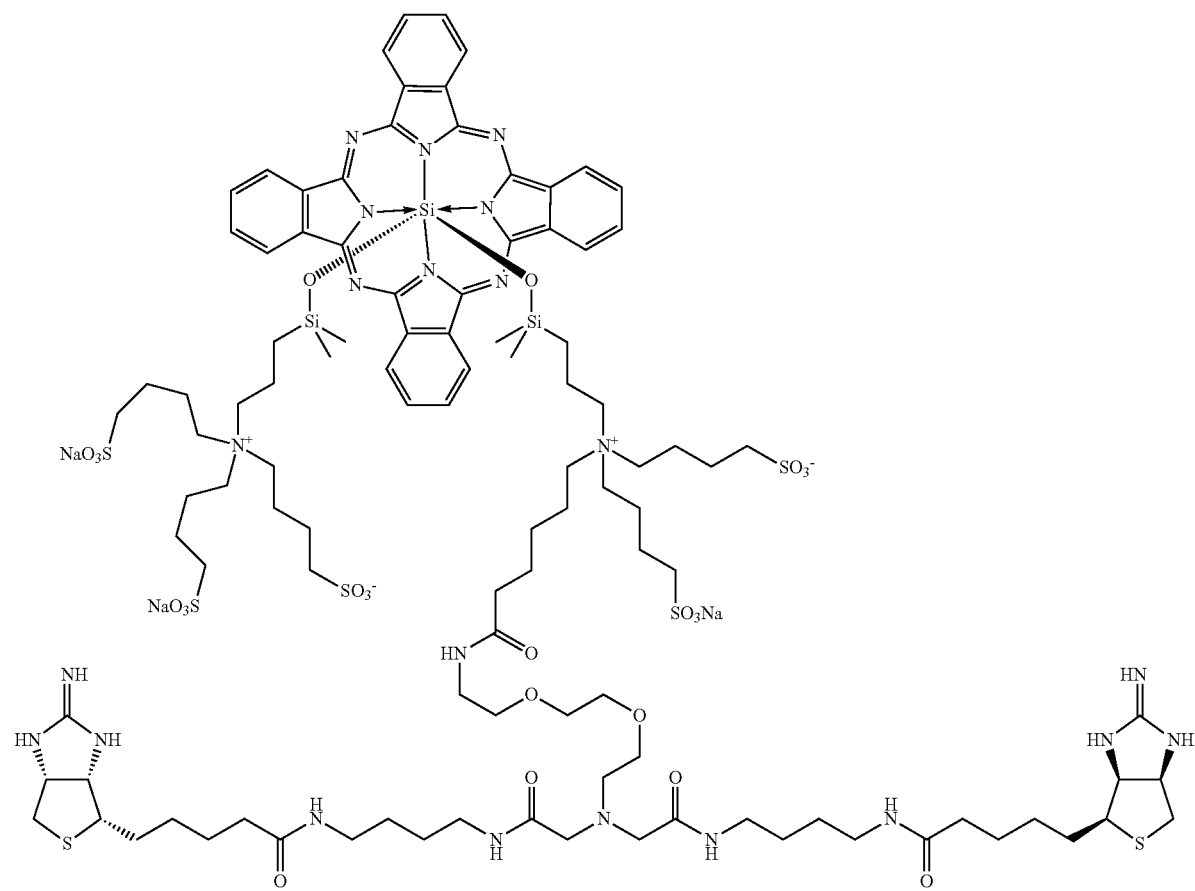

TABLE 2A-continued
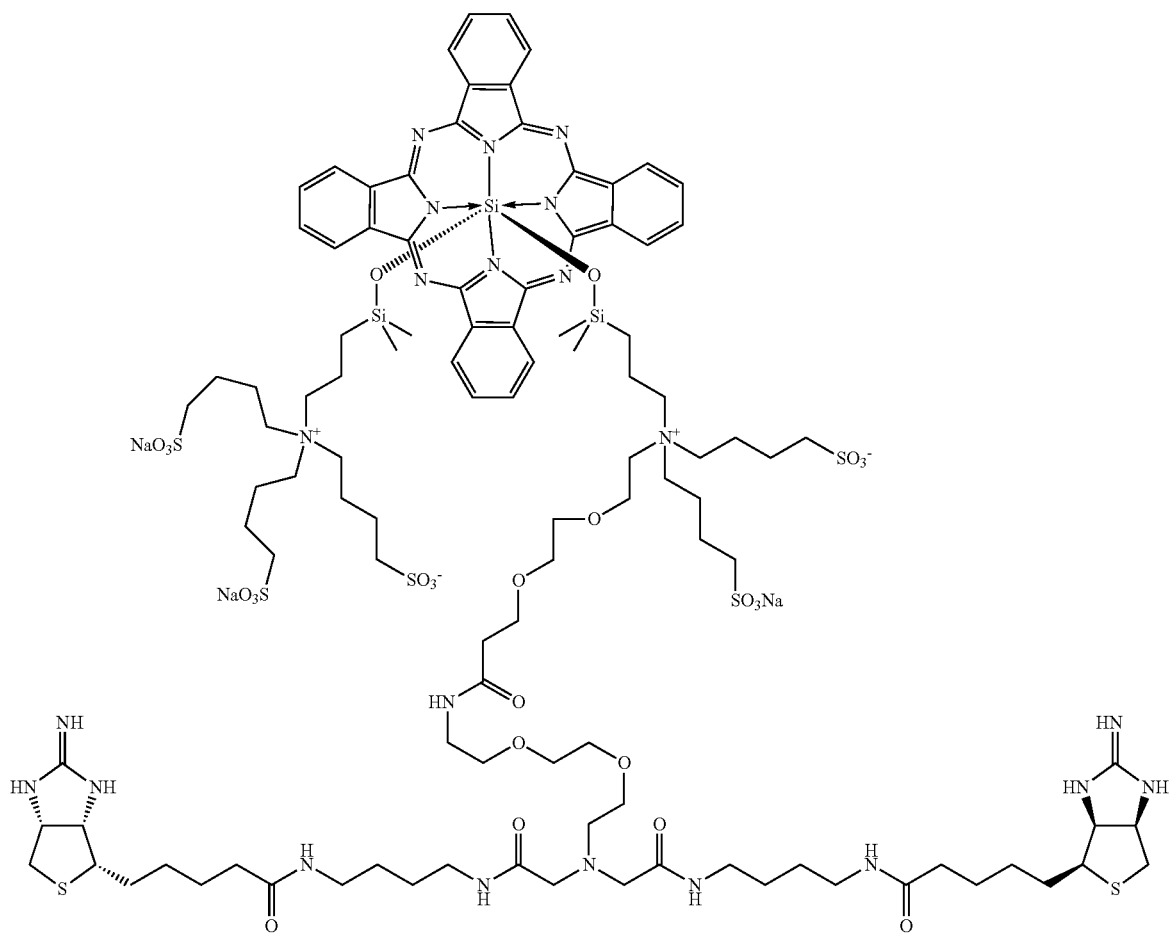

TABLE 2A-continued
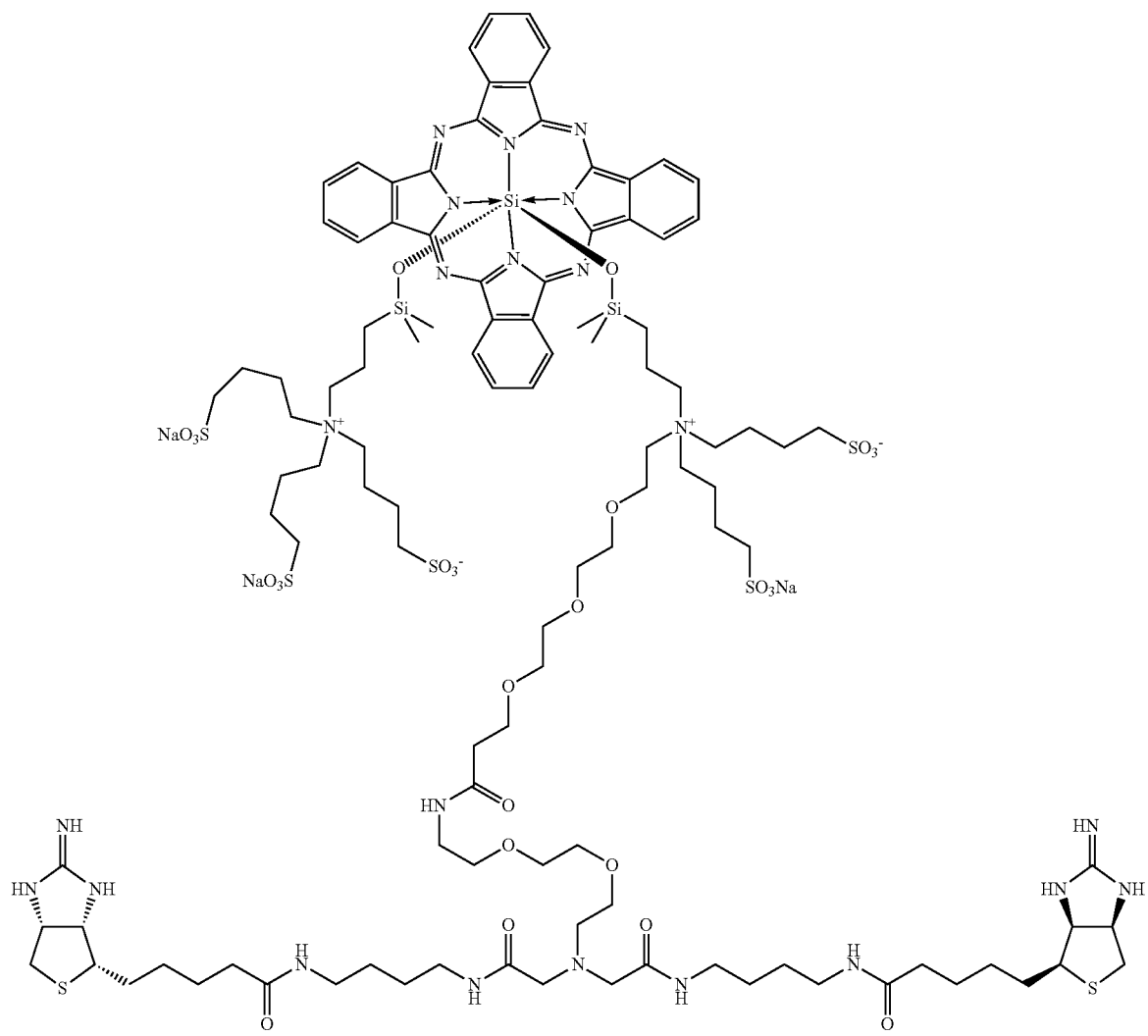

TABLE 2A-continued
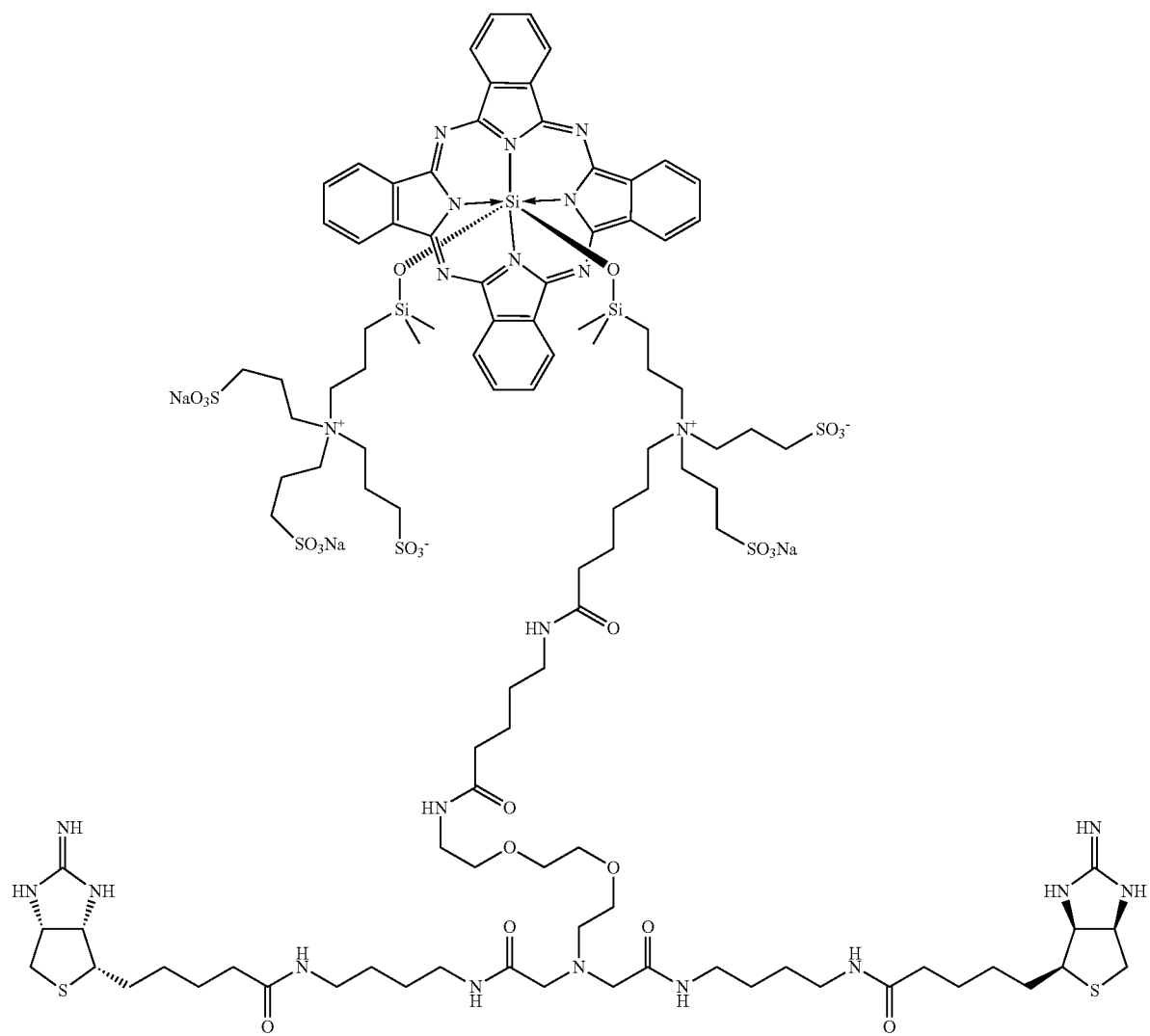

One embodiment provides a compound, or a salt, stereoisomer, or tautomer thereof, having the structure of Formula (II):

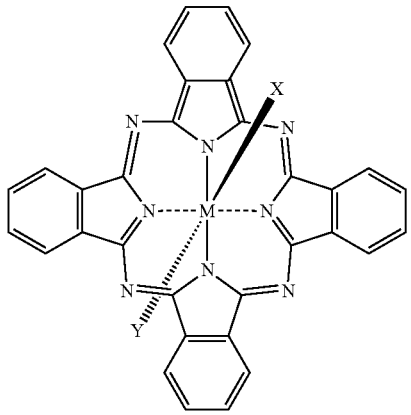

wherein,

M is a metal or metalloid;

X is

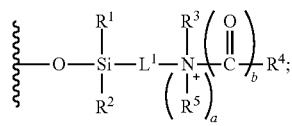

Y is

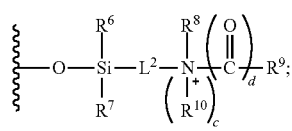

$R^1$ and $R^2$ are each independently optionally substituted alkyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl or optionally substituted heteroaralkyl;

$R^3$, $R^4$ or $R^5$ are selected from substituent group (a) or substituent group (b) wherein, (a) $R^3$ is hydrogen, $-L^3$-H, $-L^3$-A, or $-L^3$-Z;

$R^4$ is $-L^4$-H, $-(NH)_m-L^4$-A, $-(NH)_m-L^4$-Z, $-(O)_m-L^4$-A, or $-(O)_m-L^4$-Z $R^5$ is $-L^5$-H, or $-L^5$-A; and (b) $R^3$ and $R^4$ are connected with a bond to form a heterocyclyl substituted with $L^4$-A, and $R^5$ is $-L^5$-H or $-L^5$-A;

provided at least one of $R^3$, $R^4$ and $R^5$ is a group containing A;

A is a reactive group capable of forming a covalent bond with a second moiety, or a protected form thereof or a reacted form thereof;

$R^6$ and $R^7$ are each methyl;

$R^8$ is $-L^8$-Z;

$R^9$ is $-L^9$-Z;

$R^{10}$ is $-L^{10}$-Z; and

Z is a water soluble group optionally substituted with A, or L'-A;

$L^1$ is selected from optionally substituted alkylene, optionally substituted heteroalkylene, optionally substituted alkenylene, or optionally substituted heteroalkenylene;

$L^2$ is propylene;

$L^3$, $L^4$, and $L^5$ are each independently selected from optionally substituted alkylene, optionally substituted heteroalkylene, optionally substituted alkenylene, optionally substituted heteroalkenylene, optionally substituted cycloalkylene, optionally substituted heterocyclene, optionally substituted arylene, optionally substituted aralkylene, optionally substituted heteroaralkylene, or optionally substituted heteroarylene where the carbon atom of the alkylene, heteroalkylene, alkenylene, heteroalkenylene, cycloalkylene, heterocyclene, arylene, aralkylene, heteroaralkylene, or optionally substituted heteroarylene is further optionally substituted with a Z, and each nitrogen atom of the heteroalkylene or heteroalkenylene is optionally substituted with one or two L'-Z;

L' is each independently optionally substituted alkylene, optionally substituted heteroalkylene, optionally substituted alkenylene, optionally substituted heteroalkenylene, optionally substituted cycloalkylene, optionally substituted heterocyclene, optionally substituted arylene, optionally substituted aralkylene, optionally substituted heteroaralkylene, or optionally substituted heteroarylene;

$L^8$, $L^9$ and $L^{10}$ are each propylene;

a is 0 or 1;

b is 0 or 1;

c is 0 or 1;

d is 0 or 1;

m is 0 or 1;

n is 0 or 1;

provided that if b is 1, then a is 0; if d is 1, then c is 0; if m is 1, then b is 1; and if n is 1, then c is 1.

Another embodiment provides the compound of Formula (II), or salt, stereoisomer, or tautomer thereof, selected from the group consisting of:

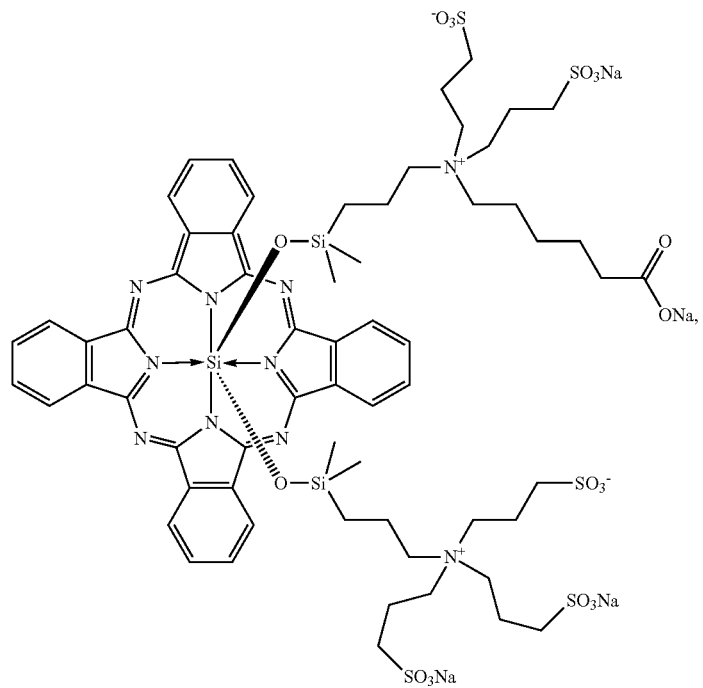
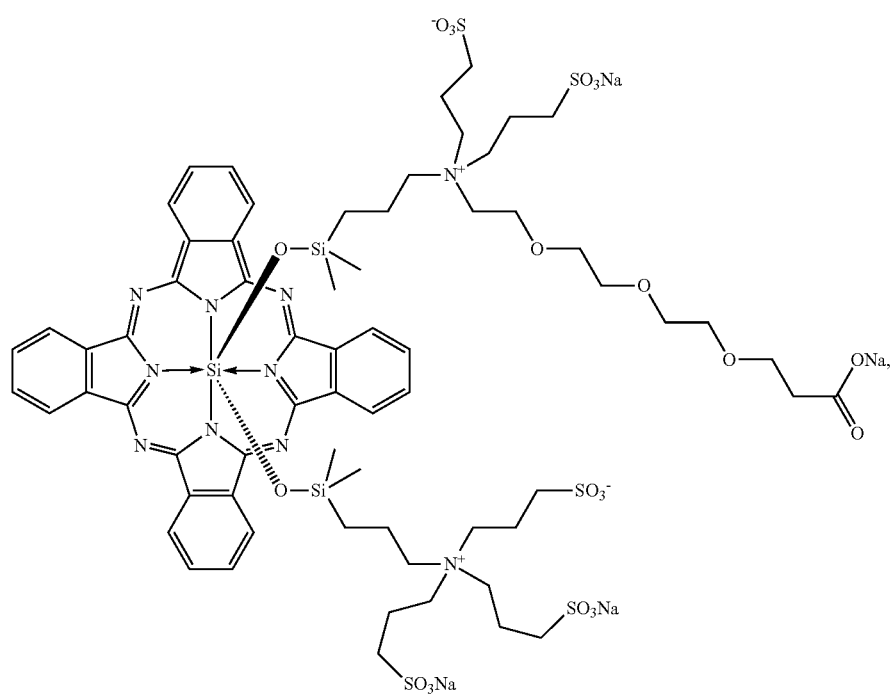

-continued

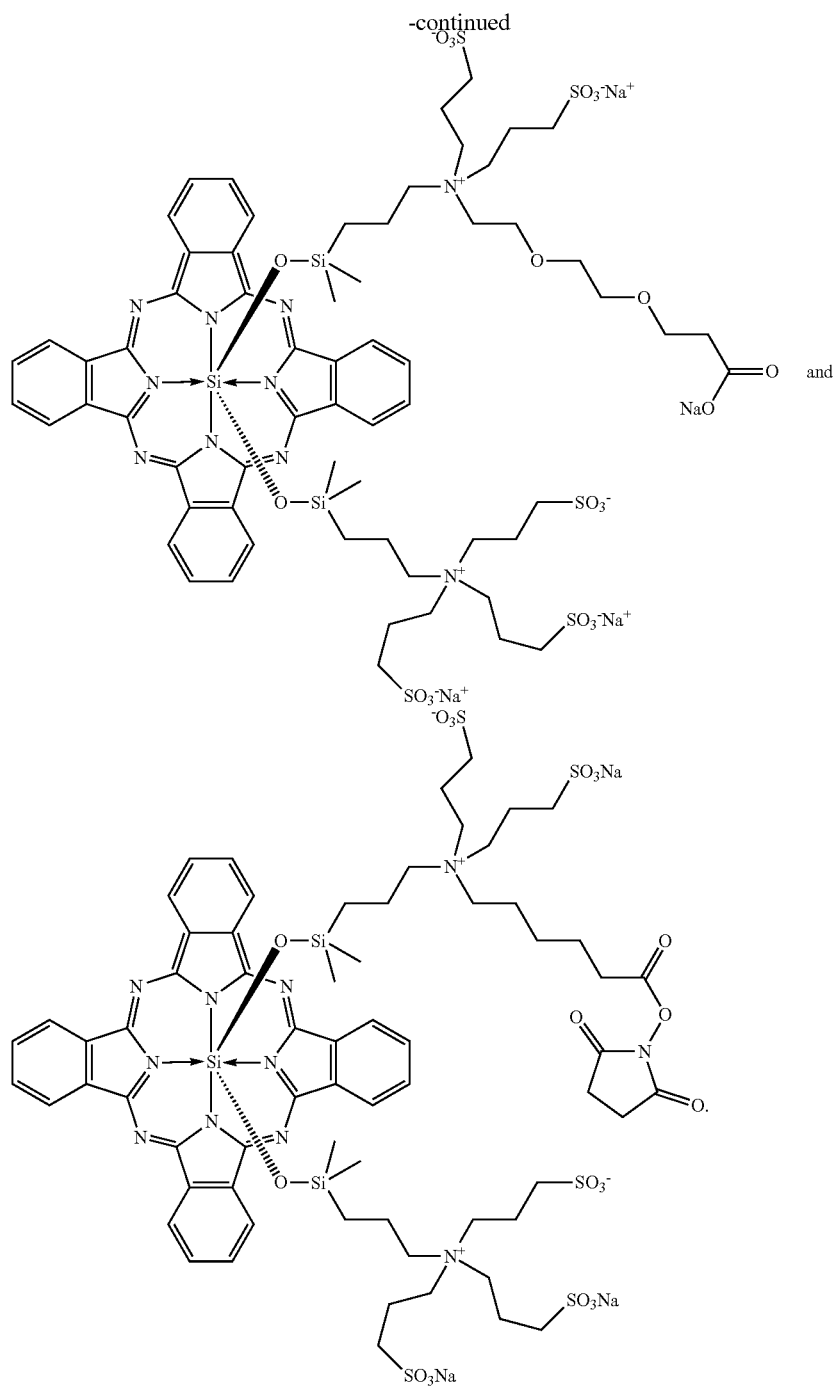

One embodiment provides a compound of Formula (III), or a salt, stereoisomer, tautomer thereof, having the structure:

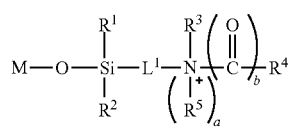

(III)

wherein M is a metal or metalloid selected from Si, Ge, Sn, Al, or Zn, optionally further ligated on the metal or metalloid;

$R^1$ and $R^2$ are each independently optionally substituted alkyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl or optionally substituted heteroaralkyl;

$R^3$, $R^4$ or $R^5$ are selected from substituent group (a) or substituent group (b) wherein, (a) $R^3$ is hydrogen, $-L^3-H$, $-L^3-A$, or $-L^3-Z$;
$R^4$ is $-L^4-H$, $-(NH)_m-L^4-A$, $-(NH)_m-L^4-Z$, $-(O)_m-L^4-A$ or $-(O)_m-L^4-Z$
$R^5$ is $-L^5-H$ or $-L^5-A$; and (b) $R^3$ is $-L^3-H$, or $-L^5-A$;
$R^4$ is $-L^4-H$, $-(NH)_m-L^4-A$, or $-(O)_m-L^4-A$; wherein $R^3$ and $R^4$ are connected with a bond to form a heterocyclyl substituted with $-L^4-A$; and
$R^5$ is $-L^5-H$ or $-L^5-A$;

provided at least one of $R^3$, $R^4$ and $R^5$ is a group containing A;

A is a reactive group capable of forming a covalent bond with a thiol, hydroxyl, carboxyl or amino group of a second moiety, or a protected form thereof or a reacted form thereof;

$L^1$ is optionally substituted alkylene, optionally substituted heteroalkylene, optionally substituted alkenylene or optionally substituted heteroalkenylene;

Z is a water soluble group optionally substituted with A or L'-A;

$L^3$, $L^4$, and $L^5$ are each independently optionally substituted alkylene, optionally substituted heteroalkylene, optionally substituted alkenylene, optionally substituted heteroalkenylene, optionally substituted cycloalkylene, optionally substituted heterocyclene, optionally substituted arylene, optionally substituted aralkylene, optionally substituted heteroaralkylene, or optionally substituted heteroarylene where the carbon atom of the alkylene, heteroalkylene, alkenylene, heteroalkenylene, cycloalkylene, heterocyclene, arylene, aralkylene, heteroaralkylene, or heteroarylene is further optionally substituted with Z and each nitrogen atom of the heteroalkylene or heteroalkenylene is optionally substituted with one or two L'-Z;

L' is each independently optionally substituted alkylene, optionally substituted heteroalkylene, optionally substituted alkenylene, optionally substituted heteroalkenylene, optionally substituted cycloalkylene, optionally substituted heterocyclene, optionally substituted arylene, optionally substituted aralkylene, optionally substituted heteroaralkylene, or optionally substituted heteroarylene;

a is 0 or 1;
b is 0 or 1;
m is 0 or 1;
provided that if b is 1, then a is 0; and
if m is 1, b is 1.

Another embodiment provides a compound of Formula (II), or a salt, stereoisomer, tautomer thereof, wherein $L^3$, $L^4$, $L^5$, are each independently optionally substituted alkylene, optionally substituted heteroalkylene, optionally substituted alkenylene or optionally substituted heteroalkenylene, where each nitrogen atom of the heteroalkylene or heteroalkenylene is further optionally substituted with one or two L'-Z; and L' is independently optionally substituted alkylene, optionally substituted heteroalkylene, optionally substituted alkenylene or optionally substituted heteroalkenylene.

Another embodiment provides a compound of Formula (III), or a salt, stereoisomer, tautomer thereof, wherein $L^1$ and $L^2$, are each independently optionally substituted $C_{1-10}$alkylene, optionally substituted hetero$C_{1-10}$alkylene, optionally substituted $C_{2-10}$alkenylene or hetero $C_{2-10}$alkenylene.

Another embodiment provides a compound of Formula (III), or a salt, stereoisomer, tautomer thereof, wherein $L^1$ and $L^2$, are each independently $C_{2-4}$alkylene, hetero$C_{2-4}$alkylene, optionally substituted $C_{2-4}$alkenylene or optionally substituted hetero $C_{2-4}$alkenylene.

Another embodiment provides a compound of Formula (III), or a salt, stereoisomer, tautomer thereof, wherein $L^1$ and $L^2$ are each optionally substituted $C_{2-4}$alkylene.

Another embodiment provides a compound of Formula (III), or a salt, stereoisomer, tautomer thereof, wherein the reactive group A is each independently selected from;
—$C(O)OR^{11}$,
—$NR^{12}R^{13}$,
—$NHC(O)R^{14}$,
—$C(O)R^{15}$,
—$OR^{16}$,
—$SR^{16}$,
—$OS(O)_2R^{17}$,
—$OP(OR^{18})(NR^{19}R^{20})$,
—N=C=O;
—N=C=S,
—S—C≡N,
—$SO_2$—F,
—$SO_2$—Cl,
—$SO_2$—Br,
—S—$SR^{21}$; or
5- or 6-membered dioxo-substituted heterocyclyl;

each $R^{11}$ is independently hydrogen, alkyl, haloalkyl, alkenyl, heterocyclyl, aryl or heteroaryl, wherein each $R^{11}$ is independently optionally substituted with one to five groups each independently selected from halo, —$SO_3$— and —$SO_2F$;

each $R^{12}$ is independently hydrogen, alkyl or haloalkyl;

each $R^{12}$ is aryl or heteroaryl, each $R^{13}$ independently optionally substituted with one to five groups each independently selected from halo, —$SO_3$— and —$SO_2F$; or optionally $R^{12}$ and $R^{13}$, together with the nitrogen to which they are attached, form a cyclic imide;

each $R^{14}$ is independently optionally substituted haloalkyl or optionally substituted aralkyl;

each $R^{15}$ is independently aryl optionally substituted with one to five groups each independently halo, heterocyclyl, —$SO_3$— or —$SO_2F$;

each $R^{16}$ is independently aryl optionally substituted with one to five groups each independently halo or heterocylyl;

each $R^{17}$ is independently optionally substituted alkyl, optionally substituted haloalkyl, optionally substituted alkenyl, optionally substituted cycloalkyl, optionally substituted heterocyclyl, optionally substituted aryl or optionally substituted heteroaryl, wherein the heterocyclyl, aryl or heteroaryl is optionally substituted with one to five groups each independently selected from halo. —$SO_3$—, —$SO_2F$ and —$C(O)OR^c$;

each $R^c$ is independently optionally substituted alkyl, optionally substituted haloalkyl, optionally substituted cycloalkyl or optionally substituted aryl;

$R^{18}$, $R^{19}$ and $R^{20}$ are each independently optionally substituted alkyl or optionally substituted haloalkyl; and $R^{21}$ is heteroaryl.

Another embodiment provides a compound of Formula (III), or a salt, stereoisomer, tautomer thereof, wherein the reactive group A is selected from the group consisting of;

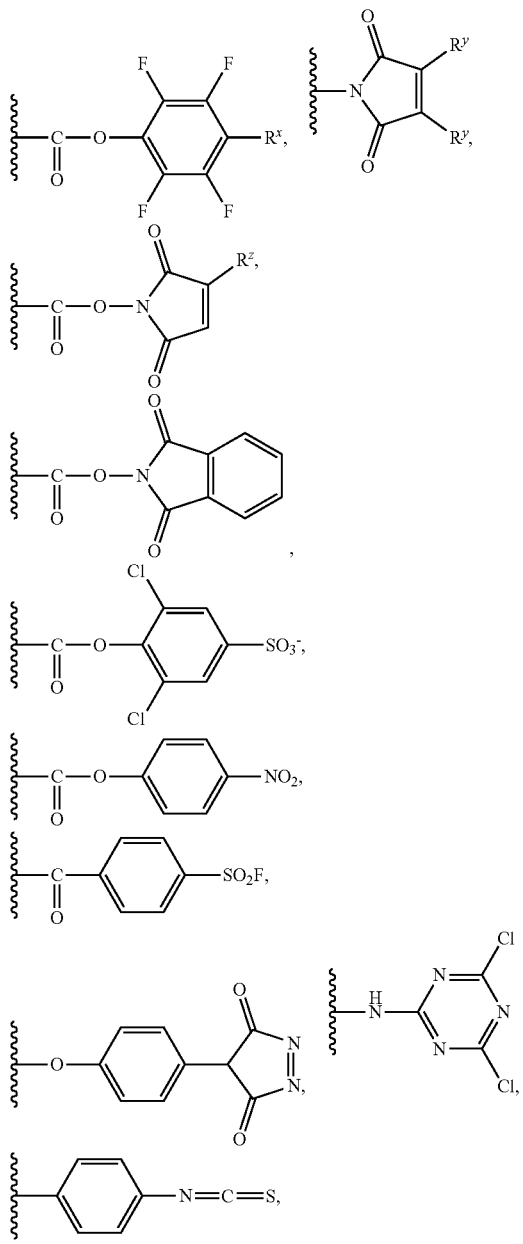

—NHC(O)R$^{14}$, —COOH and —OSO$_2$R$^{17}$ where each R$^x$ and R$^y$ are independently hydrogen or halo, and R$^z$ is hydrogen or —SO$_3$—;

R$^{14}$ is optionally substituted haloalkyl or optionally substituted aralkyl; and R$^{17}$ is independently optionally substituted alkyl, optionally substituted haloalkyl, optionally substituted alkenyl, optionally substituted cycloalkyl, optionally substituted heterocyclyl, optionally substituted aryl or optionally substituted heteroaryl, wherein the heterocyclyl, aryl or heteroaryl is optionally substituted with one to five groups each independently selected from halo, —SO$_3$—, —SO$_2$F and —C(O)OR$^c$; and each R$^c$ is independently optionally substituted alkyl, optionally substituted haloalkyl, optionally substituted cycloalkyl or optionally substituted aryl.

Another embodiment provides a compound of Formula (III), or a salt, stereoisomer, tautomer thereof, wherein the reactive group is each independently —C(O)OR$^{11}$ or —NR$^{12}$R$^{13}$.

Another embodiment provides a compound of Formula (III), or a salt, stereoisomer, tautomer thereof, wherein the water soluble group Z is —C(O)OH,
—(CH$_2$)$_q$(OCH$_2$CH$_2$)$_v$(CH$_2$)$_q$C(O)OH,
—(CH$_2$CH$_2$O)$_v$(CH$_2$)$_p$C(O)OH,
—(CH$_2$)$_v$(OCH$_2$CH$_2$)$_v$OR$^{22}$,
—(CH$_2$CH$_2$O)$_v$(CH$_2$)$_p$OR$^{22}$,
—(CH$_2$)$_q$(OCH$_2$CH$_2$)$_v$SR$^{22}$,
—(CH$_2$CH$_2$O)$_v$(CH$_2$)$_p$SR$^{22}$,
—O(CH$_2$)$_v$N[(CH$_2$CH$_2$O)$_n$CH$_2$CH$_2$OR$^{22}$]$_t$,
—(CH$_2$)$_q$(OCH$_2$CH$_2$)$_v$N[(CH$_2$CH$_2$O)$_w$CH$_2$CH$_2$OR$^{22}$]$_t$,
—(CH$_2$CH$_2$O)$_m$(CH$_2$)$_p$N[(CH$_2$CH$_2$O)$_w$CH$_2$CH$_2$OR$^{22}$]$_t$,
—NH$_2$,
—(CH$_2$)$_q$N[(CH$_2$CH$_2$O)$_v$CH$_2$CH$_2$OR$^{22}$]$_t$,
—(CH$_2$)$_q$NR$^b$[(CH$_2$CH$_2$O)$_w$CH$_2$CH$_2$OR$^{22}$]$_u$,
—(CH$_2$)$_q$N[(CH$_2$)$_p$(OCH$_2$CH$_2$)$_v$OR$^{22}$]$_t$,
—(CH$_2$)$_q$N[(CH$_2$)$_p$SO$_3$—]$_t$,
—(CH$_2$)$_q$NR$^b$[(CH$_2$)$_p$SO$_3$—]$_u$,
—(CH$_2$)$_q$NR$^b$(CH$_2$)$_p$CH(SO$_3$—)$_2$,
—(CH$_2$)$_q$N[(CH$_2$)$_p$S(O)$_u$OH]$_t$,
—(CH$_2$)$_q$N[(CH$_2$)$_p$OSO$_3$—]$_t$,
—(CH$_2$)$_q$(OCH$_2$CH$_2$)$_v$(CH$_2$)$_q$SO$_3$—,
—(CH$_2$)$_q$(OCH$_2$CH$_2$)$_v$(CH$_2$)$_q$S(O)$_u$OH,
—(CH$_2$)$_q$(OCH$_2$CH$_2$)$_v$(CH$_2$)$_q$OSO$_3$$^{2-}$,
—SO$_3$—,
—CH(SO$_3$—)$_2$,
—OSO$_3$$^{2-}$,
—S(O)$_u$OH,
—PO$_3$$^{2-}$,
—CH(PO$_3$$^{2-}$)$_2$,
—(CH$_2$)$_q$N[(CH$_2$)$_p$PO$_3$—]$_t$,
—(CH$_2$)$_q$(OCH$_2$CH$_2$)$_v$(CH$_2$)$_q$PO$_3$—,
—(CH$_2$)$_q$N[(CH$_2$)$_p$OPO$_0$—]$_t$,
—OPO$_3$—,
—(CH$_2$)$_q$(OCH$_2$CH$_2$)$_v$(CH$_2$)$_q$P(O)(OH)$_2$,
—(CH$_2$)$_q$N[(CH$_2$)$_p$P(O)(OH)$_2$]$_t$,
—P(O)(OH)$_2$,
glutamate,
aspartate,
histidine,
1,3-beta-glucan, or
1,4-beta-glucan;

each R$^{22}$ is independently alkyl, haloalkyl, cycloalkyl or aryl;

each R$^b$ is independently hydrogen, alkyl optionally substituted with —CO$_2$H, heteroalkylene optionally substituted with —CO$_2$H, haloalkyl or cycloalkyl;

each v, w and p are independently an integer from 1 to 10;

each q is independently an integer from 0 to 10;

t is 2 or 3; and u is 1 or 2.

Another embodiment provides a compound of Formula (III) or a salt, stereoisomer, tautomer thereof, wherein the water soluble group Z is —(CH$_2$)$_q$(OCH$_2$CH$_2$)$_v$OR$^{22}$,
—(CH$_2$)$_q$O(CH$_2$)$_v$N[(CH$_2$CH$_2$O)$_w$CH$_2$CH$_2$OR$^{22}$]$_t$,
—(CH$_2$)$_q$N[(CH$_2$)$_p$(OCH$_2$CH$_2$)$_v$OR$^{22}$]$_t$,
—(CH$_2$)$_q$N[(CH$_2$)$_p$SO$_3$—]$_t$,
—(CH$_2$)$_q$NR$^b$[(CH$_2$)$_p$SO$_3$—]$_u$,
—(CH$_2$)$_q$NR$^b$[(CH$_2$)$_p$CH(SO$_3$—)$_2$]$_u$,
—SO$_3$—,
—CH(SO$_3$—)$_2$, —$PO_3^{2-}$,
—$(CH_2)_qN[(CH_2)_pPO_3]_t$,
—$(CH_2)_qNR^b[(CH_2)_pPO_3—]_u$ or
—$(CH_2)_qNR^b(CH_2)_pCH(PO_3—)_2$;

each $R^{22}$ is independently alkyl, haloalkyl, cycloalkyl or aryl;

each $R^b$ is independently hydrogen, alkyl optionally substituted with —$CO_2H$, heteroalkylene optionally substituted with —$CO_2H$, haloalkyl or cycloalkyl;

each v, w and p are independently an integer from 1 to 10;
each q is independently an integer from 0 to 10;
t is 2 or 3; and
u is 1 or 2.

Another embodiment provides a compound of Formula (III), or a salt, stereoisomer, tautomer thereof, wherein a is 0, and b is 1.

Another embodiment provides a compound of Formula (III), or a salt, stereoisomer, tautomer thereof, wherein a is 1, and b is 0.

Another embodiment provides a compound of Formula (III), or a salt, stereoisomer, tautomer thereof, wherein the compound of Formula (III) has the structure:

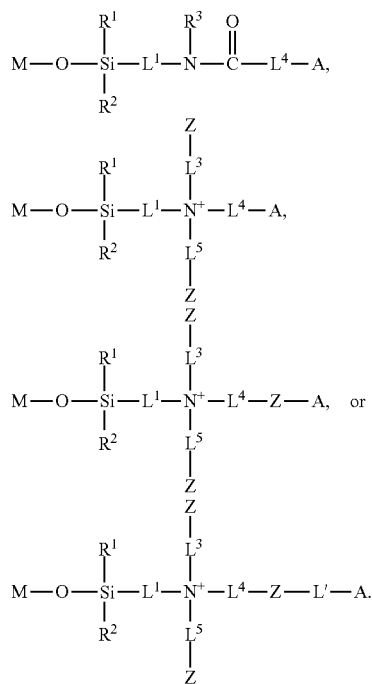

Another embodiment provides a compound of Formula (III), or a salt, stereoisomer, tautomer thereof, wherein $L^1$ is selected from —$(CH_2)_2$—, —$(CH_2)_3$ or —$(CH_2)_4$—.

Another embodiment provides a compound of Formula (III), or a salt, stereoisomer, tautomer thereof, wherein $L^1$ is —$(CH_2)_3$—.

Another embodiment provides a compound of Formula (III), or a salt, stereoisomer, tautomer thereof, wherein $L^4$ is selected from —$(CH_2)$—, —$(CH_2)$—, —$(CH_2)_3$—, —$(CH_2)_4$—, or —$(CH_2)$—. Another embodiment provides a compound of Formula (III), or a salt, stereoisomer, tautomer thereof, wherein $L^4$ is —$(CH_2)$— or $(CH_2)_2$—. Another embodiment provides a compound of Formula (III), or a salt, stereoisomer, tautomer thereof, wherein $L^4$ is —$(CH_2)_3$—.

Another embodiment provides a compound of Formula (III), or a salt, stereoisomer, tautomer thereof, wherein $L^4$ is —$(CH_2)_4$—. Another embodiment provides a compound of Formula (III), or a salt, stereoisomer, tautomer thereof, wherein $L^4$ is —$(CH_2)_5$—.

Another embodiment provides a compound of Formula (III), or a salt, stereoisomer, tautomer thereof, wherein $L^5$ is selected from —$(CH_2)_3$—, —$(CH_2)_4$— or —$(CH_2)_5$—. Another embodiment provides a compound of Formula (III), or a salt, stereoisomer, tautomer thereof, wherein $L^5$ is —$(CH_2)_3$—. Another embodiment provides a compound of Formula (III), or a salt, stereoisomer, tautomer thereof, wherein $L^5$ is —$(CH_2)_4$—. Another embodiment provides a compound of Formula (III), or a salt, stereoisomer, tautomer thereof, wherein $L^5$ is —$(CH_2)$—.

Another embodiment provides a compound of Formula (III), or a salt, stereoisomer, tautomer thereof, wherein $R^3$, $R^4$ or R are selected from substituent group (a).

Another embodiment provides a compound of Formula (III), or a salt, stereoisomer, tautomer thereof, wherein $R^3$ is hydrogen. Another embodiment provides a compound of Formula (III), or a salt, stereoisomer, tautomer thereof, wherein $R^3$ is hydrogen, a is 0, and b is 1.

Another embodiment provides a compound of Formula (III), or a salt, stereoisomer, tautomer thereof, wherein $R^3$ is -$L^3$-Z.

Another embodiment provides a compound of Formula (III), or a salt, stereoisomer, tautomer thereof, wherein $R^4$ is —$(NH)_m$-$L^4$-Z. Another embodiment provides a compound of Formula (III), or a salt, stereoisomer, tautomer thereof, wherein $R^4$ is —$(O)_m$-$L^4$-Z.

Another embodiment provides a compound of Formula (III), or a salt, stereoisomer, tautomer thereof, wherein m is 0.

Another embodiment provides a compound of Formula (III), or a salt, stereoisomer, tautomer thereof, wherein $L^4$ is alkylene, and the carbon atom of the alkylene is further substituted with a second Z. Another embodiment provides a compound of Formula (III), or a salt, stereoisomer, tautomer thereof, wherein the L alkylene is a $C_{2-5}$ alkylene. Another embodiment provides a compound of Formula (III), or a salt, stereoisomer, tautomer thereof, wherein said second Z is —$(CH_2)_qN[(CH_2)_pSO_3—]_t$ Another embodiment provides a compound of Formula (III), or a salt, stereoisomer, tautomer thereof, wherein t is 3, q is 2-6, and p is 2-4.

Another embodiment provides a compound of Formula (III), or a salt, stereoisomer, tautomer thereof, wherein $R^5$ is -$L^5$-A.

Another embodiment provides a compound of Formula (III), or a salt, stereoisomer, tautomer thereof, wherein $R^3$, $R^4$ or $R^5$ are selected from substituent group (b).

Another embodiment provides a compound of Formula (III), or a salt, stereoisomer, tautomer thereof, wherein $L^4$ is $C_{2-5}$ alkylene, and Z is —$(CH_2)_qN[(CH_2)_pSO_3—]_t$, wherein q is 0.

Another embodiment provides a compound of Formula (III), or a salt, stereoisomer, tautomer thereof, wherein p is 2-5. Another embodiment provides a compound of Formula (III), or a salt, stereoisomer, tautomer thereof, wherein p is 3. Another embodiment provides a compound of Formula (III), or a salt, stereoisomer, tautomer thereof, wherein p is 4.

Another embodiment provides a compound of Formula (III), or a salt, stereoisomer, tautomer thereof, wherein $L^4$ is $C_{2-5}$ alkylene, and Z is —$(CH_2)_qN[(CH_2)_pPO_3—]_t$, wherein q is 0. Another embodiment provides a compound of Formula (III), or a salt, stereoisomer, tautomer thereof, wherein p is 2-5, and t is 3. Another embodiment provides a compound of Formula (III), or a salt, stereoisomer, tautomer thereof, wherein p is 3. Another embodiment provides a compound of Formula (III), or a salt, stereoisomer, tautomer thereof, wherein p is 4.

Another embodiment provides a compound of Formula (III), or a salt, stereoisomer, tautomer thereof, wherein $L^4$ is $C_{2-5}$ alkylene, and Z is —$(CH_2)_qNR^b(CH_2)_pCH(SO_3—)_2$, wherein q is 0.

Another embodiment provides a compound of Formula (III), or a salt, stereoisomer, tautomer thereof, wherein $R^b$ is alkyl optionally substituted with —$CO_2H$, or heteroalkylene optionally substituted with —$CO_2H$.

Another embodiment provides a compound of Formula (III), or a salt, stereoisomer, tautomer thereof, wherein $R^b$ is hydrogen.

Another embodiment provides a compound of Formula (III), or a salt, stereoisomer, tautomer thereof, wherein p is 2-5.

Another embodiment provides a compound of Formula (III), or a salt, stereoisomer, tautomer thereof, wherein $L^4$ is $C_{2-5}$ alkylene, and Z is —$(CH_2)_qNR^b[(CH_2)_pPO_3—]_2$, wherein q is 0.

Another embodiment provides a compound of Formula (III), or a salt, stereoisomer, tautomer thereof, wherein $R^b$ is alkyl optionally substituted with —$CO_2H$, or heteroalkylene optionally substituted with —$CO_2H$.

Another embodiment provides a compound of Formula (III), or a salt, stereoisomer, tautomer thereof, wherein $R^b$ is hydrogen.

Another embodiment provides a compound of Formula (III), or a salt, stereoisomer, tautomer thereof, wherein p is 2-5.

Another embodiment provides a compound of Formula (III), or a salt, stereoisomer, tautomer thereof, wherein $L^4$ is $C_{1-5}$ alkylene or heteroalkylene, and Z is —C(O)OH, or —$(CH_2)_q(OCH_2CH_2)_vOR^{22}$.

Another embodiment provides a compound of Formula (III), or a salt, stereoisomer, tautomer thereof, wherein q is 1-3 and v is 1-3.

Another embodiment provides a compound of Formula (III), or a salt, stereoisomer, tautomer thereof, wherein m is 1.

Another embodiment provides a compound of Formula (III), or a salt, stereoisomer, tautomer thereof, wherein $L^4$ is $C_{1-5}$ alkylene, and Z is —$SO_3$, or —$CH(SO_3—)_2$.

Another embodiment provides a compound of Formula (III), or a salt, stereoisomer, tautomer thereof, wherein $L^4$ is $C_{2-5}$ alkylene, and Z is —$(CH_2)_qN[(CH_2CH_2-O)_vCH_2CH_2OR^{22}]_2$ wherein q is 0, and v is 1-3.

Another embodiment provides a compound of Formula (III), or a salt, stereoisomer, tautomer thereof, wherein $R^4$ is —$(NH)_m$-$L^4$-A.

Another embodiment provides a compound of Formula (III), or a salt, stereoisomer, tautomer thereof, wherein $R^4$ is —$(O)_m$-$L^4$-A.

Another embodiment provides a compound of Formula (III), or a salt, stereoisomer, tautomer thereof, wherein m is 0.

Another embodiment provides a compound of Formula (III), or a salt, stereoisomer, tautomer thereof, wherein $L^4$ is $C_{1-5}$ alkylene or heteroalkylene.

Another embodiment provides a compound of Formula (III), or a salt, stereoisomer, tautomer thereof, wherein A is selected from the group consisting of:

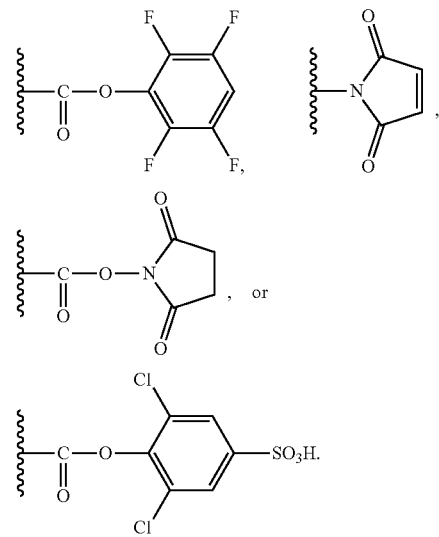

Another embodiment provides a compound of Formula (III), or a salt, stereoisomer, tautomer thereof, wherein M is Si or Ge.

Another embodiment provides a compound of Formula (III), or a salt, stereoisomer, tautomer thereof, selected from the group consisting of.

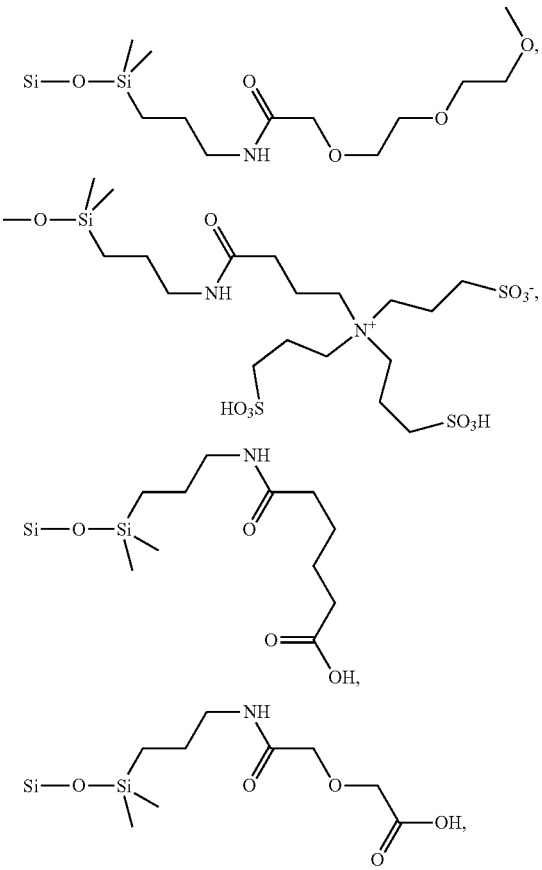

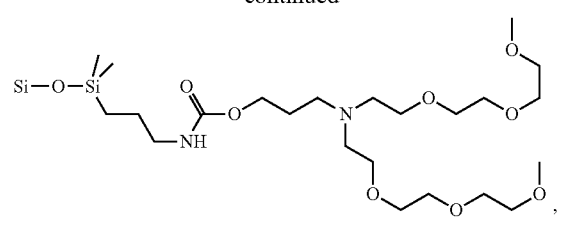
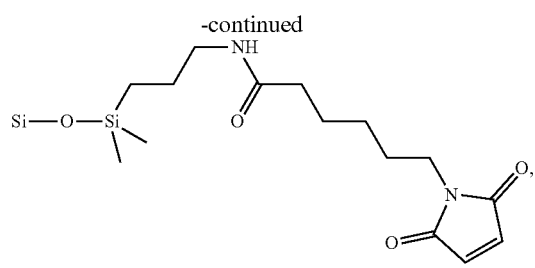
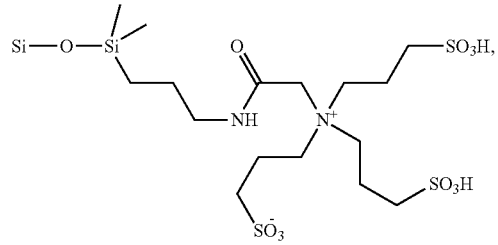
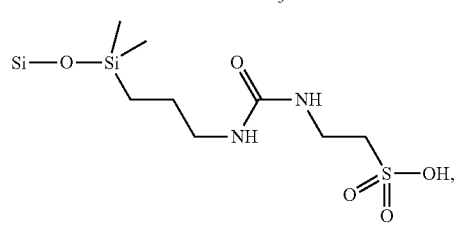
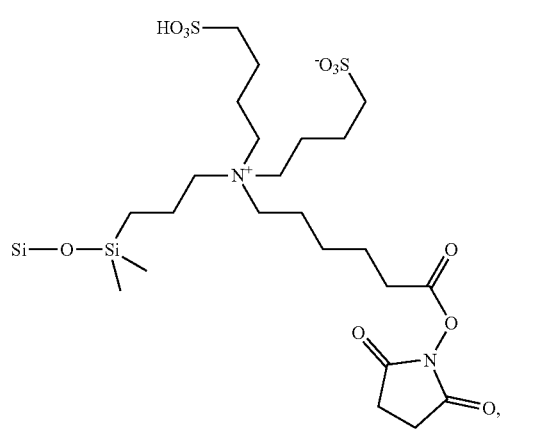
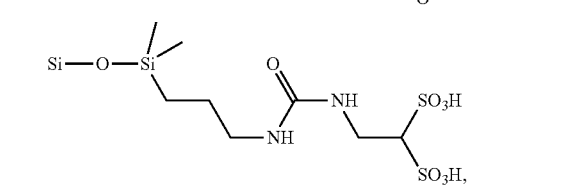
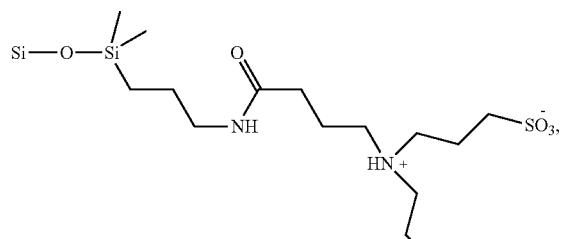
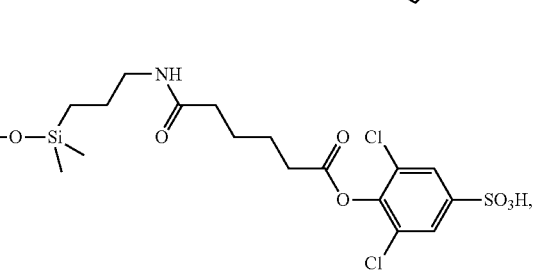
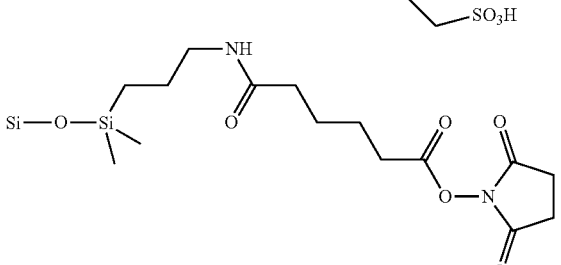
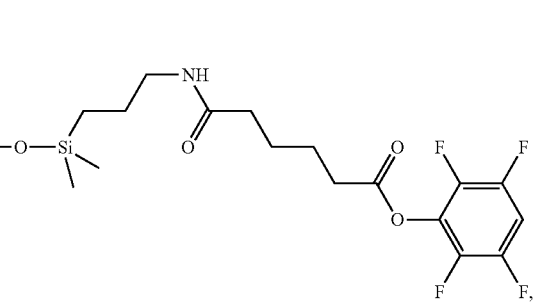
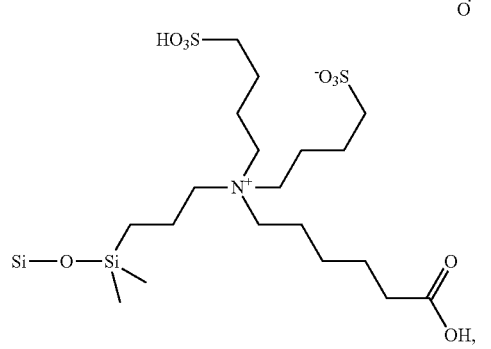
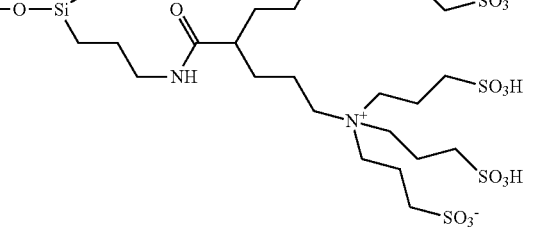

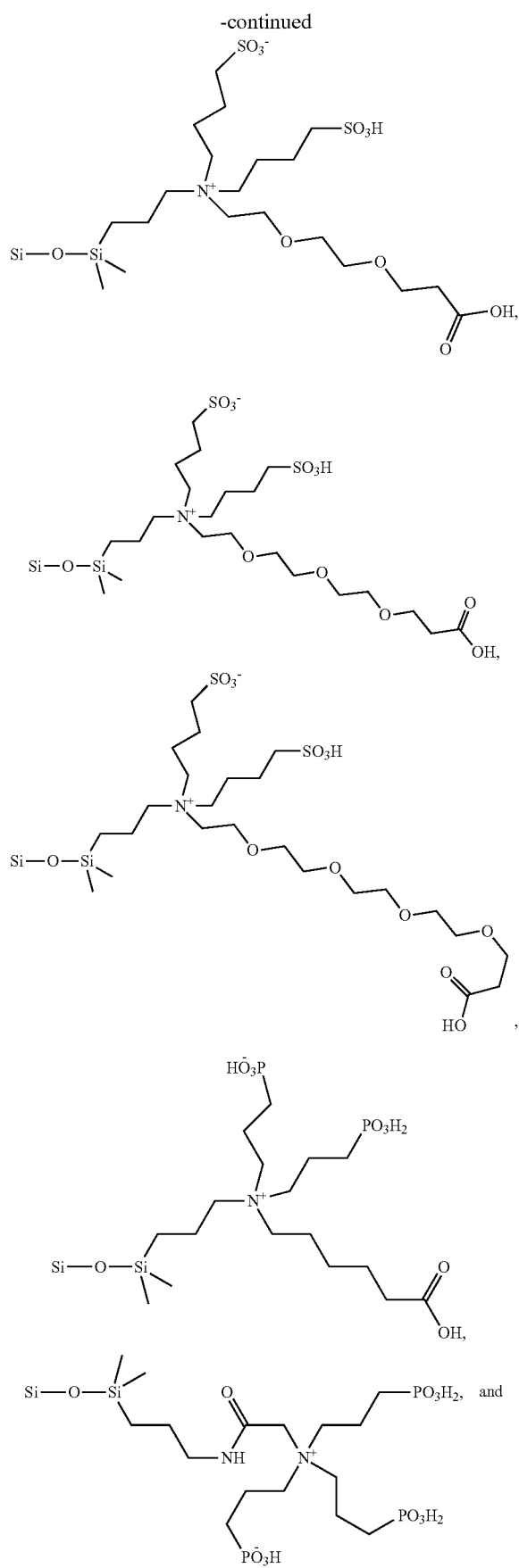

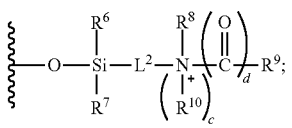

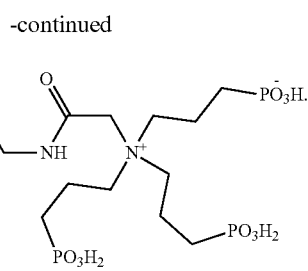

In certain embodiments, provided herein is a compound of Formula (0) comprising a silicon atom coordinated by (a) an unsubstituted phthalocyanine, (b) an axial silicon-containing ligand having a conjugatable group A'; and (c) an axial silicon-containing ligand having a water-solubilizing group Z that is not a conjugatable group.

One embodiment provides a compound, or salt, stereoisomer, or tautomer thereof, comprising a silicon atom coordinated by (a) an unsubstituted phthalocyanine, (b) a first axial silicon-containing ligand comprising a conjugatable group; and (c) a second axial silicon-containing ligand comprising a water-solubilizing group, but not a conjugatable group; and wherein the chemical structures of the first and second axial ligands are different. Another embodiment provides the compound, or salt, stereoisomer, or tautomer thereof, wherein the axial silicon-containing ligand having a conjugatable group further comprises a water-solubilizing group. Another embodiment provides the compound, or salt, stereoisomer, or tautomer thereof, wherein the water-solubilizing group is a group comprising one or more polar and/or ionic substituents. Another embodiment provides the compound, or salt, stereoisomer, or tautomer thereof, wherein the one or more polar and/or ionic substituents on the water-solubilizing group are selected from carboxylate (—$CO_2$), poly(ethyleneglycol), sulfonate (—$SO_3H$) group, a sulfonyl (—$SO_2H$) group, a sulfate (—$SO_4$) group, a hydroxyl (—OH) group, a phosphate (—$OPO_3H$) group, a phosphonate (—$PO_3H$) group, an amine (—$NH_2$) group and an optionally substituted quaternized nitrogen. Another embodiment provides the compound, or salt, stereoisomer, or tautomer thereof, wherein the one or more polar and/or ionic substituents on the water-solubilizing group are selected from a trivalent or tetravalent nitrogen-containing group, tris-sulfoalkyl quaternary ammonium, tris-sulfonate quaternary ammonium, bis-sulfoalkyl amine, bis-sulfonate amine, or bis-alkoxypolyethylene glycol amine. Another embodiment provides the compound, or salt, stereoisomer, or tautomer thereof, wherein the axial silicon-containing ligand having a water-solubilizing group has the structure of $$\xi-O-\underset{\underset{R^7}{|}}{\overset{\overset{R^6}{|}}{Si}}-L^2-\underset{\underset{(R^{10})_c}{|}}{\overset{R^8}{\underset{|}{N^+}}}\left(\overset{O}{\underset{||}{C}}\right)_d R^9;$$

$R^6$ and $R^7$ are each independently optionally substituted alkyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl or optionally substituted heteroaralkyl;

R⁸, R⁹ or R¹⁰ are selected from substituent group (a) or substituent group (b) wherein,
(a) R⁸ is hydrogen, -L⁸-H or -L⁸-Z;
R⁹ is -L⁹-H, —(NH)$_n$-L⁹-Z or —(O)$_n$-L⁹-Z;
R¹⁰ is -L¹⁰-Z; and
(b) R⁸ and R⁹ are connected with a bond to form a heterocyclyl substituted with -L⁹-Z and R¹⁰ is -L¹⁰-H or -L¹⁰-Z; provided at least one of R⁸, R⁹ and R¹⁰ is a group containing Z; Z is a water-solubilizing group;
L² is an optionally substituted alkylene, optionally substituted heteroalkylene, optionally substituted alkenylene or optionally substituted heteroalkenylene;
L⁸, L⁹ and L¹⁰ are each independently optionally substituted alkylene, optionally substituted heteroalkylene, optionally substituted alkenylene, optionally substituted heteroalkenylene, optionally substituted cycloalkylene, optionally substituted heterocyclene, optionally substituted arylene, optionally substituted aralkylene, optionally substituted heteroaralkylene, or optionally substituted heteroarylene, where the carbon atom of the alkylene, heteroalkylene, alkenylene, heteroalkenylene, cycloalkylene, heterocyclene, arylene aralkylene, optionally substituted heteroaralkylene, or optionally substituted heteroarylene, is further optionally substituted with Z and each nitrogen atom of the heteroalkylene or heteroalkenylene is optionally substituted with one or two L'-Z;
L' is each independently optionally substituted alkylene, optionally substituted heteroalkylene, optionally substituted alkenylene, optionally substituted heteroalkenylene, optionally substituted cycloalkylene, optionally substituted heterocyclene, optionally substituted arylene, optionally substituted aralkylene, optionally substituted heteroaralkylene, or optionally substituted heteroarylene;
c is 0 or 1;
d is 0 or 1;
n is 0 or 1;
if d is 1, then c is 0;
if n is 1, c is 1 and
provided that when R⁶ and R⁷ are both methyl, and L is propylene, c is 1 and d is 0, then L⁸, L⁹ and L¹⁰ are each not propylene.

Another embodiment provides the compound, or salt, stereoisomer, or tautomer thereof, wherein the axial silicon-containing ligand having a water-solubilizing group has the structure of

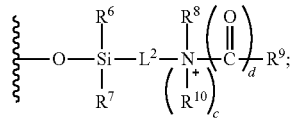

R⁶ and R⁷ are each independently optionally substituted alkyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl or optionally substituted heteroaralkyl;
R⁸, R⁹ or R¹⁰ are selected from substituent group (a) or substituent group (b) wherein,
(a) R⁸ is hydrogen, -L⁸-H or -L⁸-Z;
R⁹ is -L⁹-H, —(NH)$_n$-L⁹-Z or —(O)$_n$-L⁹-Z;
R¹⁰ is -L¹⁰-Z; and
(b) R⁸ and R⁹ are connected with a bond to form a heterocyclyl substituted with -L⁹-Z and R¹⁰ is -L¹⁰-H or -L¹⁰-Z; provided at least one of R⁸, R⁹ and R¹⁰ is a group containing Z;
Z is a water-solubilizing group;
L² is an optionally substituted alkylene, optionally substituted heteroalkylene, optionally substituted alkenylene or optionally substituted heteroalkenylene;
L⁸, L⁹ and L¹⁰ are each independently optionally substituted alkylene, optionally substituted heteroalkylene, optionally substituted alkenylene, optionally substituted heteroalkenylene, optionally substituted cycloalkylene, optionally substituted heterocyclene, optionally substituted arylene, optionally substituted aralkylene, optionally substituted heteroaralkylene, or optionally substituted heteroarylene, where the carbon atom of the alkylene, heteroalkylene, alkenylene, heteroalkenylene, cycloalkylene, heterocyclene, arylene aralkylene, optionally substituted heteroaralkylene, or optionally substituted heteroarylene, is further optionally substituted with Z and each nitrogen atom of the heteroalkylene or heteroalkenylene is optionally substituted with one or two L'-Z;
L' is each independently optionally substituted alkylene, optionally substituted heteroalkylene, optionally substituted alkenylene, optionally substituted heteroalkenylene, optionally substituted cycloalkylene, optionally substituted heterocyclene, optionally substituted arylene, optionally substituted aralkylene, optionally substituted heteroaralkylene, or optionally substituted heteroarylene;
c is 0 or 1;
d is 0 or 1;
n is 0 or 1;
if d is 1, then c is 0; and
if n is 1, c is 1.

Another embodiment provides a phthalocyanine dye having the Formula (XX):

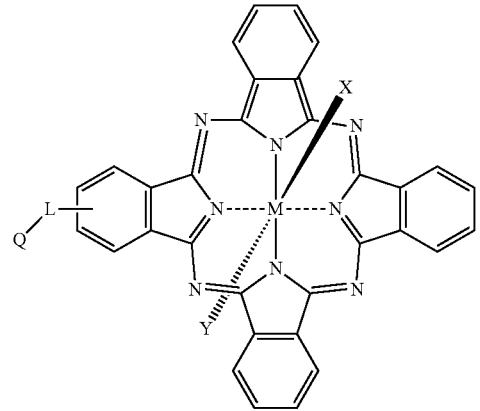

or a salt, stereoisomer, or tautomer thereof, wherein,
M is a metal or metalloid;
each Y is independently selected and Y is

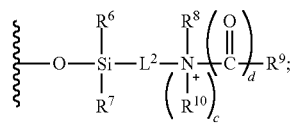

L is a member selected from the group consisting of a direct link, or a covalent linkage, wherein said covalent linkage is linear or branched, cyclic or heterocyclic, saturated or unsaturated, having 1-60 atoms selected from the group consisting of C, N, P, O, and S, wherein L can have additional hydrogen atoms to fill valences, and wherein said linkage contains any combination of ether, thioether, amine, ester, carbamate, urea, thiourea, oxy or amide bonds; or single, double, triple or aromatic carbon-carbon bonds; or phosphorus-oxygen, phosphorus-sulfur, nitrogen-nitrogen, nitrogen-oxygen, or nitrogen-platinum bonds; or aromatic or heteroaromatic bonds;

Q is a reactive or an activatable group;

$R^6$ and $R^7$ are each independently optionally substituted alkyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl or optionally substituted heteroaralkyl;

$R^8$, $R^9$ or $R^{10}$ are selected from substituent group (a) or substituent group (b) wherein, (a) $R^8$ is hydrogen, $-L^8$-H, $-L^8$-A or $-L^8$-Z;
$R^9$ is $-L^9$-H, $-L^9$-A, $-(NH)_n$-$L^9$-Z or $-(O)_n$-$L^9$-Z;
$R^{10}$ is $-L^{10}$-A $-L^{10}$-Z; and (b) $R^8$ and $R^9$ are connected with a bond to form a heterocyclyl substituted with $-L^9$-Z and $R^{10}$ is $-L^{10}$-H or $-L^{10}$-Z;

provided at least one of $R^8$, $R^9$ and $R^{10}$ is a group containing Z;

Z is a water soluble group optionally substituted with A or L'-A;

$L^8$, $L^9$ and $L^{10}$ are each independently optionally substituted alkylene, optionally substituted heteroalkylene, optionally substituted alkenylene, optionally substituted heteroalkenylene, optionally substituted cycloalkylene, optionally substituted heterocyclene, optionally substituted arylene, optionally substituted aralkylene, optionally substituted heteroaralkylene, or optionally substituted heteroarylene, where the carbon atom of the alkylene, heteroalkylene, alkenylene, heteroalkenylene, cycloalkylene, heterocyclene, arylene, aralkylene, heteroaralkylene, or optionally substituted heteroarylene is further optionally substituted with Z and each nitrogen atom of the heteroalkylene or heteroalkenylene is optionally substituted with one or two L'-Z;

L' is each independently optionally substituted alkylene, optionally substituted heteroalkylene, optionally substituted alkenylene, optionally substituted heteroalkenylene, optionally substituted cycloalkylene, optionally substituted heterocyclene, optionally substituted arylene, optionally substituted aralkylene, optionally substituted heteroaralkylene, or optionally substituted heteroarylene;

A is a reactive group capable of forming a covalent bond with a thiol, hydroxyl, carboxyl or amino group of a second moiety, or a protected form thereof or a reacted form thereof;

c is 0 or 1;
d is 0 or 1;
n is 0 or 1;
provided that if d is 1, then c is 0; and if n is 1, then c is 0.

In some embodiments, M is Si or Ge.

In some embodiments, each group Z is independently selected from;
—C(O)OH,
—$(CH_2)_q(OCH_2CH_2)_v(CH_2)_pC(O)OH$,
—$(CH_2CH_2O)_v(CH_2)_pC(O)OH$,
—$(CH_2)_q(OCH_2CH_2)_vOR^{22}$,
—$(CH_2CH_2O)_v(CH_2)_pOR^{22}$,
—$(CH_2)_q(OCH_2CH_2)_vSR^{22}$,
—$(CH_2CH_2O)_v(CH_2)_pSR^{22}$,
—$O(CH_2)_vN[(CH_2CH_2O)_nCH_2CH_2OR^{22}]_t$,
—$(CH_2)_q(OCH_2CH_2)_vN[(CH_2CH_2O)_wCH_2CH_2OR^{22}]_t$,
—$(CH_2CH_2O)_m(CH_2)_pN[(CH_2CH_2O)_wCH_2CH_2OR^{22}]_t$,
—$NH_2$,
—$(CH_2)_qN[(CH_2CH_2O)_vCH_2CH_2OR^{22}]_t$,
—$(CH_2)_qNR^b[(CH_2CH_2O)_wCH_2CH_2OR^{22}]_u$,
—$(CH_2)_qN[(CH_2)_p(OCH_2CH_2)_vOR^{22}]_t$,
—$(CH_2)_qN[(CH_2)_pSO_3H]_t$,
—$(CH_2)_qNR^b[(CH_2)_pSO_3H]_u$,
—$(CH_2)_qNR^b(CH_2)_pCH(SO_3H)_2$,
—$(CH_2)_qN[(CH_2)_pS(O)_uOH]_t$,
—$(CH_2)_qN[(CH_2)_pOSO_3H]_t$,
—$(CH_2)_q(OCH_2CH_2)(CH_2)_qSO_3H$,
—$(CH_2)_q(OCH_2CH_2)_v(CH_2)_qS(O)_uOH$,
—$(CH_2)_q(OCH_2CH_2)_v(CH_2)_qOSO_3H$,
—$SO_3H$,
—$CH(SO_3H)_2$,
—$OSO_3H$,
—$S(O)_uOH$,
—$PO_3H$,
—$CH(PO_3H)_2$,
—$(CH_2)_qN[(CH_2)_pPO_3—]_t$,
—$(CH_2)_q(OCH_2CH_2)_v(CH_2)_qPO_3H$,
—$(CH_2)_pN[(CH_2)_pOPO_3H]_t$,
—$OPO_3H$,
—$(CH_2)_q(OCH_2CH_2)_v(CH_2)_qP(O)(OH)_2$,
—$(CH_2)_qN[(CH_2)_pP(O)(OH)_2]_t$,
—$P(O)(OH)_2$,
glutamate, aspartate, histidine, 1,3-beta-glucan and 1,4-beta-glucan;

each $R^{22}$ is independently alkyl, haloalkyl, cycloalkyl or aryl;

each $R^b$ is independently hydrogen, alkyl optionally substituted with —$CO_2H$, heteroalkylene optionally substituted with —$CO_2H$, haloalkyl or cycloalkyl;

each v, w and p are independently an integer from 1 to 10;
each q is independently an integer from 0 to 10;
t is 2 or 3; and
u is 1 or 2.

In some embodiments, each group Z is independently selected from:
—$(CH_2)_q(OCH_2CH)_vOR^{22}$,
—$(CH_2)_qO(CH_2)_vN[(CH_2CH_2O)_wCH_2CH_2OR^{22}]_t$,
—$(CH_2)_qN[(CH_2)_p(OCH_2CH_2)_vOR^{22}]_t$,
—$(CH_2)_qN[(CH_2)_pSO_3H]_t$,
—$(CH_2)_qNR^b[(CH_2)_pSO_3H]_u$,
—$(CH_2)_qNR^b[(CH_2)_pCH(SO_3H)_2]_u$,
—$SO_3H$,
—$CH(SO_3H)_2$,
—$PO_3H$,
—$(CH_2)_qN[(CH_2)_pPO_3H]_t$,
—$(CH_2)_qNR^b[(CH_2)_pPO_3H]_u$, or
—$(CH_2)_qNR^b(CH_2)_pCH(PO_3H)_2$, each $R^{22}$ is independently alkyl, haloalkyl, cycloalkyl or aryl;

each $R^b$ is independently hydrogen, alkyl, haloalkyl or cycloalkyl;

each v, w and p are independently an integer from 1 to 10;
each q is independently an integer from 0 to 10;
t is 2 or 3; and u is 1 or 2.

In some embodiments, each group A is independently selected from
- —C(O)OR¹¹,
- —NR¹²R¹³,
- —NHC(O)R¹⁴,
- —C(O)R¹⁵,
- —OR¹⁶,
- —SR¹⁶,
- —OS(O)₂R¹⁷,
- —OP(OR¹⁸)(NR¹⁹R²⁰),
- —N═C═O;
- —N═C═S,
- —S—C≡N,
- —SO₂—F,
- —SO₂—Cl,
- —SO₂—Br,
- —S—SR²¹, or
- a 5- or 6-membered dioxo-substituted heterocyclyl;

wherein each $R^{11}$ is independently hydrogen, alkyl, haloalkyl, alkenyl, heterocyclyl, aryl or heteroaryl, and each $R^{11}$ is independently optionally substituted with one to five groups each independently selected from halo, —SO₃H and —SO₂F;

each $R^{12}$ is independently hydrogen, alkyl or haloalkyl;

each $R^{13}$ is aryl or heteroaryl, and each $R^{13}$ is independently optionally substituted with one to five groups each independently selected from halo, —SO₃H and —SO₂F; or optionally $R^{12}$ and $R^{13}$, together with the nitrogen to which they are attached, form a cyclic imide;

each $R^{14}$ is independently optionally substituted haloalkyl or optionally substituted aralkyl;

each $R^{15}$ is independently aryl optionally substituted with one to five groups each independently halo, heterocyclyl, —SO₃H or —SO₂F;

each $R^{16}$ is independently aryl optionally substituted with one to five groups each independently halo or heterocyclyl;

each $R^{17}$ is independently optionally substituted alkyl, optionally substituted haloalkyl, optionally substituted alkenyl, optionally substituted cycloalkyl, optionally substituted heterocyclyl, optionally substituted aryl or optionally substituted heteroaryl, wherein the heterocyclyl, aryl or heteroaryl is optionally substituted with one to five groups each independently selected from halo, —SO₃H, —SO₂F, and —C(O)OR^c;

each $R^c$ is independently optionally substituted alkyl, optionally substituted haloalkyl, optionally substituted cycloalkyl or optionally substituted aryl;

$R^{18}$, $R^{19}$ and $R^{20}$ are each independently optionally substituted alkyl or optionally substituted haloalkyl; and $R^{21}$ is heteroaryl.

In some embodiments, each group Y is independently selected from:

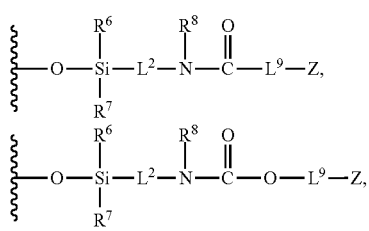

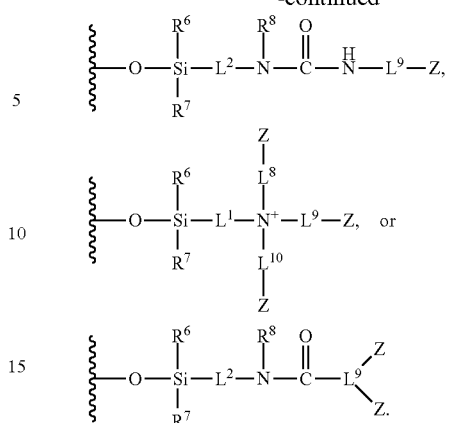

One embodiment provides a phthalocyanine dye having the regiochemistry indicated with Formula (XXa);

(XXa)

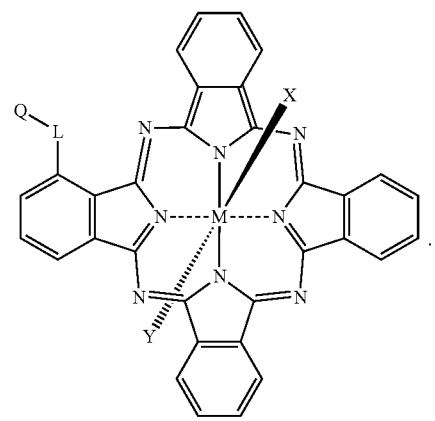

One embodiment provides a phthalocyanine dye having the Formula (XXb):

(XXb)

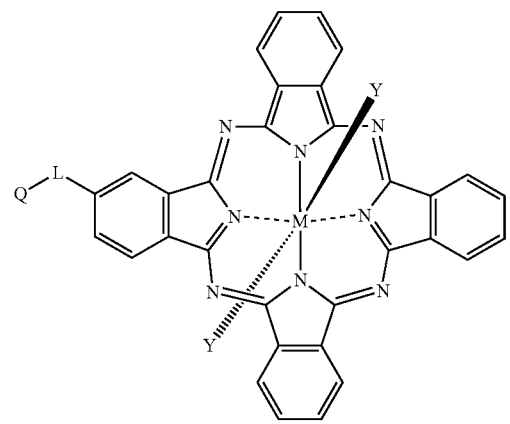

Another embodiment provides a compound of Formula (XX), wherein the M-Y group is independently selected from the group consisting of:

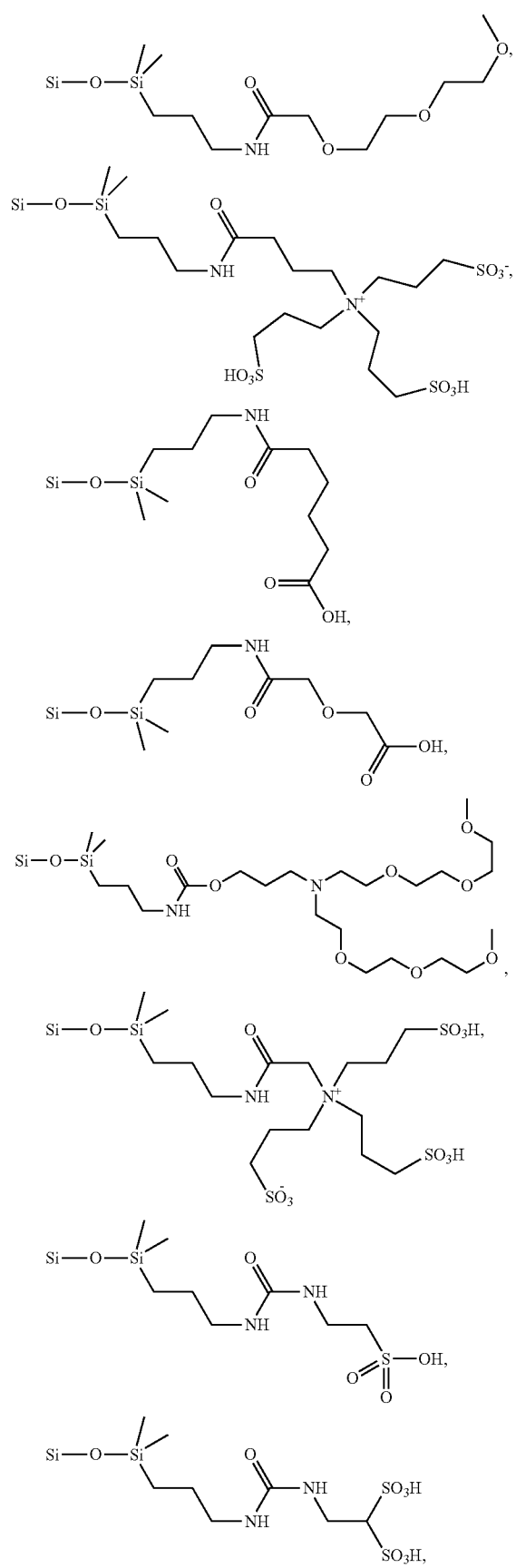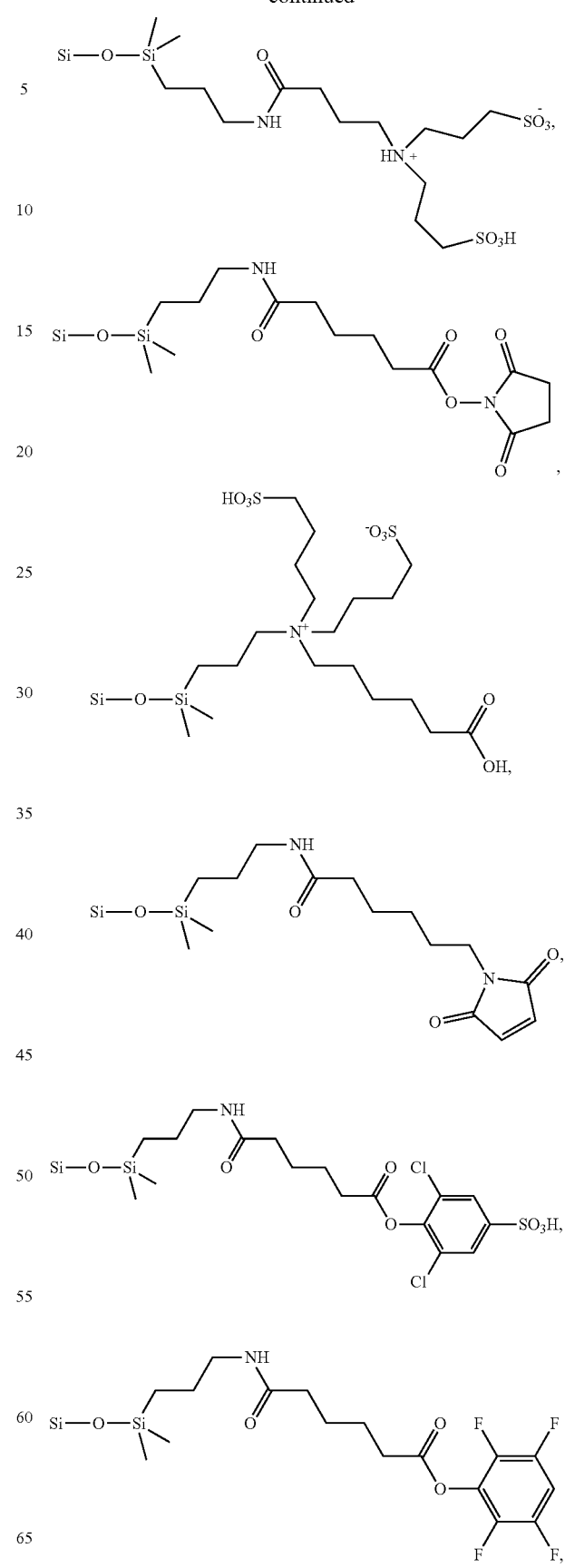

119
-continued
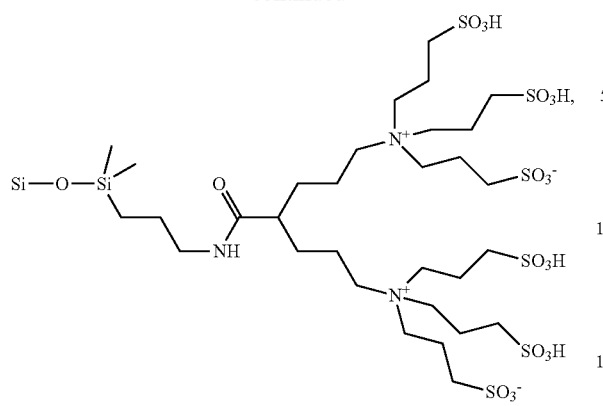
120
-continued
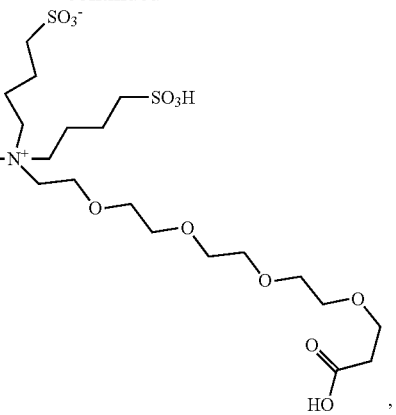
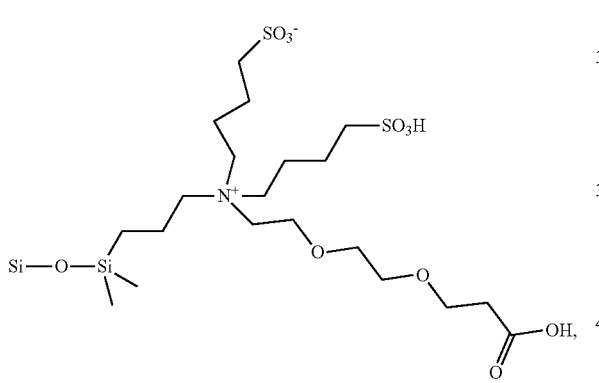
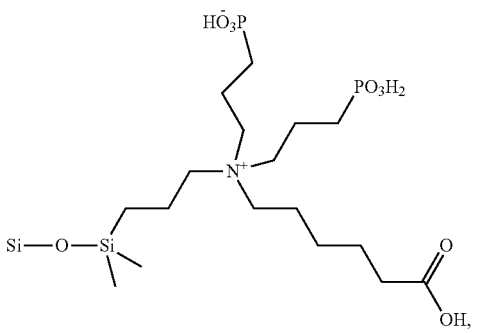
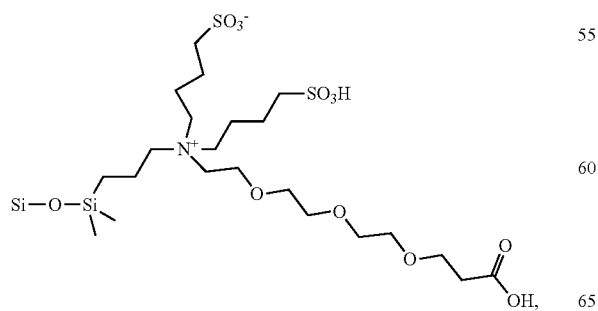
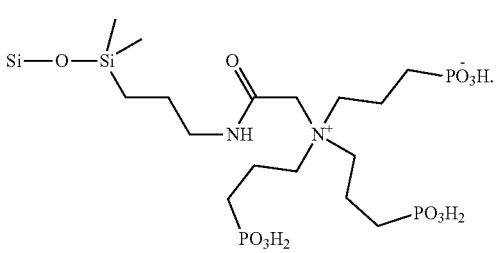

In some embodiments, the compound of Formula (XX) is selected from a compound in Table 2B.
TABLE 2B
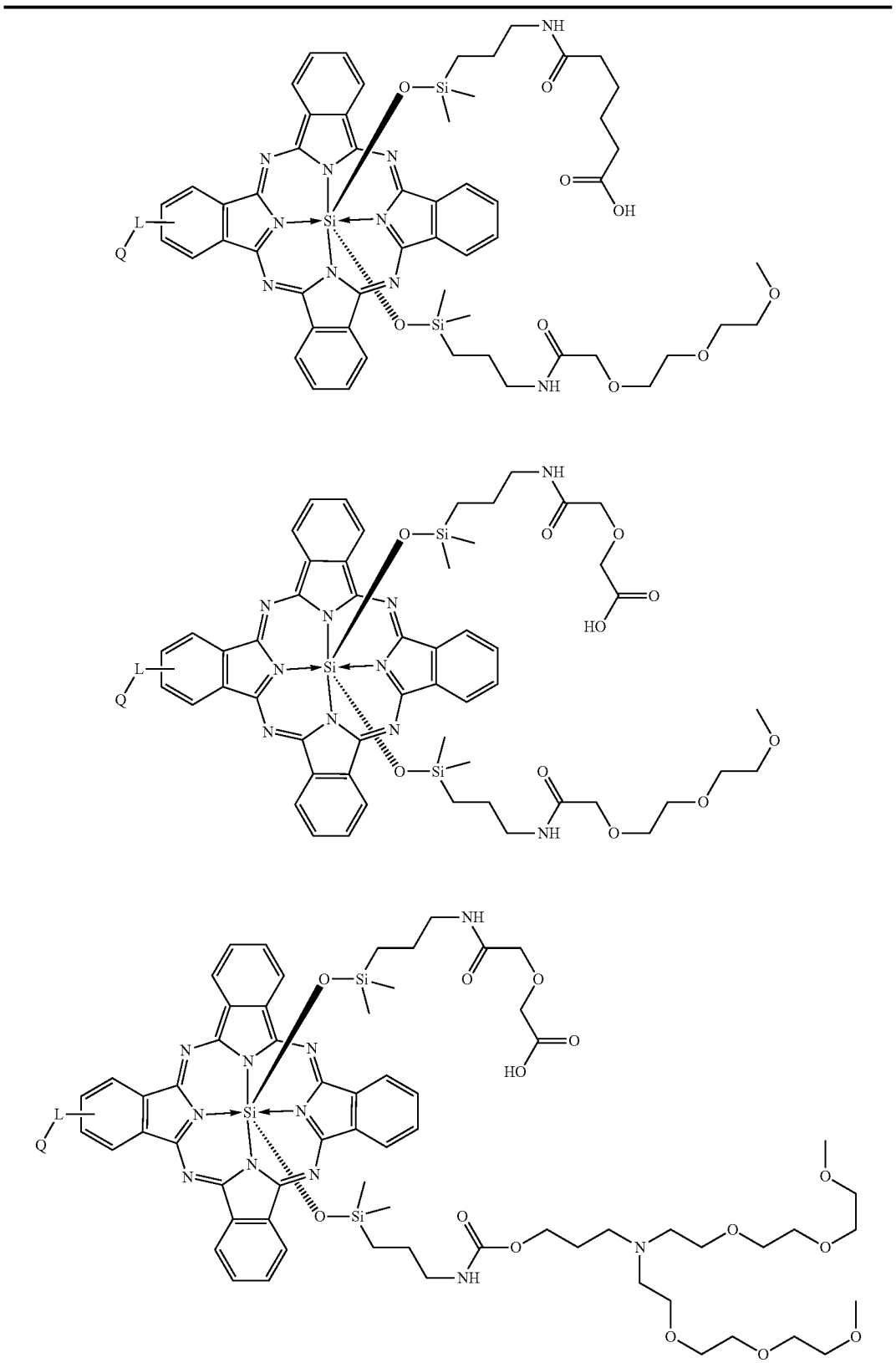

TABLE 2B-continued
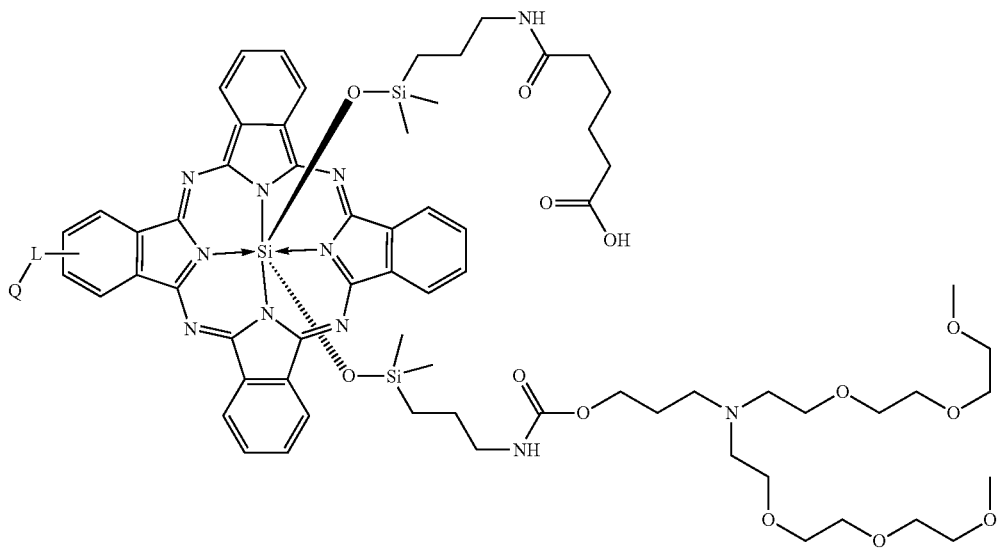
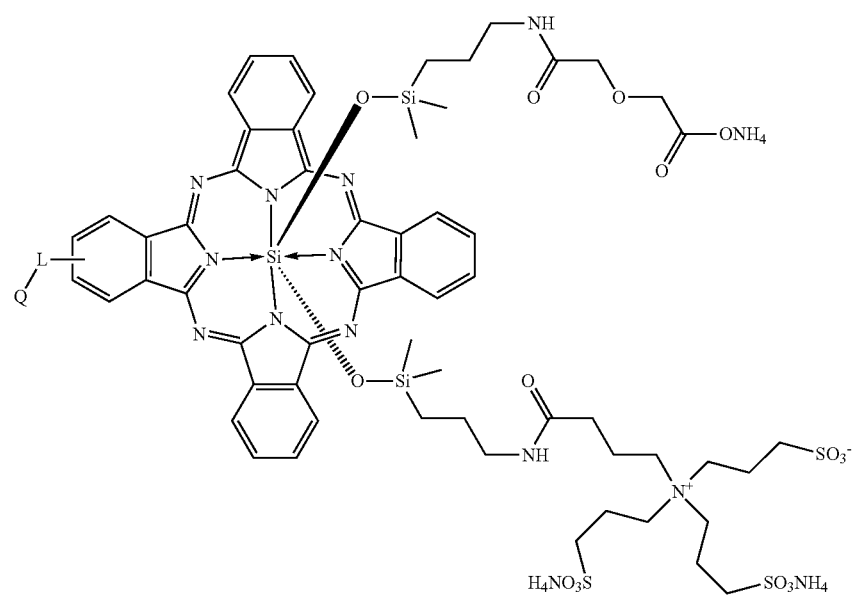

TABLE 2B-continued
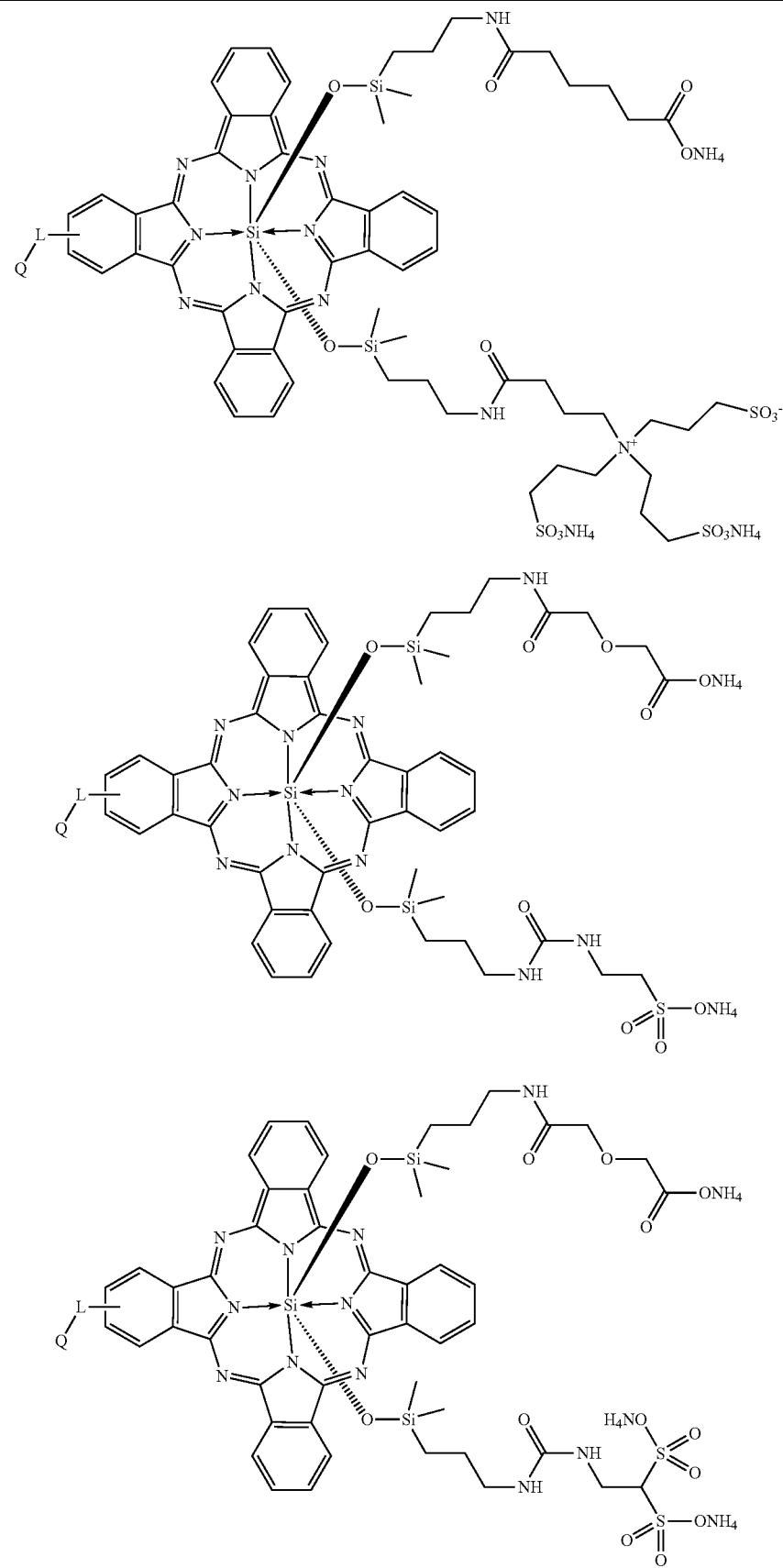

TABLE 2B-continued
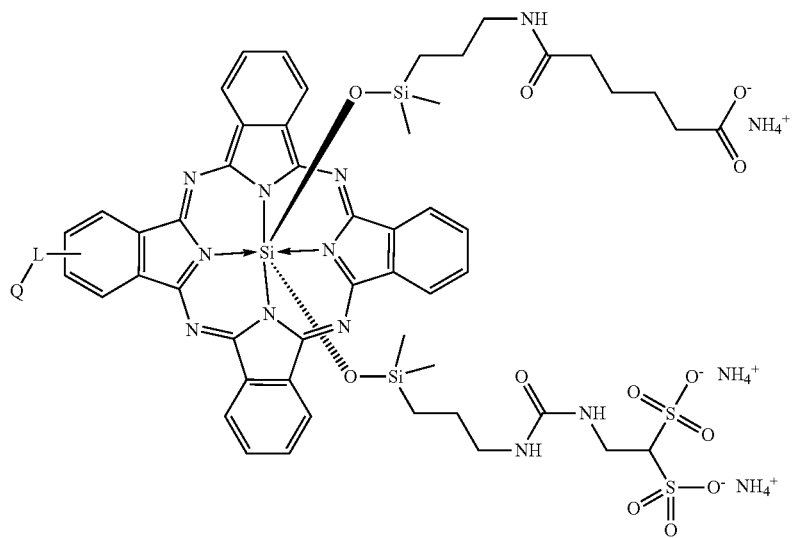
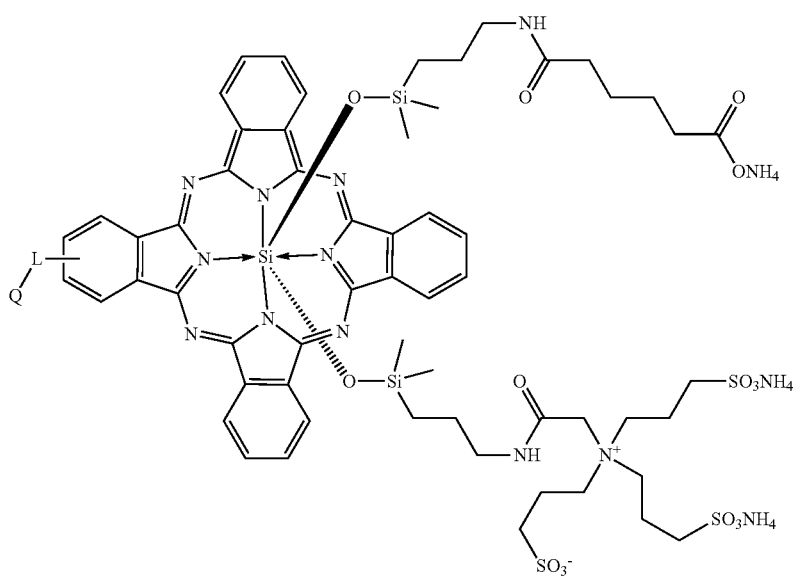

TABLE 2B-continued
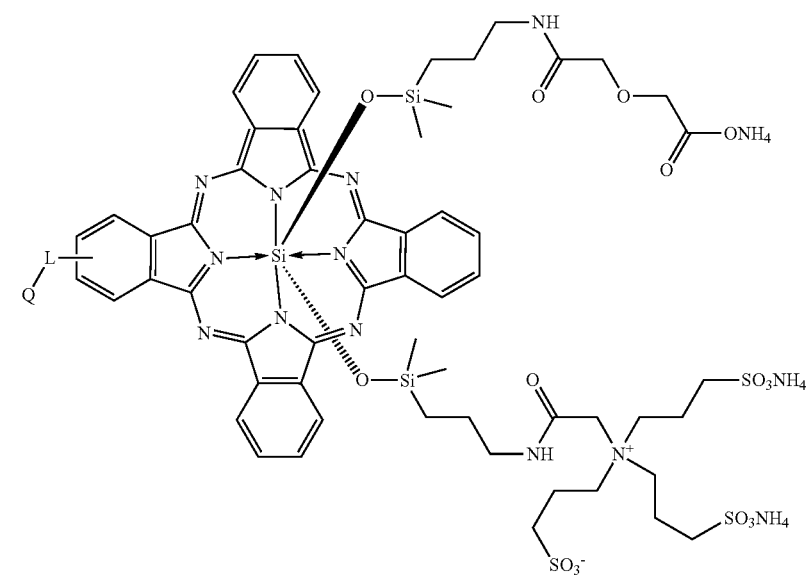
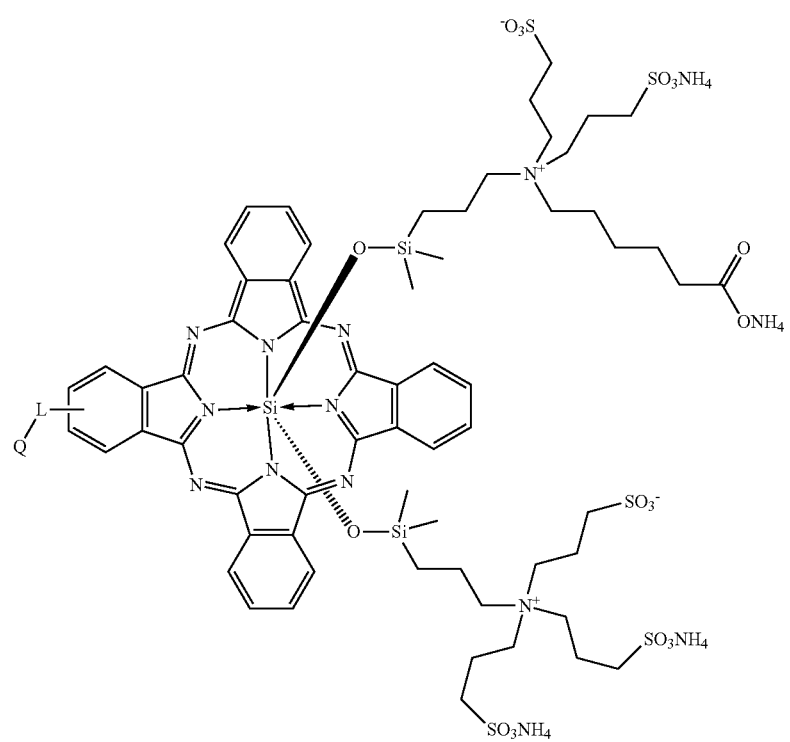

TABLE 2B-continued
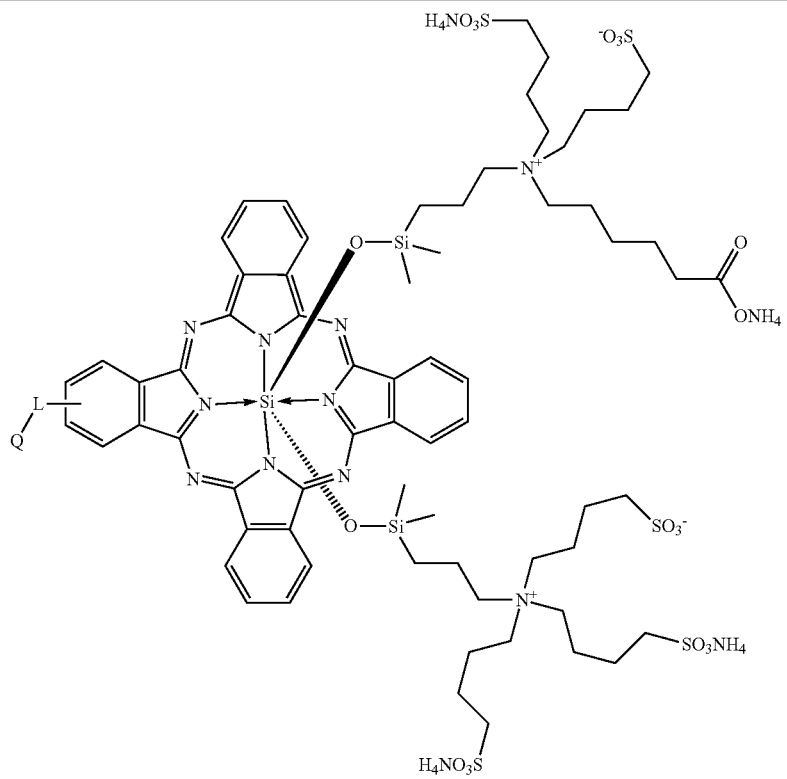
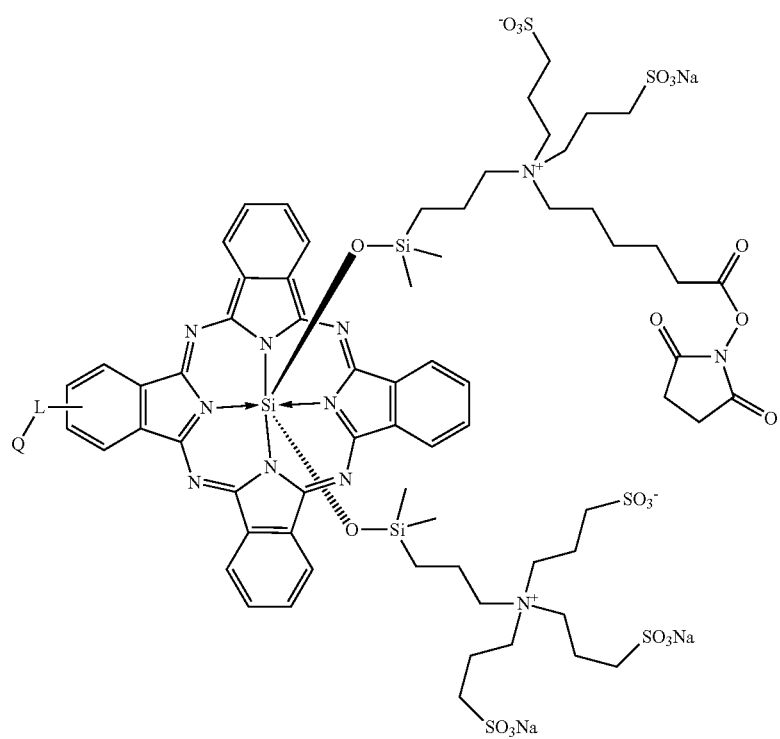

TABLE 2B-continued
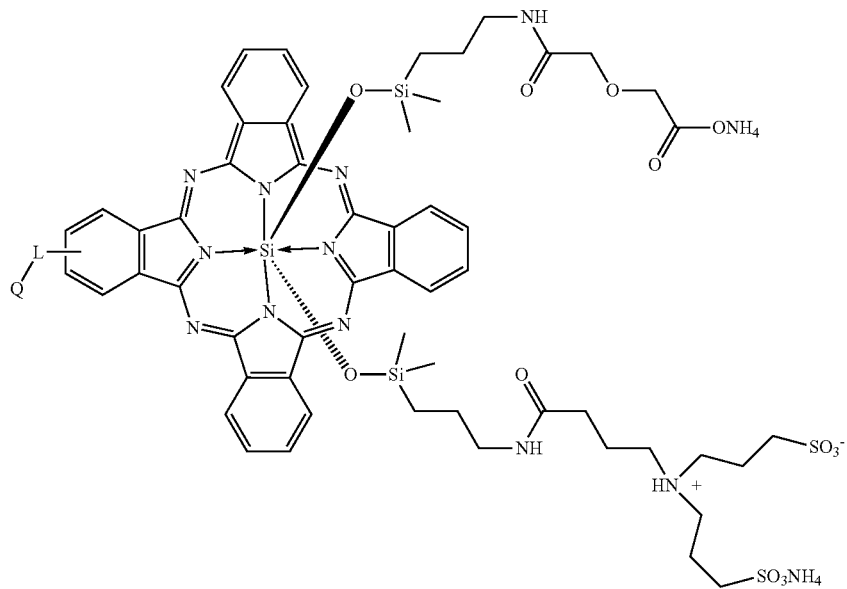
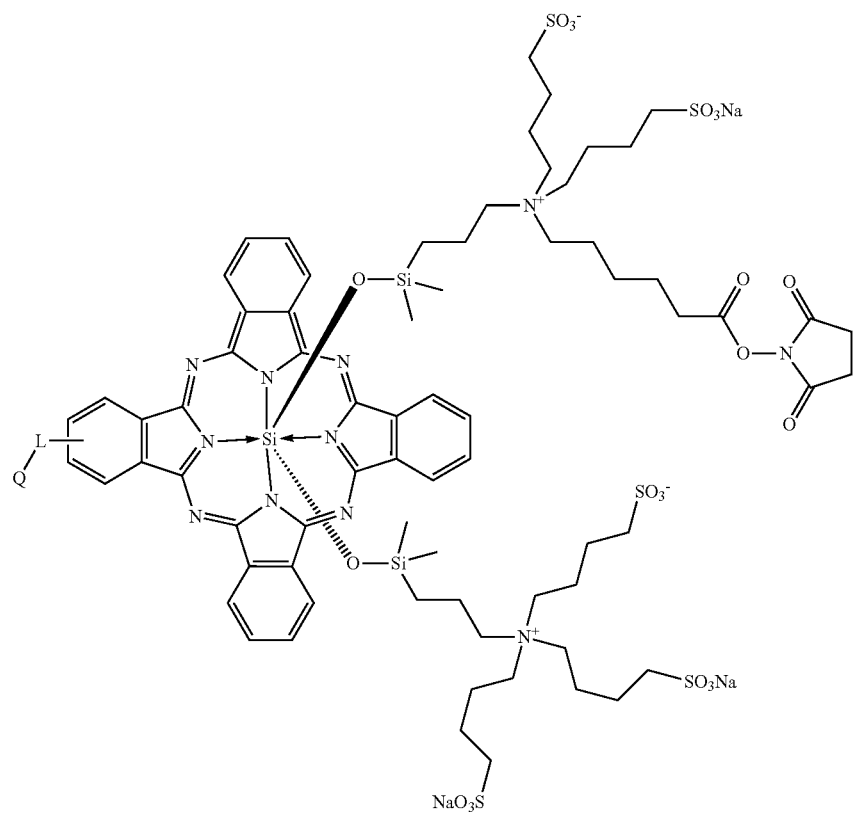

TABLE 2B-continued
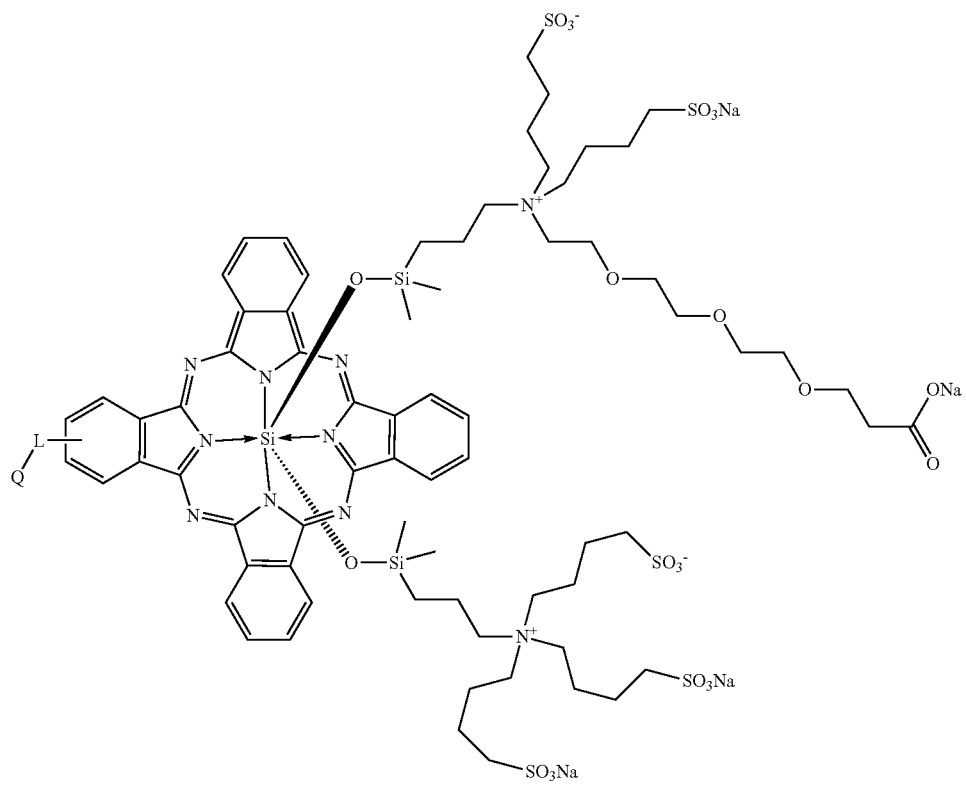
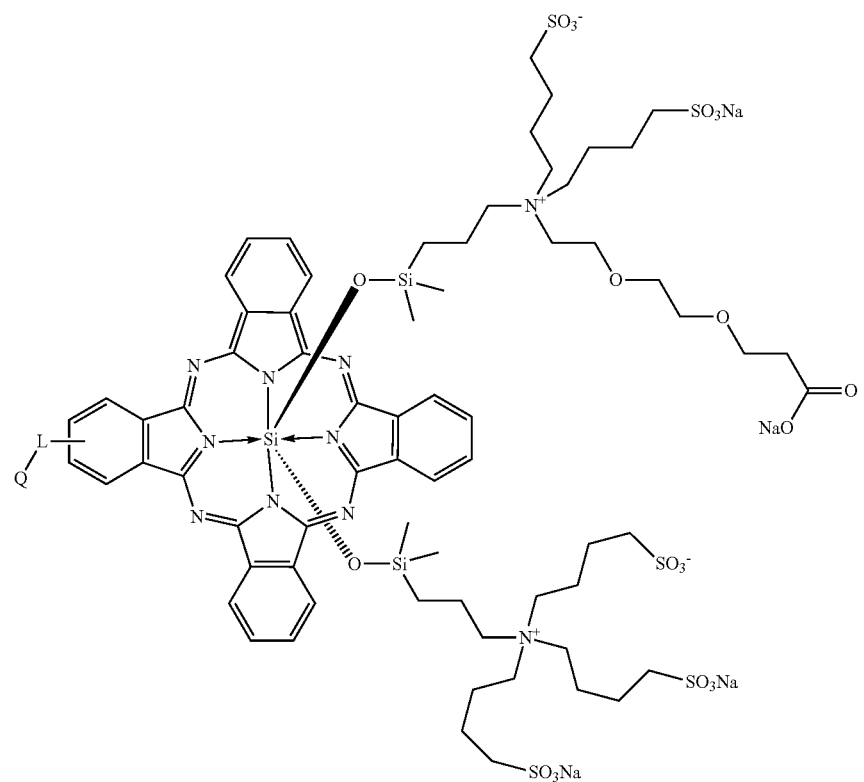

TABLE 2B-continued
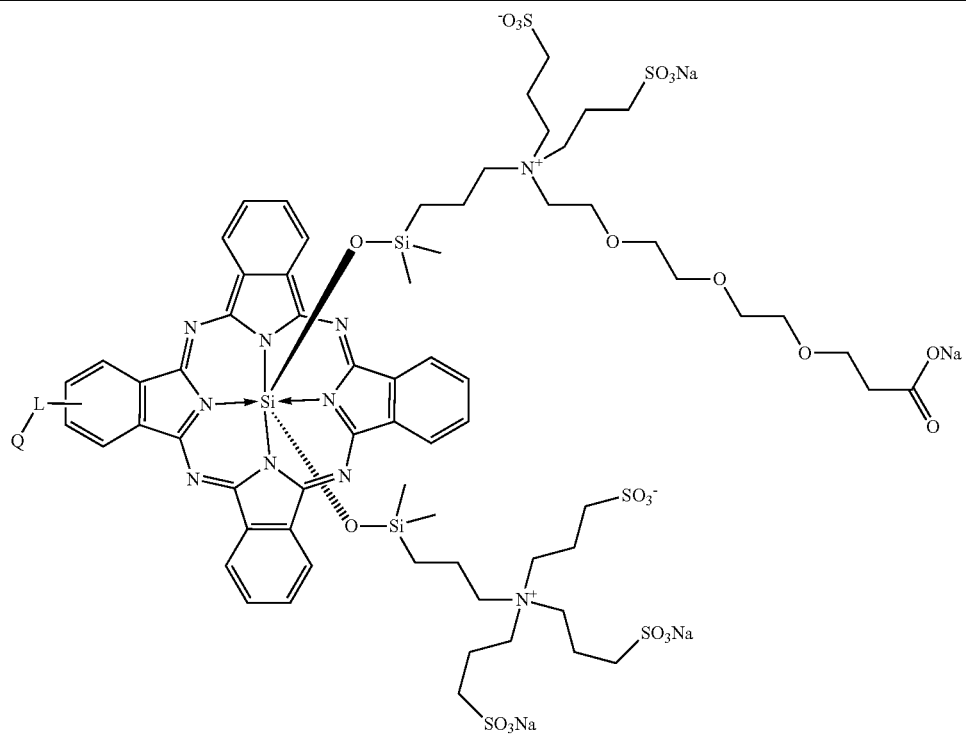
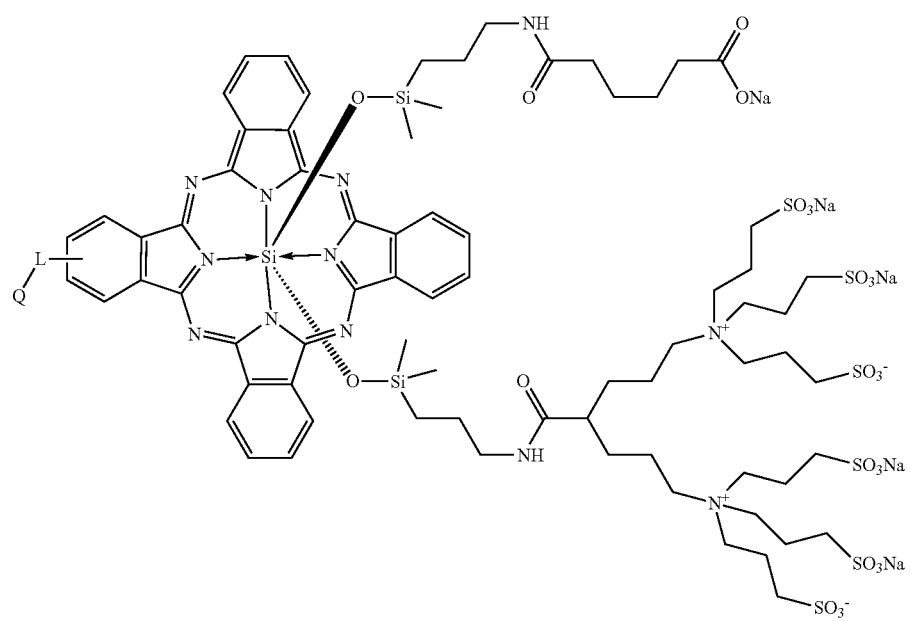

TABLE 2B-continued
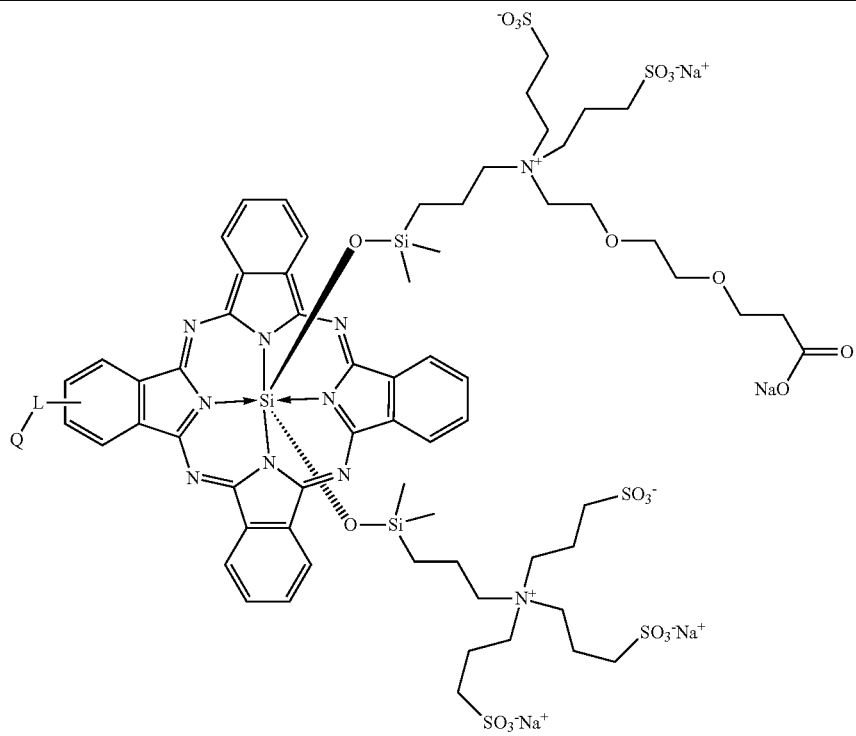
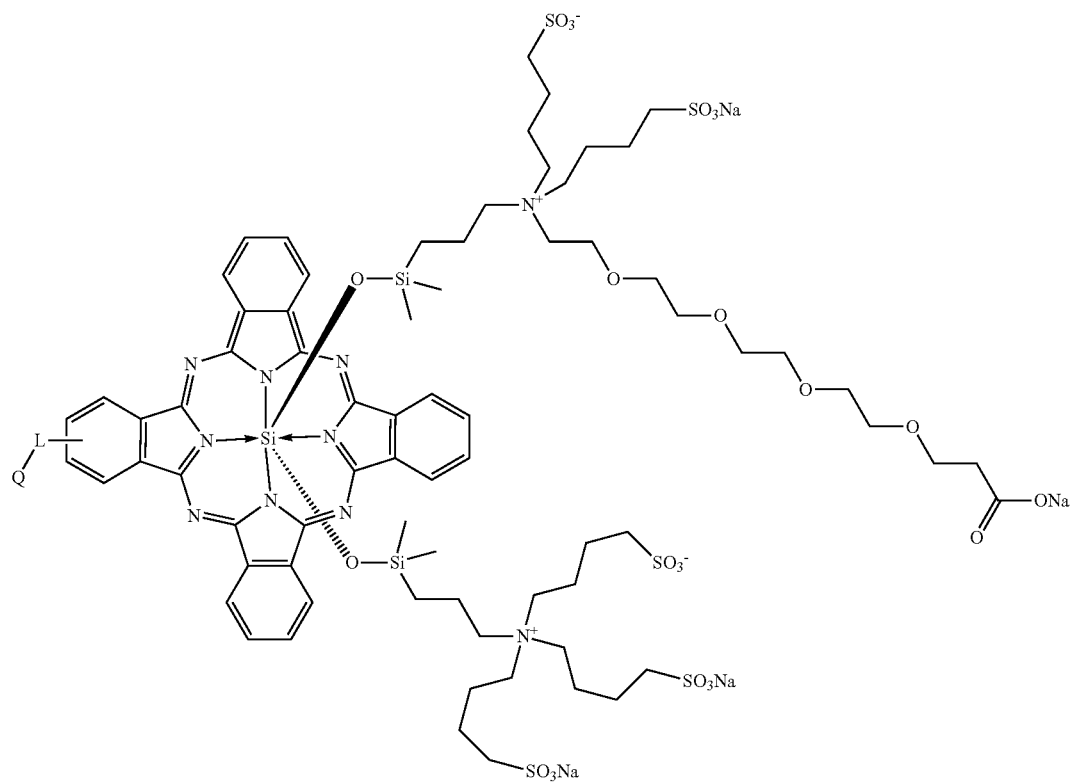

TABLE 2B-continued
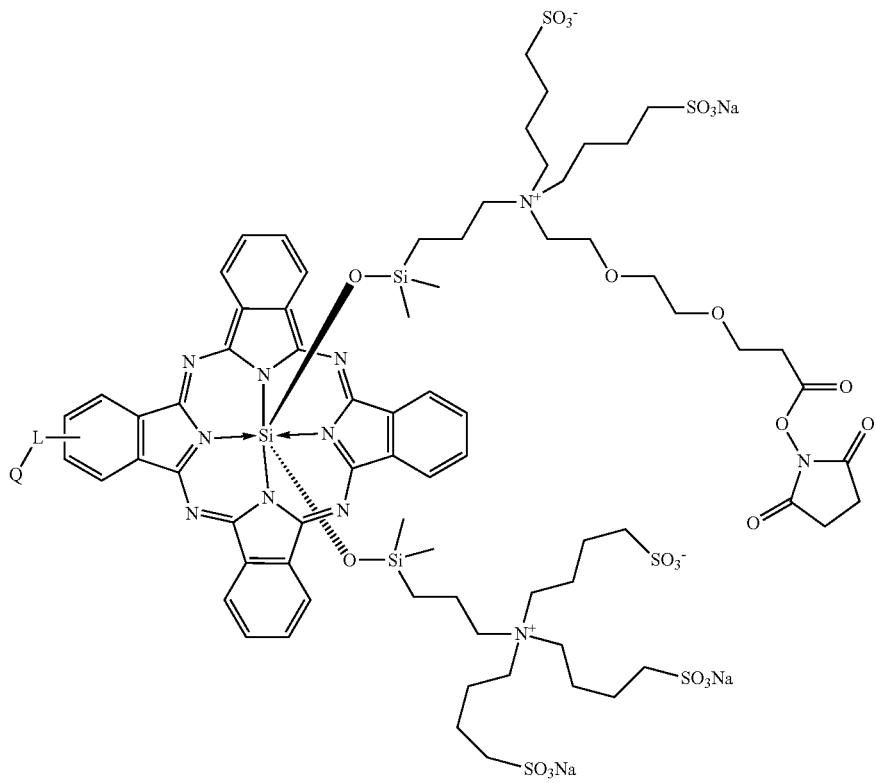
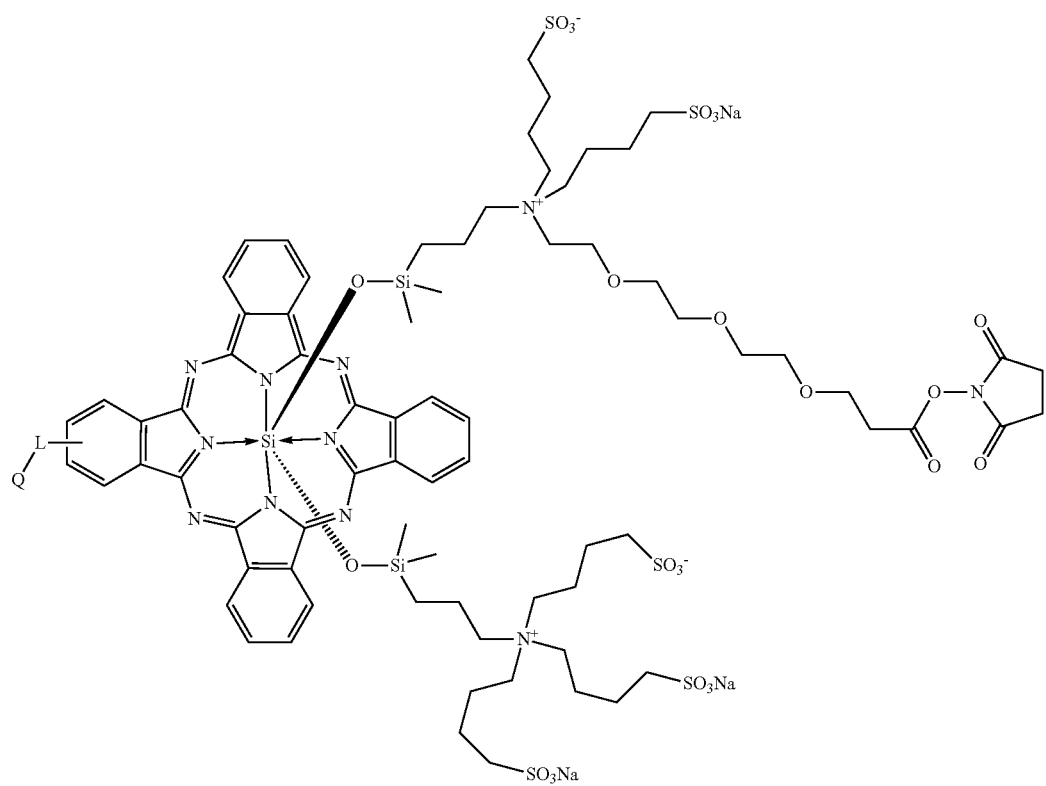

TABLE 2B-continued
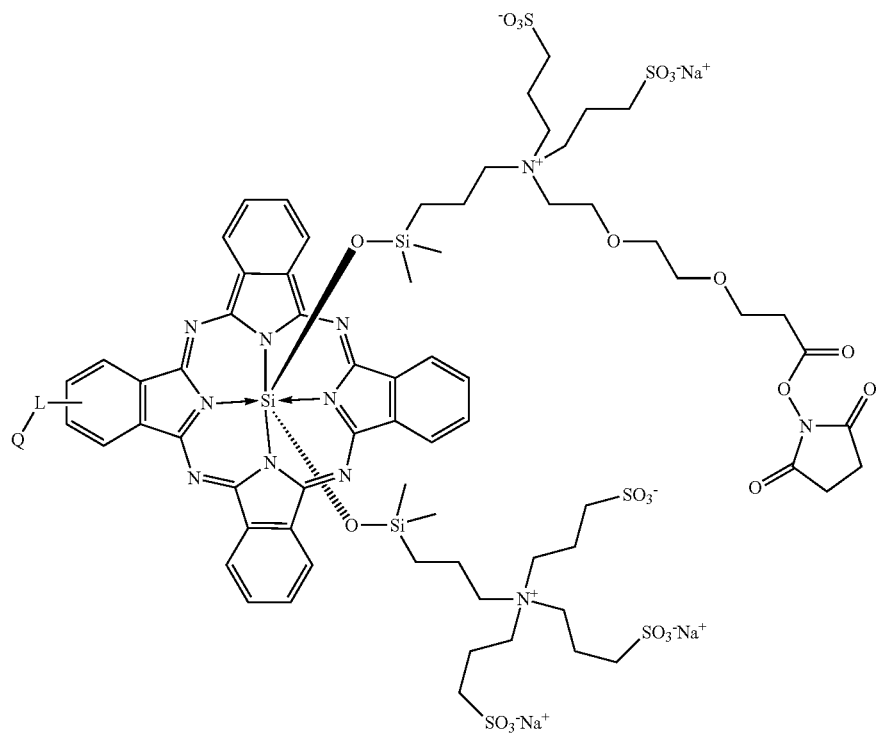
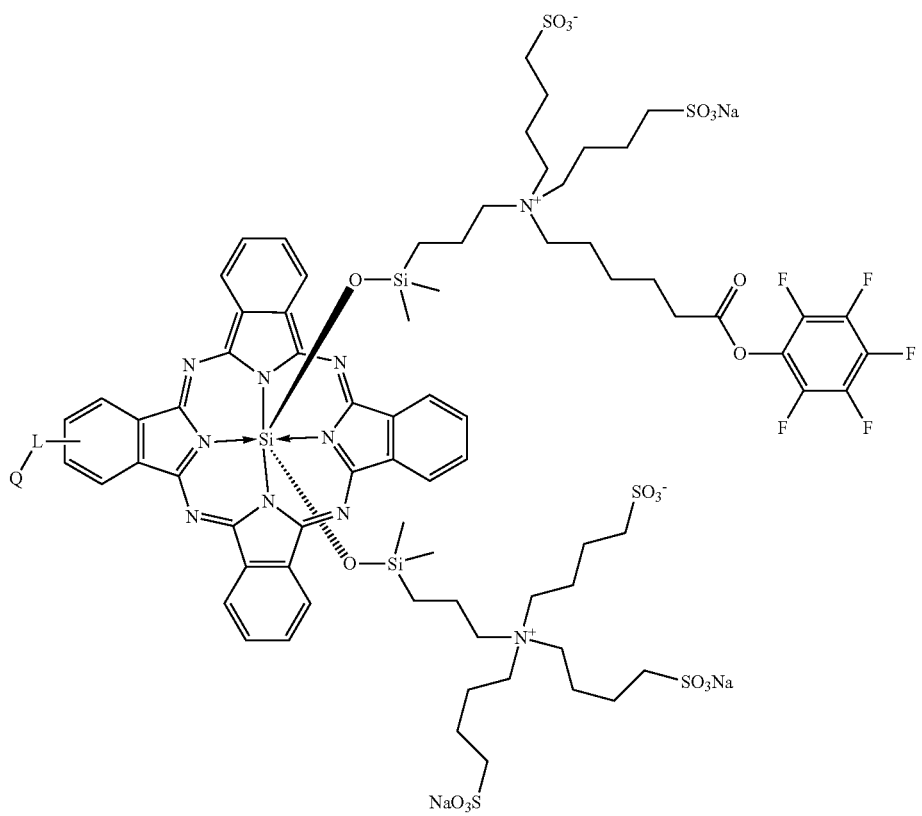

TABLE 2B-continued

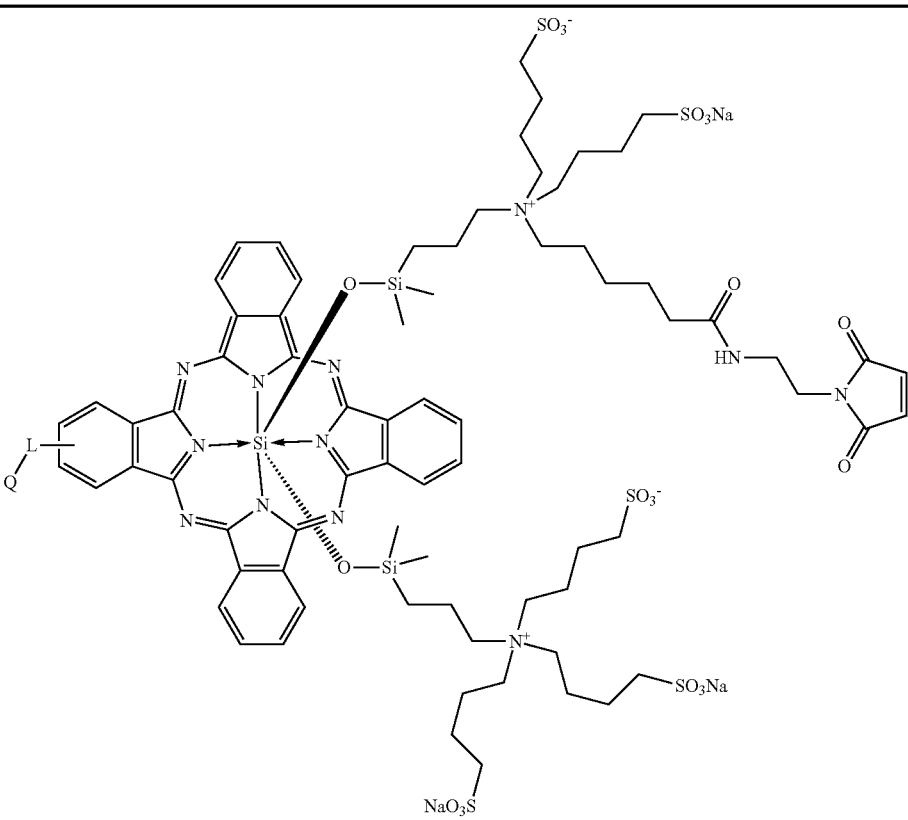

The compounds of this disclosure may contain one or more stereogenic centers and thus occur as racemates and racemic mixtures, enantiomerically enriched mixtures, single enantiomers, individual diastereomers and diastereomeric mixtures. The compounds of the present disclosure may, either by nature of stereogenic centers or by restricted rotation, be present in the form of isomers (e.g., enantiomers, diastereomers).

It will also be appreciated that when two or more stereogenic centers are present in the compounds of the disclosure, several diastereomers and enantiomers of the exemplified structures will often be possible. It is intended that pure stereoisomers, pure diastereomers, pure enantiomers, and mixtures thereof, are within the scope of the disclosure. When compounds contain stereochemistry, the compounds are designated as '(racemic)' or "rac" if the stereoisomers have not been separated and '(R) or (S)' if the stereoisomers have been resolved.

All isomers, whether separated, pure, partially pure, or in racemic mixture, of the compounds of this disclosure are encompassed within the scope of this disclosure. The purification of said isomers and the separation of said isomeric mixtures may be accomplished by various methods. For example, diastereomeric mixtures can be separated into the individual isomers by chromatographic processes or crystallization, and racemates can be separated into the respective enantiomers either by chromatographic processes on chiral phases or by resolution.

The compounds of the present disclosure include all cis, trans, syn, anti, entgegen (E), and zusammen (Z) isomers as well as mixtures thereof. The compounds of the present disclosure may also be represented in multiple tautomeric forms, in such instances, the present disclosure expressly includes all tautomeric forms of the compounds described herein, even though only a single tautomeric form may be represented. In addition, where a term used in the present disclosure encompasses a group that may tautomerize, all tautomeric forms are expressly included there under. For example, hydroxy substituted heteroaryl includes 2-hydroxypyridine as well as 2-pyridone, 1-hydroxyisoquinoline as well as 1-oxo-1,2-dihydroisoquinoline, and the like. All such isomeric forms of such compounds are expressly included in the present disclosure.

The compounds of the present disclosure include the compounds themselves, as well as their salts, solvate, solvate of the salt and their prodrugs, if applicable. Salts for the purposes of the present disclosure are preferably pharmaceutically acceptable salts of the compounds according to the present disclosure. Salts which are not themselves suitable for pharmaceutical uses but can be used, for example, for isolation or purification of the compounds according to the disclosure are also included. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion.

The present disclosure also encompasses all suitable isotopic variants of the compounds according to the present disclosure, whether radioactive or not. An isotopic variant of a compound according to the present disclosure is understood to mean a compound in which at least one atom within the compound according to the present disclosure has been exchanged for another atom of the same atomic number, but with a different atomic mass than the atomic mass which usually or predominantly occurs in nature. Examples of isotopes which can be incorporated into a compound according to the present disclosure are those of hydrogen, carbon, nitrogen, oxygen, fluorine, chlorine, bromine and iodine, such as $^{2}H$ (deuterium), $^{3}H$ (tritium), $^{13}C$, $^{14}C$, $^{15}N$, $^{17}O$, $^{18}O$, $^{18}F$, $^{36}Cl$, $^{82}Br$, $^{123}I$, $^{124}I$, $^{125}I$, $^{129}I$ and $^{131}I$. Particular isotopic variants of a compound according to the present disclosure, especially those in which one or more radioactive isotopes have been incorporated, may be beneficial, for example, for the examination of the mechanism of action or of the active compound distribution in the body. Compounds labelled with $^{3}H$, $^{14}C$ and/or $^{15}F$ isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required. In some embodiments, hydrogen atoms of the compounds described herein may be replaced with deuterium atoms. In certain embodiments, "deuterated" as applied to a chemical group and unless otherwise indicated, refers to a chemical group that is isotopically enriched with deuterium in an amount substantially greater than its natural abundance. Isotopic variants of the compounds according to the present disclosure can be prepared by various, including, for example, the methods described below and in the working examples, by using corresponding isotopic modifications of the particular reagents and/or starting compounds therein.

In certain embodiments, the phthalocyanine dye compound of Formula (I) is unconjugated or used as a free dye for biomedical imaging, including, but not limited to, magnetic resonance imaging (MRI), fluorescence imaging, positron emission tomography (PET) and photoacoustic imaging. In certain embodiments, provided herein are kits comprising the phthalocyanine dye compound of Formula (I) and instructions for its use. In certain embodiments, provided herein are kits comprising the phthalocyanine dye compounds of Formula (I) and an additional reagent, such as an additional detection reagent, reference or standards, luminescence standards, enzymes, antibodies, enzyme inhibitors, or solvents.

The phthalocyanine dye compounds provided herein are photoactivatable dyes, that absorb at a wavelength generally between 600 nm and 810 nm. In some embodiments, the wavelengths at which the phthalocyanine dye compounds absorb and are excited is between about 600 nm and 810 nm, between about 640 nm and 750 nm, or between about 660 and 710 nm. In some embodiments, the wavelengths at which the phthalocyanine dye compounds absorb and are excited is about 650 nm, 660 nm, 670 nm, 680 nm, 690 nm, or 700 nm. In some embodiments, the maximum wavelength for absorption is no more than about 690 nm, about 680 nm, about 675 nm, or about 670 nm.

B. Conjugates of Phthalocyanine Dye Compounds

Provided are compositions and combinations containing the phthalocyanine dye compounds described herein conjugated to a targeting molecule that binds to a target molecule, such as a target molecule on the surface of a cell or pathogen. In some embodiments, the conjugates contain the phthalocyanine dye compounds described herein conjugated to a biomolecule, such an antibody, antibody fragment, antibody-like molecule, DNA probe, avidin, streptavidin, lipid, biochemical analog, polymer, peptide, or drug. In some embodiments, the provided conjugates and combinations are to be employed in methods and uses described herein.

In some embodiments, conjugates of the phthalocyanine dye compounds described herein, such as a Formula (X), Formula (0), Formula (I), or Formula (II) compound conjugated to a targeting molecule are used in methods of treatment, such as to inhibit growth and/or kill cells, such as cancer tumor cells. In some embodiments, conjugates of the phthalocyanine dye compounds described herein, such as a Formula (X), Formula (0), Formula (I), or Formula (II) compound conjugated to a targeting molecule are used in methods of imaging, whereby the conjugates as a result of the targeting molecule bind to a target, such as on a cell (e.g., a specific type of tumor cell) or on a pathogen, and the Formula (X), Formula (0), Formula (I), or Formula (II) compound of the conjugate, when exposed to an appropriate wavelength of light permits imaging of the targeted cell type. Such imaging can be used in conjunction with treatment with the conjugate or separately.

In some embodiments, the targeting molecule of the conjugate binds to a target molecule expressed on the surface of a cell or pathogen, such as a proliferating cell, a cancer cell, a cell in hyperplasia, a tumor cell, a cell in the tumor microenvironment (TME), a cell of the immune system, a neuron, or a pathogen. In some embodiments, the cell is a stem cell, a proliferating cell, a cell in a hyperplasia, or a pathogen-infected cell. In some embodiments, the pathogen is selected from among viruses, bacteria, fungi, biofilms, and other prokaryote cell systems. In some examples, the targeting molecule in the provided compositions binds to a target molecule on the surface of a certain cancer or tumor cell or a cell in the TME. In some embodiments, the cell of the immune system is a leukocyte, such as a neutrophil, an eosinophil, a basophil, a lymphocyte, or a monocyte. In some embodiments, the targeting molecule bind to a target molecule expressed on the surface of one or more immune cells, such as lymphocytes (T-cells, B-cells, and NK cells), neutrophils, and/or monocytes or macrophages. In some examples, the targeting molecule in the provided compositions binds a target molecule expressed on the surface of immunosuppressive cells, e.g., TAMs, tDCs, MDSCs, TANs, CAFs, and/or regulatory T cells (Tregs). In some of the provided compositions, the targeting molecule binds an immune checkpoint inhibitor on the surface of immunosuppressive cells. In some embodiments, the targeting molecule bind to a target molecule on the surface of a neuron, such as a peripheral nervous system neuron or a central nervous system neuron. In some embodiments, the neuron is a nociceptor such as a thermal nociceptor, mechanical nociceptor, chemical nociceptor, or polymodal nociceptor. In some embodiments, the targeting molecule binds to a pathogen, such as a virus, bacterium, fungus, biofilm, or other prokaryote cell system. In some embodiments, the pathogen is a gram-negative or gram-positive bacterium.

In some embodiments, the target molecule to which the targeting molecule of the stable conjugate binds includes an antigen, a polypeptide, a peptide, a lipid, or a carbohydrate, or a combination thereof. In some embodiments, the target molecule is a cell surface molecule.

In some embodiments, the one or more target molecule(s) is/are selected from among cell membrane phospholipids, prokaryotic peptidoglycans, bacterial cell envelop proteins, viral capsid proteins, 1-40-β-amyloid, 1AR, 2AR, 4-1BB (CD137), 5AC, 5'-nucleotidase, 5T4, ACTHR, activated factor IX, activin receptor-like kinase 1, ACVR2B, adenocarcinoma antigen, ALK, alpha-4-integrin, alpha-5-beta-3 integrin, alpha-5-beta-5 integrin, alpha-fetoprotein (AFP), aminopeptidase N, amyloid, Ang-2, angiopoietin 2, angiopoietin 3, ANPA, ANPB, anthrax protective antigen, anthrax toxin, Anti-alpha 1 Fetoprotein, AOC3, AOC3 (VAP-1), APA, APN, APP, AT1, AXL, B1, B2, B7-DC, B7-H3, *Bacillus anthracis* anthrax, bacterial cell envelop proteins, BAFF, BAFF-R. BAGE1, BAGE2, B-cell receptor BB1, BB2, BB4, BCMA, BCR complex, Bcr-Abl, beta amyloid, B1, B-lymphoma cell, Bombesin receptor, BRAF, BRAF(V600E), BRCA, BTK, C1s, C242 antigen, C5, CAIX, calcitonin gene-related peptide (CGRP), calcitonin gene-related peptide alpha, calcitonin receptor, cancer antigen 125 (CA125), *Canis lupus familiaris* IL31, Caprin-1, carbonic anhydrase 9 (CA-IX), cardiac myosin, CCK1, CCK2, CCL11 (eotaxin-1), CCR2, CCR4, CCR5, CD2, CD3, CD3 epsilon, CD3 T cell co-receptor, CD4, CD5, CD6, CD7, CD10, CD11, CD11a, CD13, CD14, CD15, CD18, CD19, CD20, CD22, CD23 (IgE receptor), CD25, CD27, CD28, CD30 (TNFRSF8), CD33, CD34, CD37, CD38, CD40, CD41 (integrin alpha-IIb), CD44, CD44 v6, CD45, CD47, CD51, CD52, CD68, CD70, CD74, CD79B, CD80, CD90, CD97B, CD123, CD125, CD133, CD134/OX40/TNFRSF4, CD147 (Basigin), CD154 (CD40L), CD200, CD206, CD271, CD276, CD276/B7-H3, CD278 (aka ICOS), CD319, CDK 4/6, CDS, CEA (Carcinoembryonic Antigen), CEACAM1, CEACAM3, CEACAM5, CEACAM6, CEA-related antigen, cell membrane phospholipids, cell surface plectin-1, cell-surface annexin-1, CFD, chemokine receptors, c-KIT, Claudin 18 Isoform 2, CLDN18.2, *Clostridium difficile*, clumping factor A, c-Met, coagulation factor III, complement C5a, Cripto-1, CRLR, CSF1, CSF1R, CSF2, CTGF, CTLA-4, CXCR2, CXCR4 (CD184), CXCR4 antagonist, cytomegalovirus, cytomegalovirus glycoprotein B, dabigatran, DCC, dendritic cell-associated lectin 2, DLL3, DLL4, DPP4, DR5, *E. coli* shiga toxin type-1, *E. coli* shiga toxin type-2, E2 glycoprotein, ebolavirus glycoprotein, EGFL7, EGFR/ERBB1/HER1, EGFR extracellular domain III, EGFRvIII, EML4-ALK, EMR1, endoglin, Endosialin, endothelial cell Anxa-1, endotoxin, EP2, EP4, EpCAM, EphA2, Ephrin ligands, Ephrin receptor, ephrin receptor A3, *Escherichia coli*, ET receptors, F protein of respiratory syncytial virus, Factor X, FAP, FAS-ligand, FCGRT, FGF 23, FGFR, FGFR2, fibrin II, beta chain, Fibronectin, Fibronectin ED-B, fibronectin extra domain-B, folate hydrolase, folate receptor 1, folate receptor alpha, folate-binding protein, frizzled receptors, G protein coupled receptors of the Family B (Secretin receptor-like) like), GAGE1, GAGE2, GAGE3, GAGE4, GAGE6, gangliosides (such as GD2, GD3, GM1 and GM2), GARP/inactive TGF-β complex, GCGR, GD2 ganglioside, GD3 ganglioside, GDF-8, gelatinase B, GITR (glucocorticoid-induced tumor necrosis factor receptor), GLP-1 receptor, Glypican-3, GMCSF receptor α-chain, GP120, gp172, gpA33, GP100, GPNMB, G-protein coupled receptors of the Family A (Rhodopsin-like), G-protein coupled receptors of the Family C (Metabotropic Glutamate Receptor-like), growth differentiation factor 8, GUCY2C, hemagglutinin (HA), Heparin sulfates, hepatitis B surface antigen, hepatitis B virus, HER1/EGFR, HER2/ERBB2/neu, HER2/neu, HER3/ERBB3, HER4, HGF receptor, histone complex, HIV-1, HLA-DR 10β, HLA-DR antigen, HMFG, HNGF, HPV 16/18 and E6/E7 antigens, Hsp90, hTERT, human scatter factor receptor kinase, human TNF, human beta-amyloid, ICAM-1, ICAM-1 (CD54). ICOSL, IgE, IgE Fc region, IGF-1 receptor (CD221), IGHE, ILGF2, ILT3, influenza A virus hemagglutinin, integrin α4β7, integrin α5β1, integrin αVβ3, integrin α4, integrin α4β7, integrin α5β1, integrin αIIbβ3, integrin αvβ3, integrin β7, interferon receptor, interferon α/β receptor, interferon gamma-induced protein, interleukin-1 (IL-1), interleukin-1 alpha, interleukin-1β, interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), interleukin-13 (IL-13), interleukin-15 (IL-15), interleukin-17 (IL-17), interleukin-17A (IL-17A), interleukin-17F (IL-17F), interleukin-19 (IL-19), interleukin-20, interleukin-22, interleukin-23, interleukin-23 (IL-23), interleukin-23A, interleukin receptor (e.g., IL-2R, IL-3R, IL-4Rα, IL-6R, IL-11R, IL-13R, IIL-31RA), ITGA2 (CD49b), ITGAM, ITGB2 (CD18), JAK1, JAK2, Kalikrien-9, kallikrein, KIR, KIR2D, KIT, LAG-3, Lewis-Y antigen, LFA-1 (CD11a). LH receptor (LHR), luteinizing-releasing hormone receptor, LINGO-1, lipoteichoic acid, LIV-1, LOXL2, LPA1, LRRC15, L-selectin (CD62L), LTA, LYPD3, MAC-1, MAGE 1, MAGE 2, MAGE 3, MAGE 4, MART1, MASP-2, MCAM, MC1R, MCP-1, MCSF, MEK1, MEK2, member 1 (SLITRK1), member 2 (SLITRK2), member 3 (SLITRK3), member 4 (SLITRK4), member 5 (SLITRK5), member 6 (SLITRK6), Mesothelin, MET, metalloproteinases, MIF, MS4A1, MSLN, MST1R (aka RON), mTOR, MUC1 (episialin), MUC16, mucin CanAg, mucins, mucosal addressin cell adhesion molecule 1 (MAdCAM-1), mutant p53, mutant Ras, myelin-associated gly coprotein, myostatin, NACP, NCA-90 (granulocyte antigen), nectin-4. Neprilysin, Neu (cell-surface Nucleolin), neural apoptosis-regulated proteinase 1, Neuropilin-1 (NRP1). Neuropilin-2, NG2, NGNA ganglioside, NK1, NK2, NK3, NKG2A, NMB-R, NOGO-A, Notch receptor, Notch-1, NRP1, NTR2, NTR3, nuC242, NY-ESO-1, OT-R, OX40, oxLDL, *P. aeruginosa* type III secretion system, p32 (p32/gC1qR/HABP1), p75, p97 melanoma antigen, PAC1. PAR1, Patched (PTCH), PCDC1, PCSK9, PD-1, PDFG receptors, PDGF receptor, PDGF-R α, PD-L1, PDT, PEM antigen, phosphate-sodium co-transporter, phosphatidylserine, platelet-derived growth factor receptor beta, plexins, PMSA, prohibitin, prokaryotic peptidoglycans, prostatic carcinoma cells, Protease-cleaved collagen IV, protein tyrosine kinase 7, proteinase 3, PSA, *Pseudomonas aeruginosa*. PSMA, PTK7, purinergic P2X family (e.g. P2X1-5), rabies virus G glycoprotein, rabies virus glycoprotein, RAMP1, RAMP2, RAMP3 patched, RANKL, RBB3, respiratory syncytial virus, RET, RET receptor, RGMA, RHD, Rhesus factor, root plate-specific spondin 3. ROR1, ROS, ROS1, RSVFR, RTN4, *S. aureus* alpha toxin. *S. aureus* bi-component leukocidin, sclerostin, SDC1, selectin P, serum amyloid A protein, serum amyloid P component, SK1 antigen, SLAMF7, SMO, smoothened, SOST, sphingosine-1-phosphate. SRC, sst1, sst2A, sst2B, sst3, sst4, sst5. *Staphylococcus aureus, Staphylococcus aureus* alpha toxin, STEAP1, TAG-72, tau protein, T-cell receptor (TCR), TEM1, TEMs, tenascin C, tenascin glycoproteins, TFPI, TGFBR2, TGFBR1, TGF-β, Tie-1, Tie-2, TIGIT, TIM-3, TNF, TNFR superfamily member 4, TNF-α, TR1, TRAIL-R1. TRAIL-R², TRAP, Trk-A, Trk-B, Trk-C, TROP-2, TRPA, TRPC, TRPM, TRPML, TRPP (e.g. TRPV1-6, TRPA1. TRPC1-7, TRPM1-8, TRPP1-5, TRPML 1-3), TRPV, TSC1, TSC2, TSH receptor, TSLP, tumor antigen CTAA16.88, tumor necrosis factor alpha (TNF-α), tumor specific glycosylation of MUC1, tumor-associated glycoprotein 72 (TAG72), TWEAK receptor, TYRP1 (glycoprotein 75), VEGF receptors (VEGFR1 or Flt-1, VEGFR2 or FLK-1/KDR and VEGF-3 or FLT-4), VEGFA, vimentin, viral capsid proteins, voltage-gated ion channels, VPAC1, VPAC2, VSIR, VWF, Wilms tumor 1, Y1 receptor, Y2 receptor, Y4 receptor, Y5 receptor, and Zaire ebolavirus glycoprotein.

In some embodiments, the one or more target molecule(s), such as a cell surface target molecule, is/are selected from among HER1/EGFR, HER2/ERBB2, CD20. CD25 (IL-2Ra receptor), CD33, CD52, CD133, CD206, CEA, CEACAM1, CEACAM3, CEACAM5, CEACAM6, cancer antigen 125 (CA125), alpha-fetoprotein (AFP), Lewis Y, TAG72, Caprin-1, mesothelin, PDGF receptor, PD-1, PD-L1, CTLA-4, IL-2 receptor, vascular endothelial growth factor (VEGF), CD30, EpCAM, EphA2, Glypican-3, gpA33, mucins, CAIX, PSMA, folate-binding protein, gangliosides (such as GD2, GD3, GM1 and GM2). VEGF receptor (VEGFR), VEGFR2, VEGF-A, integrin αVβ3, integrin α5β1, ERBB3, MET, IGF1R, EPHA3, TRAILR1, TRAILR2, RANKL, FAP, tenascin, AFP, BCR complex, CD3, CD18, CD44, CTLA-4, gp72, HLA-DR 10β, HLA-DR antigen, IgE, MUC-1, nuC242, PEM antigen, metalloproteinases, Ephrin receptor, Ephrin ligands, HGF receptor, CXCR4, CXCR4, Bombesin receptor, SK1 antigen, Bcr-Abl, RET, MET, TRKB, TIE2, ALK, ROS, EML4-ALK, ROS1, BRAFV600E, SRC, c-KIT, PDGFR, mTOR, TSC1, TSC2, BTK, KIT, BRCA, CDK 4/6, JAK1, JAK2, BRAF, FLT-3, MEK1, MEK2, and SMO. In some embodiments, the one or more cell surface target molecule(s) is/are HER1/EGFR, HER2, PD-L1, CD25, EpCAM, EphA2, FAP. CD206, CD20, CD44, CD133, Mesothelin, MUC1, PSMA, Glypican-3, and carcinoembryonic antigen (CEA). In some embodiments, the cell surface target molecule is one or more of CD25, CEA, FAP, HER1/EGFR, HER2, MUC1, PD-L1, or PSMA.

A "dye-containing conjugate" or a "conjugate" as used herein has a targeting molecule linked to a phthalocyanine dye compound provided herein, such as the phthalocyanine dye compound of Formula (X), Formula (0), Formula (I), or Formula (II). In some embodiments, at least part of the targeting molecule is or is a combination of a protein, a glycoprotein, an antibody, an antibody fragment, an affibody, an antigen, an antigen binding fragment, a peptide, a polypeptide, a tissue homing peptide, a small molecule, a polymeric synthetic molecule, a polymeric nanoparticle, a liposome, an enzyme substrate, a hormone, a neurotransmitter, a cell metabolite, a viral particle, a viral capsid, a viral nanoparticle, a bacterial particle, a marker, a cell, a hapten, an avidin, a streptavidin, a monomeric streptavidin, a biotin, a carbohydrate, an oligosaccharide, a polysaccharide, a nucleic acid, a deoxy nucleic acid, a fragment of DNA, a fragment of RNA, an aptamer, nucleotide triphosphates, acyclo terminator triphosphates, PNA. In some instances, the targeting molecule can include an antigen binding molecule, such as an antibody or antibody fragment (e.g., antigen-binding fragment), or other protein, peptide or small molecule that binds to a target molecule, such as a target molecule on the surface of a cell. In some aspects, an exemplary conjugate contains a targeting molecule that is an antibody or an antibody fragment. In some aspects, and exemplary conjugate contains a targeting molecule that is an antigen-binding fragment derived from an antibody, a functional equivalent thereof, or an antibody fragment. In some examples, the targeting molecule in the provided conjugates contains a bispecific antibody, an scFv, a single domain antibody (sdAb) or nanobody, a VHH, an isolated single variable domain, an affibody, or a z-domain structure, a DARPin, a monobody, an anticalin, an affilin, an affimer type 1 molecule, an affimer type 2 molecule, an affitin, an alphabody, an anticalin, an avimer, a fynomer, a kunitz domain peptide, or a nanoclamp.

In some embodiments, the targeting molecule binds to the target molecule, such as an antigen or protein, directly or indirectly. For example, in some embodiments, the targeting molecule is a second binding molecule that binds to a first binding molecule which is capable of binding to the target molecule, such as an antigen or protein. For example, the targeting molecule can be a secondary antibody, which binds to a first binding molecule, e.g., a primacy antibody, capable of binding the protein or antigen, e.g., a cell surface protein or a cell surface receptor. Thus, in some embodiments, the phthalocyanine dye is conjugated to a secondary antibody.

In some embodiments, the targeting molecule is an RGD polypeptide, an iRGD polypeptide, a Lyp-1 polypeptide, a cripto-1 binding polypeptide, a somatostatin receptor binding polypeptide, a prohibitin binding polypeptide, an NGR polypeptide, an iNGR polypeptide, or an activatable cell penetrating peptide (ACPP) comprised of a polycationic cell penetrating peptide (CPP) connected via a cleavable linker to a neutralizing poly anion.

In some embodiments, the targeting molecule is a viral particle, such as a virus-like particle, a viral-like nanoparticle, or a viral capsid. In some embodiments, the targeting molecule is a viral-like nanoparticle. In some embodiments, the viral-like nanoparticle is assembled from L1 capsid proteins. In some embodiments, the viral-like nanoparticle is assembled from a combination of L1 and L2 capsid proteins. In some embodiments, the targeting molecule and bind to and infect cells. In some embodiments, the targeting molecule is one such as described in WO2015042325.

In some embodiments, a virus-like particle (VLP) refers to an organized capsid-like structure, such as roughly spherical or cylindrical in shape, that comprises self-assembling ordered arrays of L1 or L1 and L2 capsomers and does not include a viral genome. In some embodiments, virus-like particles are morphologically and antigenically similar to authentic virions, but they lack viral genetic material, such as viral nucleic acid, rendering the particles noninfectious. A VLP may be used to deliver to a recipient cell an agent, such as prophylactic agent, therapeutic agent or diagnostic agent, or an enclosed circular or linear DNA or RNA molecule.

In some embodiments, VLPs may have modified immunogenicity and/or antigenicity with respect to the wild type VLPs. The VLPs may, for example, be assembled from capsomers having a variant capsid protein with modified immunogenicity and/or antigenicity. In some embodiments, a variant capsid protein with modified immunogenicity and/or antigenicity is one that is modified naturally or synthetically, such as mutated, substituted, deleted, pegylated or inserted, at an amino acid to reduce or prevent recognition of the capsid protein by pre-existing, such as endogenous, viral serotype-specific antibodies. A variant capsid protein may be a human papillomavirus (HPV) L1 variant, a non-human papillomavirus L1 variant, or a papillomavirus L1 variant based on a combination of amino acids from different HPV serotypes.

In some embodiments, a VLP is a papilloma virus VLP. The VLP may be a human papilloma virus VLP, such as derived from a virus that can infect human, while in other embodiments, the VLP may be a non-human papilloma virus VLP. Examples of nonhuman VLPs include those derived from, without limitation, bovine papilloma viruses, murine papilloma viruses, cotton-rabbit papilloma viruses and macaque or rhesus papilloma virus particles. In some embodiments, the VLPs are bovine papilloma virus viral-like nanoparticles, such as type 1 viral-like nanoparticles, such as assembled from BPV L1 capsid proteins or a combination of BPV L1 and BPV L2 capsid proteins. In some embodiments, a capsid protein refers to a protein monomer, several of which form a capsomer oligomer. In some embodiments, a capsomer refers to the basic oligomeric structural unit of a viral capsid, which is an outer covering of protein that protects the genetic material of a virus. Capsid proteins may include in some embodiments, papillomavirus $L^1$ major capsid proteins and papillomavirus L2 minor capsid proteins. In some embodiments, the VLPs contain only L1 capsid proteins, while in other embodiments, the VLPs contain a mixture, or combination, of L1 and L2 capsid proteins.

In some embodiments, the percentage of L1 capsid proteins in a virus-like particle is greater than the percentage of L2 capsid proteins in the virus-like particle. For example, in some embodiments, the percentage of L1 capsid proteins in a virus-like particle is 80% to 100% of the total number of capsid proteins in the virus-like particle. In some embodiments, the percentage of L1 capsid proteins in a virus-like particle is at least or is about 80%, 85%, 90%, 91%, 92%, 93%, 94%, 95%, 96%, 97%, 98%, 99% or 100%. In some embodiments, the percentage of L2 capsid proteins in a virus-like particle is 1% to 25% of the total number of capsid proteins in the virus-like particle. For example, in some embodiments, the percentage of L2 capsid proteins in a virus-like particle is at least or about 1%, 2%, 3%, 4%, 5%, 6%, 7%, 8%, 9%, 10%, 11%, 12%, 13%, 14%, 15%, 16%, 17%, 18%, 19% or 20%.

In some embodiments, a virus-like particle contains 12 to 72 L2 proteins. In some embodiments, a virus-like particle contains 360 $L^1$ proteins and 12 to 72 L2 proteins. In some embodiments, capsid proteins assemble into viral-like nanoparticles having a diameter of 20 to 60 nm. For example, capsid proteins may assemble into viral-like nanoparticles having a diameter of at least or about 20, 25, 30, 35, 40, 45, 50, 55 or 60 nm.

In some embodiments, the targeting molecule is a DARPin (designed ankyrin repeat protein). Typically, DARPins are derived from natural ankyrin repeat proteins and bind to proteins including e.g., human receptors, cytokines, kinases, human proteases, viruses and membrane proteins (Molecular Partners AG Zurich Switzerland; see Chapter 5. "Designed Ankyrin Repeat Proteins (DARPins); From Research to Therapy", Methods in Enzymology, vol 503: IOC134 (2012); and "Efficient Selection of DARPins with Sub-nanomolar Affinities using SRP Phage Display", J. Mol. Biol. (2008) 382, 1211-1227, the entire disclosures of which are hereby incorporated by reference. In some embodiments, the DARPin is an antibody mimetic protein having high specificity and high binding affinity to a target protein, which is prepared via genetic engineering. In some embodiments, DARPins have a structure comprising at least 2 ankyrin repeat motifs, for example, comprising at least 3, 4 or 5 ankyrin repeat motifs. The DARPins can have any suitable molecular weight depending on the number of repeat motifs. For example, the DARPins including 3, 4 or 5 ankyrin repeat motifs may have a molecular weight of about 10 kDa, about 14 kDa, or about 18 kDa, respectively.

In some embodiments, the DARPin includes a core part that provides structure and a target binding portion that resides outside of the core and binds to a target. In some embodiments, the structural core includes a conserved amino acid sequence and the target binding portion includes an amino acid sequence that differs depending on the target.

In some embodiments, the targeting molecule is an affibody molecule. An "affibody" refers to a protein engineered to bind a target protein or peptide with high affinity. In some examples, an affibody mimics an antibody. Typically, an affibody molecule is composed alpha helices, such as three alpha helices, that confer binding to the target molecule. In some examples the affibody protein scaffold is based on the B or Z domain of staphylococcal protein A or an amino acid-substituted protein scaffold thereof. Affibodies can be engineered and synthesized, and molecules with desired binding properties can be identified and selected, for example, using phage display. Affibody molecules are reviewed in Lofblom et al. (2010), FEBS Letters 584(12): 2670-2680, which is incorporated by reference.

In some embodiments, the targeting molecule is selected from among adrenocorticotropic hormone (ACTH), angiotensin II, atrial natriuretic factor (ANF), bombesin, bradykinin, brain derived neurotrophic factor (BDNF), bone morphogenetic protein 2 (BMP-2), bone morphogenetic protein 6 (BMP-6), bone morphogenetic protein 7 (BMP-7), bone morphogenetic protein 2 (BMP-2), calcitonin, cardiotrophin 1 (CT-1), CD22, CD40, cholecystokinin (CCK), ciliary neurotrophic factor (CNTF), CCL1-CCL28, CXCL1-CXCL17, XCL1, XCL2, CX3CL1, crypto-1 binding peptide, vascular endothelial cell growth factor (VEGF), epidermal growth factor (EGF), endothelin 1, endothelin 1/3, FAS-ligand, fibroblast growth factor 1 (FGF-1), fibroblast growth factor 2 (FGF-2), fibroblast growth factor 4 (FGF-4), fibroblast growth factor 5 (FGF-5), fibroblast growth factor 6 (FGF-6), fibroblast growth factor 1 (FGF-7), fibroblast growth factor 1 (FGF-10), Flt-3, gastrin, gastrin releasing peptide (GRP), granulocyte colony-stimulating factor (G-CSF), granulocyte macrophage stimulating factor (GM-CSF), glucagon like peptide (GLP-1), hepatocyte growth factor (HGF), interferon alpha (IFN-a), interferon beta (IFN-b), interferon gamma (IFNγ), insulin-like growth factor 1 (IGF-1), insulin-like growth factor 2 (IGF-2), interleukin 1 (IL-1), interleukin 2 (IL-2), interleukin 3 (IL-3), interleukin 4 (IL-4), interleukin 5 (IL-5), interleukin 6 (IL-6), interleukin 7 (IL-7), interleukin 8 (IL-8), interleukin 9 (IL-9), interleukin 10 (IL-10), interleukin 11 (IL-11), interleukin 12 (IL-12), interleukin 13 (IL-13), interleukin 15 (IL-15), interleukin 17 (IL-17), interleukin 19 (IL-19), luteinizing hormone (LH), luteinizing-releasing hormone (LHRH), macrophage colony-stimulating factor (M-CSF), monocyte chemotactic protein 1 (MCP-1), macrophage inflammatory protein 3a (MIP-3a), macrophage inflammatory protein 3b (MIP-3b), nerve growth factor (NGF), neuromedin B, neurotrophin 3 (NT-3), neurotrophin 4 (NT-4), neurotensin, neuropeptide Y, oxytocin, pituitary adenylate cyclase activating peptide (PACAP), platelet derived growth factor AA (PDGF-AA), platelet derived growth factor AB (PDGF-AB), platelet derived growth factor BB (PDGF-BB), platelet derived growth factor CC (PDGF-CC), platelet derived growth factor DD (PDGF-DD), netrin-1 (NTN1), netrin-2 (NTN2), netrin-4 (NTN4), netrin-G1 (NTNG1) and netrin-G2 (NTNG2), ephrin A1 (EFNA1), ephrin A2 (EFNA2), ephrin A3 (EFNA3), ephrin A4 (EFNA4), ephrin A5 (EFNA5), semaphorin 3A (SEMA3A), semaphorin 3B (SEMA3B), semaphorin 3C (SEMA3C), semaphorin 3D (SEMA3D), semaphorin 3F (SEMA3F), semaphorin 3G (SEMA3G), semaphorin 4A (SEMA4A), semaphorin 4B (SEMA4B), semaphorin 4C (SEMA4C), semaphorin 4D (SEMA4D), semaphorin 4F (SEMA4F), semaphorin 4G (SEMA4G), semaphorin 5A (SEMA5A), semaphorin 5B (SEMA5B), semaphorin 6A (SEMA6A), semaphorin 6B (SEMA6B), semaphorin 6D (SEMA6D), semaphorin 7 A (SEMA7A), SLIT1, SLIT2, SLIT3, SLIT and NTRK-like family, member 1 (SLITRK1), SLIT and NTRK-like family, member 2 (SLITRK2), SLIT and NTRK-like family, member 3 (SLITRK3), SLIT and NTRK-like family, member 4 (SLITRK4), SLIT and NTRK-like family, member 5 (SLITRK5), SLIT and NTRK-like family, member 6 (SLITRK6), prostaglandin E2 (PGE2), RANTES, Somatostatin-14, Somatostatin-28, stem cell factor (SCF), stromal cell derived factor 1 (SDF-1), substance P, thyroid stimulating hormone (TSH), transforming growth factor alpha (TGF-a), transforming growth factor beta (TGF-β), tumor necrosis factor alpha (TNF-α), thrombin, vasoactive intestinal peptide (VIP), Wnt1, Wnt2, Wnt2b/13, Wnt3, Wnt3a, Wnt4, Wnt5a. Wnt5b, Wnt6, Wnt7a, Wnt7b, Wnt7c, Wnt8, Wnt8a, Wnt8b, Wnt8c, Wnt10a, Wnt10b, Wnt11, Wnt14, Wnt15, or Wnt16. Sonic hedgehog, Desert hedgehog, and Indian hedgehog.

In some embodiments, the targeting molecule is an antibody, an antibody fragment, or a functional equivalent of an antibody or antibody fragments (e.g., an affibody) that specifically binds to an antigen, such as a cell surface molecule on a tumor cell or immune cell(s). Included among such antibodies are antibodies, affibodies, or antigen-binding antibody fragments capable of binding to a cell surface molecule, such as a cell surface protein, e.g., cell surface receptor, described herein. In some cases, the antibody can bind to an antigen of a protein expressed on a cell in a tumor, including a tumor-specific protein. In some cases, the antibody can bind to an antigen of a protein expressed on an immune cell, such as lymphocyte (T-cell, B-cell, and NK cell), neutrophil, and/or monocyte or macrophage.

An "antibody" is a polypeptide ligand comprising at least a light chain or heavy chain immunoglobulin variable region that specifically recognizes and binds an epitope of an antigen, such as a tumor-specific protein. Generally, antibodies are composed of a heavy and a light chain, each of which has a variable region, termed the variable heavy (VH) region and the variable light (VL) region. Together, the VH region and the VL region are responsible for binding the antigen recognized by the antibody.

Antibodies include intact immunoglobulins and fragments of antibodies that exhibit antigen-binding, such as Fab fragments, Fab' fragments, F(ab)'2 fragments, single chain Fv proteins ("scFv"), and disulfide stabilized Fv proteins ("dsFv"). An scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies, for example, humanized murine antibodies, and heteroconjugate antibodies, such as bispecific antibodies. See also, Pierce Catalog and Handbook, 1994-1995 (Pierce Chemical Co., Rockford, Ill.); Kuby, J. Immunology, 3rd Ed., W. H. Freeman & Co., New York, 1997.

Typically, a naturally occurring immunoglobulin has heavy (H) chains and light (L) chains interconnected by disulfide bonds. There are two types of light chain, lambda (λ) and kappa (κ). There are five main heavy chain classes, or isotypes, which determine the functional activity of an antibody molecule: IgM, IgD, IgG, IgA and IgE.

Each heavy and light chain contains a constant region and a variable region, also known as "domains." In combination, the heavy and the light chain variable regions generally specifically bind the antigen. Light and heavy chain variable regions may contain a "framework" region interrupted by three hypervariable regions, also called "complementarity-determining regions" or "CDRs." The precise amino acid sequence boundaries of a given CDR or framework regions (FR, the non-CDR portions of the variable regions of the heavy and light chains) can be determined using any of a number of known schemes, including those described by Kabat et al. (1991), "Sequences of Proteins of Immunological Interest," 5th Ed. Public Health Service, National Institutes of Health, Bethesda, Md. ("Kabat" numbering scheme); Al-Lazikani et al., (1997) JMB 273, 927-948 ("Chothia" numbering scheme); MacCallum et al., J. Mol. Biol. 262:732-745 (19%), "Antibody-antigen interactions: Contact analysis and binding site topography," J. Mol. Biol. 262, 732-745." ("Contact" numbering scheme); Lefranc M P et al., "IMGT unique numbering for immunoglobulin and T cell receptor variable domains and Ig superfamily V-like domains," Dev Comp Immunol, 2003, 27(1):55-77 ("IMGT" numbering scheme). Honegger A and Plückthun A, "Yet another numbering scheme for immunoglobulin variable domains: an automatic modeling and analysis tool," J Mol Biol, 2001, 309(3):657-70, ("Ahom" numbering scheme); and Martin et al., "Modeling antibody hypervariable loops: a combined algorithm." PNAS, 1989, 86(23): 9268-9272, ("AbM" numbering scheme). The sequences of the framework regions of different light or heavy chains are relatively conserved within a species, such as humans. The framework region of an antibody, that is the combined framework regions of the constituent light and heavy chains, serves to position and align the CDRs in three-dimensional space.

The CDRs are typically responsible for binding to an epitope of an antigen. The CDRs of each chain are typically referred to as CDR1, CDR2, and CDR3, numbered sequentially starting from the N-terminus, and are also generally identified by the chain in which the particular CDR is located. Thus, a VH CDR3 is located in the variable domain of the heavy chain of the antibody in which it is found, whereas a VL CDR1 is the CDR1 from the variable domain of the light chain of the antibody in which it is found. Antibodies with different specificities, such as different combining sites for different antigens, have different CDRs. Although it is the CDRs that vary from antibody to antibody, only a limited number of amino acid positions within the CDRs are directly involved in antigen binding. These positions within the CDRs are called specificity determining residues (SDRs).

References to "VH" or "VH" refer to the variable region of an immunoglobulin heavy chain, including that of an Fv, scFv, dsFv or Fab. References to "V L" or "V L" refer to the variable region of an immunoglobulin light chain, including that of an Fv, scFv, dsFv or Fab.

Among the provided antibodies are antibody fragments. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g., scFv); and multispecific antibodies formed from antibody fragments. Other antibody fragments or multispecific antibodies formed from antibody fragments include a multivalent scFv, a bispecific scFv or an scFv-CH3 dimer. Antibody fragments can be made by various techniques, including but not limited to proteolytic digestion of an intact antibody as well as production by recombinant host cells.

A "monoclonal antibody" is an antibody produced by a single clone of B lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimeric antibody" has framework residues from one species, such as human, and CDRs, which generally confer antigen binding, from another species, such as a murine antibody that specifically binds mesothelin.

A "humanized" immunoglobulin is an immunoglobulin including a human framework region and one or more CDRs from a non-human (for example a mouse, rat, or synthetic) immunoglobulin. The non-human immunoglobulin providing the CD Rs is termed a "donor," and the human immunoglobulin providing the framework is termed an "acceptor." In some embodiments, the CDRs are from the donor immunoglobulin in a humanized immunoglobulin. Constant regions need not be present, but if they are, they may be substantially identical to human immunoglobulin constant regions, such as at least about 85-90%, such as about 95% or more identical. Hence, parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

A "human" antibody (also called a "fully human" antibody) is an antibody that includes human framework regions and CDRs from a human immunoglobulin. In some embodiments, the framework and the CDRs are from the same originating human heavy and/or light chain amino acid sequence. However, frameworks from one human antibody can be engineered to include CDRs from a different human antibody. Parts of a human immunoglobulin may be substantially identical to corresponding parts of natural human immunoglobulin sequences.

"Specifically binds" refers to the ability of a molecule, such as an antibody or antigen-binding fragment, to specifically bind an antigen, such as a tumor-specific antigen, relative to binding to unrelated proteins, such as non-tumor proteins, for example β-actin. In some embodiments, a molecule, such as an antibody or fragment, including a molecule, such as an antibody or fragment, attached to a phthalocyanine dye molecule, specifically bind s to a target, such as a cell surface protein.

In some embodiments, the phthalocyanine dye molecule, such as the phthalocyanine dye of Formula (X), Formula (0), Formula (I), or Formula (II) is conjugated to an antibody or an antigen-binding antibody fragment. For example, in some aspects, the conjugate is a phthalocyanine dye of Formula (X) and an antibody or an antigen-binding antibody fragment. In some aspects, the conjugate is a phthalocyanine dye of Formula (0) and an antibody or an antigen-binding antibody fragment. In some aspects, the conjugate is a phthalocyanine dye of Formula (I) and an antibody or an antigen-binding antibody fragment. In some aspects, the conjugate is a phthalocyanine dye of Formula (II) and an antibody or an antigen-binding antibody fragment. Exemplary antibodies which can be conjugated to one or more dyes of Formula (X), Formula (0), Formula (I), and/or Formula (II) provided herein include 3F8, 8H9, AB122, ab75705, Abagovomab, Abciximab, Abituzumab, Abrezekimab, Abrilumab, Actoxumab, Adalimumab. Adecatumumab, ADG116, ADU-1604, Aducanumab, Afasevikumab, Afelimomab, Afutuzumab. AGEN1181. AGEN1884, AGX-115, AK104, AK105, Alacizumab pegol, Alemtuzumab, Alirocumab, Altumomab pentetate, Amatuximab, AMG 404, AMP-224, AMP-514, Anatumomab mafenatox, Andecaliximab, Anetumab ravtansine, Anifrolumab. Anrukinzumab, anti-CD133, Apolizumab. Aprutumab ixadotin, Arcitumomab, arcitumomab Fab fragment, Ascrinvacumab, Aselizumab, Atezolizumab, Atidortoxumab, Atinumab, Atlizumab (Tocilizumab), ATOR-1015. Atorolimumab, Avelumab, Azintuxizumab vedotin, B72.3, Bapineuzumab, Basiliximab, Bavituximab, BCD-100, BCD-135, BCD-145, BCD-217, Bectumomab, Begelomab, Belantamab mafodotin, Belimumab, Bemarituzumab, Benralizumab, Berlimatoxumab, Bermekimab, Bersanlimab, Bertilimumab, Besilesomab, Bevacizumab, Bezlotoxumab, BGB-A333, BI 754091, Biciromab, Bimagrumab, Bimekizumab, Birtamimab, Bivatuzumab, Bivatuzumab mertansine, BL-8040, Bleselumab, Blinatumomab, Blontuvetmab, Blosozumab, BMS-936559, BMS-986218, Bococizumab, Brazikumab, Brentuximab vedotin, Briakinumab, Brodalumab, Brolucizumab, Brontictuzumab, Burosumab, Cabiralizumab, Camidanlumab tesirine, Camrelizumab, Canakinumab, Cantuzumab mertansine, Cantuzumab ravtansine, Caplacizumab, Capromab, Capromab pendetide, Carlumab, Carotuximab, Catumaxomab, cBR96-doxorubicin immunoconjugate, CBT-502, CC-90002, CDC-022, Cedelizumab, Cemiplimab, Cergutuzumab amunaleukin, Certolizumab pegol, Cetrelimab, Cetuximab, Cibisatamab, Cirmtuzumab, Citatuzumab bogatox, Cixutumumab, Clazakizumab, Clenoliximab, Clivatuzumab tetraxetan, CMAB302, Codrituzumab, Cofetuzumab pelidotin, Coltuximab ravtansine, Conatumumab, Concizumab, Cosfroviximab, Cosibelimab, CP-870,893, CR6261, Crenezumab, Crizanlizumab, Crotedumab, CS1001, CS1003, Cusatuzumab, CX-188, Dacetuzumab, Daclizumab, Dalotuzumab, Dapirolizumab pegol, Daratumumab, Dectrekumab, Demcizumab, Denintuzumab mafodotin, Denosumab, Depatuxizumab mafodotin, Derlotuximab biotin, Detumomab, Dezamizumab, Dinutuximab, Diridavumab, Domagrozumab, Dorlimomab aritox, Dostarlimab, Drozitumab, DS-8201, Duligotumab, Duligotuzumab, Dupilumab, Durvalumab, Dusigitumab, Duvortuxizumab, Ecromeximab, Eculizumab, Edobacomab, Edrecolomab, Efalizumab, Eftilagimod alpha, Efungumab, Eldelumab, Elezanumab, Elgemtumab, Elotuzumab, Elsilimomab, Emactuzumab, Emapalumab, Emibetuzumab, Emicizumab, Enapotamab vedotin, Enavatuzumab, Enfortumab vedotin, Enlimomab pegol, Enoblituzumab, Enokizumab, Enoticumab, Ensituximab, Epitumomab cituxetan, Epratuzumab, Eptinezumab, Erenumab, Erlizumab, Ertumaxomab, Etaracizumab, Etigilimab, Etrolizumab, Evinacumab, Evolocumab, Exbivirumab, F3, F520, Fanolesomab, Faralimomab, Faricimab, Farletuzumab, Fasinumab, FAZ053, FBTA05, Felvizumab, Fezakinumab, Fibatuzumab. Ficlatuzumab, Figitumumab, Firivumab, Flanvotumab, Fletikumab, Flotetuzumab, Fontolizumab, Foralumab, Foravirumab, Fremanezumab, Fresolimumab, Frovocimab, Frunevetmab, Fulranumab, Futuximab, Galcanezumab, Galiximab, Gancotamab, Ganitumab, Gantenerumab, Gatipotuzumab, Gavilimomab, GB221, Gedivumab, Gemtuzumab ozogamicin, genolimzumab, Gevokizumab, Gilvetmab, Gimsilumab, Girentuximab, Glembatumumab vedotin, GLS-010, Golimumab, Gomiliximab, Gosuranemab, Guselkumab, HD201, Hervycta, HLX02, HLX10, HLX20, HLX22, HX008, HX009, Ianalumab, Ibalizumab, IBI308, Ibritumomab tiuxetan, Icrucumab, Idarucizumab, Ieramilimab, Ifabotuzumab, Igovomab, Iladatuzumab vedotin, IMAB362, Imalumab, Imaprelimab, Imciromab, Imgatuzumab, INBRX-105, Inclacumab, Indatuximab ravtansine, Indusatumab vedotin, Inebilizumab, Infliximab, Inolimomab, Inotuzumab ozogamicin, Intetumumab, Iomab-B, IPH2101, Ipilimumab, Iratumumab, Isatuximab, Iscalimab, Istiratumab, Itolizumab, Ixekizumab, JTX-4014, Keliximab, KN035, KN046, Labetuzumab, Lacnotuzumab, Ladiratuzumab vedotin, Lambrolizumab (Pembrolizumab), Lampalizumab, Lanadelumab, Landogrozumab, Laprituximab emtansine, Larcaviximab, LDP, Lebrikizumab, Lemalesomab, Lendalizumab, Lenvervimab, Lenzilumab, Lerdelimumab, Leronlimab, Lesofavumab, Letolizumab, Lexatumumab, Libivirumab, Lifastuzumab vedotin, Ligelizumab, Lilotomab satetraxetan, Lintuzumab, Lirilumab, Lodelcizumab, Lokivetmab, Loncastuximab tesirine, Lorvotuzumab mertansine, Losatuxizumab vedotin, Lucatumumab, Lulizumab pegol, Lumiliximab, Lumretuzumab, Lupartumab, Lupartumab amadotin, Lutikizumab, LY3300054, LY3415244, LZM009, mAb114, Mapatumumab, Margetuximab, Marstacimab, Maslimomab, Matuzumab, Mavrilimumab, MCLA-145, MEDI6469, MEDI6383, Mepolizumab, Metelimumab, MGA012, MGD013, MGD019, Milatuzumab, Minretumomab, Mirikizumab, Mirvetuximab soravtansine, Mitumomab, MK-1308, MK-4166, MNRP1685 A, Modotuximab, Mogamulizumab, Monalizumab, Morolimumab, Mosunetuzumab, Motavizumab, Moxetumomab pasudotox, MOXR0916, MSB2311, Muromonab-CD3, Nacolomab tafenatox, Namilumab, Naptumomab estafenatox, Naratuximab emtansine, Namatumab, Natalizumab, Navicixizumab, Navivumab, Naxitamab, Nebacumab, Necitumumab, Nemolizumab, NEOD001, Nerelimomab, Nesvacumab, Netakimab, Nimotuzumab, Nirsevimab, Nivolumab, NM-01, Nofetumomab merpentan, Obiltoxaximab, Obinutuzumab, OC125 monoclonal antibody, Ocaratuzumab, Ocrelizumab, Odulimomab, Ofatumumab, Olaratumab, Olecumab, Olendalizumab, Olokizumab, Omalizumab, Omburtamab, OMS721, Onartuzumab, Ontuxizumab, Onvatilimab, Opicinumab, Oportuzumab monatox, Oregovomab, Orticumab, Otelixizumab, Otilimab, Otlertuzumab, Oxelumab, Ozanezumab, Ozoralizumab, Pagibaximab, Palivizumab, Pamrevlumab, Panitumumab, Pankomab, Panobacumab, Parsatuzumab, Pascolizumab, Pasotuxizumab, Pateclizumab, Patritumab, PDR001, Pembrolizumab, Pemtumomab, Perakizumab, Pertuzumab, Pexelizumab, PF-05280014, PF-06801591, Pidilizumab, Pinatuzumab vedotin, Pintumomab, Placulumab, Plozalizumab, Pogalizumab, Polatuzumab vedotin, Ponezumab, Porgaviximab, Prasinezumab, Prezalizumab, Prezalumab, Priliximab, Pritoxaximab, Pritumumab, PRO 140, Quilizumab, Racotumomab, Radretumab, Rafivirumab, Ralpancizumab, Ramucirumab, Ranevetmab, Ranibizumab, Ravagalimab, Ravulizumab, Raxibacumab, Refanezumab, Regavirumab, REGN2810, REGN3504, REGN4659, REGN-EB3, Relatlimab, Remtolumab, Reslizumab, rHIgM12B7, Rilotumumab. Rinucumab, Risankizumab, Rituximab, Rituximab, Rivabazumab pegol, Rmab, RO121661, Robatumumab, Roledumab, Romilkimab, Romosozumab, Rontalizumab, Rosmantuzumab, Rovalpituzumab tesirine, Rovelizumab, Rozanolixizumab, Ruplizumab, SA237, Sacituzumab, Sacituzumab govitecan, Samalizumab, Samrotamab vedotin, Sarilumab, Satralizumab, Satumomab pendetide, SB3, SCT-110A, SEA-CD40, Secukinumab, Selicrelumab, Seribantumab, Setoxaximab, Setrusumab, Sevirumab, SG001, SGN-CD19A, SHP647, SHR-1316, SIBP-01, Sibrotuzumab, Sifalimumab, Siltuximab, Simtuzumab, Sintilimab, Siplizumab, Sirtratumab vedotin, Sirukumab, Sofituzumab vedotin, Solanezumab, Solitomab, Sonepcizumab, Sontuzumab, Spartalizumab, Stamulumab, STI-3031, Sulesomab, Suptavumab, Sutimlimab, Suvizumab, Suvratoxumab, Sym021, Tabalumab, Tacatuzumab tetraxetan, Tadocizumab, Talacotuzumab, Talizumab, Tamtvetmab, Tanezumab, Taplitumomab paptox, Tarextumab, Tavolimab, Tefibazumab, Telimomab aritox, Telisotuzumab, Telisotuzumab vedotin, Tenatumomab, Teneliximab, Teplizumab, Tepoditamab, Teprotumumab, Tesidolumab, Tetulomab, Tezepelumab, TG-1501, TGN1412. Tibulizumab, Ticilimumab, Tigatuzumab, Tildrakizumab, Timigutuzumab, Timolumab, Tiragolumab, Tiragotumab, Tislelizumab, Tisotumab vedotin, TNX-650, Tocilizumab, Tocilizumab, Tomuzotuximab, Toralizumab, Toripalimab, Tosatoxumab. Tositumomab, Tositumomab, Tovetumab, Tralokinumab, Trastuzumab, Trastuzumab deruxtecan, Trastuzumab-anns, trastuzumab-dkst, Trastuzumab emtansine, TRBS07, Tregalizumab, Tremelimumab, Trevogrumab, TRX385, TRX518, TSR-042, Tucotuzumab celmoleukin. Tuvirumab, TX05, Ublituximab, Ulocuplumab, Urelumab, Urtoxazumab, Ustekinumab, Utomilumab, Vadastuximab talirine, Vanalimab, Vandortuzumab vedotin, Vantictumab, Vanucizumab, Vapaliximab, Varisacumab, Varlilumab, Vatelizumab, Vedolizumab, Veltuzumab, Vepalimomab, Vesencumab, Visilizumab, Vobarilizumab, Volociximab, Vonlerolizumab, Vopratelimab, Vorsetuzumabmafodotin, Votumumab, Vunakizumab, Xentuzumab, XmAb20717. XmAb22841, XMAB-5574, Zalutumumab, Zanolimumab, Zatuximab, Zenocutuzumab, Ziralimumab, ZKAB001, Zolbetuximab, and Zolimomab aritox.

In some embodiments, the antibody is Cetuximab (ERBITUX), panitumumab, zalutumumab, nimotuzumab, trastuzumab, Ado-trastuzumab emtansine, Tositumomab (Bexxar®), Rituximab (Rituxan, MabThera), Ibritumomab tiuxetan (Zevalin), Basiliximab, Daclizumab (Zenapax), Gemtuzumab (Mylotarg), Alemtuzumab, CEA-scan Fab fragment, OC125 monoclonal antibody, ab75705, B72.3, Bevacizumab (Avastin®), Afatinib, Axitinib, Bosutinib, Cabozantinib, Ceritinib, Crizotinib, Dabrafenib, Dasatinib, Erlotinib, Everolimus, Ibrutinib, Imatinib, Lapatinib, Lenvatinib, Nilotinib, Olaparib, Palbociclib, Pazopanib, Pertuzumab, Ramucirumab, Regorafenib, Ruxolitinib, Sorafenib, Sunitinib, Temsirolimus, Vandetanib, Vemurafenib, Vismodegib, Basiliximab, Ipilimumab, Nivolumab, pembrolizumab, lambrolizumab, MPDL3280A, Pidilizumab (CT-011), MS BOO 1078C, BMS-935559 or MED14736, AMP-224, or is an antigen-binding fragment thereof.

In some embodiments, the antibody is AB122. ADG116, ADU-1604, AGEN1181, AGEN1884, AK105, AMG 404, AMP-224, AMP-514 (MED10680), Atezolizumab (TECENTRIQ, MPDL3280A, RG7446), Avelumab (BAVENCIO; MSB0010718C; M7824), Basiliximab (SIMULECT), BCD-100, BCD-135, BCD-145, BGB-A333, BI 754091, BMS-936559 (MDX-1105), BMS-986218, Camidanlumab tesirine, Camrelizumab (SHR1210), Cantuzumab ravtansine, CBT-502 (TQB-2450), Cemiplimab (LIBTAYO; REGN2810), Cetrelimab (hPAM4-Cide), Cetuximab (ERBITUX), Clivatuzumab tetraxetan, Cosibelimab (CK-301), CS1001 (WPB3155), CS1003, CX-188, Daclizumab (ZINBRYTA, ZENAPAX), Depatuxizumab mafodotin, Dostarlimab, Durvalumab (IMFINZI), F520, FAZ053, Futuximab, Gatipotuzumab, Genolimzumab (APL-501; GB226; CBT-501), GLS-010, HLX10, HLX20, HX008, 1B1308, Imgatuzumab, Inolimomab, Ipilimumab (YERVOY), JTX-4014, KN035, Laprituximab emtansine, LDP, LY3300054, LZM009, Matuzumab, MGA012 (IN-CMGA0012), MK-1308, Modotuximab, MSB2311. Necitumumab (PORTRAZZA), Nimotuzumab (THERACIM, THERALOC), Nivolumab (OPDIVO), NM-01, Panitumumab (VECTIBIX; ABX-EGF), PDR001, Pembrolizumab (KEYTRUDA; lambrolizumab; MK-3475), Pemtumomab (THERAGYN), PF-06801591, RA8, REGN2810, REGN3504, REGN4659, SCT-110A, SG001, SHR-1316. Sibrotuzumab, Sintilimab (TYVYT), Spartalizumab (PDR001), STI-003, STI-3031 (IMC-001: STI-A1015), Sym021, TG-1501, Tislelizumab, Tomuzotuximab, Toripalimab, Tremelimumab (Ticilimumab), TSR-042, Xenopax, Zalutumumab (HuMax-EGFR), ZKAB001 (STI-A 1014), or is a binding fragment thereof.

In some embodiments, the targeting molecule of the conjugate binds to EGFR. For example, in some aspects, the conjugate is a phthalocyanine dye of Formula (X), or Formula (0) and an antibody or an antigen-binding fragment that binds to EGFR. In some aspects, the antibody of the conjugate that targets or binds to EGFR includes, but is not limited to, Alacizumab pegol, Cetuximab, Depatuxizumab mafodotin, Futuximab, Icrucumab, Imgatuzumab, Laprituximab emtansine, Matuzumab, Modotuximab, Necitumumab, Nimotuzumab, Panitumumab, Ramucirumab, Tomuzotuximab, Zalutumumab, or an EGFR-binding fragment thereof. In some aspects, the conjugate is a phthalocyanine dye of Formula (X), or Formula (0) and cetuximab or an antigen-binding fragment of cetuximab. In some aspects, the conjugate is a phthalocyanine dye of Formula (X), or Formula (0) and a polypeptide or small peptide that binds to EGFR. In some aspects, the conjugate is a phthalocyanine dye of Formula (I) and an antibody or an antigen-binding fragment that binds to EGFR. In some aspects, the conjugate is a phthalocyanine dye of Formula (I) and cetuximab or an antigen-binding fragment of cetuximab. In some aspects, the conjugate is a phthalocyanine dye of Formula (I) and a polypeptide or small peptide that binds to EGFR.

In some embodiments, the targeting molecule of the conjugate binds to CD25. For example, in some aspects, the conjugate is a phthalocyanine dye of Formula (X), or Formula (0) and an antibody or an antigen-binding fragment that binds to CD25. In some aspects, the antibody of the conjugate that targets or binds to CD25 includes, but is not limited to, Basiliximab, Camidanlumab tesirine, daclizumab, Inolimomab, RA8, STI-003, Xenopax, or a CD25-binding fragment thereof. In some aspects, the conjugate is a phthalocyanine dye of Formula (X), or Formula (0) and basiliximab or an antigen-binding fragment of basiliximab. In some aspects, the conjugate is a phthalocyanine dye of Formula (X), or Formula (0) and daclizumab or an antigen-binding fragment of daclizumab. In some aspects, the conjugate is a phthalocyanine dye of Formula (X), or Formula (0) and an IL-2 non-blocking CD25 antibody such as an antibody disclosed in WO2018167104 and WO2019008386. In some aspects, the conjugate is a phthalocyanine dye of Formula (I) and an antibody or an antigen-binding fragment that binds to CD25. In some aspects, the conjugate is a phthalocyanine dye of Formula (I) and basiliximab or an antigen-binding fragment of basiliximab. In some aspects, the conjugate is a phthalocyanine dye of Formula (I) and daclizumab or an antigen-binding fragment of daclizumab. In some aspects, the conjugate is a phthalocyanine dye of Formula (I) and an IL-2 non-blocking CD25 antibody, such as an antibody disclosed in WO2018167104 and WO2019008386.

In some embodiments, the targeting molecule of the conjugate is an antibody or antigen-binding fragment thereof that targets or binds PD-L1, such as an anti-PD-L1 antibody or an antigen-binding fragment thereof and the phthalocyanine dye has the Formula (X), Formula (0), Formula (I), or Formula (II). In some aspects, the antibody of the conjugate that targets or binds to PD-L1 includes, but is not limited to, Atezolizumab (MPDL3280A, TECENTRIQ), Avelumab (BAVENCIO), Durvalumab (MED14736, IMFINZI), LDP, NM-01. STI-3031, KN035, LY3300054, M7824 (MSB0011359C), BMS-936559, MSB2311, BCD-135, BGB-A333, CBT-502, Cosibelimab (CK-301), CS1001, FAZ053, MDX-1105, SHR-1316, TG-1501, ZKAB001, INBRX-105, MCLA-145, KN046, LY3415244, REGN3504, and HLX20. Exemplary anti-PD-L1 antibodies include MED14736 (Medimmune) MPDL3280A (Genentech), BMS-935559 (Bristol-Myers Squibb) and MSB0010718C and an antigen-binding fragment of any of the foregoing.

In some embodiments, the targeting molecule of the conjugate is an antibody or antigen-binding fragment thereof that targets or binds PD1, such as an anti-PD1 antibody or an antigen-binding fragment thereof and the phthalocyanine dye has the Formula (X), Formula (0), Formula (I), or Formula (II). In some aspects, the antibody of the conjugate that targets or binds to PD1 includes, but is not limited to, pembrolizumab (MK-3475, Keytruda), nivolumab (Opdivo), cemiplimab (Libtayo), toripalimab (JS001), HX008, SG001, GLS-010, dostarlimab (TSR-042), tislelizumab (BGB-A317), cetrelimab (JNJ-63723283), pidilizumab (CT-011), genolimzumab (APL-501, GB226), BCD-100, cemiplimab (REGN2810). F520, sintilimab (IBI308), GLS-010, CS1003, LZM009, camrelizumab(SHR-1210), SCT-110A, MGA012, AK105. PF-06801591. AMP-224, AB122, AMG 404, BI 754091, HLX10, JTX-4014, MEDI0680, Sym021, MGD019, MGD013, AK104, XmAb20717, RO7121661, CX-188, and spartalizumab.

In some embodiments, the targeting molecule of the conjugate is an antibody or antigen-binding fragment thereof that targets or binds CTLA-4, such as an anti-CTLA-4 antibody or an antigen-binding fragment thereof and the phthalocyanine dye has the Formula (X), Formula (0), Formula (I), or Formula (II). In some aspects, the antibody of the conjugate that targets or binds to CTLA-4 includes, but is not limited to, ipilimumab (Yervoy®), tremelimumab (ticilimumab), AGEN1181, AGEN1884, ADU-1064, BCD-145, and BCD-217.

In some embodiments, the targeting molecule of the conjugate is an antibody or antigen-binding fragment thereof that targets or binds HER2, such as an anti-HER2 antibody or an antigen-binding fragment thereof and the phthalocyanine dye has the Formula (X), Formula (0), Formula (I), or Formula (II). In some aspects, the antibody of the conjugate that targets or binds to HER2 includes, but is not limited to, CDC-022 (HERtiCAD), CMAB302 (Cipterbin), DS-8201, Gancotamab, GB221, HD201, Hervycta, HLX02, HLX22, Margetuximab, Pertuzumab (Perjeta), PF-05280014 (Trazimera), SB3, SIBP-01, Timigutuzumab, Trastuzumab (Herceptin), trastuzumab deruxtecan (ENHERTU), Trastuzumab emtansine (Kadcyla), trastuzumab-anns (Kanjinti), trastuzumab-dkst (Ogivri), and TX05.

In some embodiments, the targeting molecule of the conjugate is an antibody or antigen-binding fragment thereof that targets or binds MUC1, such as an anti-MUC1 antibody or an antigen-binding fragment thereof and the phthalocyanine dye has the Formula (X), Formula (0), Formula (I), or Formula (II). In some aspects, the antibody of the conjugate that targets or binds to MUC1 includes, but is not limited to, Cantuzumab ravtansine, Clivatuzumab tetraxetan, Gatipotuzumab, and Pemtumomab.

In some embodiments, the targeting molecule of the conjugate is an antibody or antigen-binding fragment thereof that targets or binds PSMA, such as an anti-PSMA antibody or an antigen-binding fragment thereof and the phthalocyanine dye has the Formula (X), Formula (0), Formula (I), or Formula (II). In some aspects, the antibody of the conjugate that targets or binds to PSMA includes, but is not limited to, Capromab pendetide.

In some embodiments, the targeting molecule of the conjugate is an antibody or antigen-binding fragment thereof that targets or binds CEA, such as an anti-CEA antibody or an antigen-binding fragment thereof and the phthalocyanine dye has the Formula (X), Formula (0), Formula (I), or Formula (II). In some aspects, the antibody of the conjugate that targets or binds to CEA includes, but is not limited to, Altumomab pentetate. Arcitumomab, arcitumomab Fab fragment, Besilesomab, Cibisatamab, F3, and Labetuzumab. In some embodiments, the targeting molecule of the conjugate in an antibody or antibody fragment, such as an antibody fragment disclosed in EP1505076 or a full-length antibody with the antigen binding domains of an antibody fragment disclosed in EP1505076.

In some embodiments, the targeting molecule of the conjugate is an antibody or antigen-binding fragment thereof that targets or binds FAP, such as an anti-FAP antibody or an antigen-binding fragment thereof and the phthalocyanine dye has the Formula (X), Formula (0), Formula (I), or Formula (II). In some aspects, the antibody of the conjugate that targets or binds to FAP includes, but is not limited to. Sibrotuzumab.

In some embodiments, the targeting molecule of the conjugate is a biosimilar, interchangeable or bio better of any of the targeting molecules described herein.

In some embodiments, the conjugate contains a number of dye residues per targeting molecule that is from or from about 1 to about 1000, such as from or from about 1 to about 100, from or from about 1 to about 50, from or from about 1 to about 25, from or from about 1 to about 10, from or from about 1 to about 5. In some embodiments, the ratio of dye molecules to targeting molecule is or is about 1:1, 2:1, 3:1, 4:1, 5:1, 10:1, 15:1, 20:1, 25:1, 50:1, 75:1, 100:1, 150:1, 200:1, 250:1, 300:1, 350:1, 400:1, 450:1, 500-1, 550:1, 600:1, 650:1, 700:1, 750:1, 800:1, 850:1, 900:1, 950:1 or 1000:1, or is between or between about any two of such values. In some embodiments, the targeting molecule may contain up to 2, 3, 4, 5, 6, 7, 8, 9, 10, 15, 20, 50, 75, 100, 150, 200, 250, 300, 350, 400, 450, 500, 550, 600, 650, 700, 750, 800, 850, 900, 950 or 1000 dye molecules.

In some embodiments, such as when the targeting molecule is a polypeptide, such as an antibody or antigen-binding fragment, the number of dye molecule per targeting molecule can be from or from about 1 to 5, such as from or from about 1 to 4, for example at or about 1, at or about 2, or at or about 3. In some embodiments, the number of dye residues per targeting molecule is about 3:1. In some embodiments, the number of dye residues per targeting molecule is about 4:1. In some embodiments, the number of dye residues per targeting molecule is about 2:1. In some embodiments, the number of dye residues per targeting molecule is about 1:1. In some embodiments, the number of dye residues per targeting molecule is between about 2:1 and about 3:1. In some embodiments, the number of dye residues per targeting molecule is between about 1:1 to about 2:1. In some embodiments, the number of dye residues per targeting molecule is between about 1.5:1 to about 2:1. In some embodiments, the number of dye residues per targeting molecules is between about 3:1 and about 4:1.

C. Formulations and Administration

Also provided herein are compositions, such as pharmaceutical compositions, containing any of the conjugates provided herein. In some aspects, the compositions contain the phthalocyanine dye conjugate, such as a targeting molecule and a phthalocyanine dye of Formula (X), Formula (0), Formula (I), or Formula (II), and a pharmaceutically acceptable carrier. In some embodiments, the composition containing the conjugate is for use in treatment or therapy, in accordance with any of the provided embodiments, such as for administration to a subject having a disease or condition, for the treatment of the disease or condition. The dosages of phthalocyanine dye conjugate to be administered to a subject are not subject to absolute limits but will depend on the nature of the composition: its active ingredients; and its unwanted side effects, such as immune response against the agent, the subject being treated, and the type of condition being treated and the manner of administration. Generally, the dose will be a therapeutically effective amount, such as an amount sufficient to achieve a desired biological effect, for example an amount that is effective to decrease the size, such as volume and/or weight, of the tumor, or attenuate further growth of the tumor, or decrease undesired symptoms of the tumor.

In some embodiments, the compositions used for administration of the phthalocyanine dye conjugate contain an effective amount of the agent along with conventional pharmaceutical carriers and excipients appropriate for the type of administration contemplated. For example, in some embodiments, parenteral formulations may contain a sterile aqueous solution or suspension of the conjugate. In some embodiments, compositions for enteral administration may contain an effective amount of the phthalocyanine dye conjugate in aqueous solution or suspension that may optionally include buffers, surfactants, thixotropic agents, and flavoring agents.

In some embodiments, the phthalocyanine dye conjugate or conjugate in combination with an additional therapeutic agent, can be formulated in a pharmaceutically acceptable buffer, such as that containing a pharmaceutically acceptable carrier or vehicle. Generally, the pharmaceutically acceptable carriers or vehicles, such as those present in the pharmaceutically acceptable buffer, can be any known in the art. Remington's Pharmaceutical Sciences, by E. W. Martin, Mack Publishing Co., Easton, Pa., 19th Edition (1995), describes compositions and formulations suitable for pharmaceutical delivery of one or more therapeutic compounds. Pharmaceutically acceptable compositions generally are prepared in view of approvals for a regulatory agency or other agency prepared in accordance with generally recognized pharmacopeia for use in animals and in humans.

Pharmaceutical compositions can include carriers such as a diluent, adjuvant, excipient, or vehicle with which the compound is administered. Examples of suitable pharmaceutical carriers are described in "Remington's Pharmaceutical Sciences" by E. W. Martin. Such compositions will contain a therapeutically effective amount of the compound, generally in purified form, together with a suitable amount of carrier so as to provide the form for proper administration to the patient. Such pharmaceutical carriers can be sterile liquids, such as water and oils, including those of petroleum, animal, vegetable or synthetic origin, such as peanut oil, soybean oil, mineral oil, and sesame oil. Water is a typical carrier when the pharmaceutical composition is administered intravenously. Saline solutions and aqueous dextrose and glycerol solutions also can be employed as liquid carriers, particularly for injectable solutions. Compositions can contain along with an active ingredient, a diluent such as lactose, sucrose, dicalcium phosphate, or carboxymethylcellulose; a lubricant, such as magnesium stearate, calcium stearate and talc; and a binder such as starch, natural gums, such as gum acacia, gelatin, glucose, molasses, polyvinylpyrrolidone, celluloses and derivatives thereof, povidone, crospovidones and other such binders known to those of skill in the art. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, and ethanol. A composition, if desired, also can contain minor amounts of wetting or emulsifying agents, or pH buffering agents, for example, acetate, sodium citrate, cyclodextrin derivatives, sorbitan monolaurate, triethanolamine sodium acetate, triethanolamine oleate, and other such agents.

In some embodiments, pharmaceutical preparation can be in liquid form, for example, solutions, syrups or suspensions. Such liquid preparations can be prepared by conventional means with pharmaceutically acceptable additives such as suspending agents (e.g., sorbitol syrup, cellulose derivatives or hydrogenated edible fats): emulsifying agents (e.g., lecithin or acacia); non-aqueous vehicles (e.g., almond oil, oily esters, or fractionated vegetable oils); and preservatives (e.g., methyl or propyl-p-hydroxy benzoates or sorbic acid). In some cases, pharmaceutical preparations can be presented in lyophilized form for reconstitution with water or other suitable vehicle before use.

In some embodiments, the nature of the pharmaceutically acceptable buffer, or carrier, depends on the particular mode of administration being employed. For instance, in some embodiments, parenteral formulations may comprise injectable fluids that include pharmaceutically and physiologically acceptable fluids such as water, physiological saline, balanced salt solutions, aqueous dextrose, or glycerol as a vehicle. In some embodiments, for solid compositions, for example powder, pill, tablet, or capsule forms, non-toxic solid carriers can include, for example, pharmaceutical grades of mannitol, lactose, starch, or magnesium stearate. In addition to biologically-neutral carriers, pharmaceutical compositions to be administered can in some embodiments contain minor amounts of non-toxic auxiliary substances, such as wetting or emulsifying agents, preservatives, and pH buffering agents, for example sodium acetate or sorbitan monolaurate.

The compounds can be formulated into suitable pharmaceutical preparations such as solutions, suspensions, tablets, dispersible tablets, pills, capsules, powders, sustained release formulations or elixirs, for oral administrate, as well as transdermal patch preparation and dry powder inhalers. Typically, the compounds are formulated into pharmaceutical compositions using techniques and procedures well known in the art (see e.g., Ansel Introduction to Pharmaceutical Dosage Forms, Fourth Edition, 1985, 126). Generally, the mode of formulation is a function of the route of administration.

Compositions can be formulated for administration by any route known to those of skill in the art including intramuscular, intravenous, intradermal, intralesional, intraperitoneal injection, subcutaneous, intratumoral, epidural, nasal, oral, vaginal, rectal, topical, local, otic, inhalational, buccal (e.g., sublingual), and transdermal administration or any route. Other modes of administration also are contemplated. Administration can be local, topical or systemic depending upon the locus of treatment. Local administration to an area in need of treatment can be achieved by, for example, but not limited to, local infusion during surgery, topical application, e.g., in conjunction with a wound dressing after surgery, by injection, by means of a catheter, by means of a suppository, or by means of an implant.

Parenteral administration, generally characterized by injection, either subcutaneously, intramuscularly, intratumorally, intravenously or intradermally is contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also contain an activator in the form of a solvent such as pH buffering agents, metal ion salts, or other such buffers. The pharmaceutical compositions also may contain other minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) also is contemplated herein. The percentage of active compound contained in such parenteral compositions is highly dependent on the specific nature thereof, as well as the activity of the compound and the needs of the subject.

Injectables are designed for local and systemic administration. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or non-aqueous. If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, non-aqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include Sodium Chloride Injection, Ringers Injection, Isotonic Dextrose Injection, Sterile Water Injection, Dextrose and Lactated Ringers Injection. Non-aqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers, which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate.

If administered intravenously, suitable carriers include physiological saline or phosphate buffered saline (PBS), and solutions containing thickening and solubilizing agents, such as glucose, polyethyleneglycol, and polypropylene glycol and mixtures thereof.

The composition can be formulated for single dosage administration or for multiple dosage administration. The agents can be formulated for direct administration. The composition can be provided as a liquid or lyophilized formulation. Where the composition is provided in lyophilized form it can be reconstituted just prior to use by an appropriate buffer, for example, a sterile saline solution.

Compositions also can be administered with other biologically active agents, either sequentially, intermittently or in the same composition. Administration also can include controlled release systems including controlled release formulations and device-controlled release, such as by means of a pump.

The most suitable route in any given case depends on a variety of factors, such as the nature of the disease, the progress of the disease, the severity of the disease and the particular composition which is used. For example, compositions are administered systemically, for example, via intravenous administration. Subcutaneous methods also can be employed, although increased absorption times can be necessary to ensure equivalent bioavailability compared to intravenous methods.

Pharmaceutical compositions can be formulated in dosage forms appropriate for each route of administration. Pharmaceutically and therapeutically active compounds and derivatives thereof are typically formulated and administered in unit dosage forms or multiple dosage forms. Each unit dose contains a predetermined quantity of therapeutically active compound sufficient to produce the desired therapeutic effect, in association with the required pharmaceutical carrier, vehicle or diluent. Unit dosage forms include, but are not limited to, tablets, capsules, pills, powders, granules, sterile parenteral solutions or suspensions, and oral solutions or suspensions, and oil water emulsions containing suitable quantities of the compounds or pharmaceutically acceptable derivatives thereof. Unit dose forms can be contained ampoules and syringes or individually packaged tablets or capsules. Unit dose forms can be administered in fractions or multiples thereof. A multiple dose form is a plurality of identical unit dosage forms packaged in a single container to be administered in segregated unit dose form. Examples of multiple dose forms include vials, bottles of tablets or capsules or bottles of pints or gallons. Hence, multiple dose form is a multiple of unit doses that are not segregated in packaging. Generally, dosage forms or compositions containing active ingredient in the range of 0.005% to 100% with the balance made up from non-toxic carrier can be prepared. Pharmaceutical compositions can be formulated in dosage forms appropriate for each route of administration.

The concentration of the pharmaceutically active compound is adjusted so that an injection provides an effective amount to produce the desired pharmacological effect. The exact dose depends on the age, weight and condition of the patient or animal as is known in the art. The unit-dose parenteral preparations are packaged in an ampoule, a vial or a syringe with a needle. The volume of liquid solution or reconstituted powder preparation, containing the pharmaceutically active compound, is a function of the disease to be treated and the particular article of manufacture chosen for package. All preparations for parenteral administration must be sterile, as is known and practiced in the art. In some embodiments, the compositions can be provided as a lyophilized powder, which can be reconstituted for administration as solutions, emulsions and other mixtures. They may also be reconstituted and formulated as solids or gels. The lyophilized powders can be prepared from any of the solutions described above.

The sterile, lyophilized powder can be prepared by dissolving a phthalocyanine dye-targeting molecule conjugate in a buffer solution. The buffer solution may contain an excipient which improves the stability of other pharmacological components of the powder or reconstituted solution, prepared from the powder.

In some embodiments, subsequent sterile filtration of the solution followed by lyophilization under standard conditions known to those of skill in the art provides the desired formulation. Briefly, the lyophilized powder is prepared by dissolving an excipient, such as dextrose, sorbitol, fructose, corn syrup, xylitol, glycerin, glucose, sucrose or other suitable agent, in a suitable buffer, such as citrate, sodium or potassium phosphate or other such buffer known to those of skill in the art. Then, a selected enzyme is added to the resulting mixture, and stirred until it dissolves. The resulting mixture is sterile filtered or treated to remove particulates and to ensure sterility and apportioned into vials for lyophilization. Each vial can contain a single dosage (1 mg-1 g, generally-100 mg, such as 1-5 mg) or multiple dosages of the compound. The lyophilized powder can be stored under appropriate conditions, such as at about 4° C. to room temperature. Reconstitution of this lyophilized powder with a buffer solution provides a formulation for use in parenteral administration. The precise amount depends upon the indication treated and selected compound. Such amount can be empirically determined.

In some embodiments, the pH of the composition is between or between about 6 and 10, such as between or between about 6 and 8, between or between about 6.9 and 7.3, such as about pH 7.1. In some embodiments, the pH of the pharmaceutically acceptable buffer is at least or about 5, at least or about 6, at least or about 7, at least or about 8, at least or about 9 or at least or about 10, or is 7.1.

The compositions can be formulated for single dosage administration or for multiple dosage administration. The agents can be formulated for direct administration.

In some embodiments, the compositions provided herein are formulated in an amount for direct administration of the provided conjugates, in a range from at or about 0.01 mg to at or about 3000 mg, from at or about 0.01 mg to at or about 1000 mg, from at or about 0.01 mg to at or about 500 mg, from at or about 0.01 mg to at or about 100 mg, from at or about 0.01 mg to at or about 50 mg, from at or about 0.01 mg to at or about 10 mg, from at or about 0.01 mg to at or about 1 mg, from at or about 0.01 mg to at or about 0.1 mg, from at or about 0.1 mg to at or about 2000 mg, from at or about 0.1 mg to at or about 1000 mg, from at or about 0.1 mg to at or about 500 mg, from at or about 0.1 mg to at or about 100 mg, from at or about 0.1 mg to at or about 50 mg, from at or about 0.1 mg to at or about 10 mg, from at or about 0.1 mg to at or about 1 mg, from at or about 1 mg to at or about 2000 mg, from at or about 1 mg to at or about 1000 mg, from at or about 1 mg to at or about 500 mg, from at or about 1 mg to at or about 100 mg, from at or about 1 mg to at or about 10 mg, from at or about 10 mg to at or about 2000 mg, from at or about 10 mg to at or about 1000 mg, from at or about 10 mg to at or about 500 mg, from at or about 10 mg to at or about 100 mg, from at or about 100 mg to at or about 2000 mg, from at or about 100 mg to at or about 1000 mg, from at or about 100 mg to at or about 500 mg, from at or about 500 mg to at or about 2000 mg, from at or about 500 mg to at or about 1000 mg, and from about 1000 mg to at or about 3000 mg. In some embodiments, the volume of the composition can be 0.5 mL to 1000 mL, such as 0.5 mL to 100 mL, 0.5 mL to 10 mL, 1 mL to 500 mL, 1 mL to 10 mL, such as at least or about at least or about or 0.5 mL, 1 mL, 2 mL, 3 mL, 4 mL, 5 mL, 6 mL, 7 mL, 8 mL, 9 mL, 10 mL, 15 mL, 20 mL, 30 mL, 40 mL, 50 mL or more. For example, the composition is formulated for single dosage administration of an amount between at or about 100 mg and at or about 500 mg, or between at or about 200 mg and at or about 400 mg. In some embodiments, the composition is formulated for single dosage administration of an amount between at or about 500 mg and at or about 1500 mg, at or about 800 mg and at or about 1200 mg or at or about 1000 mg and at or about 1500 mg. In some embodiments, the volume of the composition is between at or about 10 mL and at or about 1000 mL or at or about 50 mL and at or about 500 mL; or the volume of the composition is at least at or about 10 mL, 20 mL, 30 mL, 40 mL, 50 mL, 75 mL, 100 mL, 150 mL, 200 mL, 250 mL, 300 mL, 400 mL, 500 mL or 1000 mL.

In some embodiments, the entire vial contents of the formulations can be withdrawn for administration or can be divided up into a plurality of dosages for multiple administrations. Upon withdrawal of an amount of drug for administration, the formulation can be further diluted if desired, such as diluted in water, saline (e.g., 0.9%) or other physiological solution.

In some embodiments, also provided are compositions containing an additional therapeutic agent, such as an immunomodulatory agent or anti-cancer agent, for use in combination with the provided conjugates, in accordance with the provided embodiments. In some aspects, the additional therapeutic agent can be prepared in accord with known or standard formulation guidelines, such as described above. In some embodiments, the immunomodulatory agent, anti-cancer agent and/or provided conjugate are formulated as separate compositions. In some embodiments, the immunomodulatory agent is provided as a separate composition from the provided conjugate, and the two compositions are administered separately. In some embodiments, the anti-cancer agent is provided as a separate composition from the provided conjugate, and the two compositions are administered separately. The compositions can be formulated for parenteral delivery (i.e., for systemic delivery). For example, the compositions or combination of compositions are formulated for subcutaneous delivery or for intravenous delivery. The agents, such as a provided conjugate and an immunomodulatory agent and/or an anti-cancer agent can be administered by different routes of administration.

The compositions comprising the provided conjugate can be administered locally or systemically using any method known in the art, for example to subjects having a tumor, such as a cancer, or who has had a tumor previously removed, for example via surgery. Although specific examples are provided, one skilled in the art will appreciate that alternative methods of administration of the disclosed agents can be used. Such methods may include for example, the use of catheters or implantable pumps to provide continuous infusion over a period of several hours to several days into the subject in need of treatment.

In some embodiments, the provided conjugate is administered by parenteral means, including direct injection or infusion into a tumor, such as intratumorally. In some embodiments, the conjugate is administered to the tumor by applying the agent to the tumor, for example by bathing the tumor in a solution containing the conjugate, or by pouring the agent onto the tumor.

In addition, or alternatively, the conjugate can be administered systemically, for example intravenously, intramuscularly, subcutaneously, intradermally, intraperitoneally, subcutaneously, or orally, to a subject having a tumor, such as cancer.

In some embodiments, the conjugate can be administered ex vivo, for example by obtaining cells from a subject, treating such cells with a conjugate in conjunction with illumination, and administering the treated cells either to the same subject or a different subject.

In some embodiments, the composition contains an average number of dye residues per targeting molecule (e.g., DAR) that is from or from about 0.5 to about 1000, such as from or from about 0.5 to about 100, from or from about 0.5 to about 50, from or from about 0.5 to about 25, from or from about 0.5 to about 10, from or from about 0.5 to about 5. In some embodiments, the average ratio of dye molecules to targeting molecules in the composition is greater than 0.5 or greater than about 0.5, such as 0.6, 0.7, 0.8, 0.9, 1, 2, 3, 4, 5, 6, 7, 8, 9, 10, or more. In some embodiments, the ratio of dye molecules to targeting molecules in the composition is or is about 0.5:1, 0.7:1, 0.8:1, 1:1, 2:1, 3:1, 4:1, 5:1, 10:1, 15:1, 20:1, 25:1, 50:1, 75:1, 100:1, 150:1, 200:1, 250:1, 300:1, 350:1, 400:1, 450:1, 500:1, 550:1, 600:1, 650:1, 700:1, 750:1, 800:1, 850:1, 900:1, 950:1 or 1000:1, or is between or between about any two of such values.

In some embodiments, such as when the targeting molecule is a polypeptide, such as an antibody, antigen-binding fragment, or nanobody, the average number of dye molecules per targeting molecule in the composition can be from or from about 0.5 to 5, such as from or from about 0.5 to 4, for example at or about 0.5, at or about 0.6, at or about 0.7, at or about 0.8, at or about 0.9, at or about 1, at or about 2, or at or about 3. In some embodiments, the average number of dye residues per targeting molecule in the composition is about 3:1. In some embodiments, the average number of dye residues per targeting molecule in the composition about 4:1. In some embodiments, the average number of dye residues per targeting molecule in the composition about 2:1. In some embodiments, the average number of dye residues per targeting molecule in the composition is about 1:1. In some embodiments, the average number of dye residues per targeting molecule in the composition is between about 2:1 and about 3:1. In some embodiments, the average number of dye residues per targeting molecule in the composition is between about 1:1 to about 2:1. In some embodiments, the average number of dye residues per targeting molecule in the composition is between about 1.5:1 to about 2:1. In some embodiments, the average number of dye residues per targeting molecule in the composition is between about 3:1 and about 4:1. In some embodiments, the average number of dye residues per targeting molecule in the composition is between about 0.5:1 to about 1:1.

D. Devices and Illumination Methods for Use with Conjugates

In some aspects, devices that can be used with the provided embodiments include light diffusing devices that provide illumination (in some cases, also referred to as irradiation) at a wavelength (or wavelengths) of light suitable for use with the dye conjugate composition, such as a phthalocyanine dye conjugates of Formula (X), Formula (O), Formula (I), or Formula (II) and a targeting molecule described herein. Illumination devices can include a light source (for example, a laser), and a means of conveying the light to the area of interest (for example, one or more fibers to illuminate an isolated area of a subject or an isolated lesion or tumor). Exemplary illumination devices are described in U.S. Pat. Nos. 10,295,719; 10,527,771; and 10,416,366, incorporated herein by reference. Such devices deliver light to a target region of a subject using a light diffusing device, containing, a non-circular core optic fiber that is operably connected to a laser. In some embodiments, the core optic fiber is circular and is coiled or bent prior to interfacing with a light diffusing device. In particular aspects, the device delivers a "top hat" core irradiance distribution to deliver uniform light to the illuminated area. The light diffusing device can be as cylindrical diffuser for use, for example, for intratumor or intratissue irradiation. In some embodiments, the light diffusing device is a frontal diffuser, with a lens, where the illumination is projected through the lens of the frontal diffuser at the end of the optic fiber. The projected light can be a collimated or dispersing beam of light.

In some embodiments, the target area, such as a tumor, the vicinity of a tumor, a lymph node, the vicinity of the lymph node, is illuminated with light at a wavelength within a range from at or about 400 nm to at or about 900 nm, such as from or from at or about 500 nm to at or about 900 nm, such as from or from at or about 600 nm to at or about 850 nm, such as from or from at or about 600 nm to at or about 740 nm, such as from at or about 660 nm to at or about 740 nm, from at or about 660 nm to at or about 710 nm, from at or about 660 nm to at or about 700 nm, from at or about 660 to at or about 685, from at or about 665 to at or about 680, from at or about 670 to at or about 685, from at or about 670 nm to at or about 690 nm, from at or about 670 to at or about 680, from at or about 680 nm to at or about 740 nm, or from at or about 690 nm to at or about 710 nm. In some embodiments, the target area, such as a tumor, the vicinity of a tumor, a lymph node, the vicinity of the lymph node, or the tumor microenvironment, is illuminated with light at a wavelength of at or about 600 nm to at or about 850 nm, such as at or about 660 nm to at or about 740 nm. In some embodiments, the target area, such as a tumor, the vicinity of a tumor, a lymph node, the vicinity of the lymph node, or the tumor microenvironment, is illuminated with light at wavelength of at least at or about 600 nm, 620 nm, 640 nm, 660 nm, 680, nm, 700 nm, 720 nm or 740 nm, such as at or about 670±50 nm, or at or about 670±40 nm, for example at or about 670 nm or at or about 670 nm. In some embodiments, the target area, such as a tumor, the vicinity of a tumor, a lymph node, the vicinity of the lymph node, or the tumor microenvironment, is illuminated with light at a wavelength of less than or less than about 685 nm or 680 nm.

In some embodiments of the methods and uses provided herein, illumination is carried out using cylindrical diffusing fibers that includes a diffuser length of at or about 0.5 cm to at or about 10 cm and spaced at or about 1.8±0.2 cm apart. In some embodiments, the light illumination dose is from at or about 20 J/cm fiber length to at or about 500 J/cm fiber length. In some embodiments, the tumor is greater than at or about 10 mm deep or is a subcutaneous tumor.

In some embodiments, the provided methods include illuminating a target area that is an interstitial tumor in a subject with cylindrical diffusing fibers that includes a diffuser length of at or about 0.5 cm to at or about 10 cm and spaced at or about 1.8±0.2 cm apart with a light dose of at or about 100 J/cm fiber length or with a fluence rate of at or about 400 mW/cm. In some embodiments, the target area is a tumor that is greater than at or about 10 mm deep or is a subcutaneous tumor. In some embodiments, the cylindrical diffusing fibers are placed in a catheter positioned in the tumor at or about 1.8±0.2 cm apart. In some embodiments, the catheter is optically transparent.

In some embodiments, the target area, such as a tumor, the vicinity of a tumor, a lymph node, the vicinity of the lymph node, or the tumor microenvironment, is illuminated with light dose of at least at or about 1 $J/cm^2$, such as at least at or about 10 $J/cm^2$, at least at or about 30 $J/cm^2$, at least at or about 50 $J/cm^2$, at least at or about 75 $J/cm^2$, at least at or about 100 $J/cm^2$, at least at or about 150 $J/cm^2$, or at least at or about 500 $J/cm^2$. In some embodiments, the dose of illumination is from at or about 1 to at or about/$cm^2$, from at or about 1 to at or about 500 $J/cm^2$, from at or about 5 to at or about 200 $J/cm^2$, from at or about 10 to at or about 100 $J/cm^2$, from at or about 10 to at or about 50 $J/cm^2$, from at or about 30 to at or about 200 $J/cm^2$, from at or about 30 to at or about 150 $J/cm^2$, or from at or about 30 $J/cm^2$ to at or about 100 $J/cm^2$. In some embodiments, the target area is illuminated at a dose of at least at or about 2 $J/cm^2$, 5 $J/cm^2$, 10 $J/cm^2$, 25 $J/cm^2$, 50 $J/cm^2$, 75 $J/cm^2$, 100 $J/cm^2$, 150 $J/cm^2$, 200 $J/cm^2$, 300 $J/cm^2$, 400 $J/cm^2$, or 500 $J/cm^2$.

In some embodiments, the target area is a tumor that is a superficial tumor. In some embodiments, the tumor is less than 10 mm thick. In some embodiments, illumination is carried out using a microlens-tipped fiber for surface illumination. In some embodiments, the light illumination dose is from at or about 5 $J/cm^2$ to at or about 200 $J/cm^2$.

In some embodiments, the target area, such as a tumor, the vicinity of a tumor, a lymph node, the vicinity of the lymph node, or the tumor microenvironment, are illuminated at a dose of at least at or about 1 J/cm fiber length, such as at least at or about 10 J/cm fiber length, at least at or about 50 J/cm fiber length, at least at or about 100 J/cm fiber length, at least at or about 250 J/cm fiber length, or at least at or about 500 J/cm fiber length. In some embodiments, the dose of illumination is from at or about 1 to at or about 1000 J/cm fiber length, from at or about 1 to at or about 500 J/cm fiber length, from at or about 2 to at or about 500 J/cm fiber length, from at or about 50 to at or about 300 J/cm fiber length, from at or about 10 to at or about 100 J/cm fiber length, or from at or about 10 to at or about 50 J/cm fiber length. In some embodiments, the target area, such as a tumor, the vicinity of a tumor, a lymph node, the vicinity of the lymph node, or the tumor microenvironment, are illuminated at a dose of at least at or about 2 J/cm fiber length, 5 J/cm fiber length, 10 J/cm fiber length, 25 J/cm fiber length, 50 J/cm fiber length, 75 J/cm fiber length, 100 J/cm fiber length, 150 J/cm fiber length, 200 J/cm fiber length, 250 J/cm fiber length, 300 J/cm fiber length, 400/cm fiber length or 500 J/cm fiber length.

In some embodiments, the provided methods include illuminating a target area that is a superficial tumor in a subject with a microlens-tipped fiber for surface illumination with a light dose of from at or about 5 $J/cm^2$ to at or about 200 $J/cm^2$. In some embodiments, the light illumination dose is at or about 50 $J/cm^2$.

In some embodiments, the dose of illumination following administration of the composition comprising the phthalocyanine dye-targeting molecule conjugate is at least at or about 1 J/cm2 or at least at or about 1 J/cm of fiber length at a wavelength of at or about 600-800 nm, for example, at least at or about 1 J/cm2 or at least at or about 1 J/cm of fiber length at a wavelength of at or about 620-720 nm, at least at or about 10 J/cm$^2$ or at least at or about 10 J/cm of fiber length at a wavelength of at or about 620-720 nm, at least at or about 50 J/cm$^2$ or at least at or about 50 J/cm of fiber length at a wavelength of at or about 620-720 nm, or at least at or about 100 J/cm$^2$ or at least at or about 100 J/cm of fiber length at a wavelength of at or about 620-720 nm. In some embodiments, the wavelength is 640-700 nm. In some embodiments, the dose of illumination following administration of the composition comprising the phthalocyanine dye-targeting molecule conjugate is at least at or about 1.0 J/cm$^2$ or at least at or about 1 J/cm of fiber length, at a wavelength of at or about 670 nm, for example, at least at or about 10 J/cm$^2$ or at least at or about 10 J/cm of fiber length, at a wavelength of at or about 670 nm, at least at or about 50 J/cm$^2$ or at least at or about 50 J/cm of fiber length, at a wavelength of at or about 670 nm, or at least at or about 100 J/cm$^2$ or at least at or about 100 J/cm of fiber length, at a wavelength of at or about 670 nm, for example 1.0 to 500 J/cm or 1.0 to 500 J/cm of fiber length, at a wavelength of at or about 670 nm. Exemplary illumination after administration of the conjugates or compositions provided herein include illuminating the target area at a wavelength of at or about 620 nm to at or about 720 nm at a dose of at least at or about 1 J/cm$^2$ or at least at or about 1 J/cm of fiber length.

In some embodiments, illuminating is carried out at a wavelength of at or about 580 nm to at or about 830 nm and at a dose of from at or about 25 J/cm$^2$ to at or about 400 J/cm$^2$ or from at or about 2 J/cm fiber length to at or about 500 J/cm fiber length. In some embodiments, the target area is illuminated at a wavelength of 670±40 nm. In some embodiments, target area is illuminated at a dose of at or about of 50 J/cm$^2$ or at or about 100 J/cm of fiber length.

In some embodiments, a light or laser may be applied to the conjugate, such as cells containing the conjugate, for a duration from at or about 5 seconds to at or about 5 minutes. For example, in some embodiments, the light or laser is applied for at or about 5, 10, 15, 20, 25, 30, 35, 40, 45 50 or 55 seconds, or for within a range between any of two such values, to activate the dye molecule(s) of the conjugate. In some embodiments, the light or laser is applied for at or about 1, 1.5, 2, 2.5, 3, 3.5, 4, 4.5 or 5 minutes, or more, or within a range between any two of such values. In some embodiments, the length of time a light or laser is applied can vary depending, for example, on the energy, such as wattage, of the light or laser. For example, lights or lasers with a lower wattage may be applied for a longer period of time.

In some embodiments, a light or laser may be applied for at or about 30 minutes to at or about 96 hours after administering the conjugate. For example, in some embodiments, the light or laser is applied at or at about 30, 35, 40, 45, 50 or 55 minutes after administering the conjugate, or within a range between any two of such values. In some embodiments, the light or laser is applied at or at about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 hours after administering the conjugate, or is administered within a range between about any two of such values, such as, for example between at or about 20 hours to at or about 28 hours, or about 24 hours±4 hours. In some embodiments, the light or laser is applied between or between about 1 and 24 hours, such as between at or about 1 and at or about 12 hours, at or about 12 and at or about 24 hours, at or about 6 and at or about 12 hours, or may be administered more than at or about 24 hours following administration of the conjugate. In some embodiments, the light or laser is applied at or about 36, 48, 72 or 96 hours after administering the conjugate. In some embodiments, the light or laser is applied at or at about 24 hours±4 hours after administering the conjugate.

In some embodiments, the target area, such as a tumor, the vicinity of a tumor, a lymph node, the vicinity of the lymph node, or the tumor microenvironment, or subjects, can be illuminated one or more times. Thus, illumination can be completed in a single day, or can be done repeatedly on multiple days with the same or a different dosage, such as illumination at least at or about 2 different times, 3 different times, 4 different times 5 different times or 10 different times. In some embodiments, repeated illuminations may be done on the same day, on successive days, or every-3 days, every 3-7 days, every 1-2 weeks, every 2-4 weeks, every 1-2 months, or at even longer intervals. In some embodiments, multiple illuminations are performed, such as at least 2, at least 3, or at least 4 illuminations, such as 2, 3, 4, 5, 6, 7, 8, 9 or 10 separate administrations.

In some embodiments, the dose or method of illumination differs depending on the type or morphology of the target area, such as a tumor, the vicinity of a tumor, a lymph node, the vicinity of the lymph node. For example, in some embodiments, the illumination employs a device with "top hat" irradiance distribution profile, such as those described in published applications WO2018/080952 and US20180239074.

In some embodiments of the methods and uses provided herein, the illumination is administered after administration of the conjugate. In some embodiments, the illumination or illumination is carried out or effected between or between about 30 minutes and 96 hours after administering the phthalocyanine dye-targeting molecule conjugate, such as between 30 minutes and 48 hours, 30 minutes and 24 hours or 12 hours and 48 hours, such as generally at least 30 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours or more after administering the conjugate. In some embodiments, the illumination is performed within about 24 hours after administering the conjugate or within 24 hours 4 hours after administering the conjugate, or within about 20, 21, 22, 23, 24, 24, 26, 27, or 28 hours after administering the conjugate.

E. Combination Therapy

In some embodiments, also provided are methods and uses that include combination therapies, and combinations, such as combinations for use in accordance with the combination therapy. In some aspects, the combination includes a conjugate provided herein and an additional therapeutic agent, such as an immunomodulatory agent or an anti-cancer agent. In some embodiments, the targeting molecule used for the conjugate in such combination therapies is an antibody, or an antibody fragment, that binds to a target molecule, linked to a phthalocyanine dye provided herein. In some aspects, the combination therapy includes administration of the conjugate and the additional therapeutic, e.g., an immunomodulatory agent, an immune checkpoint inhibitor, and anti-cancer agent, a therapeutic agent that acts against suppressor cells, or a combination thereof. In such methods, the primary tumors, newly arising tumors, invasive tumor cells, and metastatic tumor cells can be sensitized to the treatment with the additional therapeutic agent, such as an immunomodulatory agent, an immune checkpoint inhibitor, therapeutic agent, or an anti-cancer agent. In such methods, the growth of primary tumors, newly arising tumors, invasive tumor cells, and metastatic tumor cells can be inhibited, reduced or eliminated, and/or the volume of one or more tumors is reduced.

The increase in sensitivity as a result of such combination treatments can include, but is not limited to, a reduction of inhibition of tumor growth, a reduction in tumor cell invasion and/or metastasis, an increase in tumor cell killing, an increase in systemic immune response, an increase in new T cell priming, an increase in the diversity of intratumoral CD8' T cells, an increase in the number and/or activity of intratumoral CD8+T effector cells, a decrease in the number and/or activity of intratumoral regulatory T cells, a decrease in the number and/or activity of intratumoral myeloid derived suppressor cells, a decrease in the number and/or activity of intratumoral tumor associated fibroblasts or cancer associated fibroblasts (CAFs), or any combination thereof.

In some embodiments the additional therapeutic agent is an anticancer agent. In some embodiments, the anticancer agent can be one or more of a chemotherapeutic agent, an antibody treatment and/or a radiotherapeutic agent. In some embodiments, the additional therapeutic agent is an anti-cancer agent selected from a checkpoint inhibitor, an immune adjuvant, a therapeutic that acts against suppressor cells, a chemotherapeutic agent, radiation, and a biologic comprising an anti-cancer targeting molecule that binds to a tumor cell.

In some aspects, the additional therapeutic agent is an immunomodulatory agent (also called immune modulating agent), such as an immune checkpoint inhibitor. In some aspects, such combination is employed for treatment of the tumor, lesion or cancer. In some embodiments, the methods include the administration of the immunomodulatory agent, such as an immune checkpoint inhibitor, prior to, concurrent with or subsequent to the administration of a provided conjugate.

In some embodiments, the additional therapeutic agent, such as an immunomodulatory agent, used in such combination therapies herein can include an adjuvant, immune checkpoint inhibitor, cytokine or any combination thereof. A cytokine for use in the combinations can be, for example, Aldesleukin (PROLEUKIN), Interferon alfa-2a, Interferon alfa-2b (Intron A), Peginterferon Alfa-2b (SYLATRON/PEG-Intron), IL-15, IL-18, or a cytokine that targets the IFNAR1/2 pathway, the IL-2/IL-2R pathway. An adjuvant for use in the combinations can be, for example, Poly ICLC (HILTONOL/Imiquimod), 4-1BB (CD137; TNFRS9), OX40 (CD134) OX40-Ligand (OX40L), Toll-Like Receptor 2 Agonist SUP3, Toll-Like Receptor TLR3 and TLR4 agonists and adjuvants targeting the Toll-like receptor 7 (TLR7) pathway, other members of the TNFR and TNF superfamilies, other TLR2 agonists, TLR3 agonists and TLR4 agonists.

In some embodiments, the additional therapeutic agent is an immune checkpoint inhibitor that is a PD-1 inhibitor, such as a small molecule, antibody or antigen binding fragment that inhibits PD-1 activity. Exemplary antibodies that target PD-1 include, but are not limited to, AB122, AK104, AK105, AMG 404, AMP-224, AMP-514 (MEDI0680), BCD-100, BCD-217, BI 754091, Camrelizumab(SHR1210), Cemiplimab (LIBTAYO; REGN2810), Cetrelimab (JNJ-63723283), CS1003, CX-188, Dostarlimab (TSR-042), F520, Genolimzumab (APL-501: GB226, CBT-501), GLS-010, HLX10, HX008, HX009, IBI308, JTX-4014, LZM009, MGA012 (INCMGA0012), MGD013, MGD019, Nivolumab (OPDIVO, BMS-936558), PDR001, Pembrolizumab (KEYTRUDA, Lambrolizumab, MK-3475), PF-06801591, Pidilizumab (CT-011), REGN2810, RO7121661, SCT-110A, SG001, Sintilimab (TYVYT, IBI308), Spartalizumab (PDR001), Sym021, Tislelizumab (BGB-A317), Toripalimab (JS 001), TSR-042 (ANB011), and XmAb20717.

In some embodiments, the additional therapeutic agent is an immune checkpoint inhibitor that is a PD-L1 inhibitor, such as a small molecule, antibody or antigen binding fragment that inhibits PD-L1 activity. Exemplary antibodies that target PD-L1 include but are not limited to, Atezolizumab (TECENTRIQ, MPDL3280A, RG7446), Avelumab (BAVENCIO, MSB0010718C; M7824), BCD-135, BGB-A333, BMS-936559 (MDX-1105), CBT-502 (TQB-2450), Cosibelimab (CK-301), CS1001 (WPB3155), Durvalumab (IMFINZI; MED14736), FAZ053, HLX20, INBRX-105, KN035, KN046, LDP, LY3300054, LY3415244, MCLA-145, MSB2311, NM-01, REGN3504, SHR-1316 (HTI-1088), STI-3031 (IMC-001; STI-A1015), TG-1501, and ZKAB001 (STI-A1014).

In some embodiments, the additional therapeutic agent is an immune checkpoint inhibitor that is a CTLA-4 inhibitor, such as a small molecule, antibody or antigen binding fragment that inhibits CTLA-4 activity. In some of any embodiments, the antibody that targets CTLA-4 is selected from the group consisting of ADG116, ADU-1604, AGEN1181, AGEN1884, AK104, ATOR-1015, BCD-145, BCD-217, BMS-986218, Ipilimumab (YERVOY), KN046, MGD019, MK-1308, REGN4659, Tremelimumab (Ticilimumab, CP-675,206), XmAb20717, and XmAb22841.

In some embodiments, the additional therapeutic agent is a CD25 inhibitor, such as a small molecule, antibody or antigen binding fragment that inhibits CD25 activity. In some of any embodiments, the anti-CD25 antibody is selected from the group consisting of Basiliximab (SIMULECT), Camidanlumab tesirine, daclizumab (Zinbryta; Zenapax), Inolimomab, RA8, STI-003, and Xenopax.

The administration of an additional therapeutic agent, such as a checkpoint inhibitor, adjuvant or cytokine, can be administered prior to, concurrent with, or subsequent to the administration of the provided conjugates. For example, the methods can include administering one or more doses of an immune checkpoint inhibitor, administering a conjugate, and after administration of the conjugate, illuminating with a suitable wavelength of light a target area. The methods can include first administering the conjugate, and after administration of the conjugate, illuminating a target area, and then administering an additional therapeutic agent, such as an immune checkpoint inhibitor, subsequently either to administration of the conjugate or subsequently to the illumination step. The methods can also include the administration of an additional therapeutic agent, such as an immune checkpoint inhibitor, concurrently with administration of the conjugate, followed by illuminating a target area. In some embodiments, an additional therapeutic agent, such as an immune checkpoint inhibitor, adjuvant or cytokine, is administered one or more times, prior to when a provided conjugate is administered, followed by illuminating a target area, and then one or more additional administrations of an additional therapeutic agent (the same or a different additional therapeutic agent).

F. Other Uses

Also provided are other methods and uses for the conjugates provided herein. In some embodiments, the provided conjugates are used for purposes associated with diagnostics, monitoring, or research, such as laboratory research. For example, in some embodiments, the provided conjugates are used for visualizing or detecting a target molecule or interaction of interest. Such applications include, but are not limited to, imaging, DNA sequencing, DNA microarray, immunoblotting (e.g., Western blotting), flow cytometry analysis, protein microarray, and fluorescence resonance imaging transfer (FRET). In some embodiments the provided conjugates are used for detection of enzyme activity, screening in high throughput applications, detection of protein interactions (e.g., ligand-receptor interactions), and nucleic acid hybridizations.

For example, in some embodiments, the provided conjugates are used as in vitro, in vivo, or ex vivo imaging agents of cells, tissues or organs in various biomedical applications including, but not limited to, tomographic imaging of organs, monitoring of organ functions, coronary angiography, fluorescence endoscopy, imaging of tumors, laser guided surgery, photoacoustic and sonofluorescence methods, and other similar methods.

In some embodiments, the conjugates are administered to a subject for visualization or detection in vivo. In such embodiments, the compositions are administered in doses effective to achieve the desired optical image of a tumor, tissue, or organ. Such doses may vary widely, depending upon the particular dye compound or conjugate employed, the tumor, tissue, or organ subjected to the imaging procedure, the imaging equipment being used, and other factors. In some embodiments, the provided conjugates are used for the visualization of a disease or condition. The equipment for such visualization is selected as appropriate for the disease or condition to be visualized, such as by direct microscopic imaging, endoscopic visualization, or 2D or 3D image reconstruction. Exemplary diseases or conditions for which the provided conjugates can be used to visualize include, but are not limited to, ocular diseases or conditions, skin diseases or conditions; vascular disorders, such as atherosclerotic plaques or other vascular abnormalities; gastrointestinal, oral, bronchial, cervical, and urinary diseases and tumors; and other tumors, such as breast or brain tumors.

In some aspects, the provided conjugates are used for visualization by immunofluorescence of formalin-fixed cells or tissue, or live-cell imaging, in vitro or ex vivo.

G. Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known to the skilled person in this technical field. Reference to "about" value or parameter herein includes (and describes) embodiments that are directed to that value or parameter per se. For example, description referring to "about X" includes description of "X".

As used herein, a "conjugate" refers to a targeting molecule linked directly or indirectly to a photoactivatable dye described herein, in particular a phthalocyanine dye of Formula (0), Formula (I), or Formula (II), produced by chemical conjugation and those produced by any other methods. For example, a conjugate can refer to a phthalocyanine dye provided herein linked directly or indirectly to one or more targeting molecules, such as to a polypeptide that binds to or targets to a cell surface protein. A targeting molecule can be, for example, a protein, a glycoprotein, an antibody, an antibody fragment, an affibody, an antigen, an antigen binding fragment, a peptide, a poly-peptide, a tissue homing peptide, a small molecule, a polymeric synthetic molecule, a polymeric nanoparticle, a liposome, an enzyme substrate, a hormone, a neurotransmitter, a cell metabolite, a viral particle, a viral capsid, a viral nanoparticle, a bacterial particle, a marker, a cell, a hapten, an avidin, a streptavidin, a monomeric streptavidin, a biotin, a carbohydrate, an oligosaccharide, a polysaccharide, a nucleic acid, a deoxy nucleic acid, a fragment of DNA, a fragment of RNA, an aptamer, nucleotide triphosphates, acyclo terminator triphosphates, PNA, or a chemical moiety.

As used herein, "protein" and "poly peptide" are used interchangeably. Proteins may include moieties other than amino acids (e.g., may be glycosylated, etc.) or may be otherwise processed or modified. Those of ordinary skill in the art will appreciate that a "protein" can be a complete protein chain as produced by a cell (with or without a signal sequence) or can be a protein portion thereof. A protein can sometimes include more than one protein chain, for example, non-covalently or covalently attached, e.g., linked by one or more disulfide bonds or associated by some other means. Polypeptides may contain 1-amino acids, d-amino acids, or both and may contain any of a variety of amino acid modifications or analogs known in the art. Useful modifications include, e.g., terminal acetylation, amidation, methylation. In some embodiments, proteins may comprise natural amino acids, non-natural amino acids, synthetic amino acids, and combinations thereof. In some embodiments, proteins are antibodies, antibody fragments, biologically active portions thereof and/or characteristic portions thereof.

As used herein, an "antibody" refers to a polypeptide comprising at least a light chain or heavy chain immunoglobulin variable region which specifically recognizes and binds an epitope of an antigen, such as a tumor-specific protein. Antibodies are composed of a heavy and a light chain, each of which has a variable region, termed the variable heavy ($V_H$) region and the variable light (V) region. Together, the $V_H$ region and the $V_L$ region are responsible for binding the antigen recognized by the antibody. The term "antibody" also includes intact antibodies and antigen-binding antibody fragments that exhibit antigen binding, such as Fab fragments, Fab' fragments, F(ab)'$_2$ fragments, Fab'-SH fragments, single chain Fv proteins ("scFv"), single domain antibodies (sdAb), such as heavy chain variable region only (VHH) single domain antibodies, scFv fragments, and disulfide stabilized Fv proteins ("dsFv"); diabodies; linear antibodies; and multispecific antibodies formed from antibody fragments. Other antibody fragments or multispecific antibodies formed from antibody fragments include a multivalent scFv, a bispecific scFv or an scFv-CH3 dimer. An scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term "antibody" also includes genetically engineered forms such as modified forms of immunoglobulins, chimeric antibodies, for example, humanized murine antibodies, and heteroconjugate antibodies, such as bispecific antibodies. See also, *Pierce Catalog and Handbook*, 1994-1995 (Pierce Chemical Co., Rockford, Ill.); Kuby, J., *Immunology*, 3$^{rd}$ Ed., W.H. Freeman & Co., New York, 1997.

An "antibody-like" molecule as used herein includes molecules that specifically bind to an antigen but are not structurally related to antibodies. Exemplary anti-body like molecules include, but are not limited to, affibodies, z-domain structures, DARPins, monobodies, anticalins, affilins, affimers (e.g, affimer type 1 molecules and affimer type 2 molecules), affitins, alphabodies, anticalins, avimers, fynomers, kunitz domain peptides, and nanoclamps that specifically bind to an antigen.

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

"Specifically binds" refers to the ability of individual antibodies to specifically immunologically react with an antigen relative to binding to unrelated proteins. For example, a PD-L1-specific binding agent binds substantially only the PD-L1 protein in vitro or in vivo. As used herein, the term "tumor-specific binding agent" includes tumor-specific antibodies and other agents that bind substantially only to a tumor-specific protein in that preparation.

"Antibody-dye molecule" or "antibody-dye conjugate" refers to a molecule that includes both an antibody, such as a tumor-specific antibody, conjugated to a dye molecule provided herein. In some examples the antibody is a humanized antibody (such as a humanized monoclonal antibody) that specifically binds to a surface protein on a cancer cell.

"Antigen" refers to a compound, composition, or substance that can stimulate the production of antibodies or a T cell response in an animal, including compositions (such as one that includes a tumor-specific protein) that are injected or absorbed into an animal. An antigen reacts with the products of specific humoral or cellular immunity, including those induced by heterologous antigens, such as the disclosed antigens. "Epitope" or "antigenic determinant" refers to the region of an antigen to which B and/or T cells respond. For example, an epitope is the piece of an antigen to which an antibody binds. In one embodiment, T cells respond to the epitope, when the epitope is presented in conjunction with an MHC molecule. Epitopes can be formed from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation. Methods of determining spatial conformation of epitopes include, for example, x-ray crystallography and nuclear magnetic resonance.

Examples of antigens include, but are not limited to, peptides, lipids, carbohydrates, polysaccharides, and nucleic acids containing antigenic determinants, such as those recognized by an immune cell. In some examples, an antigen includes a tumor-specific peptide (such as one found on the surface of a cancer cell) or immunogenic fragment thereof.

"Immunomodulatory agent" and "immune modulatory therapy" refer to a therapeutic agent and treatment with such agent, respectively that modulates the immune system, such as a cytokine, an adjuvant and an immune checkpoint inhibitor.

"Immune checkpoint inhibitor" refers to a type of drug that blocks certain proteins made by some types of immune system cells, such as T cells, and some cancer cells. These proteins help keep immune responses in check and can keep T cells from killing cancer cells. When these proteins are blocked, the "brakes" on the immune system are released and T cells are able to kill cancer cells better. Examples of checkpoint proteins found on T cells or cancer cells include PD-1/PD-L1 and CTLA-4/B7-1/B7-2. Some immune checkpoint inhibitors are used to treat cancer.

As used herein, a combination refers to any association between or among two or more items. The combination can be two or more separate items, such as two compositions or two collections, can be a mixture thereof, such as a single mixture of the two or more items, or any variation thereof. The elements of a combination are generally functionally associated or related.

As used herein, "combination therapy" refers to a treatment in which a subject is given two or more therapeutic agents, such as at least two or at least three therapeutic agents, for treating a single disease. In some embodiments, each therapy can result in an independent pharmaceutical effect, and together can result in an additive or synergistic pharmaceutical effect.

As used herein, "treating" a subject with a disease or condition means that the subject's symptoms are partially or totally alleviated or remain static following treatment. Hence treating encompasses prophylaxis, therapy and/or cure. Prophylaxis refers to prevention of a potential disease and/or a prevention of worsening of symptoms or progression of a disease.

As used herein, "treatment" means any manner in which the symptoms of a condition, disorder or disease or other indication, are ameliorated or otherwise beneficially altered.

As used herein, "therapeutic effect" means an effect resulting from treatment of a subject that alters, typically improves or ameliorates the symptoms of a disease or condition or that cures a disease or condition.

As used herein, amelioration of the symptoms of a particular disease or disorder by a treatment, such as by administration of a pharmaceutical composition or other therapeutic, refers to any lessening, whether permanent or temporary, lasting or transient, of the symptoms that can be attributed to or associated with administration of the composition or therapeutic.

As used herein, the term "subject" refers to an animal, including a mammal, such as a human being.

As used herein, "optional" or "optionally" means that the subsequently described event or circumstance does or does not occur, and that the description includes instances where said event or circumstance occurs and instances where it does not. For example, an optionally substituted group means that the group is unsubstituted or is substituted.

As used herein, a "tumor" refers to an abnormal mass of tissue that results when cells divide more than they should or do not die when they should. Tumors may be benign (not cancer), or malignant (cancer).

As used herein, a "lesion" refers to an area of abnormal tissue. A lesion may be benign (not cancer) or malignant (cancer).

As used herein, an "anti-cancer agent" refers to any molecules that are used for treatment to stop or prevent cancer. Examples may include, but are not limited to, small chemical molecules, antibodies, antibody conjugates, immunomodulators, or any combination thereof.

As used herein, a "suppressor cell" or an "immunosuppressor cell" refers to cells that are able to decrease or inhibit the function of immune effector cells such as CD8+T effector cells. Example for suppressor cells may include, but are not limited to, regulatory T cells, M2 macrophages, myeloid derived suppressor cells, tumor associated fibroblasts, or cancer associated fibroblasts.

As used herein, an "immunosuppressive agent" refers to an agent that decreases the body's immune responses. It reduces the body's ability to fight infections and other diseases, such as cancer.

As used herein, "resistant to treatment" refers to that a disease or a pathological condition that is not responsive to a treatment, so that this treatment is not effective or does not show efficacy in treating this disease or pathological condition.

As used herein, "systemic immune response" refers to the ability of a subject's immune system to respond to an immunologic challenge or immunologic challenges, including those associated with a tumor, a lesion or a cancer, in a systemic manner. Systemic immune response can include systemic response of the subject's adaptive immune system and/or innate immune system. Systemic immune response includes an immune response across different tissues, including the blood stream, lymph node, bone marrow, spleen and/or the tumor microenvironment, and in some cases, includes a coordinated response among the tissues and organs and various cells and factors of the tissues and organs.

As used herein, "local immune response" refers to the immune response in a tissue or an organ to an immunologic challenge or immunologic challenges including those associated with a tumor, a lesion or a cancer. Local immune response can include the adaptive immune system and/or innate immune system. Local immunity includes immune response concurrently occurring at different tissues, including the blood stream, lymph node, bone marrow, spleen and/or the tumor microenvironment.

As used herein, a "protected form" of the reactive group means certain functional groups of the reactive group or the reactive group itself, including hydroxyl, amino, mercapto and carboxylic acid groups, are protected by a suitable protecting group, using standard techniques which are well-known to those in the art and as described herein. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl and the like. Suitable protecting groups for amino, amidino and guanidino include t-butoxy carbonyl, benzyloxycarbonyl and the like. Suitable protecting groups for mercapto include —C(O)R (where R is alkyl, aryl or aralkyl), p-methoxybenzyl, trityl and the like. Suitable protecting groups for carboxylic acid include alkyl, aryl or aralkyl esters. The use of protecting groups is described in detail in Peter G. M. Wutz, *Greene's Protective Groups in Organic Synthesis,* (2014)5$^{th}$ Edition, John Wiley & Sons, Inc.

In some embodiments, the axial silicon-containing ligand is described as having a conjugatable group. In some embodiments, the axial silicon-containing ligand is described as having a reactive group. The terms "conjugatable" and "reactive", as used in this disclosure, are synonymous and interchangeable, and no distinction between the two terms shall be construed.

As used herein, the terms "reactive group" and "conjugatable group" are used interchangeably and are intended to be construed as a moiety that is capable of chemically reacting with a functional group on a different molecule (e.g., targeting molecule) to form a linkage, such as a covalent linkage. Typically, the reactive group is an electrophile or nucleophile that can form a covalent linkage through exposure to the corresponding functional group that is a nucleophile or electrophile, respectively. Alternatively, the reactive group is a photoactivatable group, and becomes chemically reactive only after illumination with light of an appropriate wavelength. Typically, the conjugation reaction between the reactive dye and the targeting molecule to be conjugated results in one or more atoms of the reactive group A incorporated into a new linkage attaching the dye to the conjugated targeting molecule.

In some embodiments, A is a reactive group that is reactive with a carboxyl group, an amine, or a thiol group on the targeting molecule. Suitable reactive groups include, but are not limited to, an activated ester, an acyl halide, an alkyl halide, an anhydride, a carboxylic acid, a carbodiimide, a carbonate, a carbamate, a haloacetamide (e.g., iodoacetamide), an isocyanate, an isothiocyanate, a maleimide, an NHS ester, a phosphoramidite, a platinum complex, a sulfonate ester and a thiocyanate for optional attachment to the targeting molecule. In some embodiments, the reactive groups are reactive with a carboxyl group, an amine, or a thiol group on a targeting molecule. In some embodiments, the reactive group is a sulfhydryl-reactive chemical group such as maleimide, haloacetyl, pyridyl disulfide, aziridines, acryloyl, arylating agents, vinylsulfones, pyridyl di-sulfides and the like. In some embodiments, the reactive group is amine-reactive. In some embodiments, the reactive group is an NHS ester.

As used herein, a "reacted form" of the reactive group means that the reactive group has undergone chemical reaction resulting in covalent linkage with another molecule.

As used herein, "water soluble group" refers to a group comprising one or more polar and/or ionic substituents that improves the solubility of the overall molecule in aqueous media. Water soluble groups include, but are not limited to a carboxylate (—CO$_2$) group, poly(ethyleneglycol), sulfonate (—SO$_3$) group, a sulfonyl (—SO$_2$) group, a sulfate (—SO$_4$) group, a hydroxyl (—OH) group, a phosphate (—OPO$_3^{-2}$) group, a phosphonate (—PO$_3^{-2}$) group, an amine (—NH$_2$) group and an optionally substituted quaternized nitrogen with each having an optional counter ion.

In certain embodiments, the water soluble group is a trivalent or tetravalent nitrogen-containing group. In yet certain embodiments, the water soluble group is tris-sulfoalkyl or tris-sulfonate quaternary ammonium, bis-sulfoalkyl or bis-sulfonate amine, or bis-alkoxypolyethylene glycol amine.

As used herein, "alkenylene" refers to a straight or branched divalent unsaturated hydrocarbon chain consisting of carbon and hydrogen atoms, having one to twelve carbon atoms, wherein the unsaturation is present only as double bonds and wherein the double bond can exist between any two carbon atoms in the chain, e.g., ethenylene, prop-1-enylene, but-2-enylene and the like. The alkenylene chain may be attached to the rest of the molecule through any two carbons within the chain.

The term "alkoxy" as used herein and unless otherwise indicated, refers to a group of formula O(alkyl). Alkoxy can be, for example, methoxy, ethoxy, n-propoxy, isopropoxy, n-butoxy, iso-butoxy, sec-butoxy, n-pentoxy, 2-pentoxy, 3-pentoxy, or hexyloxy.

The term "alkenyl" as used herein and unless otherwise indicated, refers to a straight or branched hydrocarbon chain radical containing the indicated number of carbon atoms or otherwise having from two to ten, two to eight or two to six carbon atoms, having one or more carbon-carbon double bonds and which is attached to the rest of the molecule by a single bond or a double bond. Alkenyl groups can include, e.g., vinyl, allyl, 1-butenyl, and 2-hexenyl. In some embodiments, an alkenyl is a $C_2$-$C_6$ alkenyl.

The term "alkyl" as used herein and unless otherwise indicated, refers to a saturated hydrocarbon chain radical that may be a straight chain or branched chain, containing the indicated number of carbon atoms or otherwise having from one to ten, one to eight, one to six or one to four carbon atoms, and which is attached to the rest of the molecule by a single bond. In certain embodiments, the hydrocarbon chain is optionally deuterated. For example, $C_1C_6$ alkyl indicates that the group may have from 1 to 6 (inclusive) carbon atoms in it. In some embodiments, an alkyl is a $C_1$-$C_6$ alkyl which represents a straight-chain or branched saturated hydrocarbon radical having 1 to 6 carbon atoms. Examples of alkyl include without limitation methyl, ethyl, n-propyl, isopropyl, n-butyl, isobutyl, sec-butyl, and tert-butyl.

As used herein, "alkylene" refers to a straight or branched divalent hydrocarbon chain consisting of carbon and hydrogen, containing no unsaturation, and having from one to twelve carbon atoms, e.g., methylene, ethylene, propylene or n-butylene. The alkylene chain may be attached to the rest of the molecule through any two carbons within the chain.

The term "alkynyl" as used herein and unless otherwise indicated, refers to a straight or branched hydrocarbon chain radical containing the indicated number of carbon atoms or otherwise having from two to ten, two to eight or two to six carbon atoms and having one or more carbon-carbon triple bonds. Alkynyl groups can include, e.g., ethynyl, propargyl, 1-butynyl, and 2-hexynyl. In some embodiments, an alkynyl is a $C_2$-$C_6$ alkynyl.

The term "amino" refers to a radical having the formula —NR'R" wherein R' and R" are each independently hydrogen, alkyl or haloalkyl.

The term "aralkyl" as used herein and unless otherwise indicated, refers to an alkyl radical in which an alkyl hydrogen atom is replaced by an aryl group. One of the carbons of the alkyl moiety serves as the point of attachment of the aralkyl group to another moiety. Non-limiting examples of "aralkyl" include benzyl, 2-phenylethyl, and 3-phenylpropyl groups.

The term "aryl" as used herein and unless otherwise indicated, is intended to mean any stable monocyclic or bicyclic carbon ring radical of up to 6 members in each ring, wherein at least one ring is aromatic. Examples of aryl include phenyl, naphthyl, tetrahydronaphthyl, indanyl, or biphenyl.

As used herein, "arylene" refers to a divalent aryl group having six to fourteen carbon atoms, that may be attached to the rest of the molecule through any two carbons within the carbocyclic group. For example, six-membered arylene includes 1,2-phenylene, 1,3-phenylene and 1,4-phenylene linkers wherein the attachment points of the phenylene are in the ortho, meta or para configuration, respectively.

The term "aralkylene" as used herein and unless otherwise indicated, refers to an aralkyl radical attached to the rest of the molecule through any two carbons within the moiety. Non-limiting examples of "aralkylene" include —(C$_6$H$_4$)—(CH$_2$)—, —(CH$_2$)—(C$_6$H$_4$)—(CH$_2$)—, and —(CH$_2$)—(C$_6$H$_4$)— groups. The aryl portion of an aralkylene group may have six to fourteen carbon atoms, that may be attached to the rest of the molecule through any two carbons within the aralkylene group. For example, the six-membered arylene includes 1,2-phenylene, 1,3-phenylene and 1,4-phenylene linkers wherein the attachment points of the phenylene are in the ortho, meta or para configuration, respectively.

The term "cycloalkyl" as used herein and unless otherwise indicated, refers to a monocyclic, bicyclic, tricyclic or other polycyclic hydrocarbon radical having the indicated number of ring carbon atoms or otherwise having three to ten carbon atoms and which are fully saturated or partially unsaturated. Multicyclic cycloalkyl may be fused, bridged or spiro-ring systems. Cycloalkyl groups include, but are not limited to, cyclopropyl, cyclobutyl, cyclopentyl, cyclohexyl, cycloheptyl, cyclooctyl, norbornyl, and partially unsaturated hydrocarbon rings such as cyclobutylene, cyclopentene and cyclohexene. In some embodiments, cycloalkyl is a monocyclic $C_3$-$C_8$ cycloalkyl.

As used herein, "cycloalkylene" refers to a divalent saturated or partially saturated carbocycle group having three to eight carbon atoms, that may be attached to the rest of the molecules through any two carbons of the cycloalkyl. Cycloalkylene groups include but are not limited to cyclopropylene, cyclobutylene, cyclopentylene and cyclooctylene.

The term "halo", "halogen" or "halide" as used herein and unless otherwise indicated, refers to any radical of fluorine, chlorine, bromine or iodine.

The term "haloalkyl" as used herein and unless otherwise indicated, refers to an alkyl radical in which at least one hydrogen atom is replaced by a halogen. In some embodiments, more than one hydrogen atom (e.g., 2, 3, 4, 5 or 6) are replaced by halogens. In these embodiments, the hydrogen atoms can each be replaced by the same halogen (e.g., fluoro) or the hydrogen atoms can be replaced by a combination of different halogens (e.g., fluoro and chloro). "Haloalkyl" also includes alkyl moieties in which all hydrogens have been replaced by halogens (sometimes referred to herein as perhaloalkyl, e.g., perfluoroalkyl, such as trifluoromethyl).

As used herein "heteroalkylene" refers to an alkylene group, as defined above, wherein the at least one carbon atom of the alklyene chain is replaced with a heteroatom including —NR$^d$—, —O—, —OP(R$^e$)(R$^f$)O—, —S—, —S(O)—, —S(O)$_2$—, —C(O)—, —C(S)—, or —C(NOR$^d$)— where R$^d$ is R$^e$, and R$^f$ are both =O; or one of R$^e$ and R$^f$ is =O and the other of R$^e$ and R$^f$ is OR$^a$; where Ra is alkyl as defined herein. In some embodiments, the heteroatom is within the alkylene chain (i.e., the heteroalkylene comprises at least one carbon-Z-carbon bond where Z is —NR$^g$— and R$^g$ is hydrogen or alkyl, —O—, —OP (R$^e$)(R$^f$)O—, —S—, —S(O)— or —S(O)$_2$—).

The term "heteroaryl" as used herein, and unless otherwise indicated, is intended to mean any stable monocyclic or bicyclic aromatic ring radical of up to 10 members in each ring, containing at least one hetero atom selected from N, O, S(O) and S(O)$_2$. Examples of heteroaryl include furan, pyrrole, oxazole, thiazole, imidazole, pyrazole, isoxazole, isothiazole, pyridine, pyridazine, pyrimidine, pyrazine, triazine, indolizine, indole, isoindole, benzofuran, benzothiophene, indazole, benzimidazole, benzthiazole, purine, quinoline, isoquinoline, cinnoline, phthalazine, quinazoline, quinoxaline, or naphthyridine.

The term "heteroaralkylene" as used herein and unless otherwise indicated, refers to an heteroaralkyl radical attached to the rest of the molecule through any two atoms within the moiety. Non-limiting examples of "heteroaralkylene" include -(heteroarylene)-(CH$_2$)—, —(CH$_2$)-(heteroarylene)-(CH$_2$)—, and —(CH$_2$)-(heteroarylene)-groups. The heteroaryl portion of a heteroaralkylene group may have five to ten ring atoms, that may be attached to the rest of the molecule through any two atoms within the heteroaralkylene group. For example, the heteroaralkylene group may comprise a six-membered heteroarylene comprising includes 1,2-pyridine, 1,3-pyridine and 1,4-pyridine linkers wherein the attachment points of the pyridine are in the ortho, meta or para configuration, respectively.

As used herein, "heteroarylene" refers to a divalent radical heteroaryl group containing at least one heteroatom selected from N, O, S, S(O) and S(O)$_2$, which heteroaryl group may be attached to the rest of the molecule through any two atoms of the heteroaryl.

As used herein, "heterocycloalkylene" refers to a divalent six-membered saturated or partially saturated heterocyclyl group containing at least one heteroatom selected from N, O, S, S(O) and S(O)$_2$ and wherein each carbon atom of the heterocyclyl may be optionally substituted with oxo; which heterocyclyl group may be attached to the rest of the molecules through any two carbon and/or nitrogen atoms of the heterocycle.

The term "heterocycle", "heterocyclyl" or "heterocyclic" as used herein and unless otherwise indicated, represents a stable 4-, 5-, 6- or 7-membered monocyclic- or a stable 6-, 7-, 8-, 9-, 10-, 11-, or 12-membered bicyclic heterocyclic ring system which comprises at least one non-aromatic (i.e. saturated or partially unsaturated) ring which consists of carbon atoms and from one to four, preferably up to three, heteroatoms selected from the group consisting of N, O and S, w % herein the carbon, nitrogen and sulfur atoms may optionally be oxidized as carbonyl, N-oxide, or sulfoxide/sulfone, respectively, and wherein the nitrogen atom may optionally be quaternized. A heterocycle can be bonded via a ring carbon atom or, if available, via a ring nitrogen atom. Bicyclic heterocyclic ring systems may be fused, bridged, or spiro-bicyclic heterocyclic ring system(s). In some embodiments, heterocyclyl is monocyclic having 4 to 7 or 4 to 6, ring atoms, of which 1 or 2 are heteroatoms independently selected from the group consisting of N, O and S. In some embodiments, a heterocyclyl group is bicyclic, and in which case, the second ring may be an aromatic or a non-aromatic ring which consists of carbon atoms and from one to four, preferably up to three, heteroatoms independently selected from the group consisting of N, O and S, or the second ring may be a benzene ring, or a "cycloalkyl", or a "cycloalkenyl", as defined herein. Examples of such heterocyclic groups include, but are not limited to azetidine, chroman, dihydrofuran, dihydropyran, dioxane, dioxolane, hexahydroazepine, imidazolidine, imidazoline, indoline, isochroman, isoindoline, isothiazoline, isothiazolidine, isoxazoline, isoxazolidine, morpholine, oxazoline, oxazolidine, oxetane, piperazine, piperidine, dihydropyridine, tetrahydropyridine, dihydropyridazine, pyran, pyrazolidine, pyrazoline, pyrrolidine, pyrroline, tetrahydrofuran, tetrahydropyran, thiamorpholine, tetrahydrothiophene, thiazoline, thiazolidine, thiomorpholine, thietane, thiolane, sulfolane, 1,3-dioxolane, 1,3-oxazolidine, 1,3-thiazolidine, tetrahydrothiopyran, tetrahydrotriazine, 1,3-dioxane, 1,4-dioxane, hexahydrotriazine, tetrahydro-oxazine, tetrahydropyrimidine, perhydroazepine, perhydro-1,4-diazepine, perhydro-1,4-oxazepine, 7-azabicyclo[2.2.1]heptane, 3-azabicyclo[3.2.0]heptane, 7-azabicyclo[4.1.0]heptane, 2,5-diazabicyclo[2.2.1]heptane, 2-oxa-5-azabicyclo[2.2.1]heptane, tropane, 2-oxa-6-azaspiro[3.3] heptane, dihydrobenzofuran, diydrobenzimidazolyl, dihydrobenzoxazole, and dihydrobenzothiazolyl, and N-oxides or sulfones or sulfoxides thereof.

As used herein, "metalloid" refers to a chemical element with properties intermediate between those of typical metals and nonmetals. Metalloids include the chemical elements boron, silicon, germanium, arsenic, antimony, tin, aluminium, zinc and tellurium. In some embodiments, the metal or metalloid is silicon. In some embodiments, the metal or metalloid is germanium. In some embodiments, the metal or metalloid is aluminium. In some embodiments, the metal or metalloid is tin. In some embodiments, the metal or metalloid is zinc. In some embodiments, the metal or metalloid is tellurium.

As used herein, in certain embodiments unless specified otherwise, "optionally substituted alkyl", "optionally substituted alkylene", "optionally substituted heteroalkylene", "optionally substituted alkenylene", "optionally substituted heteroalkenylene" and "optionally substituted alkynyl" refers to alkyl, alkylene, heteroalkylene, alkenylene, heteroalkenylene and alkynyl radicals, respectively, that may optionally be substituted with one or more substituents independently selected from the group consisting of halo, oxo, haloalkyl, hydroxyl, hydroxyalkyl, alkoxy, alkoxyalkyl, haloalkoxy, haloalkoxyalkyl, amino, aminoalkyl, sulfonate, and cyano.

As used herein, in certain embodiments unless specified otherwise, "optionally substituted cycloalkyl", "optionally substituted aryl, "optionally substituted heterocyclyl" and "optionally substituted heteroaryl" refers to cycloalkyl, aryl, heterocyclyl and heteroaryl radicals, respectively, that are optionally substituted with one or more substituents selected from the group consisting of halo, oxo, alkyl, alkenyl, alkynyl, haloalkyl, haloalkenyl, hydroxyl, hydroxyalkyl, alkoxy, alkoxyalkyl, haloalkoxy, haloalkoxyalkyl, amino, aminoalkyl, sulfonate, cyano and nitro.

As used herein, "protein" and "polypeptide" are used interchangeably. Proteins may include moieties other than amino acids (e.g., may be glycosylated, etc.) or may be otherwise processed or modified. Those of ordinary skill in the art will appreciate that a "protein" can be a complete protein chain as produced by a cell (with or without a signal sequence) or can be a protein portion thereof. Those or ordinary skill will appreciate that a protein can sometimes include more than one protein chain, for example, non-covalently or covalently attached, e.g., linked by one or more disulfide bonds or associated by some other means. Polypeptides may contain l-amino acids, d-amino acids, or both and may contain any of a variety of amino acid modifications or analogs known in the art. Useful modifications include, e.g., terminal acetylation, amidation, methylation. In some embodiments, proteins may comprise natural amino acids, non-natural amino acids, synthetic amino acids, and combinations thereof. In some embodiments, proteins are antibodies, antibody fragments, biologically active portions thereof and/or characteristic portions thereof.

H. Preparation of Phthalocyanine Derivative Compounds

In some embodiments, the phthalocyanine compounds disclosed herein are prepared by the general synthetic routes described below in Schemes 1-3. These schemes are intended to be exemplary to one of skill in the art and are not limiting. Additional methods for the synthesis of the phthalocyanine compounds disclosed herein are readily available to one of skill in the art.

A method for preparing phthalocyanine compounds disclosed herein is provided in Scheme 1:

Scheme 1

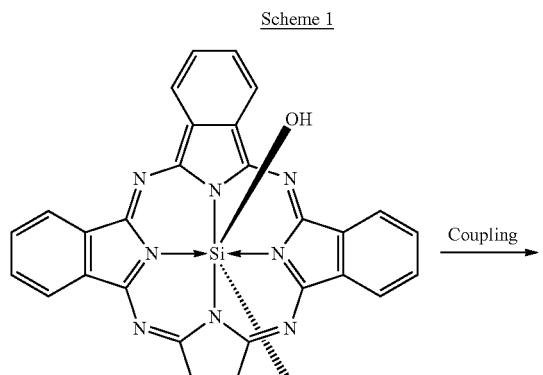

(1-1)

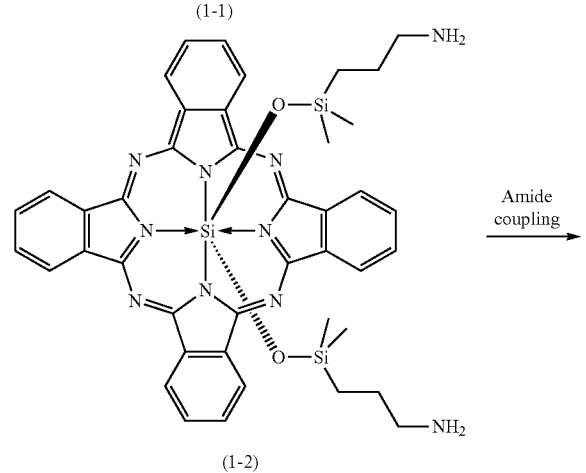

(1-2)

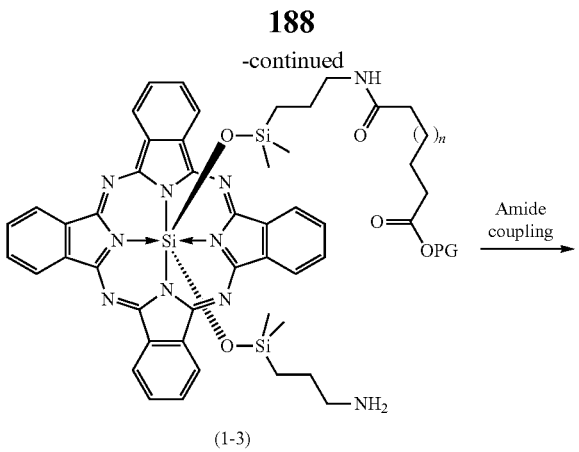

(1-3)

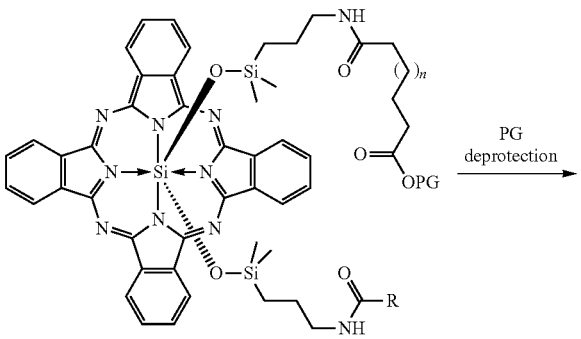

(1-4)

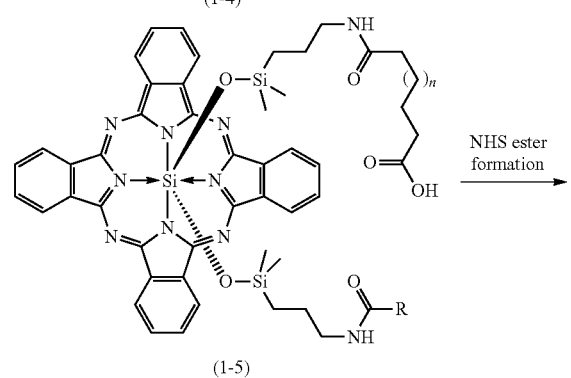

(1-5)

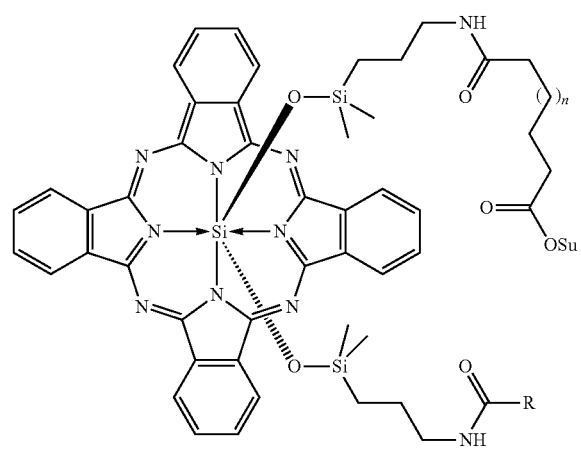

(1-6)

According to Scheme 1, the compound silicon phthalocyanine dihydroxide(1-1) is treated with 3-(ethoxydimethylsilyl)propan-1-amine to afford the axially disubstituted compound (1-2). Amide coupling of (1-2) with a suitable carboxylic acid derivative provides compound (1-3). Further amide coupling with a substituted carboxylic acid derivative affords compound (1-4). Removal of the protective group of (1-4) followed by activation of the generated carboxylic acid, such as by formation of its NHS ester, provides the desired product (1-6).

A method for preparing phthalocyanine compounds disclosed herein is provided in Scheme 2:

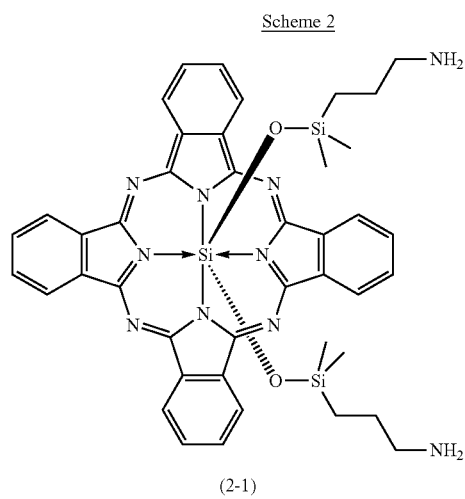

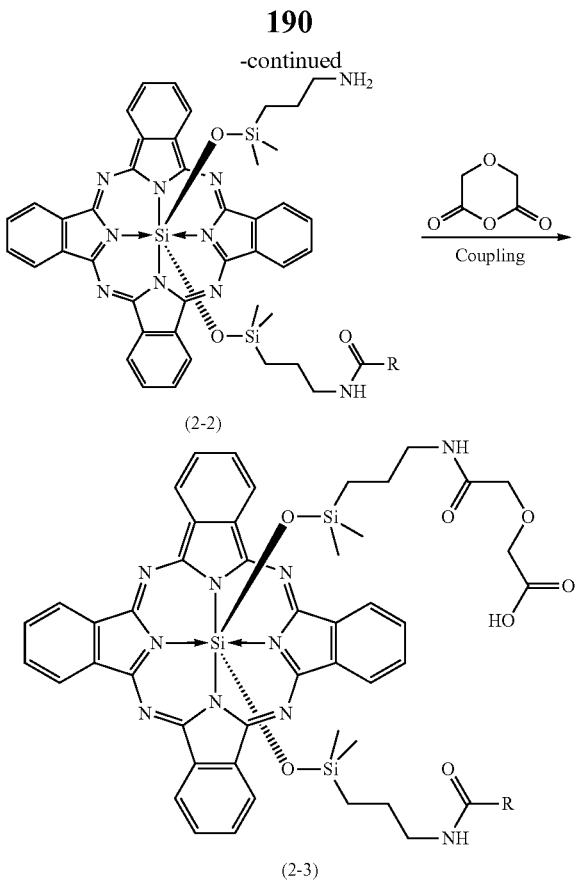

According to the method provided in Scheme 2, compound (2-1) is treated with a substituted carboxylic acid derivative to afford compound (2-2). Further amide coupling with a suitable carboxylic acid derivative provides compound (2-3).

Phthalocyanine compounds disclosed herein may also be prepared by the process outlined in Scheme 3:

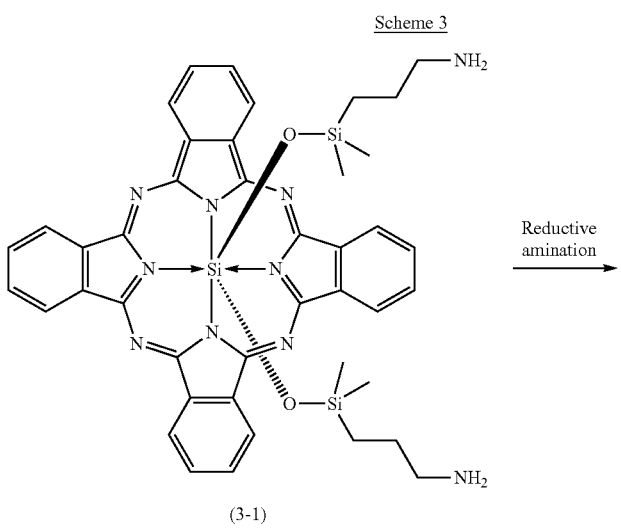

-continued
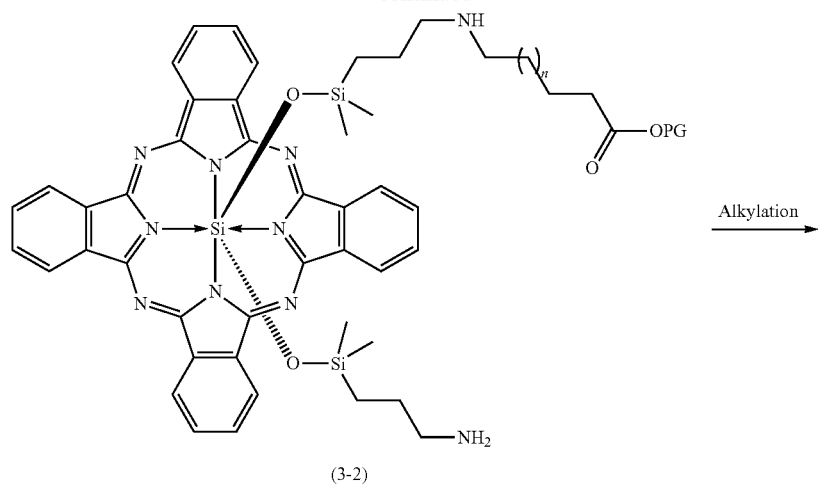
(3-2)
Alkylation →
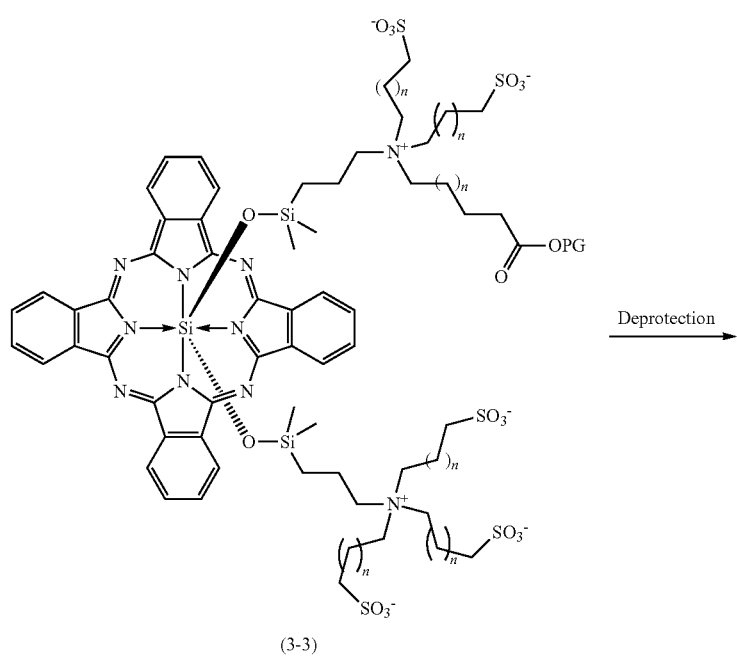
(3-3)
Deprotection →

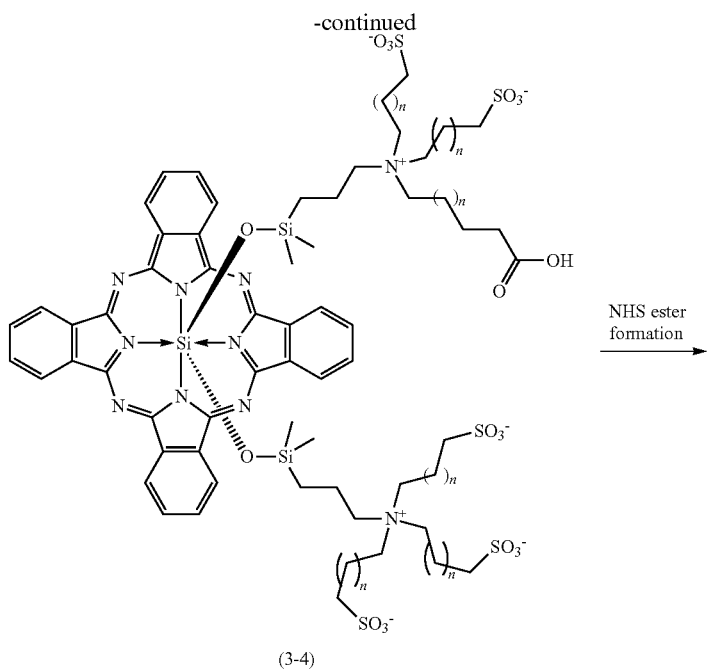

(3-4)

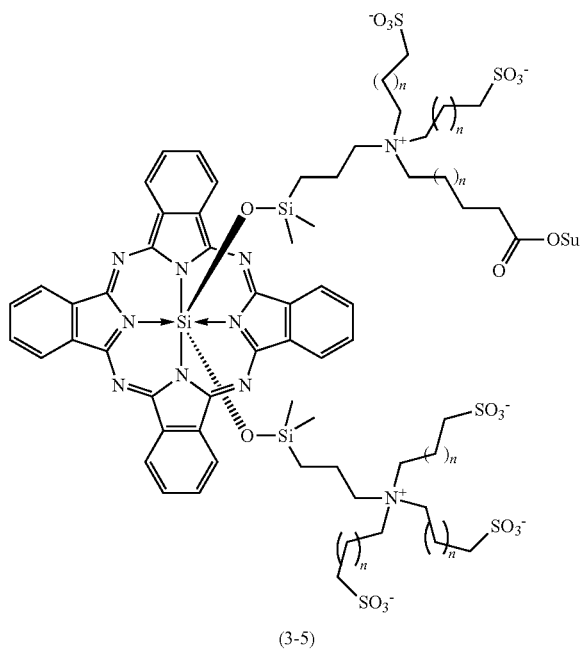

(3-5)

According to Scheme 3, the axially disubstituted compound (3-1) was submitted to reductive alkylation with the corresponding aldehyde to afford the mono-substituted derivative (3-2). Alkylation with the appropriate sulfonate-substituted haloalkyl provides compound (3-3). Removal of the protective group of (3-3) followed by activation of the generated carboxylic acid (3-4), such as by formation of its NHS ester, provides the desired product (3-5).

The subject matter has been described in an illustrative manner, and it is to be understood that the terminology used is intended to be in the nature of description rather than of limitation. Thus, it will be appreciated by those of skill in the art that conditions of solvent, temperature of reaction, volumes, reaction time may vary while still producing the desired compounds. In addition, one of skill in the art will also appreciate that many of the reagents provided in the following examples may be substituted with other suitable reagents. See, e.g., Smith & March, *Advanced Organic Chemistry*, $5^{th}$ ed. (2001). Such changes and modifications, including without limitation those relating to the chemical structures, substituents, derivatives, intermediates, syntheses, formulations and/or methods of use provided herein,

EXAMPLES

I. Chemical Synthesis

Example 1

Preparation of 6-((3-(dimethyl((19-((15-methyl-10-oxo-2,5,8-trioxa-11-aza-15-silahexadecan-15-yl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)silyl)propyl)amino)-6-oxohexanoic Acid Step 1: 3,3'-(((19H-6,11-(azeno)-17,21-(azeno[3]episoindoloazeno)benzo[7,8][1,3,5,10]tetraaza[2]silacycloundecino[4,3-a:11,1-a']diisoindole-19,19-diyl)bis(oxy))bis(dimethylsilanediyl))bis(propan-1-amine)

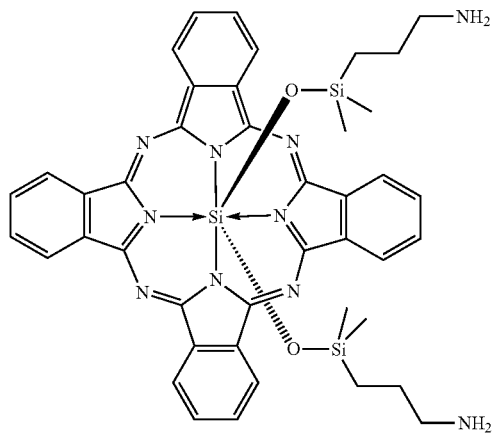

To a suspension of silicon (IV) phthalocyanine dihydroxide (0.5 g, 0.87 mmol) in dry pyridine (40 mL) under a nitrogen atmosphere was added 3-aminopropyldimethylethoxysilane (4.2 g, 26.1 mmol). The resulting mixture was heated at 140° C. for 3 h. Reaction progress was monitored by TLC on neutral alumina (10% MeOH/CH$_2$Cl$_2$). Upon reaction completion, the mixture was filtered and the mother liquor evaporated to dryness under reduced pressure. The resulting residue was suspended in hexane (50 mL), filtered and further washed with diethyl ether (2×10 mL) to afford the Step 1 intermediate (0.4 g, 57% yield) as a dark blue solid. $^1$H-NMR (400 MHz, CDCl$_3$) δ 9.70 (m, 8H), 8.39 (m, 8H), 1.23 (m, 4H), −1.22 ((m, 4H), −2.26 (m, 4H), −2.81 (s, 12H).

Step 2: methyl 6-((3-(((19-(((3-aminopropyl)dimethylsilyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)dimethylsilyl)propyl)amino)-6-oxohexanoate.dimethylsilyl)propyl)amino)-6-oxohexanoate

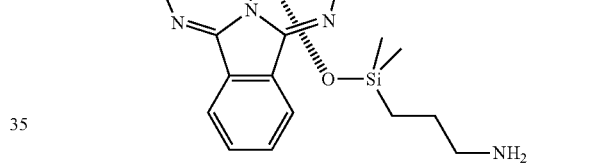

To a solution of 6-methoxy-6-oxohexanoic acid (33 mg, 0.8 eq), HOBt (39 mg, 0.96 eq) and EDCI (46 mg, 0.96 eq) in CH$_2$Cl$_2$ (7 mL) under nitrogen at room temperature was added DMAP (cat.). The reaction was stirred for 1.1 h. This mixture was added dropwise over 24 minutes to a solution of the title compound from Step 1 (200 mg, 0.25 mmol) and DIPEA (82 uL, 1.9 eq) in CH$_2$Cl$_2$ (23 mL). The reaction was stirred for 24 h at room temperature. The mixture was diluted with CH$_2$Cl$_2$ (20 mL) and washed with aqueous saturated NaHCO$_3$ (25 mL). The aqueous phase was separated and extracted with CH$_2$Cl$_2$ (3×8 mL). The combined organic layers were dried over Na$_2$SO$_4$, filtered and concentrated under reduced pressure. The blue residue was purified by silica gel column chromatography (CombiFlash, 24 g column, 0 to 90% MeOH/CH$_2$Cl$_2$) to afford the title compound (74 mg, 31% yield). LCMS: 969 (M+23)$^+$.

Step 3: methyl 6-((3-(dimethyl((19-((15-methyl-10-oxo-2,5,8-trioxa-11-aza-15-silahexadecan-15-yl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)silyl)propyl)amino)-6-oxohexanoate

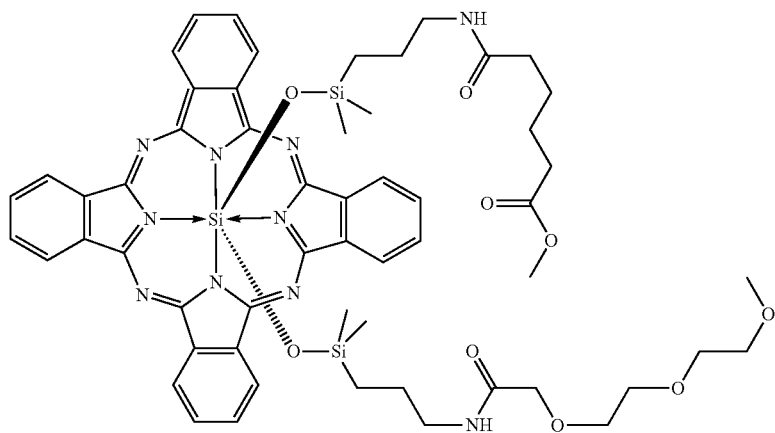

A solution of 2-(2-(2-methoxy ethoxy)ethoxy)acetic acid (14.5 mg, 1.3 eq), HOBt (14.5 mg, 1.5 eq) and EDCI (17 mg, 1.5 eq) in CH$_2$Cl$_2$ (7 mL) under nitrogen at room temperature was stirred for 1 h. A solution of the intermediate from Step 2 (56 mg, 0.059 mmol) in CH$_2$Cl$_2$ (3 mL) was added dropwise followed by $^i$Pr$_2$NEt (20 uL, 2 eq). The reaction mixture was stirred for 21 h at room temperature. It was then diluted with CH$_2$Cl$_2$ (7 mL) and sequentially washed with 0.1 N HCl (10 mL), NaHCO$_3$ (10 mL) and brine (10 mL). Each of the aqueous layers was back-extracted with CH$_2$Cl$_2$ (3 mL). The combined organic layers were dried over Na$_2$SO$_4$, filtered and concentrated under reduced pressure. The residue was purified by silica gel column chromatography (CombiFlash 12 g, 0-60% CH$_2$Cl$_2$/MeOH) to afford the Step 3 intermediate (47 mg, 72% yield) as a solid. $^1$H NMR (CD$_2$Cl$_2$, 500 MHz) δ 9.68 (m, 8H), 8.39 (m, 8H), 3.67 (s, 3H), 3.63 (s, 2H), 3.51 (m, 2H), 3.47 (m, 1H), 3.45 (m, 2H), 3.34 (m, 1H), 3.31 (m, 2H), 3.13 (s, 3H), 2.31 (dd, J=7.5, 7.5 Hz, 2H), 1.88 (dd, J=7.5, 7.5 Hz, 2H), 1.81 (m, 2H), 1.74 (m, 2H), 1.58 (m, 2H), 1.47 (m, 2H), −1.04 (m, 2H), −1.25 (m, 2H), −2.28 (m, 4H), −2.85 (s, 3H), −2.87 (s, 3H).

Step 4: 6-((3-(dimethyl((19-((15-methyl-O-oxo-2,5,8-trioxa-1-aza-15-silahexadecan-15-yl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)silyl)propyl)amino)-6-oxohexanoic Acid To a solution of the intermediate from Step 3 (46 mg, 0.04 mmol) in THF (19 mL) cooled with an ice/water bath was added 0.01N NaOH (12.5 mL, 3 eq) dropwise. The reaction was warmed up to room temperature and stirred for 22 h. The reaction mixture was diluted with EtOAc (20 mL) and washed with saturated aqueous NH$_4$Cl (15 mL). The aqueous phase was separated and extracted with CH$_2$Cl$_2$ (2×5 mL). The combined organic layers were dried over Na$_2$SO$_4$, filtered and concentrated under reduced pressure. The blue residue was purified by silica gel column chromatography (CombiFlash 12 g, 0-60% MeOH/CH$_2$Cl$_2$) to afford the title compound (37.2 mg, 82% yield) as a solid. $^1$H NMR (CD$_2$Cl$_2$. 500 MHz) δ 9.68 (m, 8H), 8.39 (m, 8H), 3.75 (s, 2H), 3.50 (dd. J=5.5, 2.5 Hz, 2H), 3.45 (m, 4H), 3.29 (dd. J=5.8, 3.8 Hz, 2H), 3.12 (s, 3H), 2.47 (dd, J=6.5, 6.5 Hz, 2H), 2.01 (dd, J=7.0, 7.0 Hz, 2H), 1.85 (m, 2H), 1.68 (m, 6H), −1.08 (m, 2H), −1.31 (m, 2H), −2.23 (m, 2H), −2.29 ((m, 2H), −2.85 (s, 3H), −2.86 (s, 3H). LCMS: 1115 (M+23)$^+$

Example 2

Preparation of 2-(2-((3-(dimethyl((19-((15-methyl-10-oxo-2,5,8-trioxa-11-aza-15-silahexadecan-15-yl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)silyl)propyl)amino)-2-oxoethoxy)acetic Acid

Step 1: Synthesis of N-(3-(((19-(((3-aminopropyl)dimethylsilyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)dimethylsilyl)propyl)-2-(2-(2-methoxyethoxy)ethoxy)acetamide

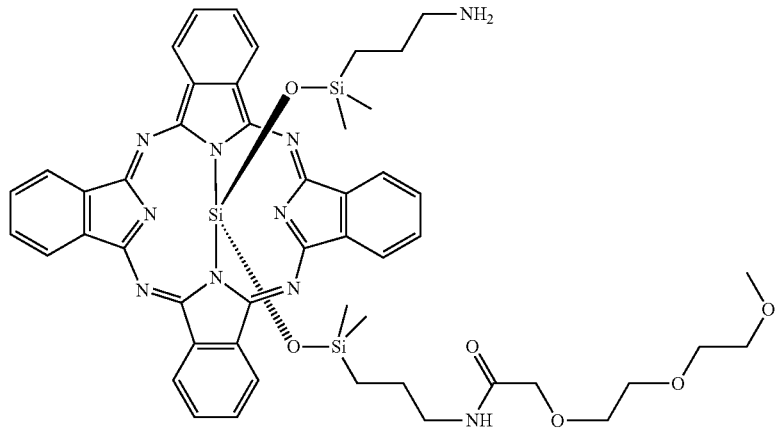 [SMILES: COCCOCCOCC(=O)NCCC[Si](C)(C)O[Si@@]1(O[Si](C)(C)CCCN)n2c3c4ccccc4c2/N=C2N=C(/N=c4/c5ccccc5/c(n41)=N/C1=NC(=N\3)/c3ccccc31)c1ccccc1\2]

To a mixture of 2-(2-(2-methoxyethoxy)ethoxy)acetic acid (5 mg, 0.026 mmol), HOBt (4.3 mg, 1 eq) and EDCI (5 mg, 1 eq) in $CH_2Cl_2$ (1.5 mL) under nitrogen at room temperature was added DMAP (cat.). The reaction was stirred for 1 h and then added dropwise over 15 minutes to a solution of the title compound from Example 1, Step 1, (25 mg, 0.031 mmol) and $Pr_2NEt$ (9 uL, 2 eq) in $CH_2Cl_2$ (3 mL). The reaction was stirred for 24 h at room temperature. It was then diluted with $CH_2Cl_2$ (3 mL) and washed with saturated aqueous $NaHCO_3$ (5 mL). The aqueous phase was separated and extracted with $CH_2Cl_2$ (2×3 mL). The combined organic layers were dried over $Na_2SO_4$, filtered and concentrated under reduced pressure. The blue residue was purified by silica gel column chromatography (Combiflash Isco, 4 g Gold column, 0 to 90% MeOH/$CH_2Cl_2$). $^1$H-NMR ($CD_2Cl_2$, 500 MHz) δ 9.67 (m, 8H), 8.38 (m, 8H), 3.63 (s, 2H), 3.52 ((m, 2H), 3.46 (m, 4H), 3.31 (m, 2H), 3.13 (s, 3H), 1.81 (dd, J=14.0, 7.0, 2H), 1.11 (m, 2H), −1.05 (m, 2H), −1.24 (m, 2H), −2.30 (m, 4H), −2.85 (s, 6H), −2.88 (s, 6H). LCMS: 965 (M+1)$^+$.

Step 2: Synthesis of 2-(2-((3-(dimethyl((19-((15-methyl-10-oxo-2,5,8-trioxa-11-aza-15-silahexadecan-15-yl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)silyl)propyl)amino)-2-oxoethoxy)acetic Acid A solution of the intermediate compound from Step 1 (4.5 mg, 0.005 mmol) and diglycolic anhydride (2.4 mg, 4.3 eq) in DMF (0.5 mL) was stirred at room temperature for 2.5 hours. The reaction mixture was diluted with EtOAc (1 mL) and washed with aqueous $NH_4Cl$ (1 mL). The aqueous phase was separated and extracted with EtOAc (3×1 mL). The combined organic layers were dried over $Na_2SO_4$, filtered and concentrated under reduced pressure. The blue residue was purified by silica gel column chromatography (Combiflash 4 g, 0-90% MeOH/$CH_2Cl_2$) to afford the title compound (3.5 mg, 69% yield). $^1$H NMR ($CD_2Cl_2$, 500 MHz) δ 9.60 (m, 8H), 8.24 (m, 8H), 3.68 (bs, 2H), 3.62 (s, 2H), 3.60 (bs, 2H), 3.47 (m, 2H), 3.42 (m, 4H), 3.27 (m, 2H), 1.81 (m, 2H), 1.26 (m, 2H), −1.06 (m, 2H), −1.34 (m, 2H), −2.31 (m, 2H), −2.50 (m, 2H), −2.85 (s, 6H), −3.00 (s, 6H). LCMS: 1080 (M+1)$^+$.

Example 3

Preparation of 2-(2-((3-(((19-((11-(2-(2-(2-methoxyethoxy)ethoxy)ethyl)-21-methyl-16-oxo-2,5,8,15-tetraoxa-1,17-diaza-2-siladocosan-21-yl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)dimethylsilyl)propyl)amino)-2-oxoethoxy)acetic Acid

Step 1: 11-(2 (2-(2-methoxyethoxy)ethoxy)ethyl)-2,5,8-trioxa-11-azatetradecan-14-yl (4-nitrophenyl) carbonate

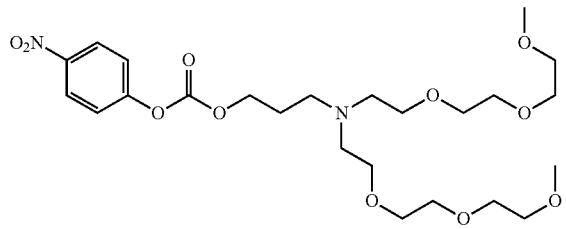 [SMILES: COCCOCCOCCN(CCCOC(=O)Oc1ccc([N+](=O)[O-])cc1)CCOCCOCCOC]

To a solution of 11-(2-(2-(2-methoxyethoxy)ethoxy)ethyl)-2,5,8-trioxa-11-azatetradecan-14-ol (1 g, 2.72 mmol) and TEA (0.75 mL, 5.44 mmol) in dichloromethane (25 mL) cooled to 0° C. was added 4-nitrophenyl chloroformate (0.821 g, 4.09 mmol) portion wise over a 15 min period. The reaction was stirred at room temperature for 6 h. It was then poured over water (50 mL) and extracted with CH$_2$Cl$_2$ (3×50 mL). The combined organic layers were dried over sodium sulfate, filtered and concentrated under reduced pressure to afford the crude Step 1 intermediate compound (1.8 g) that was used in the following step without further purification.

Step 2: 11-(2-(2-(2-methoxyethoxy)ethoxy)ethyl)-2,5,8-trioxa-11-azatetradecan-14-yl (3-(((19-(((3-aminopropyl)dimethylsilyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)dimethylsilyl)propyl)carbamate Step 3: Synthesis of 2-(2-((3-(((19-((11-(2-(2-(2-methoxyethoxy)ethoxy)ethyl)-21-methyl-16-oxo-2,5,8,15-tetraoxa-11,17-diaza-21-siladocosan-21-yl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)dimethylsilyl)propyl)amino)-2-oxoethoxy)acetic Acid To a solution of the intermediate compound from Step 2 (0.08 g, 0.07 mmol) in DMF (2 mL) at room temperature was added 1,4-dioxane-2,6-dione (0.010 g, 0.08 mmol). The reaction was stirred for 30 min and then filtered. The filtrate was diluted with ACN and lyophilized. The residue was

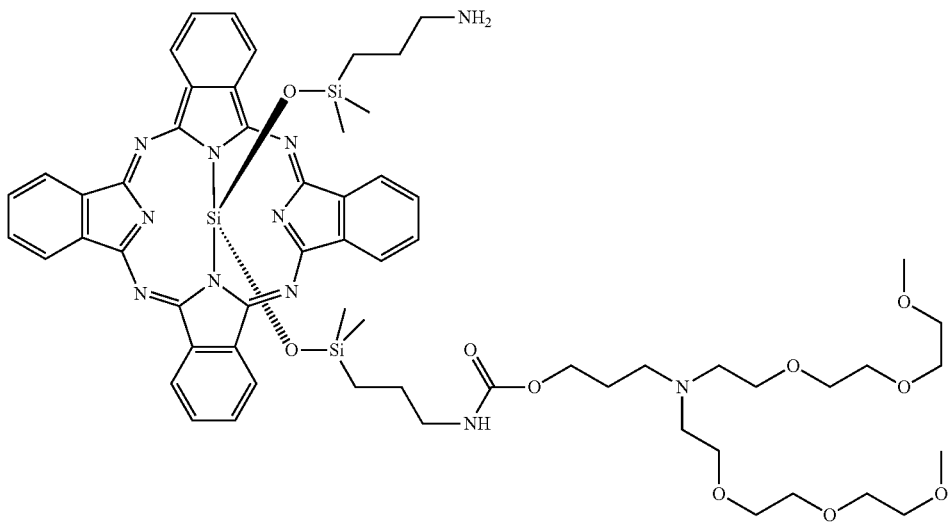 [SMILES: COCCOCCOCCN(CCCOC(=O)NCCC[Si](C)(C)O[Si@@]1(O[Si](C)(C)CCCN)n2c3c4ccccc4c2/N=C2N=C(/N=c4/c5ccccc5/c(n41)=N/C1=NC(=N\3)/c3ccccc31)c1ccccc1\2)CCOCCOCCOC]

To a solution of the intermediate compound from Example 1, Step 1, (0.4 g, 0.49 mmol) in THF (8 mL) was added TEA (0.14 ml, 0.99 mmol). The reaction was cooled to 0° C. and a solution of the title compound from Step 1 (0.26 g, 0.50 mmol) in THF (2 mL) was added drop wise. The resulting mixture was allowed to warm to room temperature and stirred for 1 h. The reaction mixture was poured over water (30 mL) and extracted with CH$_2$Cl$_2$ (3×30 mL). The combined organic layers were dried over sodium sulfate, filtered and concentrated under reduced pressure. The residue was purified by column chromatography on basic alumina (3% MeOH in CH$_2$Cl$_2$) to afford the Step 2 intermediate compound (0.2 g, 34% yield). LCMS: 1199 (M+1)$^+$.

sequentially triturated with diethyl ether (2-3 mL), hexane (2×3 mL) and dried under reduced pressure to afford the title compound (0.025 g, 34% yield) LCMS: 1314 (M+1)$^+$.

Example 4

Preparation of 6-((3-(((19-((11-(2-(2-(2-methoxyethoxy)ethyl)-21-methyl-16-oxo-2,5,8,15-tetraoxa-11,17-diaza-21-siladocosan-21-yl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)dimethylsilyl)propyl)amino)-6-oxohexanoic Acid The title compound was synthesized in a manner similar to Example 3, Step 3, by replacing 1,4-dioxane-2,6-dione for oxepane-2,7-dione (15.4 mg, 1.2 eq). LCMS: 1326 (M+1)$^+$.

Example 5

Preparation of Ammonium 3-((4-((3-(((19-(((3-(2-(carboxymethoxy)acetamido)propyl)dimethylsilyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)dimethylsilyl)propyl)amino)-4-oxobutyl)bis(3-sulfopropyl)ammonio)propane-1-sulfonate

Step 1: Synthesis of 3-((4-(benzyloxy)-4-oxobutyl)bis(3-sulfopropyl)ammonio)propane-1-sulfonate

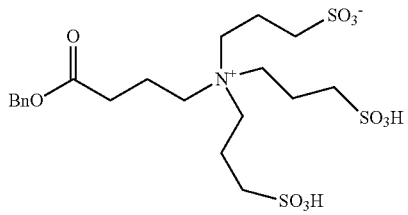

To a solution of benzyl 4-aminobutanoate hydrochloride (1 g, 4.4 mmol) in DMF (5 mL) was added DIPEA (4 mL, 43.7 mmol) followed by 1,2-oxathiolane 2,2-dioxide (2.1 g, 43.7 mmol) at room temperature under nitrogen atmosphere. The reaction mixture was stirred at 150° C. for 16 h. Upon completion, the reaction was cooled to room temperature, poured over a saturated aqueous NaHCO$_3$ solution (8 mL) and stirred for 1 h. The mixture was washed with ethyl acetate (2×15 mL). Lyophilization of the aqueous layer yielded a gummy mass that was triturated with THF (12 mL) to afford a sticky solid (8 g). A gram out of this crude was further purified by preparative HPLC to afford the Step 1 intermediate (310 mg) as its ammonium salt. LCMS: [M+H]$^+$ 560

Step 2: Synthesis of 3-((3-carboxypropyl)bis(3-sulfopropyl)ammonio)propane-1-sulfonate

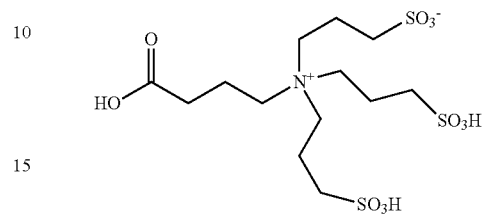

A stirred solution of the intermediate from Step 1 (310 mg, 0.56 mmol) in methanol:water (1:1, 8 mL) was purged with nitrogen for 5 min. 10% palladium on carbon was added and the resulting mixture was stirred under a hydrogen atmosphere for 30 min. Upon reaction completion, the mixture was filtered and washed with methanol:water (1:1, 10 mL). Solvent from the combined filtrates was removed under reduced pressure and the resulting aqueous phase was lyophilized to afford the Step 2 intermediate (271 mg) as a sticky solid. $^1$H-NMR (400 MHz, D$_2$O) δ 3.93 (m, 1H), 3.40-3.25 (m, 5H), 2.88-2.81 (m, 4H), 2.37 (m, 1H), 2.14-2.02 ((m, 4H), 1.91 (bs, 1H), 1.34 (m, 6H), 1.23 (m, 2H). LCMS: [M–H]$^-$ 468.

Step 3: 3-((4-((3-(((19-(((3-aminopropyl)dimethylsilyl)oxy)-19H-6,11-(azeno)-17,21-(azeno[3]episoindoloazeno) benzo[7,8][1,3,5,10]tetraaza[2]silacycloundecino[4,3-a:11,1-a']diisoindol-19-yl)oxy) dimethylsilyl) propyl)amino)-4-oxobutyl)bis(3-sulfopropyl)ammonio)propane-1-sulfonate

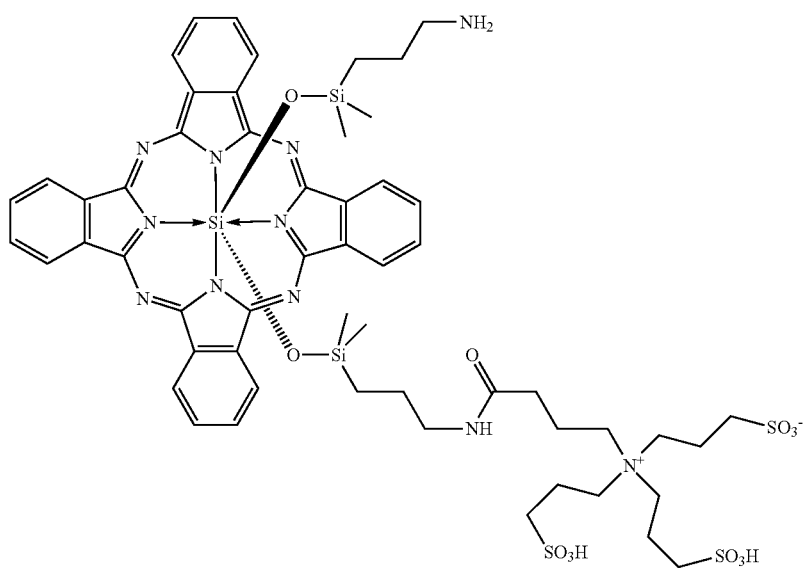

To a solution of the intermediate from Step 2 (0.187 g, 0.40 mmol) in DMF (10 mL) was added DIPEA (0.192 g, 1.49 mmol), EDC.HCl (0.143 g, 0.75 mmol) and HOBt (0.114 g 0.75 mmol) at room temperature under nitrogen atmosphere. The reaction was stirred for 2 h followed by addition of the title compound from Example 1, Step 1 (400 mg, 0.5 mmol). The resulting mixture was stirred at room temperature for 48 h. It was then poured over water (150 mL). The precipitate was collected after centrifugation and purified by preparative HPLC to afford the title compound (30 mg, 5%) as a blue solid. LCMS: [M+H]$^+$ 1256

Step 4. Synthesis of ammonium 3-((4-((3-(((19-(((3-(2-(carboxymethoxy)acetamido)propyl)dimethylsilyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)dimethylsilyl)propyl)amino)-4-oxobutyl)bis(3-sulfopropyl)ammonio)propane-1-sulfonate To a solution of the intermediate from Step 3 (10 mg, 0.008 mmol) in DMF (2 mL) at room temperature under a nitrogen atmosphere was added 1,4-dioxane-2,6-dione (2.8 mg, 0.024 mmol). The reaction mixture was stirred for 5 h and directly submitted to preparative HPLC purification. Appropriate fractions were combined and lyophilized to afford the title compound (3.2 mg, 29%) as a blue solid. $^1$H NMR (400 MHz, DMSO-d6) δ 9.71 (m, 8H), 8.50 (m, 8H), 7.04 (bs, 9H), 6.82 (s, 2H), 3.92 (m, 3H), 3.62 (s, 3H), 3.02 (m, 3H), 1.87 (m, 7H), 1.75 (m, 3H), 1.58 (m, 11H), −1.15 (m, 4H), −2.35 (m, 4H), −2.92 (s, 12H). MS: [M+H]$^+$ 1372.

Example 6

Preparation of 3-((4-((3-(((19-(((3-(6-((λ$^5$-azaneyl)oxy)-6-oxohexanamido)propyl)dimethylsilyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)dimethylsilyl)propyl)amino)-4-oxobutyl)bis(3-(((λ$^5$-azaneyl)oxy)sulfonyl)propyl)ammonio)propane-1-sulfonate The title compound was synthesized in a manner similar to Example 5, Step 4, by replacing 1,4-dioxane-2,6-dione for oxepane-2,7-dione. LCMS: 1385 (M+1)$^+$.

Example 7

Preparation of Ammonium 2-(2-((3-(((19-((dimethyl (3-(3-(2-sulfonatoethyl)ureido)propyl)silyl)oxy)-19H-6,11-(azeno)-17,21-(azeno[1]episoindoloazeno)benzo[7,8][1,3,5,10]tetraaza[2]silacycloundecino[4,3-a:11,1-a']diisoindol-19-yl)oxy)dimethylsilyl)propyl)amino)-2-oxoethoxy)acetate Step 1: Synthesis of Ammonium 2-(3-(3-(((19-(((3-aminopropyl)dimethylsilyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)dimethylsilyl)propyl)ureido)ethane-1-sulfonate

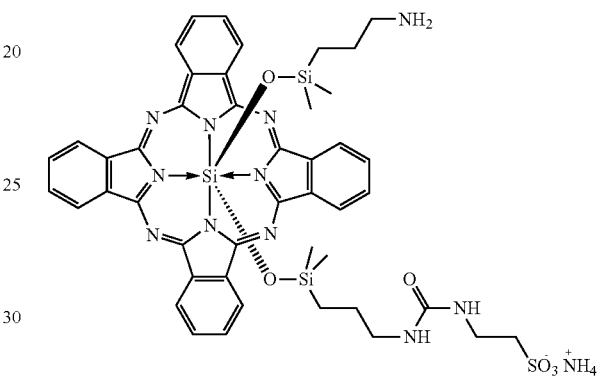

To a stirred solution of the title compound from Example 1, Step 1 (0.150 g, 0.186 mmol) in DCM (10 ml) under nitrogen atmosphere was added DIPEA (0.072 g, 0.560 mmol). The reaction mixture was cool at 0° C. and a solution of tetrabutylammonium 2-(((4-nitrophenoxy)carbonyl)amino)ethane-1-sulfonate (0.079 g, 0.149 mmol) in DCM (3.3 ml) was added dropwise. The reaction was allowed to warm up to room temperature and stirred for 16 h. The reaction mixture was concentrated under reduced pressure and triturated with DCM (3×5 ml) to obtain a crude material that was further purified by preparative HPLC. Pure fractions were lyophilized to afford the intermediate as a blue solid (6 mg, 4% yield). LCMS: [M−H]$^−$ 954.

Step 2: Synthesis of ammonium 2-(2-((3-(((19-((dimethyl(3-(3-(2-sulfonatoethyl)ureido)propyl)silyl)oxy)-19H-6,11-(azeno)-17,21-(azeno[1]episoindoloazeno)benzo[7,8][1,3,5,10]tetraaza[2]silacycloundecino[4,3-a:11,1-a']diisoindol-19-yl)oxy)dimethylsilyl)propyl)amino)-2-oxoethoxy)acetate To a solution of the intermediate from Step 1 (6 mg, 0.0063 mmol) in DMF (1 mL) at room temperature under a nitrogen atmosphere was added 1,4-dioxane-2,6-dione (2.2 mg, 0.0188 mmol). The reaction was stirred for 5 h. It was then directly purified by preparative HPLC. Appropriate fractions were combined and lyophilized to afford the title compound (2 mg, 29%) as a blue solid. $^1$H NMR (400 MHz, DMSO-d6) δ 9.71 (bs, 8H), 8.51 (bs, 8H), 7.06 (bs, 4H), 5.45 (s, 1H), 5.10 (s, 1H), 3.85 (s, 2H), 3.61 (s, 2H), 3.03 (m, 2H), 2.34 (m, 2H), 1.60 (m, 2H), 1.53 (m, 2H), −1.14 (m, 2H), −1.17 (m, 2H), −2.37 (bs, 4H), −2.91 (s, 6H), −2.92 (s, 6H). LCMS: [M−H]$^−$ 1070

Example 8

Preparation of Ammonium 2-(2-((3-(((19-(((3-(3-(2,2-disulfonatoethyl)ureido)propyl)dimethylsilyl)oxy)-19H-6,11-(azeno)-17,21-(azeno[1]episoindoloazeno)benzo[7,8][1,3,5,10]tetraaza[2]silacycloundecino[4,3-a:11,1-a']diisoindol-19-yl)oxy)dimethylsilyl)propyl)amino)-2-oxoethoxy)acetate Step 1: Synthesis of tetrabutylammonium 2-(3-(3-(((19-(((3-aminopropyl)dimethylsilyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)dimethylsilyl)propyl)ureido)ethane-1,1-disulfonate

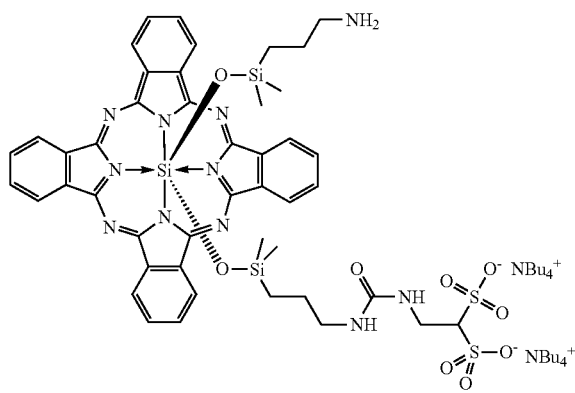

To a solution of the title compound from Example 1, Step 1, (0.2 g, 0.25 mmol) in $CH_2C_2$ (20 mL) under inert atmosphere at 0° C. was sequentially added DIPEA (0.096 g, 0.75 mmol) and a solution of bis(tetrabutyl-$\lambda^5$-azaneyl) 2-(((4-nitrophenoxy)carbonyl)amino)ethane-1,1-disulfonate (0.2 mmol) in $CH_2Cl_2$ (7.5 mL). The reaction mixture was stirred at room temperature for three hours. A blue precipitate formed. The reaction mixture was concentrated to dryness under reduced pressure and washed with $CH_2Cl_2$ to afford the Step 1 intermediate (0.17 g, 45%). LCMS: [M−H]⁻ 1034.

Step 2: Synthesis of ammonium 2-(2-((3-(((19-(((3-(3-(2,2-disulfonatoethyl)ureido)propyl)dimethylsilyl)oxy)-19H-6,11-(azeno)-17,21-(azeno[1]episoindoloazeno)benzo[7,8][1,3,5,10]tetraaza[2]silacycloundecino[4,3-a:11,1-a']diisoindol-19-yl)oxy)dimethylsilyl)propyl)amino)-2-oxoethoxy)acetate To a stirred solution of the intermediate from Step 1 (38 mg, 0.025 mmol) in DMF (4 mL) under nitrogen was added 1,4-dioxane-2,6-dione (8.7 mg, 0.075 mmol). The reaction mixture was stirred for two hours at room temperature and directly purified by preparative HPLC. Appropriate fractions were combined and lyophilized to afford the title compound (4.3 mg, 14%). ¹H NMR (400 MHz, DMSO-d₆) δ 9.71 (bs, 8H), 8.50 (bs, 8H), 7.51 (bs, 2H), 7.02 (bs, 8H), 5.52 (bs, 2H), 5.25 (bs, 2H), 3.76 (bs, 2H), 1.60 (m, 2H), 1.53 (m, 2H), −1.13 (m, 2H), −1.23 (m, 2H), −2.38 (m, 4H), −2.91 (s, 6H), −2.93 (s, 6H). LCMS: [M−H]⁻ 1150.

Example 9

Preparation of Ammonium 6-((3-(((19-(((3-(3-(2,2-disulfonatoethyl)ureido)propyl)dimethylsilyl)oxy)-19H-6,11-(azeno)-17,21-(azeno[1]episoindoloazeno)benzo[7,8][1,3,5,10]tetraaza[2]silacycloundecino[4,3-a:11,1-a']diisoindol-19-yl)oxy)dimethylsilyl)propyl)amino)-6-oxohexanoate To a solution of the intermediate from Example 8, Step 1, (45 mg, 0.03 mmol) in DMF (4.5 mL) at room temperature under a nitrogen atmosphere was added adipic anhydride (11 mg, 0.088 mmol). The reaction mixture was stirred for two hours and directly purified by preparative HPLC. Appropriate fractions were combined and lyophilized to afford the title compound (8.5 mg, 24% yield). ¹H NMR (400 MHz, DMSO-d₆) δ 9.69 (bs, 8H), 8.49 (bs, 8H), 6.68 (m, 2H), 5.50 (m, 2H), 5.25 (m, 2H), 3.16 ((m, 2H), 2.67 (bs, 1H), 2.06 (m, 2H), 1.63 (m, 2H), 1.55 (m, 2H), 1.51 (m, 2H), 1.23 (m, 4H), −1.18 (m, 2H), −1.26 (m, 2H), −2.39 (m, 4H), −2.94 (s, 6H), −2.95 (s, 6H). LCMS: [M−H]⁻ 1162.

Example 10

Preparation of 3-((2-((3-(((19-(((3-(6-(($\lambda^5$-azaneyl)oxy)-6-oxohexanamido)propyl)dimethylsilyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)dimethylsilyl)propyl)amino)-2-oxoethyl)bis(3-(($\lambda^5$-azaneyl)oxy)sulfonyl)propyl)ammonio)propane-1-sulfonate Step 1: Synthesis of 3-((2-(benzyloxy)-2-oxoethyl)bis(3-sulfopropyl)ammonio)propane-1-sulfonate

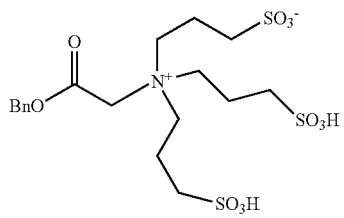

To a suspension of benzyl glycinate hydrochloride (0.5 g, 2.5 mmol) in sulfolane (8 mL) was added DIPEA (4.75 ml, 27.3 mmol). The mixture was stirred at room temperature for 15 min to obtain a clear solution, 1,2-oxathiolane 2,2-dioxide (3 g, 24.8 mmol) was added and the reaction was stirred at 140° C. for 16 h. It was then cooled to room temperature, diluted with water (15 mL) and washed with DCM (2×10 mL). The aqueous layer was separated and lyophilized to afford 3.5 g of a sticky solid residue, 900 mg of this crude were further purified by preparatory HPLC to afford the Step 1 intermediate (400 mg) as a sticky solid. LCMS: 532.7 [M+H]⁺.

Step 2: 3-((carboxymethyl)bis(3-sulfopropyl)ammonio)propane-1-sulfonate

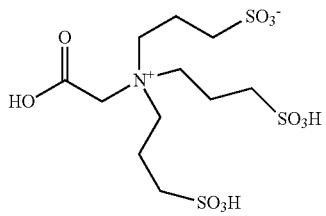

A stirred solution of the intermediate from Step 1 (350 mg, 0.66 mmol) in water (10 mL) was purged with $N_2$ for 5 min. 10% palladium on carbon was added and the resulting mixture was stirred under a hydrogen atmosphere for 2 h. The reaction was filtered and the residue was washed with water (5 mL). The combined filtrates were partially distilled under reduced pressure. The remaining solution was lyophilized to afford the Step 2 intermediate as a sticky solid. LCMS: 440 [M−H]⁻.

Step 3: Synthesis of 3-((2-((3-(((19-(((3-(6-methoxy-6-oxohexanamido)propyl)dimethylsilyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy) dimethylsilyl)propyl)amino)-2-oxoethyl)bis(3-sulfopropyl)ammonio)propane-1-sulfonate

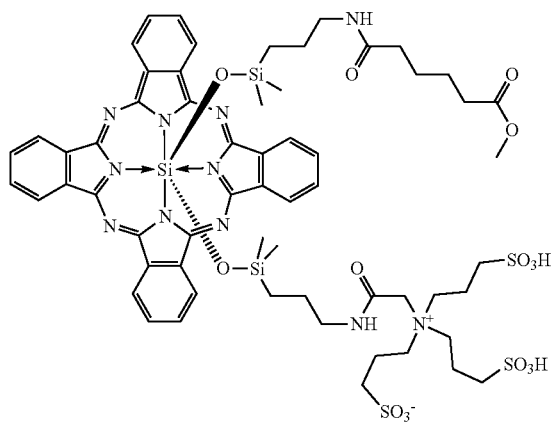

To a stirred solution of the intermediate from Step 2 (9 mg, 0.021 mmol) in DMF (1 mL) under a nitrogen atmosphere were sequentially added EDC.HCl (6 mg, 0.03 mmol), HOBt (2.8 mg, 0.02 mmol) and DIPEA (11 μL, 0.06 mmol). The mixture was stirred at room temperature for 1 h and then added to a solution of the title compound from Example 1, Step 2 (20 mg, 0.02 mmol) in DMF (0.5 mL) at 0° C. The reaction was stirred at room temperature for 8 h. Water (0.5 mL) was added and the resulting mixture was lyophilized. The residue was washed with hexanes (5 mL) and diethyl ether (2×3 mL) to afford the Step 3 intermediate (18 mg) as a blue solid that was used in the next step without further purification. LCMS: 1369 [M]⁻.

Step 4: Synthesis of 3-((2-((3-(((19-(((3-(6-((λ⁵-azaneyl)oxy)-6-oxohexanamido)propyl)dimethylsilyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)dimethylsilyl)propyl)amino)-2-oxoethyl)bis(3-((λ⁵-azaneyl)oxy)sulfonyl)propyl)ammonio)propane-1-sulfonate To a solution of the intermediate from Step 3 (18 mg, 0.01 mmol) in a 1:2 MeOH:$H_2O$ mixture (2 mL) was added $K_2CO_3$ (6 mg, 0.04 mmol). The resulting mixture was stirred at room temperature for 16 h. The reaction was directly purified by preparatory HPLC (mobile phases: 5 mM ammonium bicarbonate+0.1% $NH_3$ in water; 100% ACN; X-Bridge C18). Selected fractions were combined and lyophilized to afford the title compound (0.4 mg, 3% yield) as a blue solid. LCMS: 1354 [M−H]⁻.

Example 11

Preparation of 3-((2-(3-(((19-(((3-(2-(2-((λ⁵-azaneyl)oxy)-2-oxoethoxy)acetamido)propyl)dimethylsilyl)oxy)-19H-6,11-(azeno)-17,21-(azeno[3]episoindoloazeno)benzo[7,8][1.3.5.10]tetraaza[2]silacycloundecino[4,3-a:11,1-a']diisoindol-19-yl)oxy)dimethylsilyl)propyl)amino)-2-oxoethyl)bis(3-((λ⁵-azaneyl)oxy)sulfonyl)propyl)ammonio)propane-1-sulfonate

Step 1: Ammonium 3,3',3''-((2-((3-(((19-(((3-aminopropyl)dimethylsilyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)dimethylsilyl)propyl)amino)-2-oxoethyl)ammonio)tris(propane-1-sulfonate

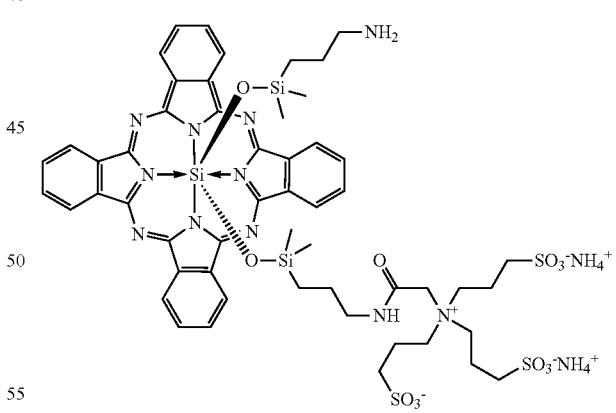

To a stirred solution of the intermediate from Example 10, Step 2 (54 mg, 0.12 mmol) in DMF (2 mL) at 0° C. under a nitrogen atmosphere was sequentially added $T_3P$ (0.16 mL of 50% solution in EtOAc, 0.25 mmol) and DIPEA (0.11 mL, 0.62 mmol). The reaction mixture was stirred at room temperature for 1 h. A solution of the title compound from Example 1, Step 1 (0.1 g, 0.12 mmol) in DMF (1 mL) was added dropwise at 0° C. The resulting mixture was stirred at room temperature for 8 h. The reaction mixture was purified by preparative HPLC (A: 5 mM ammonium bicarbonate+

0.1% NH$_3$ in water; B: 100% ACN to afford the Step 1 intermediate compound (6 mg, 4%) as a blue solid. LCMS: 1227 [M]$^-$ Step 2: 3-((2-((3-(((19-(((3-(2-(2-(($\lambda^5$-azaneyl)oxy)-2-oxoethoxy)acetamido)propyl)dimethylsilyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)dimethylsilyl)propyl)amino)-2-oxoethyl)bis(3-((($\lambda^5$-azaneyl)oxy)sulfonyl)propyl)ammonio)propane-1-sulfonate The title compound was prepared in a manner similar to Example 2, Step 2 by replacing the intermediate compound from Example 2, Step 1 with the intermediate compound from Step 1. The reaction mixture was directly purified by preparative HPLC to afford the title compound as a blue solid (1.2 mg, 49%). $^1$H NMR (400 MHz, DMSO-d$_6$) δ 9.70 (m, 8H), 8.51 (m, 8H), 7.03 (bs, 6H), 3.90 (bs, 2H), 3.62 (s, 2H), 3.53 (s, 2H), 3.44 (s, 2H), 2.67-2.61 (m, 4H), 2.34 (m, 8H), 1.83 (bs, 6H), 1.57 (m, 4H), −1.15 (m, 4H), −2.23 (m, 4H), −2.92 (s, 12H). LCMS: 1342 [M−H]$^-$.

Example 12

Preparation of 3-((6-(($\lambda$5-azanyl)oxy)-6-oxohexyl)(3-(($\lambda$5-azaneyl)oxy)sulfonyl)propyl)(3-(((19-(((3-(bis(3-(((1,5-azaneyl)oxy)sulfonyl)propyl)(3-sulfonatopropyl)ammonio)propyl)dimethylsilyl)oxy)-19H-6,11-(azeno)-17,21-(azeno[3]episoindoloazeno)benzo[7.8][1.3.5.10]tetraaza[2]silacycloundecino[4,3-a:11,1-a']diisoindol-19-yl)oxy)dimethylsilyl)propyl)ammonio)propane-1-sulfonate Step 1: Methyl 6-((3-(((19-(((3-aminopropyl)dimethylsilyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)dimethylsilyl)propyl)amino)hexanoate

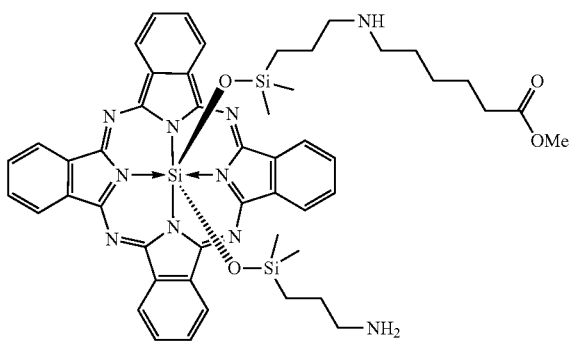

To a solution of the intermediate compound from Example 1, Step 1 (0.3 g, 0.37 mmol) in THF (50 mL) was added a solution of methyl-6-oxohexanoate (0.08 g, 0.56 mmol) in THF (2 mL) and a catalytic amount of AcOH. The solution was stirred at room temperature for one hour. It was then added to a suspension of NaBH(OAc)$_3$ (0.237 g, 1.12 mmol) in THF (10 ml) and stirred for 16 h. The reaction was quenched with saturated aqueous NaHCO$_3$ (50 mL) and extracted with DCM (3×70 ml). The combined organic layers were dried over sodium sulfate, filtered and concentrated under reduced pressure. The residue was purified by basic alumina column chromatography to afford the Step 1 intermediate (0.10 g, 29%) as a blue solid. LCMS: 933[M+H]$^+$.

Step 2: 3-((3-(((19-((dimethyl(3-((3-sulfonatopropyl)bis(3-sulfopropyl)ammonio)propyl)silyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)dimethylsilyl)propyl)(6-methoxy-6-oxohexyl)(3-sulfopropyl)ammonio)propane-1-sulfonate

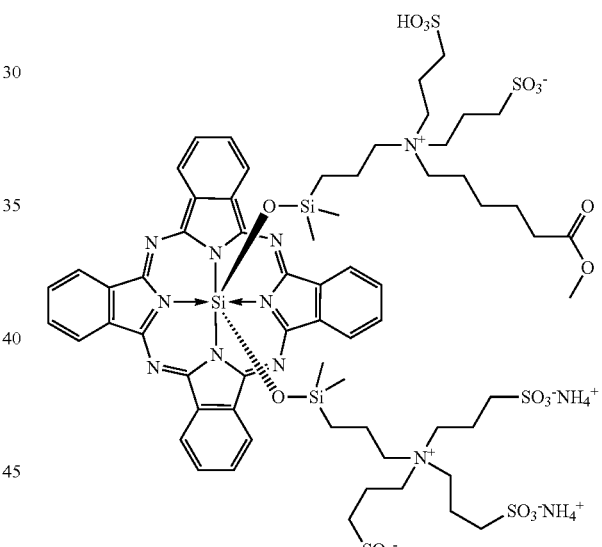

1,3-Propane sultone (0.654 g, 5.4 mmol) and DIPEA (1.4 ml, 8 mmol) were sequentially added to a solution of the intermediate compound from Step 1 (0.10 g, 0.107 mmol) in sulfolane (10 ml) under a nitrogen atmosphere followed by irradiation under microwave at 120° C. for 2 h. The reaction mixture was added drop-wise to THF (30 mL) and stirred for 30 min. The supernatant was removed. The precipitate was sequentially washed with THF (2×10 mL) and dried under reduced pressure to afford the Step 2 intermediate (0.24 g) as a blue solid. LCMS: 1542 [M]$^-$.

Step 3: 3-((6-((λ⁵-azaneyl)oxy)-6-oxohexyl)(3-((λ5-azaneyl)oxy)sulfonyl)propyl)(3-(((19-(((3-(bis(3-((λ⁵-azane)oxy)sulfonyl)propyl)(3-sulfonatopropyl)ammonio)propyl)dimethylsilyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)dimethylsilyl)propyl)ammonio)propane-1-sulfonate To a solution of the intermediate from Step 2 (120 mg, 0.08 mmol) in a 1:2 MeOH:water mixture (5 mL) was added $K_2CO_3$ (32 mg, 0.23 mmol). The reaction was stirred at room temperature for 16 h and directly purified by preparatory HPLC (mobile phases: 5 mM ammonium bicarbonate+0.1% $NH_3$ in water; 100% ACN; X-Bridge C18). Appropriate fractions were combined and lyophilized to afford the title compound (23 mg, 18%) as a blue solid, 1H NMR (400 MHz, DMSO-d6) δ 9.76 (m, 8H), 8.52 (m, 8H), 7.12 (bs, 8H), 3.49 (m, 2H), 3.42 (m, 2H), 2.64 (m, 12H), 2.27 (m, 10H), 1.88 (m, 4H), 1.43 (m, 10H), 1.11 (m, 4H), −0.89 (m, 2H), −1.03 (m, 2H), −2.30 (m, 2H), −2.37 (m, 2H), −2.89 (s, 12H). LCMS: 764 [M/2]—.

Example 13

Preparation of 4-((6-((λ5-azaneyl)oxy)-6-oxohexyl)(4-((λ5-azaneyl)oxy)sulfonyl)butyl)(3-(((19-(((3-(bis(4-((λ5-azaneyl)oxy)sulfonyl)butyl)(4-sulfonatobutyl)ammonio)propyl)dimethylsilyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)dimethylsilyl)propyl)ammonio)butane-1-sulfonate Step 1: Sodium-4-iodobutane-1-sulfonate

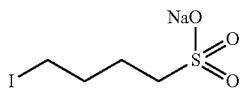

To a solution of 1,2-oxathiolane 2,2-dioxide (0.5 g, 3.7 mmol) in MeOH (5 mL) at room temperature in a sealed tube was added sodium iodide (550 mg, 3.7 mmol). The reaction mixture was heated at 80° C. for 6 h. It was then allowed to cool down to room temperature. The precipitate was filtered, washed with cold MeOH (5 mL) and dried under reduced pressure to afford the Step 1 intermediate (270 mg, 26%) as a white solid. ¹H NMR (400 MHz, Chloroform-d) δ 3.33-3.29 (m, 2H), 2.42-2.48 (m, 2H), 1.90-1.83 (m, 2H), 1.71-1.64 (m, 2H).

Step 2: Sodium 4,4',4"-((3-(((19-(((3-((6-methoxy-6-oxohexyl)bis(4-sulfonatobutyl)ammonio)propyl)dimethylsilyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)dimethylsilyl)propyl)ammonio)tris(butane-1-sulfonate)

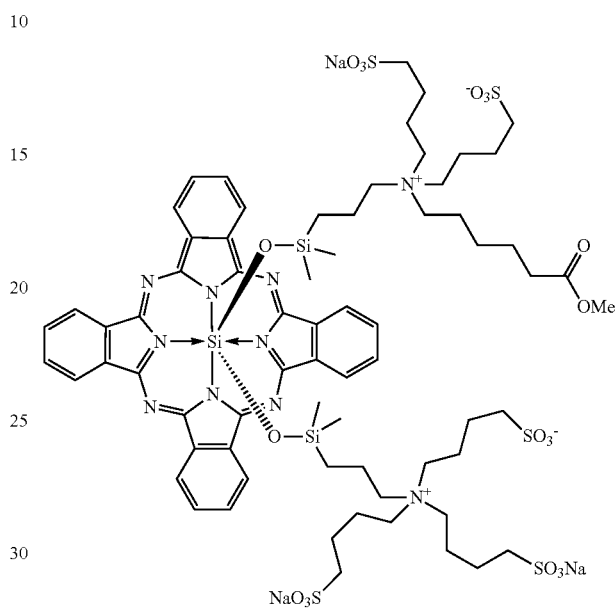

To a solution of the intermediate from Example 12, Step 1 (25 mg, 0.03 mmol) in sulfolane (3 mL) under nitrogen were added the intermediate from Step 1 (0.115 g, 0.4 mmol) and DIPEA (0.093 mL, 0.54 mmol). The reaction was irradiated under microwave at 120° C. for 4 h. The reaction mixture was added drop-wise to THF (5 mL) and stirred for 30 min. The supernatant was removed, and the residue was washed with THF (2×3 mL). The residue was dried under reduced pressure to afford the crude Step 2 intermediate (50 mg) that was used in the following step without further purification. LCMS: 805 [M/2−1]⁻

Step 3: 4-((6-((λ5-azaneyl)oxy)-6-oxohexyl)(4-(((λ5-azaneyl)oxy)sulfonyl)butyl)(3-(((19-(((3-(bis(4-((λ5-azaneyl)oxy)sulfonyl)butyl)(4-sulfonatobutyl)ammonio)propyl)dimethylsilyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)dimethylsilyl)propyl)ammonio)butane-1-sulfonate The title compound was prepared in a manner similar to Example 12, Step 3 by replacing the intermediate from Example 12, Step 3 with the intermediate from Step 2 to afford the title compound (12 mg, 24%) as blue solid. ¹H NMR (400 MHz, DMSO-d6) δ 9.77 (m, 8H), 8.54 (m, 8H), 7.12 (bs, 8H), 2.40-2.33 (m, 22H), 2.23 (m, 2H), 1.79 (m, 4H), 1.50 (m, 10H), 1.40 (m, 2H), 1.20 (m, 10H), 1.06 (m, 4H), −1.20 (m, 4H), −2.24 (m, 4H), −2.89 (s, 12H). LCMS: 798 [M−1/2]—.

Example 14

Preparation of sodium 3,3',3"-((3-(((19-(((3-((6-((2,5-dioxopyrrolidin-1-yl)oxy)-6-oxohexyl)bis(3-sulfonatopropyl)ammonio)propyl)dimethylsilyl) oxy)-19H-6,11-(azeno)-17,21-(azeno[1] episoindoloazeno)benzo[7,8][1,3,5,10]tetraaza[2] silacycloundecino[4,3-a:11,1-a']diisoindol-19-yl) oxy)dimethylsilyl)propyl)ammonio)tris(propane-1-sulfonate)

Step 1: Tetrasodium mono(6-((3-(((19-((dimethyl(3-(tris(3-sulfonatopropyl)ammonio)propyl)silyl)oxy)-19H-6,11-(azeno)-17,21-(azeno[3]episoindoloazeno) benzo[7,8][1,3,5,10]tetraaza[2]silacycloundecino[4,3-a:11,1-a']diisoindol-19-yl)oxy)dimethylsilyl) propyl)bis(3-sulfonatopropyl)ammonio)hexanoate)

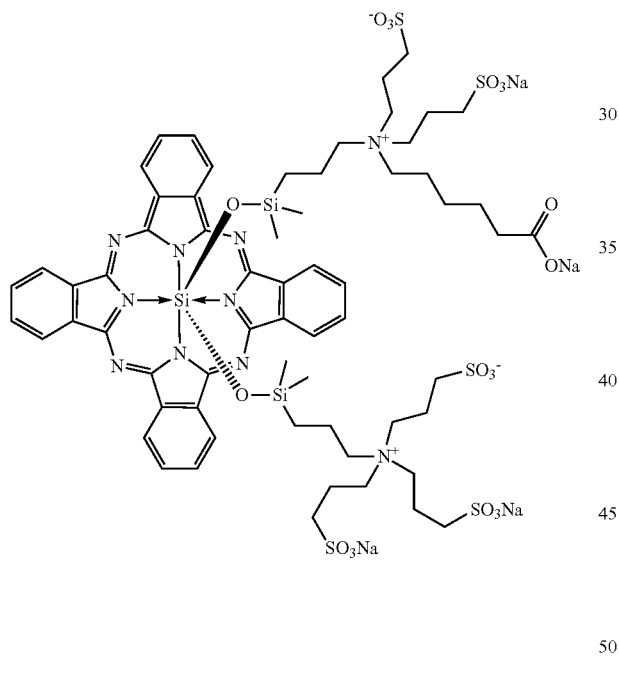

Dowex® 50WX8 hydrogen form resin (4 g, 50-100 mesh) was loaded into a column and converted to its sodium form by passing through a 1N NaCl solution (50 ml) until the pH of the eluent became neutral. The column was further washed with water to remove excess NaCl. The process was continued until no precipitate was observed upon treatment of the eluent with silver nitrate. A solution of the title compound from Example 12 (33 mg, 0.02 mmol) in water (3 ml) was passed through the column. The blue-colored fractions were collected and lyophilized to afford the Step 1 intermediate (29 mg, 91%). $^1$H NMR (400 MHz, DMSO-d6) δ 9.75 (m, 8H), 8.52 (m, 8H), 3.49 ((m, 2H), 3.42 ((m, 2H), 2.64 ((m, 12H), 2.29 (m, 10H), 1.89 (m, 4H), 1.42 (m, 10H), 1.11 (m, 4H), −0.88 (m, 2H), −1.04 (m, 2H), −2.30 (m, 2H), −2.38 (m, 2H), −2.89 (s, 12H). LCMS: 764 [M/2]—.

Step 2: Sodium 3,3',3"-((3-(((19-(((3-((6-((2,5-dioxopyrrolidin-1-yl)oxy)-6-oxohexyl)bis(3-sulfonatopropyl)ammonio)propyl)dimethylsilyl)oxy)-19H-6,11-(azeno)-17,21-(azeno[1]episoindoloazeno)benzo [7,8][1,3,5,10]tetraaza[2]silacycloundecino[4,3-a:11,1-a']diisoindol-19-yl)oxy)dimethylsilyl)propyl) ammonio)tris(propane-1-sulfonate)

To a solution of the intermediate from Step 1 (1.3 mg) in DMSO (0.3 mL) under nitrogen in an amber vial was sequentially added DIPEA (32 µL of 0.1 M DMSO solution, 4 eq) and N,N'-disuccinimidyl carbonate (64 µL of 0.1 M DMSO solution, 8 eq). The resulting mixture was stirred at room temperature overnight. The reaction was diluted with DMF (0.3 mL), filtered through a 0.45 µm filter and added dropwise to vigorously stirred MTBE (5 mL) over 20 minutes. The reaction vial was washed with DMF (0.2 mL). A blue precipitate forms. The suspension was allowed to settle, and the clear supernatant was removed. MTBE (2.5 mL) was added and the process was repeated twice. The residue after the final wash was dried under reduced pressure to afford the title compound (0.5 mg, 37%). LCMS: 812 [M−1/2]—.

Example 15

Preparation of Ammonium 2-(2-((3-(((19-(((3-(4-(bis(3-sulfonatopropyl)ammonio)butanamido)propyl)dimethylsilyl) oxy)-19H-6,11-(azeno)-17,21-(azeno[1]episoindoloazeno)benzo[7,8][1,3,5,10] tetraaza[2]silacycloundecino[4,3-a:11,1-a'] diisoindol-19-yl)oxy)dimethylsilyl)propyl)amino)-2-oxoethoxy)acetate

Step 1: 3-((4-(benzyloxy)-4-oxobutyl)(3-sulfopropyl)ammonio)propane-1-sulfonate

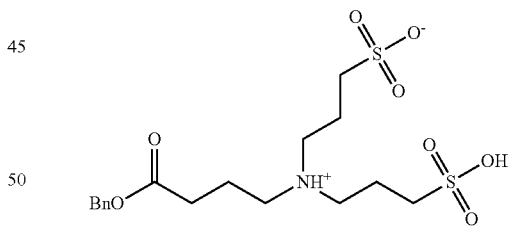

To a solution of benzyl 4-aminobutanoate hydrochloride (1 g, 4.4 mmol) in DMF (5 ml) at room temperature under a nitrogen atmosphere was added DIPEA (4 ml, 17.5 mmol) followed by 1,2-oxathiolane 2,2-dioxide (2.1 g, 44 mmol). The reaction mixture was stirred at 100° C. for 16 h. It was then cooled to room temperature, treated with a saturated aqueous NaHCO$_3$ solution (8 ml) and stirred for 1 h. The mixture was washed with ethyl acetate (2×15 ml). The aqueous layer was lyophilized to yield a residue that was triturated with THF (12 ml). A gram out of the three-gram crude was further purified by preparative HPLC to afford the Step 1 intermediate (260 mg). LCMS: 438 [M+H]$^+$ Step 2: 3-((3-carboxypropyl)(3-sulfopropyl)am-
monio)propane-1-sulfonate

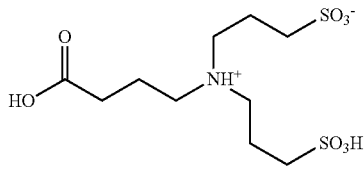

A solution of the intermediate from Step 1 (260 mg, 0.59 mmol) in a methanol:water mixture (6 ml, 1:1) was purged with nitrogen for 5 min. 10% palladium on carbon (140 mg) was added and the mixture was stirred under a hydrogen atmosphere for 30 min. The reaction mixture was filtered and the residue washed with methanol:water (10 ml, 1:1). The combined filtrates were partially rotavaped and lyophilized to afford the Step 2 intermediate (210 mg). $^1$H-NMR (400 MHz, Deuterium Oxide) δ 3.25-3.21 (m, 4H), 3.09-3.13 (m, 2H), 2.86 (t. J=7.2 Hz, 4H), 2.27 (t, J=6.9 Hz, 2H), 2.04 (m, 4H), 1.85 (m, 2H). MS: 348 [M+H]$^+$ Step 3: 3-((4-((3-(((19-(((3-aminopropyl)dimethylsi-
lyl)oxy)-19H-6,11-(azeno)-17,21-(azeno[3]episoin-
doloazeno) benzo[7,8][1,3,5,10]tetraaza[2]silacy-
cloundecino[4,3-a:11,1-a']diisoindol-19-yl)oxy)
dimethylsilyl)propyl) amino)-4-oxobutyl)(3-
sulfopropyl)ammonio)propane-1-sulfonate To a solution of the intermediate from Step 2 (69 mg, 0.18 mmol) in DMF (4 ml) at room temperature under a nitrogen atmosphere were added HOBt (57 mg, 0.37 mmol), DIPEA (96 mg, 0.75 mmol) and EDC.HCl (71 mg, 0.37 mmol). The reaction mixture was stirred for 2 h followed by addition of the title compound from Example 1, Step 1 (0.200 g, 0.25 mmol). The reaction was stirred at room temperature for 48 h. Its contents were poured over water (100 mL). The precipitate was separated by centrifugation to yield 210 mg of crude material that was purified by preparative HPLC to afford the Step 3 intermediate (10 mg, 4%) as a blue solid. LCMS: 1134 [M+H]$^+$ Step 4: Ammonium 2-(2-((3-(((19-(((3-(4-(bis(3-
sulfonatopropyl)ammonio)butanamido)propyl)dim-
ethylsilyl) oxy)-19H-6,11-(azeno)-17,21-(azeno[1]
episoindoloazeno)benzo[7,8][1,3,5,10]tetraaza[2]
silacycloundecino[4,3-a:11,1-a']diisoindol-19-yl)
oxy)dimethylsilyl)propyl)amino)-2-oxoethoxy)
acetate The title compound was prepared in a manner similar to Example 2, Step 2 by replacing the intermediate from Example 2, Step 1 with the intermediate from Step 3 (8 mg, 0.007 mmol) to afford the title compound (3.2 mg, 35%) as a blue solid. $^1$H NMR (400 MHz, DMSO-d6) δ 9.71 (bs 8H), 8.52 (bs, 8H), 6.82 (m, 2H), 3.98 (s, 2H), 3.64 (s, 2H), 3.12 (m, 3H), 1.89 (m, 7H), 1.77 (m, 2H), 1.59 (m, 8H), −1.15 (m, 4H), −2.34 (m, 4H), −2.92 (s, 12H). LCMS: 1248 [M−H]$^-$.

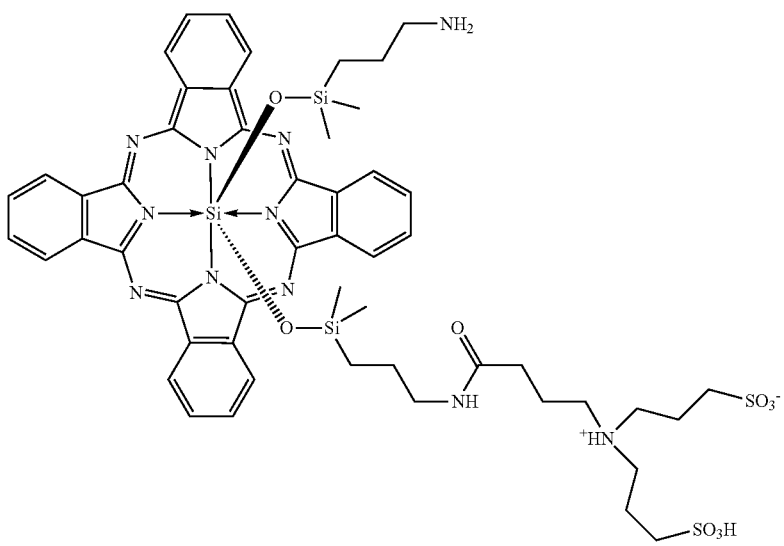

Example 16

Preparation of sodium 4,4',4"-((3-(((19-(((3-((6-((2,5-dioxopyrrolidin-1-yl)oxy)-6-oxohexyl)bis(4-sulfonatobutyl)ammonio)propyl)dimethylsilyl)oxy)-19H-6,11-(azeno)-17,21-(azeno[1]episoindoloazeno)benzo[7,8][1,3,5,10]tetraaza[2]silacycloundecino[4,3-a:11,1-a']diisoindol-19-yl)oxy)dimethylsilyl)propyl)ammonio)tris(butane-1-sulfonate)

Step 1: Sodium 6-((3-(((19-((dimethyl(3-(tris(4-sulfonatobutyl)ammonio)propyl)silyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-9-yl)oxy)dimethylsilyl)propyl)bis(4-sulfonatobutyl)ammonio)hexanoate

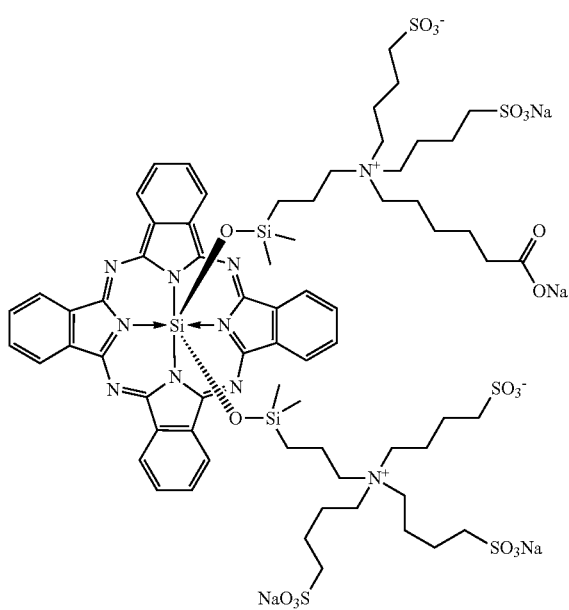

The title compound was prepared in a manner similar to Example 14, Step 1 by replacing Example 12 for Example 13 (38 mg, 0.02 mmol) to afford the title compound (34 mg, 88%), 1H NMR (400 MHz, DMSO-d6) δ 9.77 (m, 8H), 8.54 (m, 8H), 2.39-2.33 (m, 22H), 2.21 (m, 2H), 1.79 (m, 4H), 1.50 (m, 10H), 1.39 (m, 2H), 1.18 (m, 10H), 1.05 (m, 4H), −1.20 (m, 4H), −2.24 (m, 4H), −2.89 (s, 6H), −2.90 (s, 6H). LCMS: 799 [M/2]⁻

Step 2: Sodium 4,4',4"-((3-(((19-(((3-((6-((2,5-dioxopyrrolidin-1-yl)oxy)-6-oxohexyl)bis(4-sulfonatobutyl)ammonio)propyl)dimethylsilyl)oxy)-19H-6,11-(azeno)-17,21-(azeno[1]episoindoloazeno)benzo[7,8][1,3,5,10]tetraaza[2]silacycloundecino[4,3-a:11,1-a']diisoindol-19-yl)oxy)dimethylsilyl)propyl)ammonio)tris(butane-1-sulfonate)

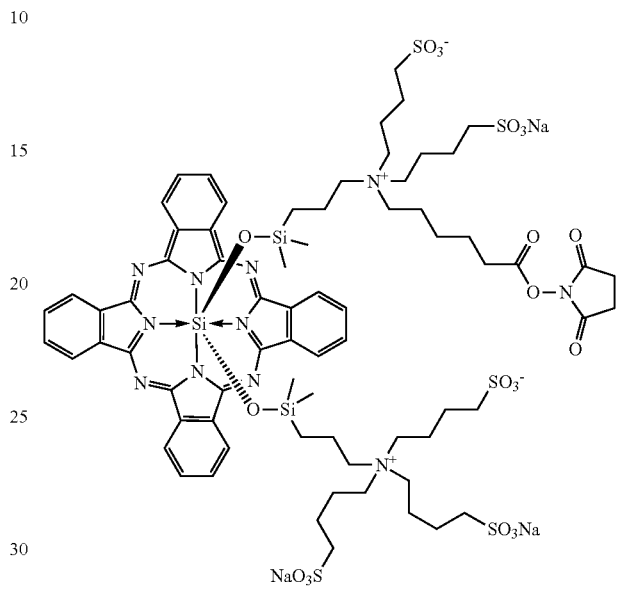

The title compound was prepared in a manner similar to Example 14, Step 2 by replacing the title compound from Example 14, Step 1 for the title compound from Step 1 (1.4 mg, 0.0008 mmol) to afford the title compound (0.0005 mmol). LCMS: 847 [M−1/2]⁻

Example 17

Preparation of Sodium 2-((19-((dimethyl(3-(tris(4-sulfonatobutyl)ammonio)propyl)silyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)-2-methyl-6,6-bis(4-sulfonatobutyl)-9,12,15-trioxa-6-aza-2-silaoctadecan-6-ium-18-oate Step 1: 3-(2-(2-(2-Hydroxyethoxy)ethoxy)ethoxy)propanoic Acid

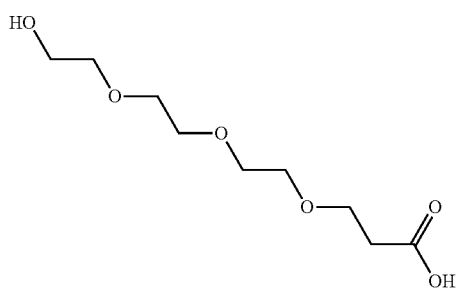 [SMILES: O=C(O)CCOCCOCCOCCO]

Tert-butyl 3-(2-(2-(2-hydroxyethoxy)ethoxy)ethoxy)propanoate (2.0 g, 7.2 mmol) was dissolved in trifluoroacetic acid (20 mL) at 0° C. The reaction mixture was stirred at room temperature for 16 h. Upon completion, solvents were removed under reduced pressure to obtain the crude title compound that was used in the following step without further purification.

Step 2: Methyl 3-(2-(2-(2-hydroxyethoxy)ethoxy)ethoxy)propanoate

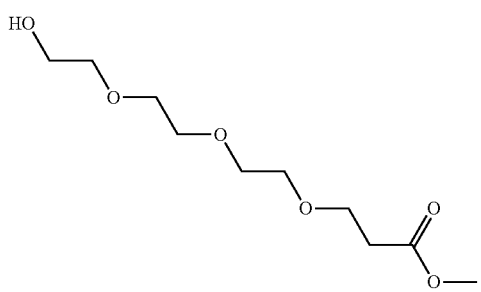 [SMILES: COC(=O)CCOCCOCCOCCO]

To a solution of the title compound from Step 1 (1.5 g, 6.7 mmol) in MeOH (20 mL) was added concentrated H$_2$SO$_4$ (0.3 mL) at room temperature. The solution was stirred at 60° C. for 3 h. The reaction mixture was concentrated under reduced pressure. The crude material was purified by column chromatography on neutral alumina to afford the title compound (1.1 g, 69%) as a liquid. 1H NMR (400 MHz, D2O) δ 3.69 (m, 2H), 3.60-3.56 (m, 15H), 2.57 (m, 2H).

Step 3: Methyl 3-(2-(2-(2-oxoethoxy)ethoxy)ethoxy)propanoate

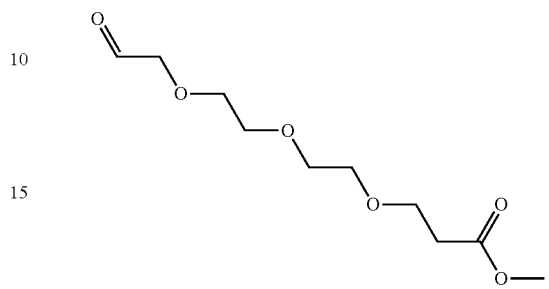

To a stirred solution of Dess-Martin periodinane (4.04 g, 9.5 mmol) and pyridine (0.92 ml, 11.4 mmol) in dichloromethane (10 mL) under nitrogen was added a solution of the title compound from Step 2 (0.9 g, 3.8 mmol) in dichloromethane (5 mL). The reaction was stirred at room temperature for 4 h. Upon completion, the reaction mixture was diluted with dichloromethane (5 mL) and treated with a saturated solution of NaHCO$_3$ (5 mL) and a 10% Na$_2$S$_2$O$_3$ solution (5 mL). The resulting mixture was stirred at room temperature for 30 min and extracted with dichloromethane (3×30 mL). The combined organic layers were dried over sodium sulphate, filtered and concentrated under reduced pressure. The residue was purified by column chromatography on neutral alumina to afford the title compound (0.45 g, 50%) that was promptly used in the next step. LCMS: 235 [M+1]$^+$ Step 4: Methyl 2-((19-(((3-aminopropyl)dimethylsilyl)oxy)-19H-6,11-(azeno)-17,21-(azeno[3]episoindoloazeno) benzo[7,8][1,3,5,10]tetraaza[2]silacycloundecino[4,3-a:11,1-a']diisoindol-19-yl)oxy)-2-methyl-9,12,15-trioxa-6-aza-2-silaoctadecan-18-oate

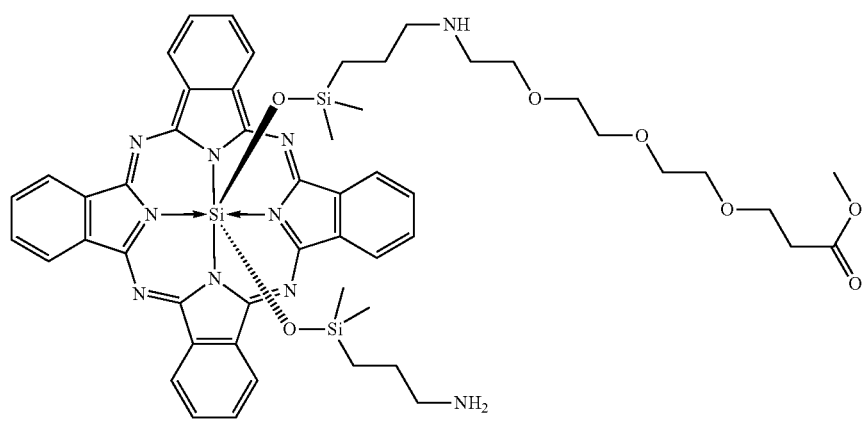

To a stirred solution of the title compound from Example 1, Step 1 (200 mg, 0.25 mmol) in THF (100 mL) at room temperature was added a solution of the title compound from Step 3 (72 mg, 0.3 mmol) in THF (2 mL) followed by a catalytic amount of AcOH (0.1 mL of a 15 mg/mL solution of AcOH in THF, 0.025 mmol). The solution was stirred at room temperature for 1 h and then added to a suspension of NaBH(OAc)$_3$ (0.16 g, 0.75 mmol) in THF (10 mL). The resulting mixture was stirred at room temperature for 4 h. The reaction contents were poured over a saturated NaHCO$_3$ aqueous solution (50 mL) and extracted with DCM (3×50 mL). The combined organic layers were dried over sodium sulphate, filtered and concentrated under reduced pressure. The residue was purified by column chromatography on basic alumina to afford the title compound (70 mg, 27%) as a blue solid. LCMS: 1023 [M+H]$^+$.

Step 5: Sodium 4,4',4"-((3-(dimethyl((19-((2-methyl-18-oxo-6,6-bis(4-sulfonatobutyl)-9,12,15,19-tetraoxa-6-aza-2-silaicosan-6-ium-2-yl)oxy)-19H-6,11-(azeno)-17,21-(azeno[1]episoindoloazeno) benzo [7,8][1,3,5,10] tetraaza [2] silacycloundecino[4,3-a:11,1-a']diisoindol-19-yl)oxy)silyl) propyl)ammonio) tris (butane-1-sulfonate)

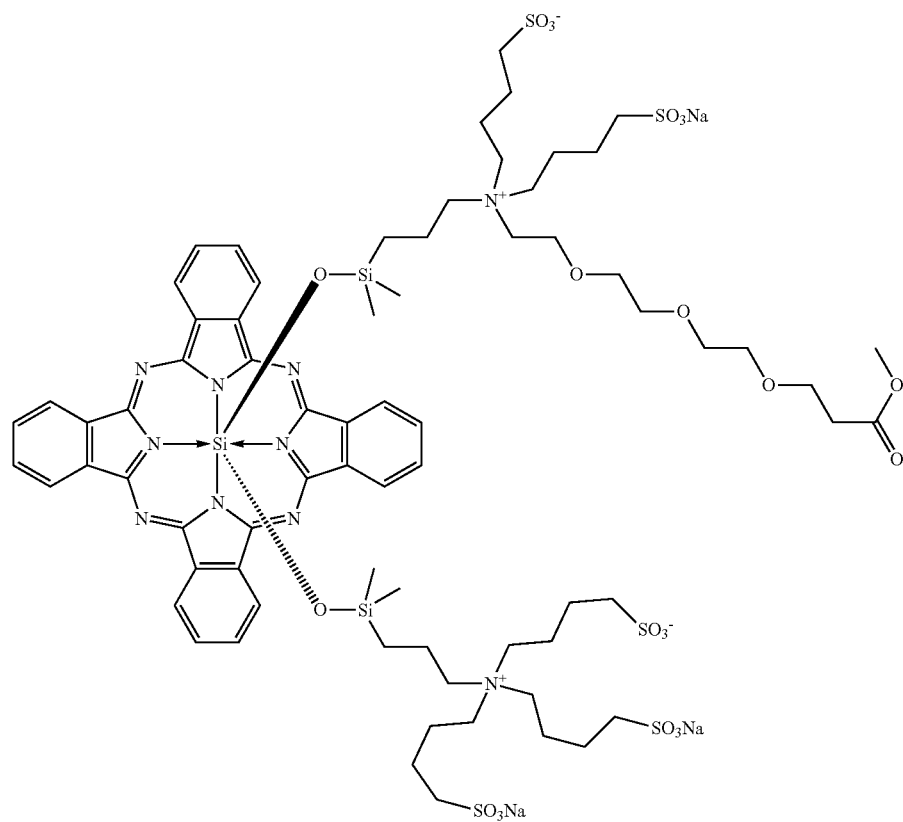

To a solution of the title compound from Step 4 (35 mg, 0.034 mmol) in sulfolane (5 mL) under nitrogen was added the title compound from Example 13, Step 1 (0.196 g, 0.68 mmol) and DIPEA (0.18 mL, 1.02 mmol). The reaction was irradiated at 120° C. in a microwave for 5 h. Upon completion, the reaction mixture was added dropwise to THF (50 mL) and stirred for 30 min. The precipitate was separated by centrifugation, washed with THF (2×10 mL) and dried under reduced pressure to afford the title compound (100 mg crude) that was used in the following step without further purification. LCMS: 853 [M+2/2]$^+$.

Step 6: Ammonium 2-((19-((dimethyl(3-(tris(4-sulfonatobutyl)ammonio)propyl)silyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)-2-methyl-6,6-bis(4-sulfonatobutyl)-9,12,15-trioxa-6-aza-2-silaoctadecan-6-ium-18-oate

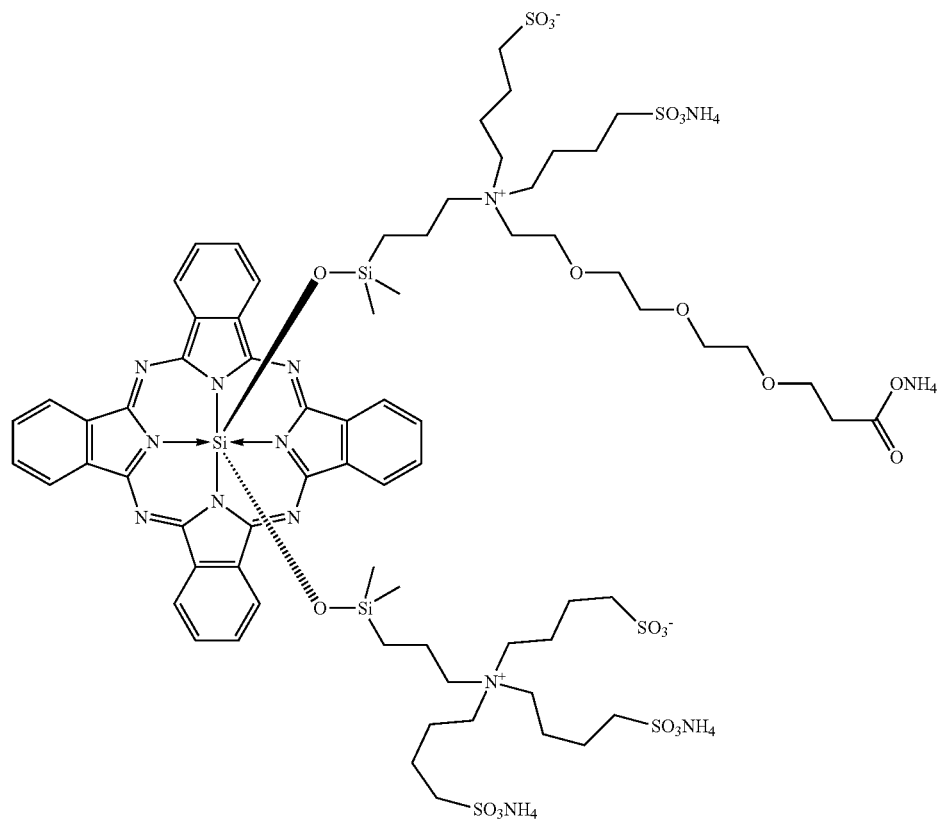

To a solution of the title compound from Step 5 (200 mg, 0.11 mmol) in MeOH:water (2:1, 7.5 mL) was added K₂CO₃ (94 mg, 0.68 mmol). The reaction was stirred at room temperature for 16 h. The reaction mixture was directly purified by preparative HPLC. Appropriate fractions were lyophilized to afford the title compound (41 mg, 34% over two steps) as a blue solid. LCMS: 844 [M−1/2]—.

Step 7: Sodium 2-((19-((dimethyl(3-(tris(4-sulfonatobutyl)ammonio)propyl)silyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)-2-methyl-6,6-bis(4-sulfonatobutyl)-9,12,15-trioxa-6-aza-2-silaoctadecan-6-ium-18-oate

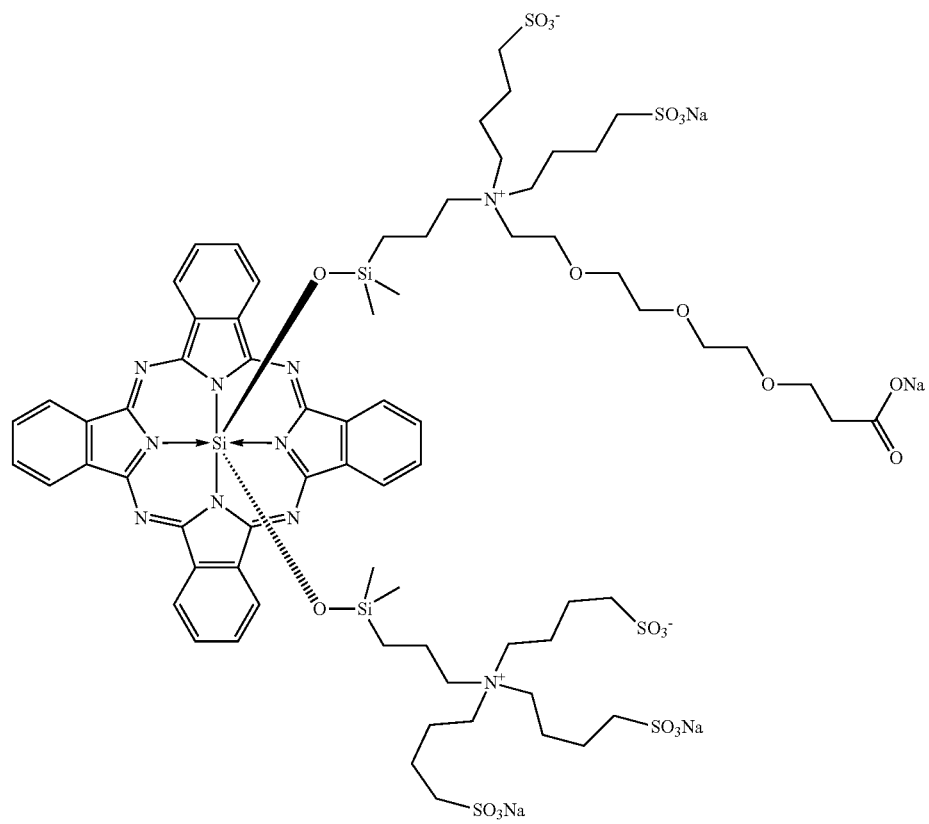

The title compound of Step 6 (41 mg, 0.027 mmol) was submitted to the ion exchange procedure described in Example 14, Step 1 to afford the title compound (39 mg, 94%). $^1$H NMR (400 MHz, DMSO-d6) δ 9.78 (m, 8H), 8.55 (m, 8H), 3.39 (m, 6H), 3.17 (m, 2H), 3.07 (m, 4H), 2.95 (m, 2H), 2.84 (m, 2H), 2.61 (m, 2H), 2.40 (m, 20H), 2.04 (m, 2H), 1.94 (m, 2H), 1.78 (m, 2H), 1.51 (m, 4H), 1.41 (m, 4H), 1.25 (m, 8H), −1.18 (m, 2H), −1.28 (m, 2H), −2.22 (m, 4H), −2.89 (s, 12H). LCMS: 844 [M−1/2]—.

Example 18

Preparation of Sodium 2-((19-((dimethyl(3-(tris(4-sulfonatobutyl)ammonio)propyl)silyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)-2-methyl-6,6-bis(4-sulfonatobutyl)-9,12-dioxa-6-aza-2-silapentadecan-6-ium-15-oate

Step 1: 3-(2-(2-hydroxyethoxy)ethoxy)propanoic Acid

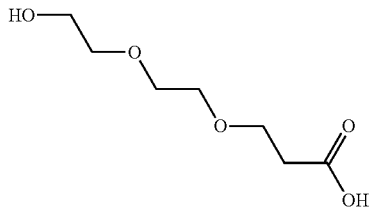 [SMILES: O=C(O)CCOCCOCCO]

The title compound was prepared in a manner similar to Example 17, Step 1 by replacing tert-butyl 3-(2-(2-(2-hydroxyethoxy)ethoxy)ethoxy)propanoate for tert-butyl 3-(2-(2-hydroxyethoxy)ethoxy)propanoate (4.5 g, 19.21 mmol) to afford the crude title compound that was used in the following step without further purification.

Step 2: Methyl 3-(2-(2-hydroxyethoxy)ethoxy)propanoate

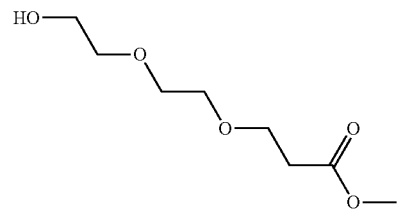

The title compound was prepared in a manner similar to Example 17, Step 2 by replacing 3-(2-(2(2-Hydroxyethoxy)ethoxy)propanoic acid for the title compound from Step 1 (3.7 g, 20.8 mmol) to afford the title compound (2.8 g, 70%) as a liquid. 1H NMR (400 MHz, CDCl3) δ 3.79 (m, 2H), 3.74 (m, 2H), 3.71 (s, 3H), 3.64 (m, 6H), 2.63 (t, J=5.6 Hz, 2H).

Step 3: Methyl 3-(2-(2-oxoethoxy)ethoxy)propanoate

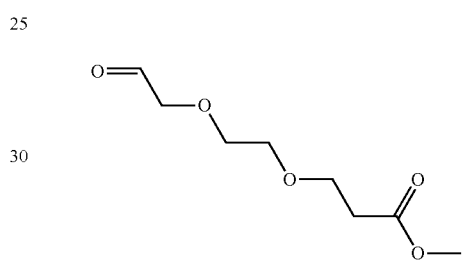

The title compound was prepared in a manner similar to Example 17, Step 3 by replacing methyl 3-(2-(2-(2-hydroxyethoxy)ethoxy)ethoxy)propanoate for the title compound from Step 2 (1 g, 5.2 mmol) to afford the title compound (470 mg, 47%) as a liquid.

Step 4: Methyl 2-((19-(((3-aminopropyl)dimethylsilyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)-2-methyl-9,12-dioxa-6-aza-2-silapentadecan-15-oate

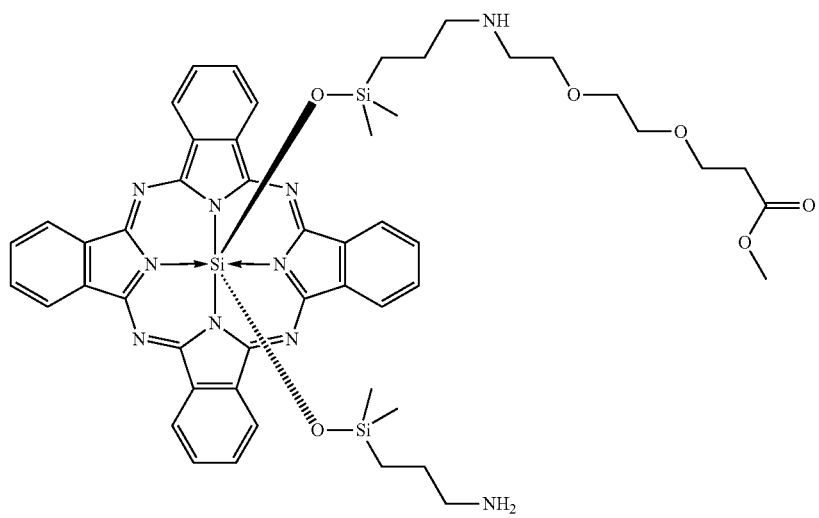

The title compound was prepared in a manner similar to Example 17, Step 4 by replacing methyl 3-(2-(2-(2-oxoethoxy)ethoxy)ethoxy)propanoate for the title compound from Step 3 (59 mg, 0.31 mmol) to afford the title compound (95 mg, 39%) as a blue solid. LCMS: 980 [M+1]$^+$.

Step 5: Sodium 4,4',4"-((3-(dimethyl((19-((2-methyl-15-oxo-6,6-bis(4-sulfonatobutyl)-9,12,16-trioxa-6-aza-2-silaheptadecan-6-ium-2-yl)oxy)-19H-6,11-(azeno)-17,21-(azeno[1]episoindoloazeno)benzo[7,8][1,3,5,10]tetraaza[2]silacycloundecino[4,3-a:11,1-a']diisoindol-19-yl)oxy)silyl)propyl)ammonio)tris(butane-1-sulfonate)

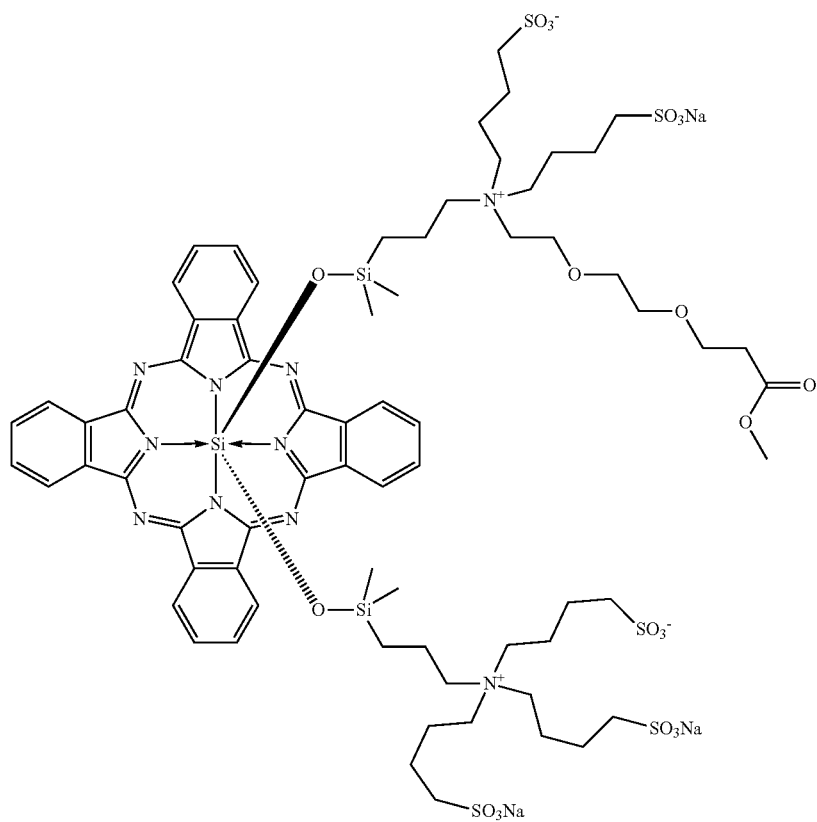

The title compound was prepared in a manner similar to Example 17, Step 5 by replacing the title compound from Example 17, Step 4 for the title compound from Step 4 (75 mg, 0.08 mmol) to afford the title compound (190 mg crude) as a blue solid. LCMS: 828 [M−2/2]—.

Step 6: Ammonium 2-((19-(((dimethyl(3-(tris(4-sulfonatobutyl)ammonio)propyl)silyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)-2-methyl-6,6-bis(4-sulfonatobutyl)-9,12-dioxa-6-aza-2-silapentadecan-6-ium-15-oate

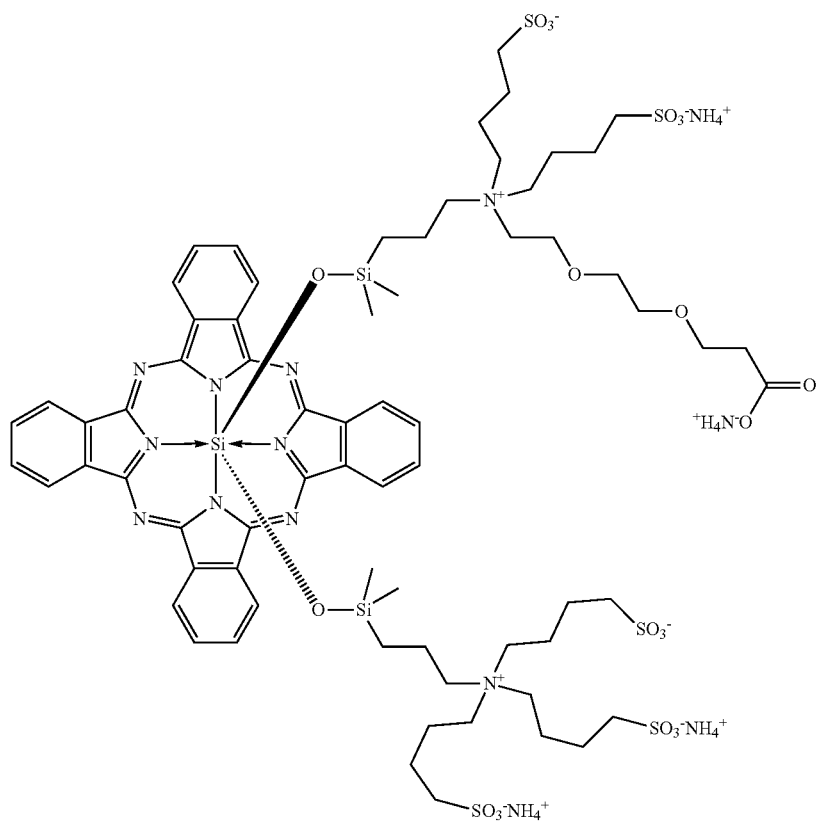

The title compound was prepared in a manna similar to Example 17, Step 6 by replacing the title compound from Example 17, Step 5 for the title compound from Step 5 (380 mg, 0.22 mmol) to afford the title compound (60 mg, 23% over two step) as a blue solid. LCMS: 822 [M−1/2]—.

Step 7: Sodium 2-((19-((dimethyl(3-(tris(4-sulfonatobutyl)ammonio)propyl)silyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)-2-methyl-6,6-bis(4-sulfonatobutyl)-9,12-dioxa-6-aza-2-silapentadecan-6-ium-15-oate

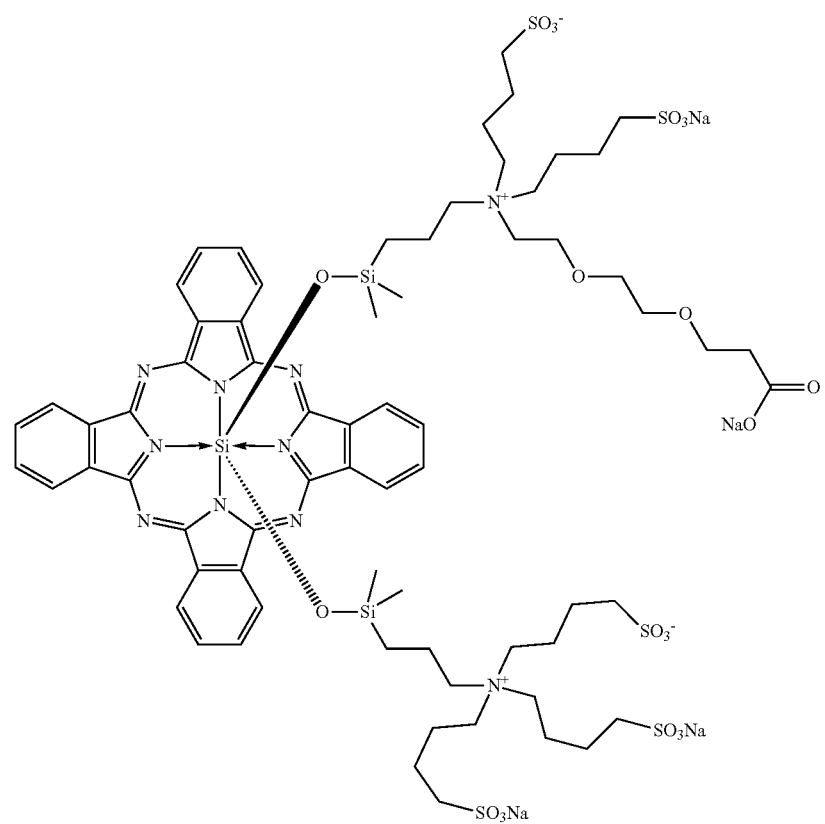

The title compound of Step 6 (70 mg, 0.04 mmol) was submitted to the ion exchange procedure described in Example 14, Step 1 to afford the title compound (66 mg, 93%). $^1$H NMR (400 MHz, D$_2$O) δ 9.66 (m, 8H), 8.46 (m, 8H), 3.29 (bs, 2H), 2.82 ((m, 4H), 2.74 (m, 6H), 2.68 (m, 8H), 2.48 (bs, 2H), 2.32 (m, 6H), 2.20 (m, 2H), 1.92 (m, 2H), 1.73 (dd, J=6.8, 6.8 Hz, 4H), 1.59 (m, 8H), 1.45 (m, 2H) 1.31 (m, 4H), 1.16 (m, 6H), −1.49 (m, 2H), −1.66 (m, 2H), −2.04 (m, 4H), −2.91 (s, 6H), −2.92 (s, 6H). LCMS: 822 [M−1/2]—.

Example 19

Preparation of sodium 2-((19-(((dimethyl(3-(tris(3-sulfonatopropyl)ammonio)propyl)silyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)-2-methyl-6,6-bis(3-sulfonatopropyl)-9,12,15-trioxa-6-aza-2-silaoctadecan-6-ium-18-oate Step 1: Sodium 3-iodopropane-1-sulfonate

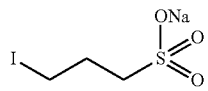

To a solution of sodium iodide (24.5 g, 164 mmol) in dry methanol (200 mL) was added 1,3-propanesultone (20 g, 164 mmol). The sealed tube was heated at 80° C. and stirred for 1 h. The reaction mixture was cooled to room temperature and filtered through a Buchner funnel. The residue was washed with DCM (50 mL) and dried under reduced pressure to afford the title compound as an off-white powder (27 g, 61%). $^1$H NMR (400 MHz, D$_2$O) δ 3.27 (t, 0.1=6.8 Hz, 2H), 2.94 (t, J=7.2 Hz, 2H), 2.16 (q, J=7.6 Hz, 2H).

Step 2: Sodium 3,3',3''-((3-(dimethyl((19-((2-methyl-18-oxo-6,6-bis(3-sulfonatopropyl)-9,12,15,19-tetraoxa-6-aza-2-silaicosan-6-ium-2-yl)oxy)-19H-6,11-(azeno)-17,21-(azeno[1]episoindoloazeno)benzo[7,8][1,3,5,10]tetraaza[2]silacycloundecino[4,3-a:11,1-a']diisoindol-19-yl)oxy)silyl)propyl)ammonio)tris(propane-1-sulfonate)

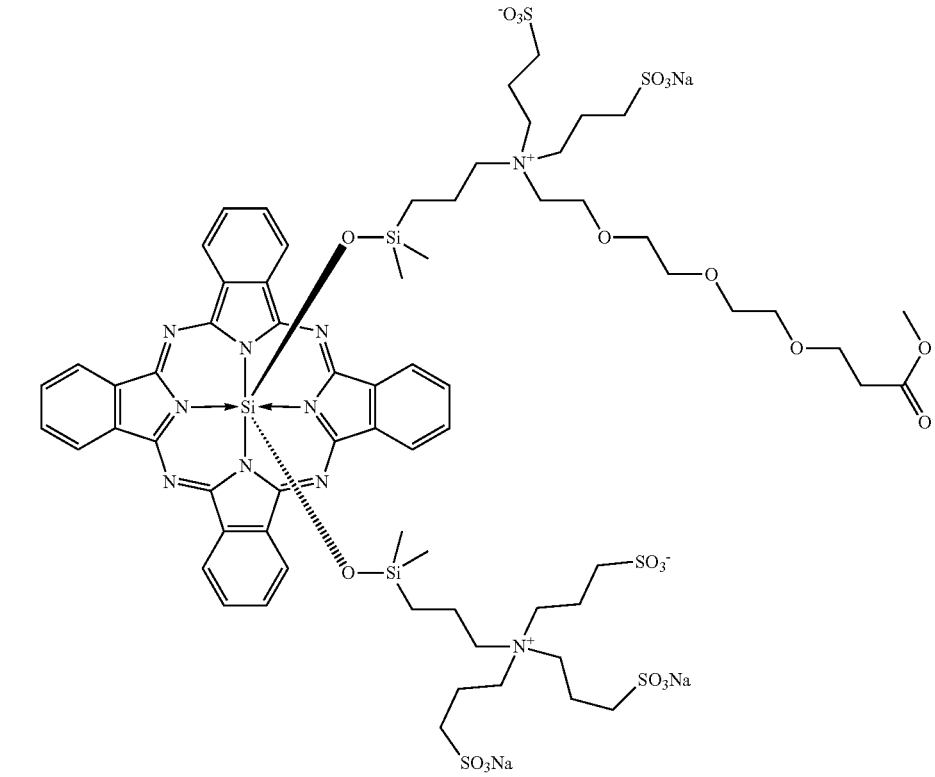

The title compound was prepared in a manner similar to Example 17, Step 5 by replacing sodium 4-iodobutane-1-sulfonate for the title compound from Step 1 (345 mg, 1.2 mmol) to afford the title compound (0.275 g, crude) as a blue solid. LCMS: 816 [M−1/2]—.

Step 3: Ammonium 2-((19-((dimethyl(3-(tris(3-sulfonatopropyl)ammonio)propyl)silyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)-2-methyl-6,6-bis(3-sulfonatopropyl)-9,12,15-trioxa-6-aza-2-silaoctadecan-6-ium-18-oate

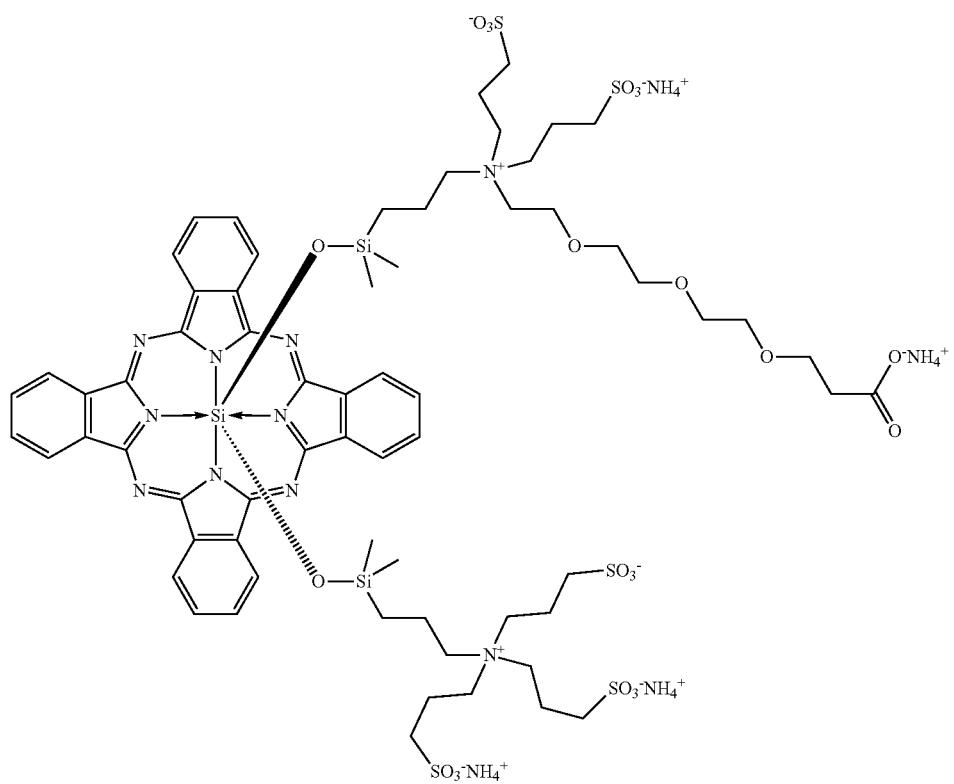

The title compound was prepared in a manner similar to Example 17, Step 6 by replacing the title compound from Example 17, Step 5 for the title compound from Step 2 (275 mg, 0.16 mmol) to afford the title compound (62 mg, 60% over two steps) as a blue solid. LCMS: 809 [M−1/2]—.

Step 4: Sodium 2-((19-((dimethyl(3-(tris(3-sulfonatopropyl)ammonio)propyl)silyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)-2-methyl-6,6-bis(3-sulfonatopropyl)-9,12,15-trioxa-6-aza-2-silaoctadecan-6-ium-18-oate

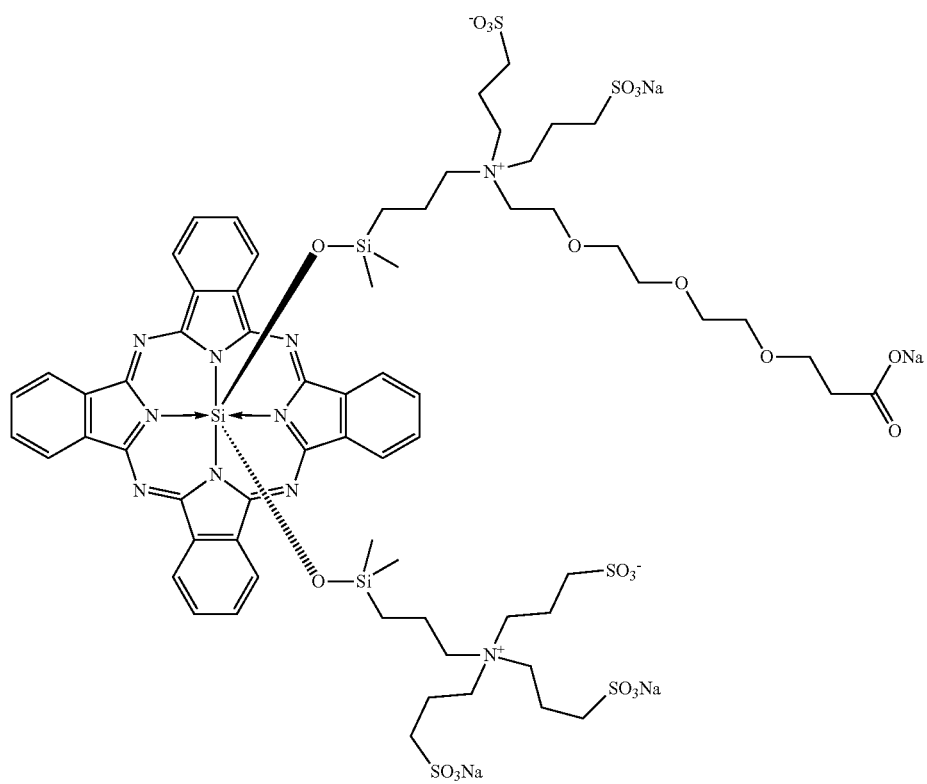

The title compound of Step 3 (62 mg, 0.04 mmol) was submitted to the ion exchange procedure described in Example 14, Step 1 to afford the title compound (58 mg, 92%). $^1$H NMR (400 MHz, D$_2$O) δ 9.66 (m, 8H), 8.47 (m, 8H), 3.30 (m, 2H), 3.23 (m, 2H), 2.87 (m, 8H), 2.72 (s, 6H), 2.60-2.39 (m, 16H), 2.09-2.07 (m, 4H), 1.91 (m, 2H), 1.67-1.50 (m, 10H), −1.56 (m, 2H), −1.67 (m, 2H), −2.02 (m, 4H), −2.89 (s, 6H), −2.93 (s, 6H). LCMS: 809 [M−1/2]−.

Example 20

Preparation of sodium 6-((3-(((19-((dimethyl(3-(5-(tris(3-sulfonatopropyl)ammonio)-2-(3-(tris(3-sulfonatopropyl) ammonio)propyl)pentanamido) propyl)silyl)oxy)-19H-6,11-(azeno)-17,21-(azeno[1] episoindoloazeno)benzo [7,8][1.3.5.10]tetraaza[2] silacycloundecino[4,3-a:11,1-a']diisoindol-19-yl) oxy)dimethylsilyl)propyl)amino)-6-oxohexanoate)

Step 1: tert-Butyl (3-bromopropyl)carbamate

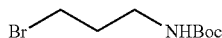

To a solution of tert-butyl (3-hydroxypropyl)carbamate (2.0 g, 11.4 mmol) in THF (30 mL) under nitrogen was added CBr$_4$ (5.68 g, 17.1 mmol) and PPh$_3$ (4.49 g, 17.1 mmol). The reaction was stirred at room temperature for 1 h. It was then diluted with an aqueous saturated NaHCO$_3$ solution (30 mL) and extracted with ethyl acetate (3×30 mL). The combined organic layers were dried over sodium sulphate, filtered and concentrated under reduced pressure. The residue was purified by silica gel chromatography to afford the title compound (2 g, 74% yield) as a white solid. $^1$H-NMR (400 MHz, CDCl$_3$) δ 4.67 (bs, 1H), 3.46 (t, J=6.4 Hz, 2H), 3.29 (m, 2H), 2.06 (t, J=6.4 Hz, 2H), 1.45 (s, 9H).

Step 2: Di-tert-utyl 2,2-bis(3-((tert-butoxycarbonyl) amino)propyl)malonate

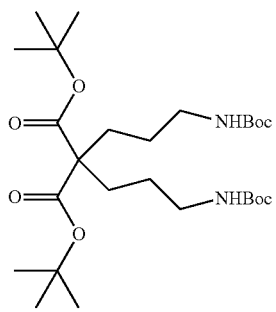 [SMILES: CC(C)(C)OC(=O)NCCCC(CCCNC(=O)OC(C)(C)C)(C(=O)OC(C)(C)C)C(=O)OC(C)(C)C]

To a solution of the title compound from Step 1 (2.0 g, 8.4 mmol) and di-tert-butyl malonate (726 mg, 3.36 mmol) in THF (20 mL) at 0° C. under nitrogen was added NaH (60%) (403 mg, 10.1 mmol) portion wise. The reaction was warmed up to room temperature and stirred for 4 h. The reaction contents were slowly added to ice-cold water (50 mL) and extracted with ethyl acetate (2×50 ml). The combined organic layers were dried over sodium sulphate, filtered and concentrated under reduced pressure. The crude residue was purified by silica gel column chromatography to afford the title compound (1.2 g, 67% yield). LCMS: 531 [M+H]$^+$.

Step 3: 5-Amino-2-(3-aminopropyl)pentanoic Acid

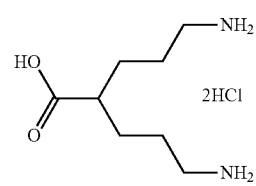

A mixture of the title compound from Step 2 (5 g, 9.4 mmol) in AcOH (50 mL) and 3N HCl (50 mL) was heated at 80° C. for 48 h. The reaction mixture was cooled to room temperature and concentrated under reduced pressure to afford the title compound (2.5 g Crude). $^1$H-NMR (400 MHz, D$_2$O) δ 2.91 (bs, 4H), 2.41 (bs, 1H), 1.58-1.50 (m, 8H).

Step 4: 5-(((((9H-fluoren-9-yl)methoxy)carbonyl) amino)-2-(3-(((((9H-fluoren-9-yl)methoxy)carbonyl) amino) propyl)pentanoic Acid

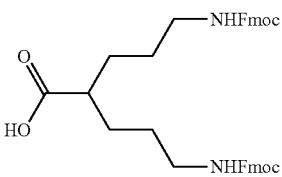

To a solution of the title compound from Step 3 (790 mg, 4.5 mmol) in a THF (10 mL) and aqueous saturated NaHCO$_3$ (10 mL) mixture was added Fmoc-OSu (3.8 g, 11.3 mmol) at room temperature. The reaction mixture was stirred at room temperature for 4 h. The pH was adjusted to between 7 and 8 by using 1N HCl and the reaction was then extracted with ethyl acetate (3×50 mL). The combined organic layers were dried over sodium sulphate, filtered and concentrated under reduced pressure. The residue was purified by silica gel column chromatography to afford the title compound (1.5 g, 76%) as white solid. LCMS: 619 [M+H]$^+$.

245

Step 5: Methyl 6-((3-(((19-((8-(3-((((9H-fluoren-9-yl)methoxy)carbonyl)amino)propyl)-1-(9H-fluoren-9-yl)-14-methyl-3,9-dioxo-2-oxa-4,10-diaza-14-silapentadecan-14-yl)oxy)-19H-6,11-(azeno)-17,21-(azeno[1]episoindoloazeno)benzo[7,8][1,3,5,10]tetraaza[2]silacycloundecino[4,3-a:11,1-a']diisoindol-19-yl)oxy)dimethylsilyl)propyl)amino)-6-oxohexanoate

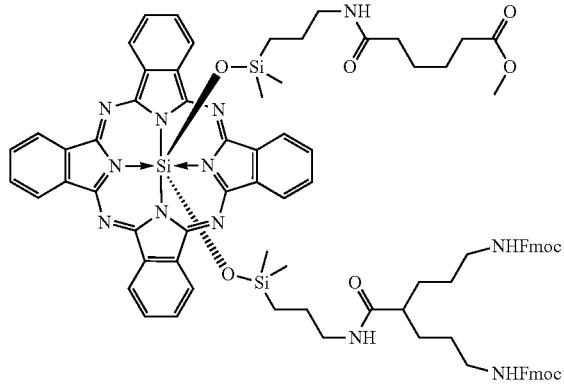

To a solution of the title compound from Step 4 (144 mg, 0.23 mmol) in THF (10 mL) under nitrogen was added EDC.HCl (71 mg, 0.35 mmol) and HOBt (57 mg, 0.35 mmol) at room temperature. The solution was stirred at room temperature for 1 h followed by addition of the title compound from Example 1, Step 2 (220 mg, 0.23 mmol) and DIPEA (0.12 mL, 0.7 mmol). The resulting mixture was stirred for 2 h. The reaction contents were poured over ice cold water (30 mL) and extracted with DCM (3×30 mL). The combined organic layers were dried over sodium sulphate, filtered and concentrated under reduced pressure. The residue was purified by column chromatography on basic alumina to afford the title compound (230 mg, 64%) as a blue solid.

246

Step 6: Methyl 6-((3-(((19-(((3-(5-amino-2-(3-aminopropyl)pentanamido)propyl)dimethylsilyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)dimethylsilyl)propyl)amino)-6-oxohexanoate

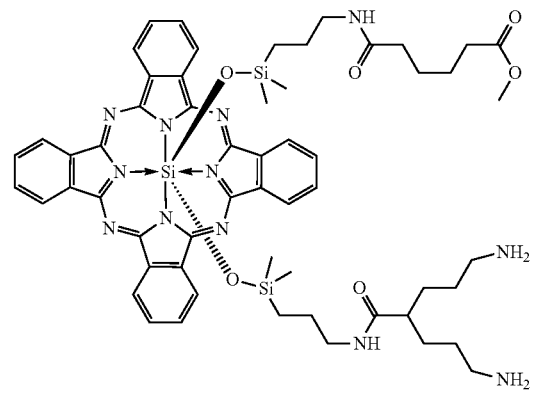

To a solution of the title compound from Step 5 (75 mg, 0.05 mmol) in THF (2 mL) was added DBU (24 mg, 0.1 mmol) at room temperature. The resulting mixture was stirred for 2 h followed by concentration under reduced pressure. The crude residue was purified by trituration using diethyl ether (2×3 mL) to afford the title compound (65 mg, crude) as a blue solid. LCMS: 1104 $[M+H]^+$.

Step 7: 3,3'-((4-((3-(((19-(((3-(6-Methoxy-6-oxohexanamido)propyl)dimethylsilyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)dimethylsilyl)propyl)carbamoyl)heptane-17-diyl)bis(bis(3-sulfopropyl)ammoniumdiyl))bis(propane-1-sulfonate)

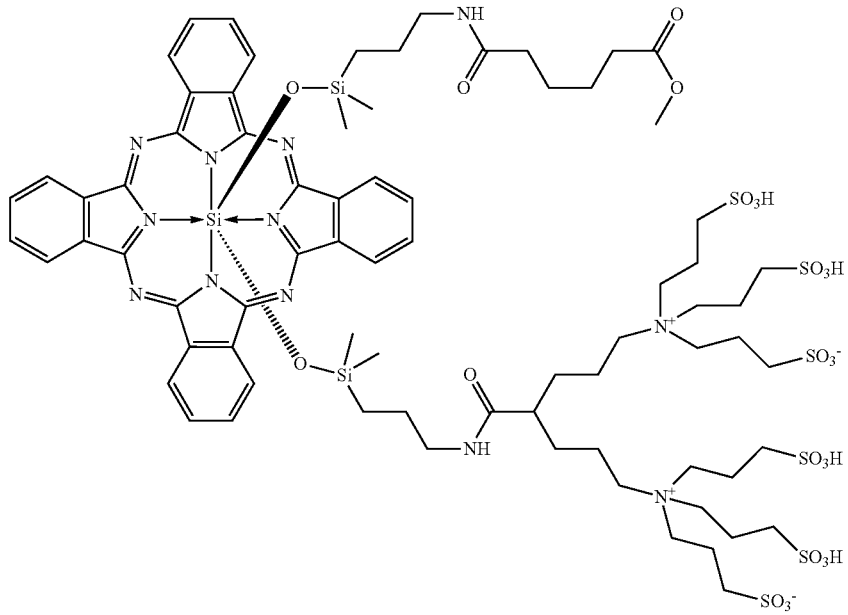

To a solution of the title compound of Step 6 (65 mg, 0.06 mmol) in sulfolane (5 mL) at room temperature under nitrogen was added 1,3-propanesultone (360 mg, 2.9 mmol) and DIPEA (0.77 mL, 4.4 mmol). The reaction was heated at 120° C. for 10 h. The reaction mixture was cooled to room temperature, added drop-wise to THF (20 mL) and stirred for 30 minutes. The supernatant was removed, and the solids were further washed with THF (2×10 mL) and dried under vacuum to afford the title compound (410 mg crude). LCMS: 917 [M−1/2]—.

Step 8: Ammonium 6-((3-(((19-((dimethyl(3-(5-(tris (3-sulfonatopropyl)ammonio)-2-(3-(tris(3-sulfonato-propyl) ammonio)propyl)pentanamido)propyl)silyl) oxy)-19H-6,11-(azeno)-17,21-(azeno[1] episoindoloazeno)benzo [7,8][1,3,5,10]tetraaza[2] silacycloundecino[4,3-a:11,1-a']diisoindol-19-yl) oxy)dimethylsilyl)propyl)amino)-6-oxohexanoate

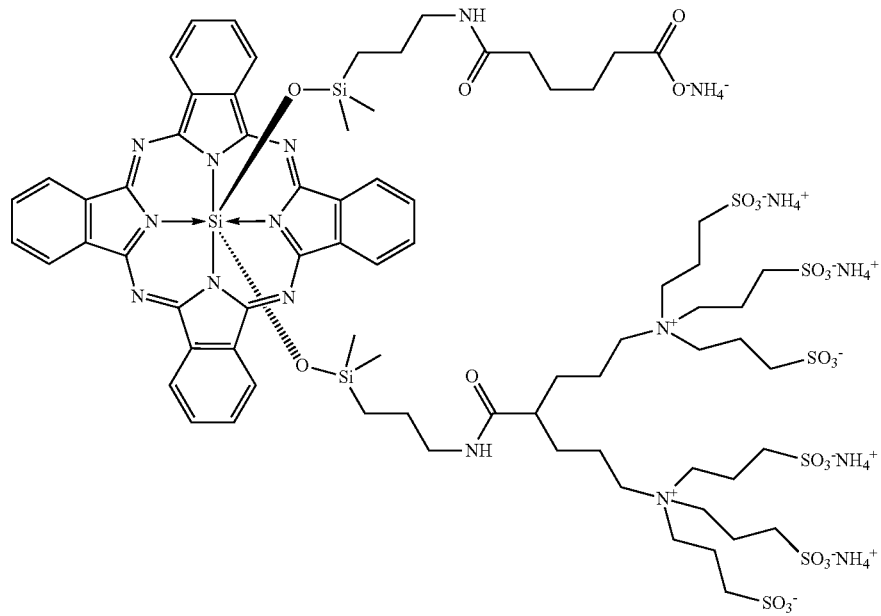

The title compound was prepared in a manner similar to Example 17, Step 6 by replacing the title compound from Example 17, Step 5 for the title compound from Step 5 (410 mg, 0.22 mmol) to afford the title compound (14 mg, 12% over two step) as a blue solid. LCMS: 910 [M−1/2]—.

Step 9: Sodium 6-((3-(((19-((dimethyl(3-(5-(tris(3-sulfonatopropyl)ammonio)-2-(3-(tris(3-sulfonatopropyl) ammonio)propyl)pentanamido)propyl)silyl) oxy)-19H-6,11-(azeno)-17,21-(azeno[1] episoindoloazeno)benzo[17,8][1,3,5,10]tetraaza[2] silacyloundecino[4,3-a:11,1-a']diisoindol-19-yl) oxy)dimethylsilyl)propyl)amino)-6-oxohexanoate)

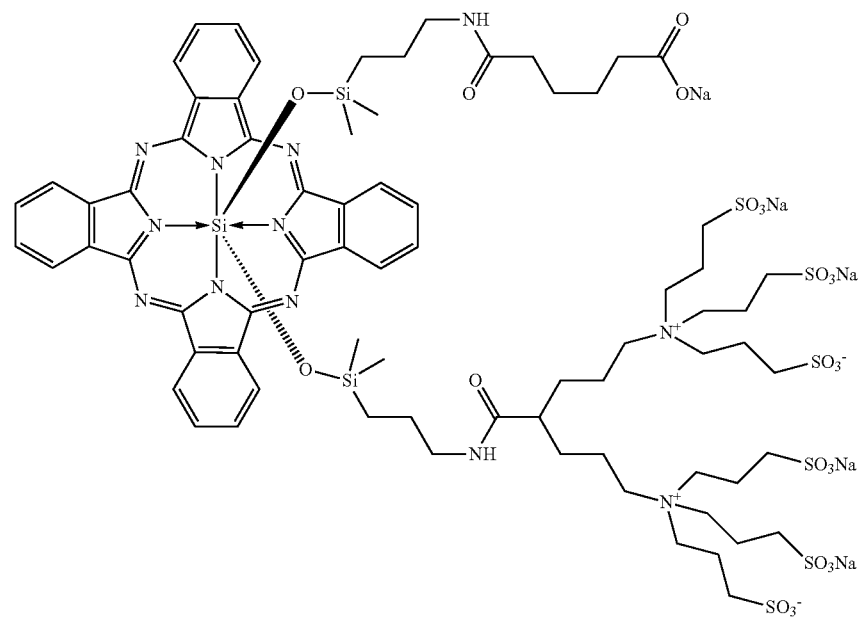

The title compound of Step 8 (18 mg, 0.009 mmol) was submitted to the ion exchange procedure described in Example 14, Step 1 to afford the title compound (16 mg, 88%). $^1$H NMR (400 MHz, D$_2$O) δ 9.57 (m, 8H), 8.40 (m, 8H), 3.19 (m, 12H), 3.03 (m, 4H), 2.73 (m, 12H), 1.94 (m, 15H), 1.81 (m, 4H), 1.25 (m, 2H), 1.25 (m, 6H), 1.14 (m, 6H), −1.16 (m, 2H), −1.28 (m, 2H) −2.23 (m, 4H), −2.92 (s, 6H), −2.96 (s, 6H). LCMS: 910 [M−1/2]—.

Example 21

Preparation of sodium 2-((19-((dimethyl(3-(tris(3-sulfonatopropyl)ammonio)propyl)silyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)-2-methyl-6,6-bis(3-sulfonatopropyl)-9,12-dioxa-6-aza-2-silapentadecan-6-ium-15-oate Step 1: Sodium 3,3',3''-((3-(dimethyl((19-((2-methyl-15-oxo-6,6-bis(3-sulfonatopropyl)-9,12,16-trioxa-6-aza-2-silaheptadecan-6-ium-2-yl)oxy)-19H-6,11-(azeno)-17,21-(azeno[1]episoindoloazeno)benzo[7,8][1,3,5,10]tetraaza[2]silacycloundecino[4,3-a:11,1-a']diisoindol-19-yl)oxy)silyl)propyl)ammonio)tris(propane-1-sulfonate)

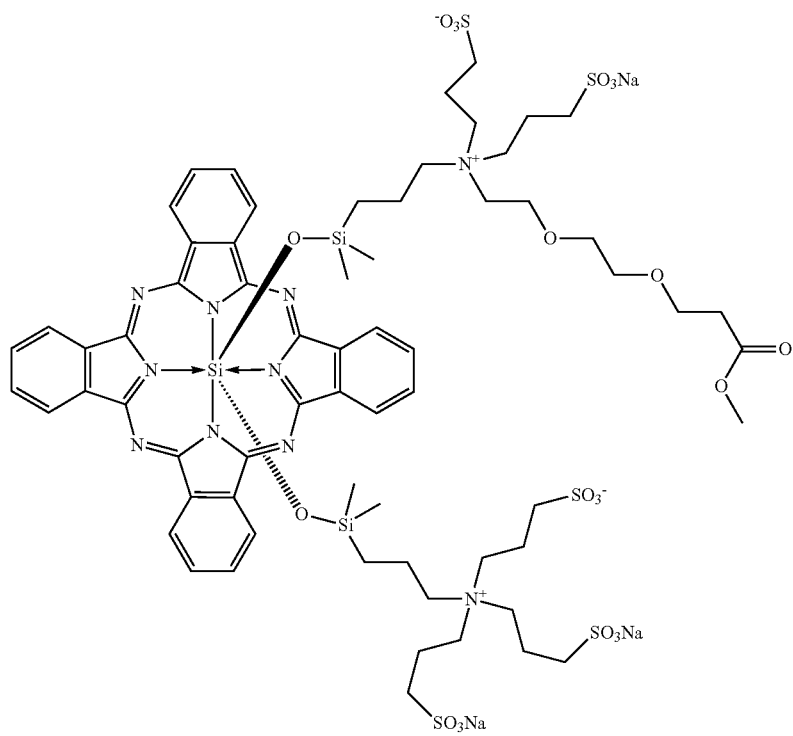

The title compound was prepared in a manner similar to Example 18, Step 5 by replacing sodium 4-iodobutane-1-sulfonate for sodium 3-iodopropane-1-sulfonate (444 mg, 1.6 mmol) to afford the title compound (500 mg crude). LCMS: 794 [M−1/2]—.

Step 2: Ammonium 2-((19-((dimethyl(3-(tris(3-sulfonatopropyl)ammonio)propyl)silyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)-2-methyl-6,6-bis(3-sulfonatopropyl)-9,12-dioxa-6-aza-2-silapentadecan-6-ium-15-oate

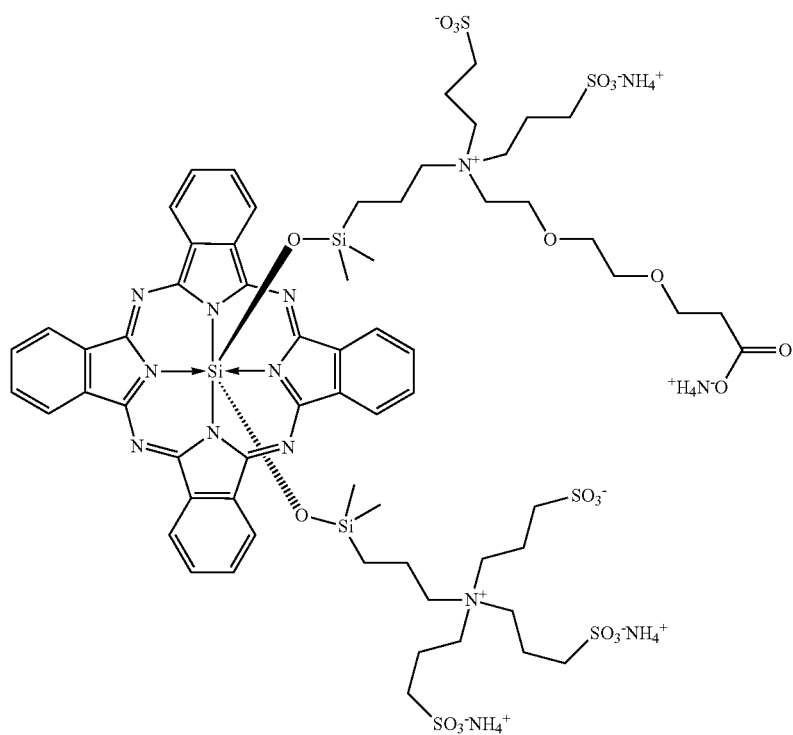

The title compound was prepared in a manner similar to Example 17, Step 6 by replacing the title compound from Example 17, Step 5 for the title compound from Step 1 (480 mg, 0.29 mmol) to afford the title compound (30 mg, 22% over two steps) as a blue solid. LCMS: 787 [M−1/2]—.

Step 3: Sodium 2-((19-((dimethyl(3-(tris(3-sulfonatopropyl)ammonio)propyl)silyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)-2-methyl-6,6-bis(3-sulfonatopropyl)-9,12-dioxa-6-aza-2-silapentadecan-6-ium-15-oate

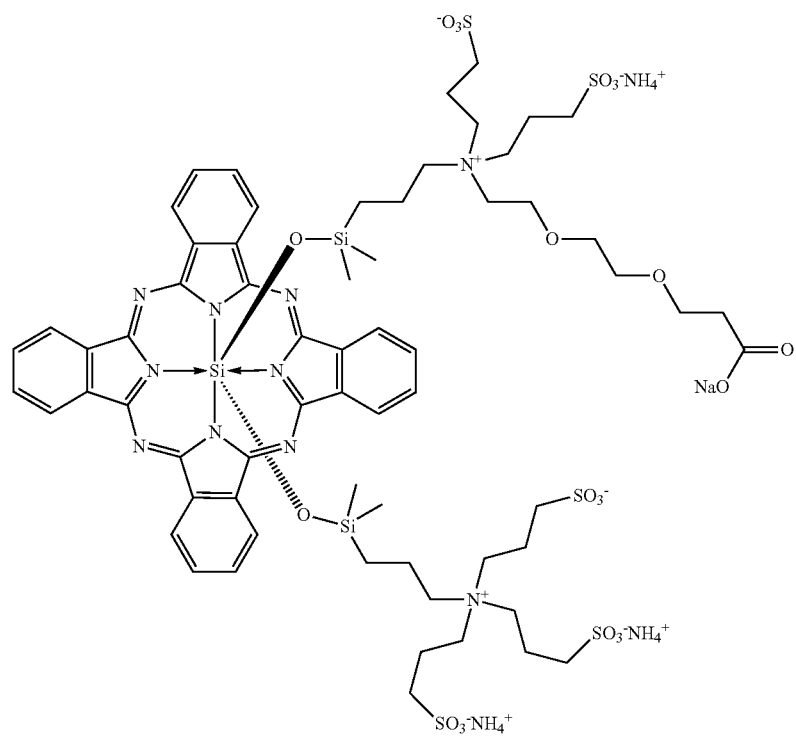

The title compound of Step 2 (30 mg, 0.02 mmol) was submitted to the ion exchange procedure described in Example 14, Step 1 to afford the title compound (28 mg, 92%). $^1$H NMR (400 MHz, D$_2$O) δ 9.66 (m, 8H), 8.46 (m, 8H), 3.30 (m, 2H), 3.23 (m, 2H), 2.87-2.83 ((m, 6H), 2.72 (m, 8H), 2.59-2.36 (m, 12H), 2.03 (m, 2H), 1.92 (m, 2H), 1.73 (t, J=6.8 Hz, 2H), 1.64 (m, 2H) 1.54 (m, 8H), −1.55 (m, 2H), −1.68 (m, 2H), −2.01 (m, 4H), −2.88 (s, 6H), −2.92 (s, 6H). LCMS: 787 [M−1/2]—.

Example 22

Preparation of sodium 2-((19-(((dimethyl(3-(tris(4-sulfonatobutyl)ammonio)propyl)silyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl) oxy)-2-methyl-6,6-bis(4-sulfonatobutyl)-9,12,15,18-tetraoxa-6-aza-2-silahenicosan-6-ium-21-oate Step 1: 1-Hydroxy-3,6,9,12-tetraoxapentadecan-15-oic Acid

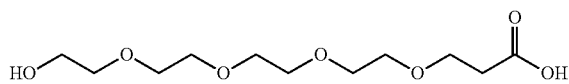 [SMILES: O=C(O)CCOCCOCCOCCOCCO]

The title compound was prepared in a manner similar to Example 17, Step 1 by replacing tert-butyl 3-(2-(2-(2-hydroxyethoxy)ethoxy)ethoxy)propanoate for tert-butyl 1-hydroxy-3,6,9,12-tetraoxapentadecan-15-oate (2 g, 6.2 mmol) to afford the crude title compound (1.6 g) that was used in the following step without further purification.

Step 2: Methyl 1-hydroxy-3,6,9,12-tetraoxapentadecan-15-oate

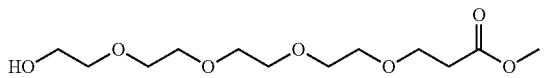 [SMILES: COC(=O)CCOCCOCCOCCOCCO]

The title compound was prepared in a manner similar to Example 17, Step 2 by replacing 3-(2-(2-(2-Hydroxyethoxy)ethoxy)ethoxy)propanoic acid for the title compound from Step 1 (1.6 g, 6.0 mmol) to afford the title compound (1.2 g, 71%), 1H NMR (400 MHz, D2O) δ 3.69 (t, J=5.8 Hz, 2H), 3.60-3.52 ((m, 17H), 3.53 (m, 2H), 2.57 (t, J=6.0 Hz, 2H).

Step 3: Methyl 1-oxo-3,6,9,12-tetraoxapentadecan-15-oate

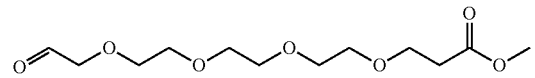 [SMILES: COC(=O)CCOCCOCCOCCOCC=O]

The title compound was prepared in a manner similar to Example 17, Step 3 by replacing methyl 3-(2-(2-(2-hydroxyethoxy)ethoxy)ethoxy)propanoate for the title compound from Step 2 (0.5 g, 1.8 mmol) to afford the title compound (210 mg, 42%) as a liquid.

Step 4: Methyl 2-((19-(((3-aminopropyl)dimethylsilyl)oxy)-19H-6,11-(azeno)-17,21-(azeno[3]episoindoloazeno) benzo[7,8][11,3,5,10]tetraaza[2]silacycloundecino[4,3-a:11,1-a']diisoindol-19-yl)oxy)-2-methyl-9,12,15,18-tetraoxa-6-aza-2-silahenicosan-21-oate

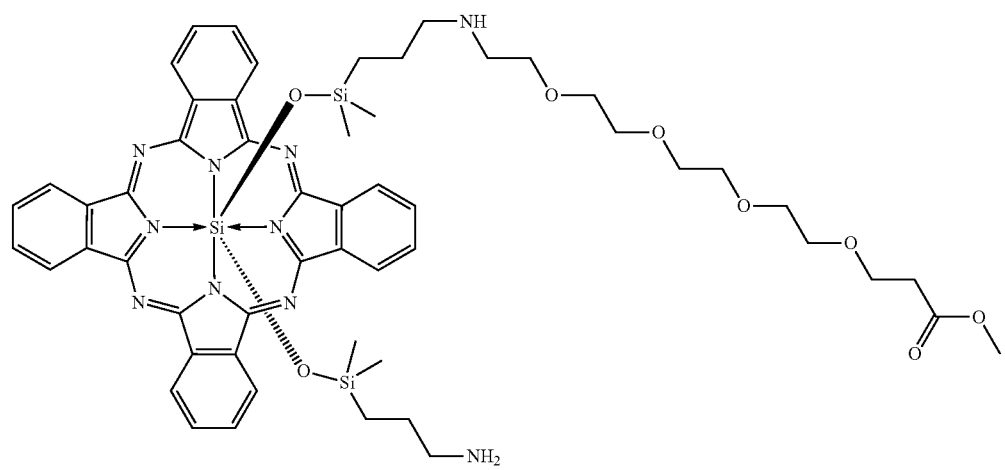

The title compound was prepared in a manner similar to Example 17, Step 4 by replacing methyl 3-(2-(2-(2-oxoethoxy)ethoxy)ethoxy)propanoate for the title compound from Step 3 (83 mg, 0.3 mmol) to afford the title compound (30 mg, 19%) as a blue solid. LCMS: 1068 [M+2H]$^+$.

Step 5: Sodium 4,4',4''-((3-(dimethyl((19-((2-methyl-21-oxo-6,6-bis(4-sulfonatobutyl)-9,12,15,18,22-pentaoxa-6-aza-2-silatricosan-6-ium-2-yl)oxy)-19H-6,11-(azeno)-17,21-(azeno[1]episoindoloazeno)benzo[7,8][1,3,5,10]tetraaza[2]silacycloundecino[4,3-a:11,1-a']diisoindol-19-yl)oxy)silyl)propyl)ammonio)tris(butane-1-sulfonate)

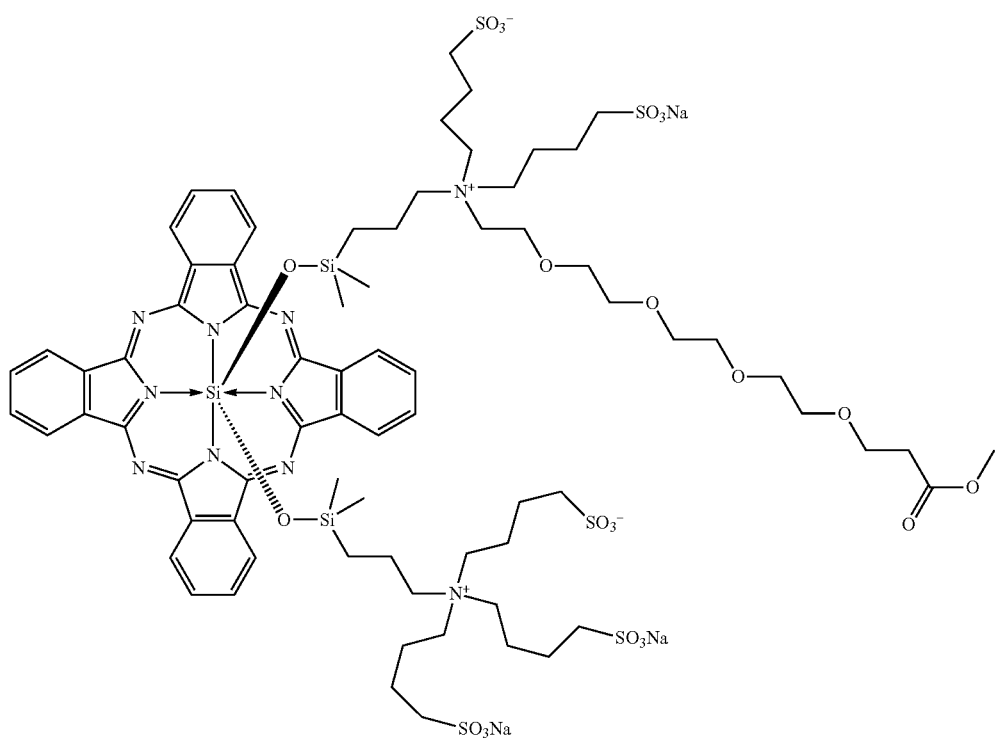

The title compound was prepared in a manner similar to Example 17, Step 5 by replacing the title compound from Example 17, Step 4 for the title compound from Step 4 (35 mg, 0.03 mmol) to afford the title compound (81 mg crude) as a blue solid. LCMS: 875 [M/2+2H]$^+$.

Step 6: Ammonium 4,4',4"-((3-(((19-((20-carboxy-2-methyl-6,6-bis(4-sulfonatobutyl)-9,12,15,18-tetraoxa-6-aza-2-silaicosan-6-ium-2-yl)oxy)-19H-6,11-(azeno)-17,21-(azeno[1]episoindoloazeno)benzo[7,8][1,3,5,101]tetraaza[2]silacycloundecino[4,3-a:11,1-a']diisoindol-19-yl)oxy)dimethylsilyl)propyl)ammonio)tris(butane-1-sulfonate)

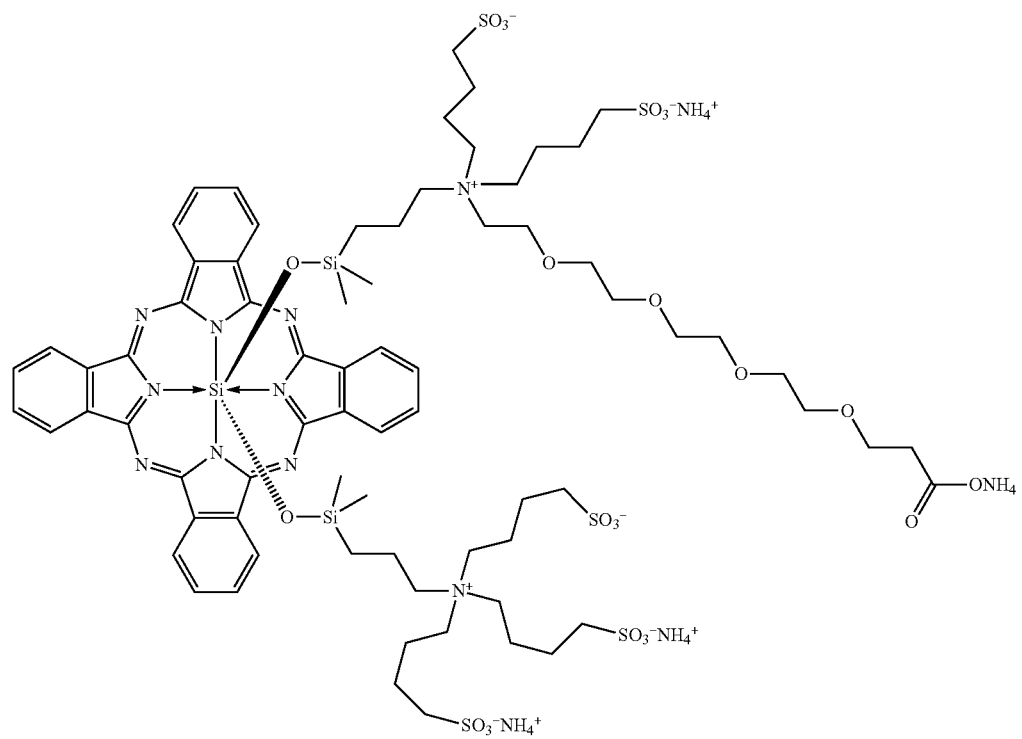

The title compound was prepared in a manner similar to Example 17, Step 6 by replacing the title compound from Example 17, Step 5 for the title compound from Step 5 (140 mg, 0.08 mmol) to afford the title compound (18 mg, 18% over two step) as a blue solid. LCMS: 866 [M−1/2]—.

Step 7: Sodium 2-((19-((dimethyl(3-(tris(4-sulfonatobutyl)ammonio)propyl)silyl)oxy)-19H-6,11-(azeno)-17,21-(azeno[3]episoindoloazeno)benzo[7,8][1,3,5,10]tetraaza[2]silacycloundecino[4,3-a:11,1-a']diisoindol-19-yl)oxy)-2-methyl-6,6-bis(4-sulfonatobutyl)-9,12,15,18-tetraoxa-6-aza-2-silahenicosan-6-ium-21-oate

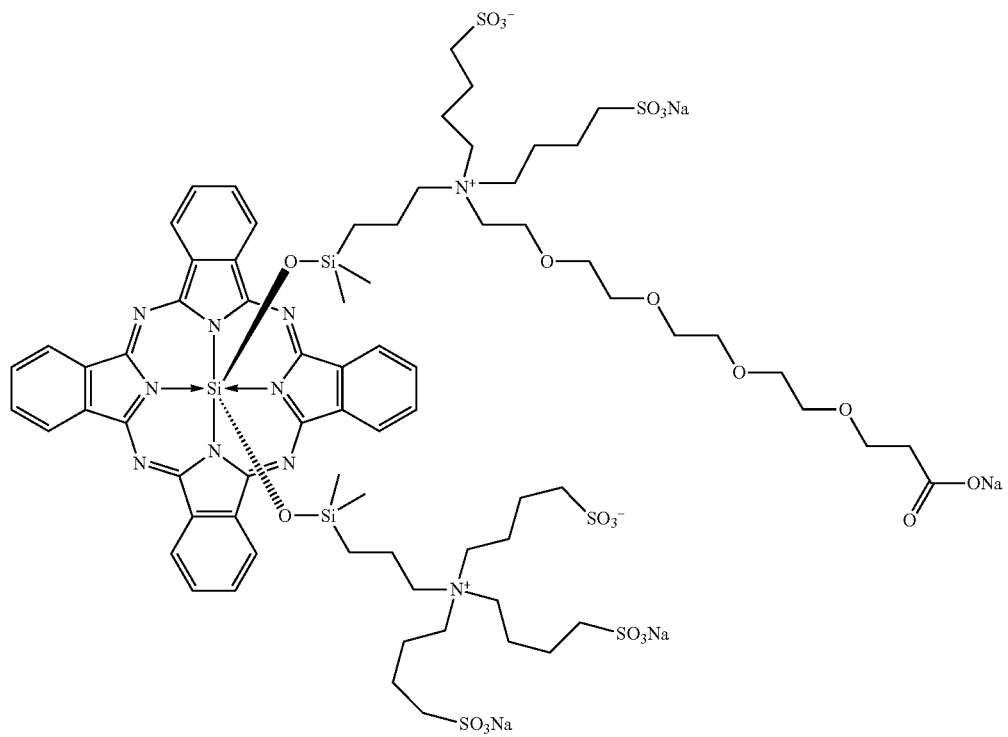

The title compound of Step 6 (18 mg, 0.01 mmol) was submitted to the ion exchange procedure described in Example 14, Step 1 to afford the title compound (16 mg, 87%). $^1$H NMR (400 MHz, D$_2$O) δ 9.65 (m, 8H), 8.46 (m, 8H), 3.40 (t, J=6.8 Hz, 2H), 3.30 (m, 2H), 3.24 (m, 2H) 3.11 (m, 2H), 2.85 (m, 6H), 2.73 (m, 8H), 2.65 (m, 6H), 2.59 (m, 4H), 2.30 (m, 4H), 2.18 (t, J=6.8 Hz, 4H), 1.92 (m, 2H), 1.58 (m, 8H), 1.44 (m, 2H), 1.31 (m, 4H), 1.15 (m, 8H), −1.50 (m, 2H), −1.64 (m, 2H), −2.06 (m, 4H), −2.91 (s, 6H), −2.93 (s, 6H). LCMS: 866 [M−1/2]—.

Example 23

Preparation of sodium 4,4',4"-((3-(((19-((15-((2,5-dioxopyrrolidin-1-yl)oxy)-2-methyl-15-oxo-6,6-bis(4-sulfonatobutyl)-9,12-dioxa-6-aza-2-silapentadecan-6-ium-2-yl)oxy)-19H-6,11-(azeno)-17,21-(azeno[1]episoindoloazeno)benzo[7,8][1,3,5,10]tetraaza[2]silacycloundecino[4,3-a:11,1-a']diisoindol-19-yl)oxy)dimethylsilyl)propyl)ammonio)tris(butane-1-sulfonate)

The title compound was prepared in a manner similar to Example 14, Step 2 by replacing the title compound from Example 14, Step 1 for the title compound from Example 18 (2.8 mg, 1.6 μmol) to afford the title compound (0.7 μmol). LCMS: 869.8 [M−2/2]—.

Example 24

Preparation of sodium 4,4',4"-((3-(((19-((18-((2,5-dioxopyrrolidin-1-yl)oxy)-2-methyl-18-oxo-6,6-bis(4-sulfonatobutyl)-9,12,15-trioxa-6-aza-2-silaoctadecan-6-ium-2-yl)oxy)-19H-6,11-(azeno)-17,21-(azeno[1]episoindoloazeno)benzo[7,8][1,3,5,10]tetraaza[2]silacycloundecino[4,3-a:11,1-a']diisoindol-19-yl)oxy)dimethylsilyl)propyl)ammonio)tris(butane-1-sulfonate)

The title compound was prepared in a manner similar to Example 14, Step 2 by replacing the title compound from Example 14, Step 1 for the title compound from Example 17 (2.5 mg, 1.4 μmol) to afford the title compound (1.3 μmol). LCMS: 891.5 [M−2/2]—.

Example 25

Preparation of sodium 3,3',3"-((3-(((19-((15-((2,5-dioxopyrrolidin-1-yl)oxy)-2-methyl-15-oxo-6,6-bis(3-sulfonatopropyl)-9,12-dioxa-6-aza-2-silapentadecan-6-ium-2-yl)oxy)-19H-6,11-(azeno)-17,21-(azeno[1]episoindoloazeno)benzo[7,8][1,3,5,10]tetraaza[2]silacycloundecino[4,3-a:11,1-a']diisoindol-19-yl)oxy)dimethylsilyl)propyl)ammonio)tris(propane-1-sulfonate)

The title compound was prepared in a manner similar to Example 14, Step 2 by replacing the title compound from Example 14, Step 1 for the title compound from Example 21 (2.4 mg, 1.4 μmol) to afford the title compound (0.8 μmol). LCMS: 834.4 [M−2/2]—.

Example 26

Preparation of sodium 4,4',4"-((3-(((19-((dimethyl(3-((6-oxo-6-(perfluorophenoxy)hexyl)bis(4-sulfonatobutyl)ammonio)propyl)silyl)oxy)-19H-6,11-(azeno)-17,21-(azeno[1]episoindoloazeno)benzo[7,8][1,3,5,10]tetraaza[2]silacycloundecino[4,3-a:11,1-a']diisoindol-19-yl)oxy)dimethylsilyl)propyl)ammonio)tris(butane-1-sulfonate)

To a solution of the title compound from Example 16, Step 1 (4.5 mg, 0.002 mmol) in DMSO (0.2 mL) under nitrogen was sequentially added EDCI (27 μL of 0.1 M solution in DMSO, 1.2 eq). After ten minutes, 2,3,4,5,6-pentafluorophenol (27 μL of 0.1 M solution in DMSO, 1.2 eq) and DMAP (3 μL of 0.1 M solution in DMSO, 0.1 eq) were sequentially added. The resulting mixture was stirred at room temperature for four days. The reaction was diluted with DMF (0.2 mL) and filtered through a 0.45 μm syringe filter into vigorously stirred MTBE (3.5 mL) over a ten-minute period. The reaction vial was washed with DMF (0.06 mL). A blue precipitate forms. The suspension was stirred for 2 min and then allowed to settle over a 30-minute period. The clear supernatant was removed and fresh MTBE (3.5 mL) was added. The suspension was stirred for 30 seconds and allowed to settle for 30 min. The clear supernatant was removed to afford the title compound as a solid. LCMS: 881.2 (M−2/2)−.

Example 27

Preparation sodium 4,4',4"-((3-(((19-(((3-((6-((2-(2,5-dioxo-2,5-dihydro-1H-pyrrol-1-yl)ethyl)amino)-6-oxohexyl)bis(4-sulfonatobutyl)ammonio)propyl)dimethylsilyl)oxy)-19H-6,11-(azeno)-17,21-(azeno[1]episoindoloazeno)benzo[7,8][1,3,5,10]tetraaza[2]silacycloundecino[4,3-a:11,1-a']diisoindol-19-yl)oxy)dimethylsilyl)propyl)ammonio)tris(butane-1-sulfonate)

N,N-Diisopropylethylamine (3 μL of a 0.1 M solution in DMSO, 5 eq) and 1-(2-aminoethyl)-1H-pyrrole-2,5-dione hydrochloride (1.2 μL of a 0.1 M solution in DMSO, 2 eq) were sequentially added to the title compound from Example 16, Step 1 (10 μL of a 5.7 mM solution in DMSO). The resulting solution was kept in the dark for 1 h. The reaction mixture was diluted with DMF (20 uL) and added dropwise to MTBE (0.28 mL) with stirring. The reaction vial was washed with DMF (10 μL) that was added to the MTBE. A blue precipitate formed. The suspension was allowed to settle over a 30-minute period. The clear supernatant was removed, and fresh MTBE (0.3 mL) was added. The suspension was sonicated for five seconds and allowed to settle for 15 min. The clear supernatant was removed, and the residue dried under reduced pressure to afford the title compound as a blue solid. LCMS: 859.0 (M−2/2)−.

II. Evaluation of Properties

Example 1

Determination of Kinetic and Thermodynamic Solubility

A working 1 mM stock solution of the test compound in DMSO was prepared from a 10 mM DMSO stock solution. A spectrum scan from 220 nm to 1000 nm of this working solution was performed in a 96-well UV plate to identify the wavelength maxima. If peaks were merged and/or optical density saturation was observed, the spectrum scan was repeated with a diluted stock (i.e. 100 µM, 50 µM, 25 µM, 12.5 µM). The selected stock solution was serially diluted in DMSO to confirm linearity and generate a seven to eight-point calibration curve. Of note, only linear points were considered in the curve.

To determine the aqueous solubility of the test compound, 50 µL of its 10 mM stock solution was added to 950 µL of pH 7.4 Dulbecco's phosphate-buffered saline (DPBS) without calcium, magnesium and Phenol red. The resulting solution was placed on a RotoSpin™ shaker at 50 rpm for 4 hours at room temperature (25° C.). The solution was then filtered using a 0.45 µm PVDF filter to remove any insoluble fraction of the compound. A 150 uL aliquot of the filtrate was taken for quantification using UV spectroscopy (POLARstar Omega BMG Plate Reader). The optical densities of the standard solutions and the test sample were acquired at the same wavelength maxima. The test sample concentration was calculated from its optical density using the linearity/calibration curve.

To determine the thermodynamic solubility of the test compound, x mg (powder form of the compound) was added toy mL of pH 7.4 Dulbecco's phosphate-buffered saline (without calcium, magnesium and Phenol red) so the final concentration of the solution was 1 mg/mL. The resulting solution was placed on a RotoSpin™ shaker at 50 rpm for 24 hours at room temperature (25° C.). The solution was then filtered using a 0.45 µm PVDF filter to remove any insoluble fraction of the compound. A 150 µL aliquot of the filtrate was taken for quantification using UV spectroscopy (POLARstar Omega BMG Plate Reader). The optical densities of the standard solutions and the test sample were acquired at the same wavelength maxima. The test sample concentration was calculated from its optical density using the linearity/calibration curve.

The solubility of various compounds is shown in Table 3, in which data are designated within the following ranges: A: ≤1 µg/mL; B: >1 µg/mL to ≤100 µg/mL; C: >100 µg/mL.

TABLE 3

Example Solubility*

| No. | (µg/mL) |
|---|---|
| 3 | A |
| 5 | C |
| 7 | A |
| 8 | A |
| 9 | A |
| 12 | C |
| 13 | C |
| 15 | B |
| 17 | C |
| 18 | C |
| 19 | C |
| 20 | C |
| 21 | C |
| 22 | C |

*Kinetic solubility for all Examples except thermodynamic for 20, 21 and 22.

Example 2

Measurement of UV-Vis Absorption

The UV-Vis absorption spectra of the compounds in either an organic solvent or aqueous media was recorded in a Varian Cary® 50 UV-Vis spectrophotometer. Compounds of the invention show absorption in the 600-800 nm region of the spectra.

Figure 2:
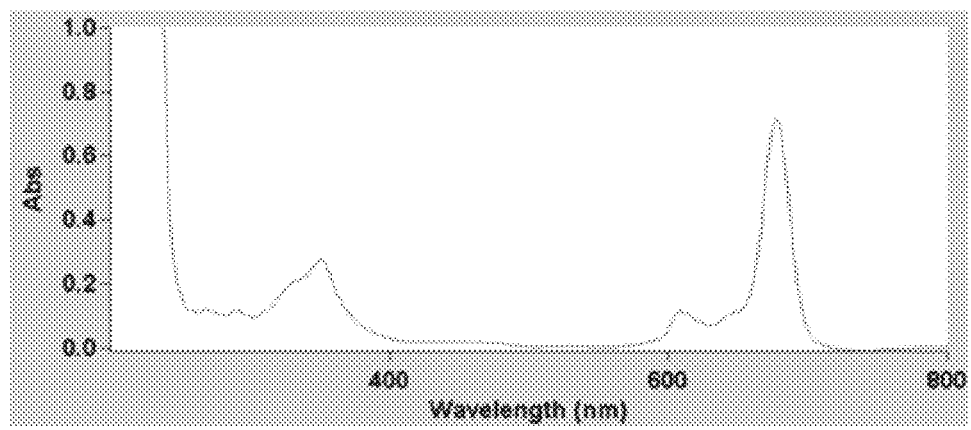
FIG. 2 provides the UV-Vis spectra of Chemical Synthesis Example 12.

The UV-Vis spectra of Chemical Synthesis Example 1 is shown in FIG. 1. The UV-Vis spectra of chemical Synthesis Example 12 is shown in FIG. 2.

Example 3

Determination of Single Oxygen Quantum Yield

Photogeneration quantum yields of singlet oxygen ($\Phi_\Delta$) were obtained by an indirect method, using either diphenylisobenzofuran (DBPF) or anthracene-9,10-bis-methylmalonate (ADMA) as chemical quenchers in either N,N-dimethylformamide or aqueous media, respectively. Typically, a solution of the phthalocyanine and the quencher was irradiated with a red LED lamp (670 nm) at 5 mW/cm$^2$. The initial DPBF or ADMA concentrations were kept the same for both the reference and the test samples. The degradation of the DPBF band at 414 nm or ADMA at 401 nm was monitored in a Varian CaryF50 UV-Vis spectrophotometer, every five seconds in the case of DPBF (up to 30 seconds) and every minute in the case of ADMA (up to five minutes). ZnPc ($\Phi_\Delta$=0.67) and AlPcSmix ($\Phi_\Delta$=0.42) were used as references in N,N-dimethylformamide or aqueous media, respectively.

The relative method shown by Eq. (1) was employed for calculations of the $\Phi_\Delta$:

$$\Phi_\Delta = \Phi_{\Delta ref} \frac{m \times I_{ref}}{m_{ref} \times I} \tag{1}$$

where $\Phi_\Delta$ and $\Phi_{\Delta ref}$ are the $^1O_2$ generation quantum yields for the sample and reference, respectively, m and $m_{ref}$ are the DPBF or ADMA photobleaching rates in the presence of the phthalocyanine of the invention and the reference, respectively, and I and $I_{ref}$ are the rates of light absorption by the phthalocyanine derivative and reference, respectively. Concentrations of the test compound and reference were chosen such that their respective absorptions at the irradiation wavelength were the same.

The singlet oxygen quantum yield of various compounds is shown in Table 4, in which $\Phi_\Delta$ data are designated within the following ranges: A: ≤0.5; B: >0.5.

TABLE 4

| Dye Compound No. | Quencher | $\Phi_\Delta$ |
|---|---|---|
| 1 | DPBF | A |
| 5 | ADMA | B |
| 12 | ADMA | B |
| 13 | ADMA | B |
| 17 | ADMA | B |
| 18 | ADMA | B |
| 19 | ADMA | B |

Example 4

Cell Killing of Free Dye PIT

The PIT killing activity of free dyes were evaluated using the molecules synthesized as Example 12 and Example 13. BxPC3 cells (#CRL-1687, ATCC, Manassas Va.) were plated, 5,000 cells per well, in RPMI-1640 media supplemented with 10% FBS and 1% Penicillin/Streptomycin (complete culture media) in a deep-well 96-well plate. Following overnight incubation at 37° C., the culture media were removed and the cells were incubated in 100 µL complete media with 1, 0.333, 0.111, 0.03704, 0.01235, 0.0412, 0.00137, or 0 µg/mL Example 12, Example 13, or IRDye 700DX carboxylate (control) for one hour at 4° C. Following incubation, the cells were illuminated with a 690 nm laser at a light dose of 64 J/cm$^2$ or protected from light (0 J/cm$^2$).

The effect of different treatment regimens on cell death was measured using the CellTox™ Green Cytotoxicity Assay (Cat No: G8742, Promega, Madison, Wis.). After the light treatment, all cells were incubated with 1× CellTox™ Green reagent diluted complete culture media. Wells that did not include any cells were also incubated with 1×CellTox Green reagent diluted in complete culture media to serve as background subtraction wells during fluorescent signal detection. The CellTox™ Green fluorescence signal was measured at 24 hours after light treatment using a fluorescence plate reader. The cells were then lysed with diluted lysis solution (Cat No: G1821, Promega, Madison, Wis.), incubated at 37° C. for 30 minutes, and the CellTox™ Green fluorescence signal was measured again post-lysis. The percentages of dead cells were calculated by taking the ratio between background (1× CellTox™ Green in complete culture media without cells)—subtracted CellTox™ Green signal per well prior to and post lysis and multiplying the ratio by 100.

Figure 3:
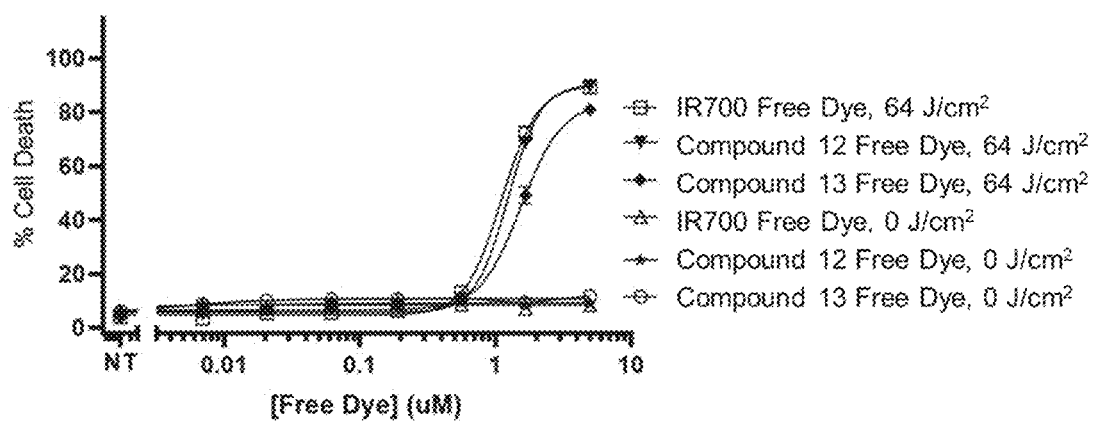
FIG. 3 depicts the dose-dependent cytotoxicity of free dyes Compound 12 and Compound 13 following illumination.

As shown in FIG. 3, no effect on cell death was observed for any sample exposed to 0 J/cm$^2$ during the PIT treatment at any dose of the free dyes, indicating that the dyes were not cytotoxic in the absence of light irradiation. In contrast, dose-dependent cell killing was observed for samples that were irradiated with a 690 nm laser at a light dose 64 J/cm$^2$.

Example 5

Generation of Dye Conjugates

This example describes a method for preparing exemplary conjugates containing a dye described herein linked to exemplary biomolecules. In this example, dye molecules such as those described herein, are conjugated to several types of biomolecules. The provided methods are exemplary and similar methods may be employed to conjugate other antibodies or targeting molecules to any of the provided dyes.

Antibody Conjugates

In this example, dye molecules such as those described herein, are conjugated to exemplary antibody biomolecules.

1) Cetuximab (CTX) Conjugates a) CTX-C12 and CTX-C13 Conjugates

A volume of 1 mL of Cetuximab (2 mg/mL solution) was buffer-exchanged into 100 mM sodium phosphate buffer (pH 8.65) using an Amicon® Ultra-15 centrifugal filter (50 kDa cutoff). The resulting Cetuximab antibody solution (approximately 1 mL) was transferred to a translucent 2 mL plastic vial. Dye Compound Example 14 (NHS ester of Compound 12 sodium salt) (89 µL, 0.6 M DMSO solution) was added with gentle swirling to create the conjugate CTX-C12. This step was carried out at room temperature under green light. The conjugation reaction was performed to a final molar ratio of 4:1 (dye: Cetuximab). The vial was placed inside an opaque container protected from light. The conjugation reaction was allowed to proceed for 270 min.

The conjugation reaction was quenched by the addition of 1 M glycine (20 µL) and mixing for 50 mm. The solution was transferred to an Amicon® Ultra-15 centrifugal filter (50 kDa cutoff) and its volume reduced to 0.7 mL. 1×PBS buffer pH 7.1 (10 mL) was added, and the resulting solution was centrifuged to a volume of approximately 1 mL. The 1×PBS buffer exchange was repeated two more times (2×10 mL). The resulting Cetuximab conjugate was stored in the dark at 2-6° C.

The conjugate was submitted for SEC-HPLC analysis to determine concentration, dye to antibody ratio (DAR) and purity. A 30 µL sample was run in a Shodex Protein® 5 µm KW-803 (8×300 mm, 300 Å) size-exclusion chromatography column on an Agilent 1100 HPLC instrument. Samples were run in a 1×PBS pH 7.1 mobile phase at a flow rate of 1 mL/min for a total of 20 minutes. Dye to antibody ratio (DAR) was determined by measuring the absorbance of the conjugates at wavelengths of 280 nm and 677 nm. The percent area of the main peak for the monomer content of the sample was determined, as well as calculation for high molecular weight species (HMW).

The CTX-C13 conjugate was prepared and analyzed in a manner similar to that of CTX-C12, replacing Compound 14 with the Compound 16 (NHS ester of Compound 13 sodium salt). The results and protein concentration of the conjugates are provided in Table 5a below.

TABLE 5a

| Conjugate | % HMW | Avg. DAR | Concentration (mg/mL) |
|---|---|---|---|
| CTX-C12 | 1.5 | 2.8 | 1.7 |
| CTX-C13 | 2.3 | 3.4 | 2.7 | b) Dye Conjugates CTX-C17, CTX-C18, and CTX-C21 Conjugates

The title compound from Example 24 (NHS ester of Compound 17)(36.5 µL, 10 mg/mL DMSO solution) was added to the Cetuximab antibody (0.65 mL, 7.7 mg/mL 100 mM phosphate. pH 8.65 solution). The reaction container was protected from light and mixed by gentle inversion. No continuous mixing was performed during the two-hour reaction at room temperature. In process SEC analysis indicated a DAR of 2.5. A second portion of dye (4.9 µL, 10 mg/mL DMSO solution) was added, and the solution was allowed to stand for one hour.

The conjugation reaction was quenched by addition of 1 M glycine (35 µL). The container was protected from light and mixed by gentle inversion at the beginning and end of the overnight reaction time at room temperature. The contents of the container were transferred to an Amicon® Ultra-15 centrifugal filter (30 kDa cutoff), topped off with 1×PBS buffer pH 7.1, and centrifuged at 3,500 rpm for 30 min. The 1×PBS buffer exchange was repeated three more times. The resulting Cetuximab conjugate was transferred to a 15 mL conical tube and stored in the dark at 2-6° C.

The conjugate was submitted for SEC-HPLC analysis to determine concentration, dye to antibody ratio (DAR) and purity. A 35 µL sample was run in a Shodex Protein® 5 µm KW-803 (8×300 mm, 300 Å) size-exclusion chromatography column on an Agilent 1100 HPLC instrument. Samples were run in a 1×PBS pH 7.1 mobile phase at a flow rate of 1 mL/min for a total of 20 minutes. Dye to antibody ratio (DAR) was determined by measuring the absorbance of the conjugates at wavelengths of 280 nm and 677 nm. The percent area of the main peak for the monomer content of the sample was determined, as well as calculation for high molecular weight species (HMW).

The CTX-C18 and CTX-C21 conjugates were prepared and analyzed in a manner similar to that of CTX-C17, replacing the compound of Example 24 with the compound of Example 23 (NHS ester of Compound 18) or Example 25 (NHS ester of Compound 21), respectively. The results and protein concentration of the conjugates are provided in Table 5b below.

TABLE 5b

| Conjugate | % HMW | Avg. DAR | Concentration (mg/mL) |
|---|---|---|---|
| CTX-C17 | 1.0 | 2.7 | 3.0 |
| CTX-C18 | 1.3 | 2.9 | 2.8 |
| CTX-C21 | 1.6 | 3.2 | 3.3 |

2) Anti-EphA2 Conjugates

Approximately 30 mg of mouse anti-human EphA2, clone 1C1 (Absolute Antibody, Catalog Number Ab00430-1.1) was buffer-exchanged into 25 mM phosphate buffer (pH 8.2) using a 30 kDa Amicon® centrifugal filter. Approximately 12 mg of the anti-EphA2 antibody solution (at a concentration of 4.59 mg/mL) were transferred to an appropriately sized container. 14.46 µL of a stock solution of dye Compound 16 (NHS ester of Compound 13 sodium salt), at a concentration of 10 mg/mL DMSO, was added with gentle swirling, at room temperature under green light for 1 hour, to create the conjugate anti-EphA2-C13. The conjugation reaction was performed to a final molar ratio of approximately 6.5:1 (dye: anti-EphA2).

The conjugation reaction was quenched by the addition of 89.2 µL of 1 M glycine, to achieve a final concentration of 20 mM glycine and mixing overnight at room temperature, protected from light. The solution was buffer-exchanged into 1× phosphate-buffered saline (1× PBS) using an Amicon® Ultra-15 centrifugal filter (30 kDa cutoff). The resulting anti-EphA2-C13 conjugate was stored in the dark at 4° C.

The conjugate was submitted for SEC-HPLC analysis to determine concentration, dye to antibody ratio (DAR) and purity. A 37 µL sample was run in a Sepax Zenix™-C 300 Å size-exclusion chromatography column on an Agilent 1100 HPLC instrument. Samples were run in a 1× PBS pH 7.1 mobile phase at a flow rate of 1 mL/min for a total of 20 minutes. Dye to antibody ratio (DAR) was determined by measuring the absorbance of the conjugates at wavelengths of 280 nm and 677 nm. The results and protein concentration of the conjugates are provided in Table 5c below.

TABLE 5c

| Conjugate | Avg. DAR | Concentration (mg/mL) |
|---|---|---|
| anti-EphA2-C13 | 2.5 | 1.5 |

3) Anti-CTLA-4 Conjugates

Approximately 6 mg of mouse anti-CTLA-4 antibody, with a heavy chain of the amino acid sequence set forth in SEQ ID NO: 1 and a light chain of the amino acid sequence set forth in SEQ ID NO: 2, in 1×PBS was buffer-exchanged into 25 mM phosphate buffer (pH 8.2) using a 30 kDa Amicon®, centrifugal filter, to a final concentration of 2.38 mg/mL. Approximately 2 mg of the anti-EphA2 antibody solution (840 µL) were transferred to two appropriately sized containers. 9.70 or 12.13 µL of a stock solution of dye Compound 16 (NHS ester of Compound 13 sodium salt)(, at a concentration of 10 mg/mL DMSO, for a molar ratio of 4:1 or 5:1 (dye: anti-CTLA-4), respectively) was added with gentle inversion at the start of the reaction time and no further mixing. The reaction continued at room temperature, protected from light for 1 hour, to create the conjugate anti-CTLA-4-C13.

The conjugation reaction was quenched by the addition of 17 µL of 1 M glycine, to achieve a final concentration of 20 mM glycine and mixing overnight at room temperature, protected from light. The mixture was gently inverted at the beginning and end of the overnight reaction. The solution was buffer exchanged into 1×PBS using an Amicon® Ultra-15 centrifugal filter (30 kDa cutoff). The resulting anti-CTLA-4-C13 conjugates were stored in the dark at 4° C.

The conjugates were submitted for SEC-HPLC analysis to determine concentration, dye to antibody ratio (DAR) and purity. A 33 µL sample was run in a Sepax Zenix™-C 300 Å size-exclusion chromatography column on an Agilent 1100 HPLC instrument. Samples were run in a 1× PBS pH 7.1 mobile phase at a flow rate of 1 mL/min for a total of 20 minutes. Dye to antibody ratio (DAR) was determined by measuring the absorbance of the conjugates at wavelengths of 280 nm and 677 nm. The results and protein concentration of the conjugates are provided in Table 5d below.

TABLE 5d

| Conjugate | Molar Ratio | Avg. DAR | Concentration (mg/mL) |
|---|---|---|---|
| anti-CTLA-4-C13 (MR4) | 4 | 2.6 | 2.3 |
| anti-CTLA-4-C13 (MR5) | 5 | 2.9 | 2.0 |

Antibody Fragment Conjugates

In this example, dye molecules such as those described herein, were conjugated to an exemplary antibody-binding fragment (Fab). The exemplary Fab contains the constant and variable domains of the heavy and light chains of the anti-EGFR antibody, Cetuximab, the amino acid sequences of which are set forth in SEQ ID NOs: 3 and 4, respectively.

Approximately 1.16 mL (3.8 mg) of the anti-EGFR Fab in 1×PBS were transferred to an appropriately sized container and diluted to a concentration of 1.2 mg/mL with 100 mM Sodium Phosphate, pH8.5. 70 µL of a stock solution of dye Compound 16 (NHS ester of Compound 13 sodium salt), at a concentration of 10 mg/mL DMSO, to achieve a molar ratio of 5:1 (dye: Fab), was added with pipette mixing at the start of the reaction time, but no further mixing. The reaction continued at room temperature, protected from light for 2 hours, to create the conjugate anti-EGFR Fab-C13.

The conjugation reaction was quenched by the addition of 65.1 µL of 1 M glycine, to achieve a final concentration of 20 mM glycine. The mixture was mixed by pipetting at the beginning of the reaction, and then incubated for 1 hour at room temperature, without further mixing and protected from light. The solution was injected into a HiLoad® 16/600 Superdex® 200 SEC column on an AKTA Pure 150 instrument to remove excess dye and exchange the buffer into 1×PBS. The main peak fractions were collected and concentrated to 1.5 mL using a 10 kDa Amicon® filter. A 80 µL sample was run in a Sepax Zenix™-C 100 Å size-exclusion chromatography column on an Agilent 1100 HPLC instrument. Samples were run in a 1×PBS pH 7.1 mobile phase at a flow rate of 1 mL/min for a total of 20 minutes. Dye to antibody ratio (DAR) was determined by measuring the absorbance of the conjugates at wavelengths of 280 nm and 677 nm. % Monomer was determined by measuring the absorbance at 280 nm. The main peak fractions were collected and concentrated to 1.5 mL using a 10 kDa Amicon® filter. The resulting anti-EGFR Fab-C13 conjugates were stored in the dark at 4° C. The results and protein concentration of the conjugates are provided in Table 5e below.

TABLE 5e

| Conjugate | Avg. DAR | Concentration (mg/mL) | A280% Monomer |
| --- | --- | --- | --- |
| anti-EGFR Fab-C13 | 1.7 | 1.9 | 99.9 |

Nanobody/VHH Domain Conjugates

In this example, dye molecules such as those described herein, were conjugated to an exemplary nanobody/VHH domain, 7D12. 7D12 is approximately 14.58 kDa, binds epidermal growth factor receptor (EGFR), and has the amino acid sequence set forth in SEQ ID NO: 5.

Approximately 1.02 mL (3.8 mg) of the VHH solution were transferred to an appropriately sized container and diluted to a concentration of 1.2 mg/mL with 100 mM Sodium Phosphate, pH8.5. 202.4 µL of a stock solution of dye Compound 16 (NHS ester of Compound 13 sodium salt), to achieve a molar ratio of 5:1 (dye: VHH), was added with pipette mixing at the start of the reaction time, but no further mixing. The reaction continued at room temperature, protected from light for 2 hours, to create the conjugate anti-EGFR VHH-C13.

The conjugation reaction was quenched by the addition of 67.7 µL of 1 M glycine, to achieve a final concentration of 20 mM glycine. The mixture was mixed by pipetting at the beginning of the reaction and then incubated overnight at room temperature, without further mixing and protected from light. The resulting solution was injected into a HiLoad® 16/600 Superdex® 75 SEC column on an AKTA Pure 150 instrument to remove excess dye and exchange the buffer into 1×PBS. The main peak fractions were collected and concentrated to 1.5 mL using a 3 kDa Amicon® filter. A 80 µL sample was run in a Sepax Zenix™-C 100 Å size-exclusion chromatography column on an Agilent 1100 HPLC instrument. Samples were run in a 1×PBS pH 7.1 mobile phase at a flow rate of 1 mL/min for a total of 20 minutes. Dye to antibody ratio (DAR) was determined by measuring the absorbance of the conjugates at wavelengths of 280 nm and 677 nm. The resulting anti-EGFR VHH-C13 conjugates were stored in the dark at 4° C. The results and protein concentration of the conjugates are provided in Table 5f below.

TABLE 5f

| Conjugate | Avg. DAR | Concentration (mg/mL) |
| --- | --- | --- |
| anti-EGFR-VHH-C13 | 1.0 | 1.4 |

Peptide Conjugates

GE11 is an EGF-competitive peptide that binds to epidermal growth factor receptor (EGFR). In this example, Compound 16 was conjugated to GE11 peptide, modified by adding a short GGG linker to the C-terminus, followed by a terminal lysine to generate a modified GE11 peptide with the sequence Ac-YHWYGYTPQNVIGGGK (SEQ ID NO: 6), as an exemplary peptide for conjugation.

To prepare the conjugate, 1 µL of a 0.1 M solution of N, N-Diisopropylethylamine (DIPEA) in DMSO and 0.9 µL of a 5.7 mM solution of dye Compound 16 (NHS ester of Compound 13 sodium salt) were sequentially added to 4.8 µL of a 1 mM solution of the modified GE11 peptide in DMSO in a 0.5 mL Eppendorf tube. The resulting mixture was incubated 6 hours in the dark. Liquid chromatography/mass spectrometry (LCMS) analysis, in negative ion mode, confirmed formation of the peptide conjugate with an [(M−2)/2]— ion of mass 1729.1 Da. The reaction was diluted with DMF (10 µL) and added to MTBE (0.25 mL). The reaction tube was washed with DMF (10 µL) that was added to the MTBE. A light blue precipitate formed. The suspension was allowed to stand for 30 minute and the precipitate was isolated by filtration.

Example 6

Cell Killing Activity of CTX-C12 and CTX-C13 PIT

To evaluate PIT killing activity of the CTX-C12 and CTX-C13 conjugates in pancreatic carcinoma cells, BxPC3 cells (#CRL-1687, ATCC, Manassas Va.) were plated, 5,000 cells per well in RPMI-1640 media supplemented with 10% FBS and 1% Penicillin/Streptomycin (complete culture media) in a deep-well 96-well plate. Following overnight incubation at 37° C., the culture media were removed, and the cells were incubated in 100 µL complete media with 1, 0.333, 0.111, 0.03704, 0.01235, 0.00412, 0.00137, or 0 µg/mL CTX-C12, CTX-C13, or cetuximab-IRDye 700DX (CTX-IR700)(control) for one hour at 4° C. Following incubation, the cells were illuminated with a 690 nm laser at a light dose of 64 J/cm$^2$ or protected from light (0 J/cm$^2$).

The effect of different treatment regimens on cell death was measured using the CellTox™ Green Cytotoxicity Assay 24 hours after illumination as described above.

Figure 4:
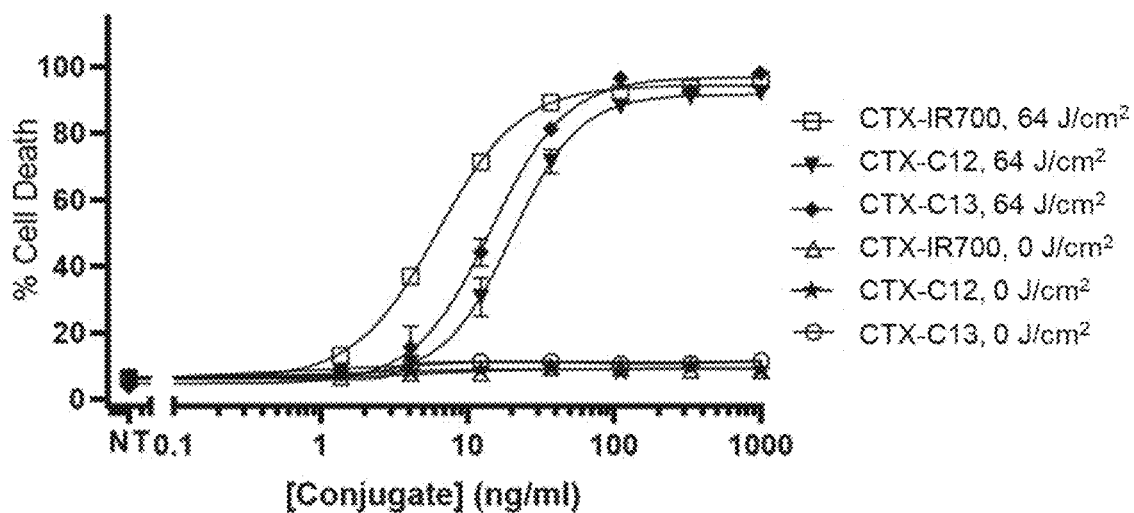
FIG. 4 depicts the dose-dependent cytotoxicity of CTX-C12 and CTX-C13 conjugates following photoimmunotherapy (PIT).

As shown in FIG. 4, no effect on cell death was observed for any sample exposed to 0 J/cm$^2$ during the PIT treatment at any dose of the antibody conjugates, indicating that the conjugates were not cytotoxic in the absence of light irradiation. In contrast, dose-dependent cell killing was observed for samples that were irradiated with a 690 nm laser at a light dose of 64 J/cm$^2$.

Example 7

Cell Killing Activity of EGFR-Targeted C13 Conjugates

In this example, PIT killing activity of EGFR-targeted-C13 conjugates, was measured on A431 squamous carcinoma cells. The conjugates evaluated were anti-EGFR antibody (Cetuximab (CTX)), anti-EGFR Fab, and an anti-EGFR VHH conjugated to C13, as described above. The same antibody, Fab, VHH domain were also conjugated to IR700 as reference molecules.

A431 cells (#CRL-1555, ATCC Manassas Va.) were plated at 5,000 cells per well in deep-well 96-well plates in complete RPMI-1640 media Following overnight incubation at 37° C., the culture media were removed, and the cells were incubated in 100 µL complete media with 20, 5, 1.25, 0.313, 0.078, 0.02, 0.005, or 0 nM CTX-C13, anti-EGFR Fab-C13, anti-EGFR VHH-C13, or the corresponding IR700 conjugates for one hour at 4° C. Following incubation, the cells were illuminated with a 690 nm laser at a light dose of 64 J/cm$^2$ or protected from light (0 J/cm$^2$). The effect of different treatment regimens on cell death was measured using the CellTox™ Green Cytotoxicity Assay 24 hours after illumination as described above. Dose response curves of percent cell death following PIT for the antibody, Fab, and VHH conjugates are shown in FIGS. 5A, 5B, and 5C, respectively.

Figure 5A:
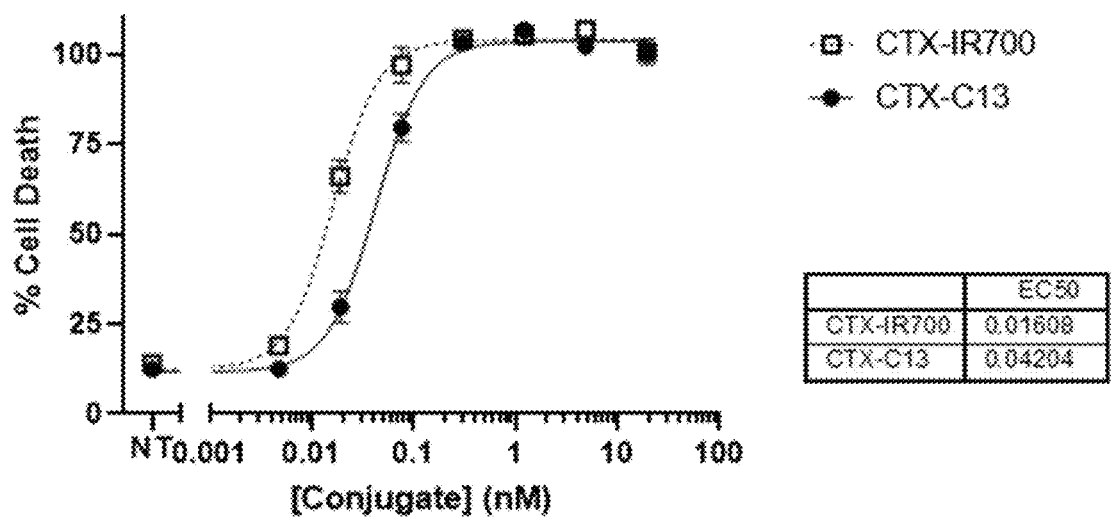
FIG. 5A depicts the dose response curves of percent cell death following PIT for an antibody conjugate.
Figure 5B:
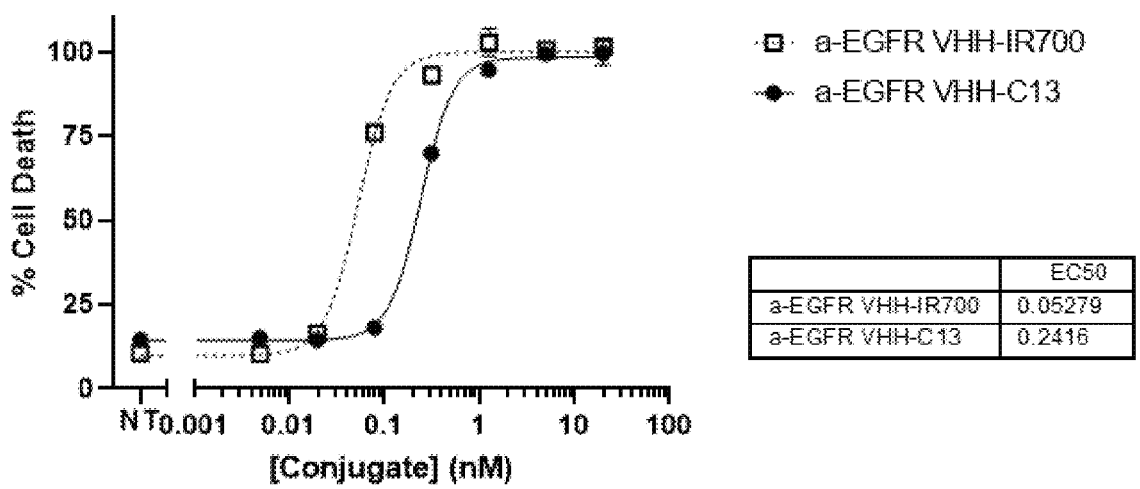
FIG. 5B depicts the dose response curves of percent cell death following PIT for a Fab conjugate.
Figure 5C:
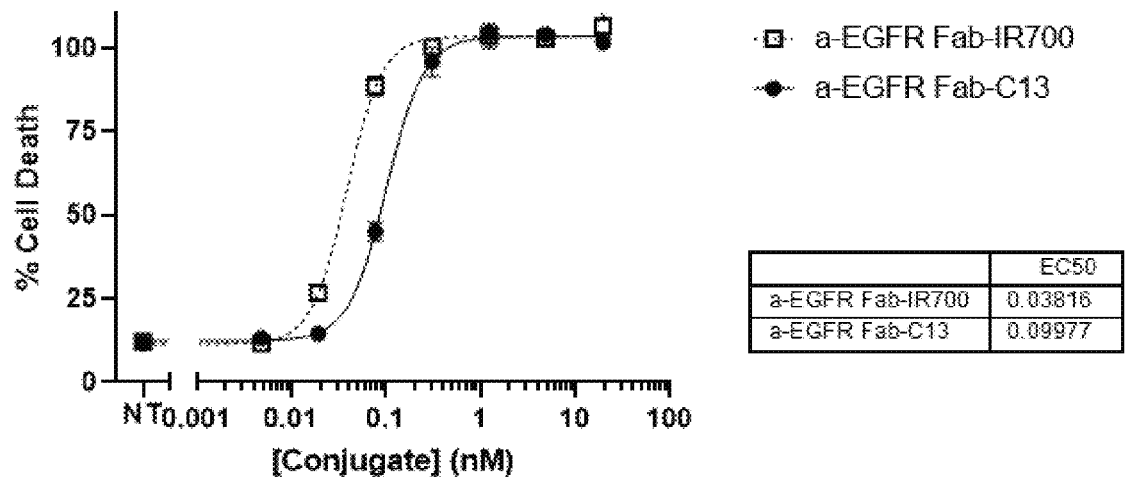
FIG. 5C depicts the dose response curves of percent cell death following PIT for a VHH/nanobody conjugate.

As shown in FIGS. 5A-5C, dose-dependent A431 cell killing was observed for all the EGFR-Targeted C13 and IR700 conjugates following irradiation with a 690 nm laser at a dose of 64 J/cm$^2$.

Example 8

Photoimmunotherapy (PIT) Using CTX-C13 Conjugates

To evaluate direct photoimmunotherapy (PIT) killing activity of tumor cells by the CTX-C13 conjugates, in vivo, immunocompromised NuNu mice were inoculated with 5×10$^6$ BxPC3 pancreatic cancer cells engineered to express luciferase (BxPC3-luc) subcutaneously on the right hind flank. On Day 6 after tumor cell inoculation, when allograft tumors grew to a volume of about 150 mm$^3$, the mice were retro-orbitally administered CTX-C13 (100 µg), generated as described above. On Day 7, the tumors in the right flank of half of the animals were illuminated at 690 nm at a dosage of 200 J/cm$^2$. Tumor cell depletion was determined by measuring bioluminescence (BLI) of the tumors, using quantitative luciferase activity, prior to illumination and 4-6 hours, 1 day, 5 days, and 7 days post-illumination. The average BLI of the tumors over time for CTX-C13 and CTX-C13 with illumination (CTX-C13+PIT) groups is plotted in FIG. 6.

Figure 6:
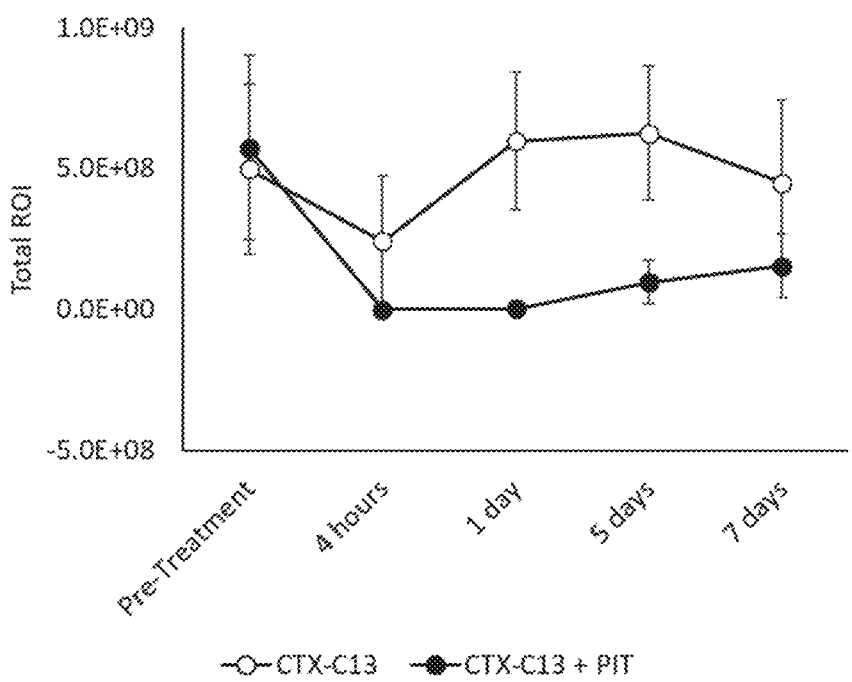
FIG. 6 depicts the response to treatment of tumors over time for CTX-C13 and CTX-C13 with illumination (CTX-C13+PIT) as described in Example 8.

As shown in FIG. 6, illumination of the CTX-C13 conjugates (CTX-C13+PIT group; closed circles) resulted in a reduction in the tumor cell BLI by 4 hours after illumination, followed by gradual tumor regrowth beginning 5 days after illumination in this immunocompromised model. Tumors treated with the CTX-C13 conjugate without illumination (FIG. 6, open circles), did not significantly reduce the tumor BLI. These results demonstrate tumor cell depletion resulting from CTX-C13 photoimmunotherapy.

Example 9

Photoimmunotherapy (PIT) Using Anti-EphA2-C13 Conjugate

To evaluate photoimmunotherapy (PIT) killing activity of the Anti-EphA2-C13 conjugates, in vivo, BALB/c mice were inoculated with 1×10$^6$ CT26-EphA2 cells subcutaneously on the right hind flank. On Day 8 after tumor cell inoculation, when allograft tumors grew to a volume of about 135 mm$^3$, the mice were retro-orbitally administered saline (100 µL; n=10) or anti-Eph A2-C13 (100 µg: n=20), generated as described above. On Day 9, the tumors of half of the animals administered anti-EphA2-C13 were illuminated at 690 nm at a dosage of 100 J/cm$^2$. The tumors of the remaining mice were not illuminated as controls. The growth of the tumors was observed over time, and tumor volumes were calculated using the formula: tumor volume= (width×length)×height/2. Average tumor volumes for each group are plotted in FIG. 7.

Figure 7:
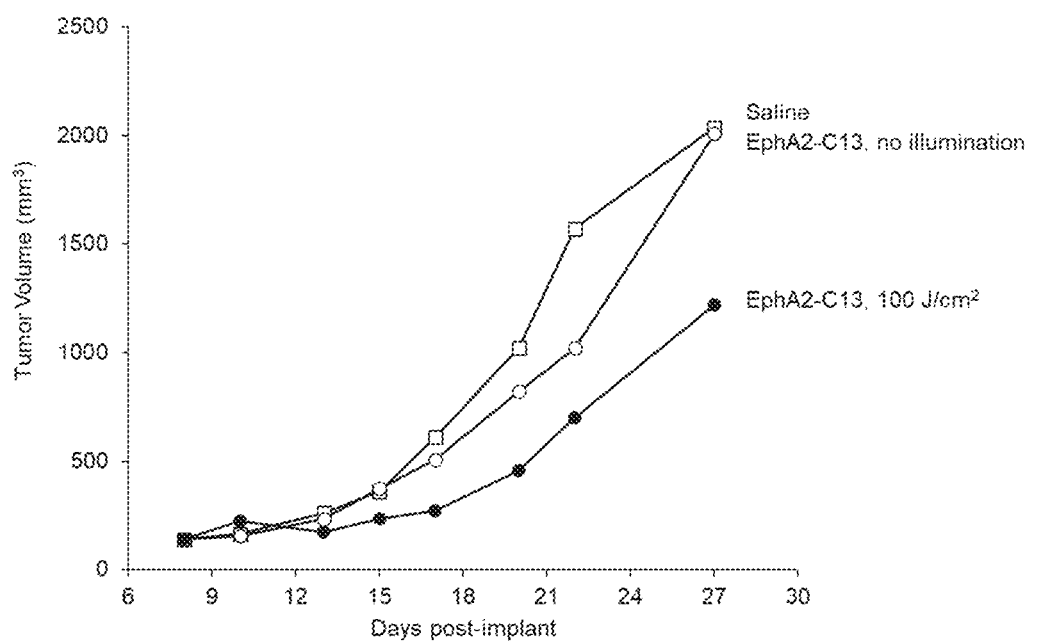
FIG. 7 depicts the response to treatment of tumors over time for anti-EphA2-C13 conjugates and anti-EphA2-C13 conjugates with illumination as described in Example 9.

As shown in FIG. 7, the average tumor volumes of non-illuminated tumors in animals treated with saline (open squares, solid line), or EphA2-C13 conjugate alone (open circle, solid line) exhibited rapid, continuous tumor growth over the course of the study. Tumors treated with EphA2-C13 with illumination at 100 J/cm$^2$ (closed circles, solid line) exhibited reduced tumor growth compared to the saline and EphA2-C13 conjugate controls. These results demonstrate that EphA2-C13 PIT inhibits tumor growth in vivo.

Sequence Listings

Table 6 Provides the Sequence Listing Recited in the Specification

TABLE 6

| SEQ ID NO. | Description | Sequence |
|---|---|---|
| 1 | CTLA-4 VH | QVQLVESGGGVVQPGRSLRLSCAASGFTFSSYTMHWVRQAPGKGLEWVTFI SYDGNNKYYADSVKGRFTISRDNSKNTLYLQMNSLRAEDTAIYYCARTGWLG PFDYWGQGTLVTVSSASTKGPSVFPLAPSSKSTSGGTAALGCLVKDYFPEPVT VSWNSGALTSGVHTFPAVLQSSGLYSLSSVVTVPSSSLGTQTYICNVNHKPSN TKVDKRVEPKSCDKTHTCPPCPAPELLGGPSVFLFPPKPKDTLMISRTPEVTCV VVDVSHEDPEVKFNWYVDGVEVHNAKTKPREEQYNSTYRVVSVLTVLHQD WLNGKEYKCKVSNKALPAPIEKTISKAKGQPREPQVYTLPPSRDELTKNQVSL TCLVKGFYPSDIAVEWESNGQPENNYKTTPPVLDSDGSFFLYSKLTVDKSRW QQGNVFSCSVMHEALHNHYTQKSLSLSPGK |
| 2 | CTLA-4 VL | EIVLTQSPGTLSLSPGERATLSCRASQSVGSSYLAWYQQKPGQAPRLLIYGAFS RATGIPDRFSGSGSGTDFTLTISRLEPEDFAVYYCQQYGSSPWTFGQGTKVEI KRTVAAPSVFIFPPSDEQLKSGTASVVCLLNNFYPREAKVQWKVDNALQSGN SQESVTEQDSKDSTYSLSSTLTLSKADYEKHKVYACEVTHQGLSSPVTKSFNRG EC |
| 3 | CTX Fab heavy chain | QVQLKQSGPGLVQPSQSLSITCTVSGFSLTNYGVHWVRQSPGKGLEWLGVI WSGGNTDYNTPFTSRLSINKDNSKSQVFFKMNSLQSNDTAIYYCARALTYYD YEFAYWGQGTLVTVSACSTKGPSVFPLAPSSKSTSGGTAALGCLVKDYFPEPV TVSWNSGALTSGVHTFPAVLQSSGLYSLSSVVTVPSSSLGTQTYICNVNHKPS NTKVDKRVEPKSCDKTHT |
| 4 | CTX light chain | DILLTQSPVILSVSPGERVSFSCRASQSIGTNIHWYQQRTNGSPRLLIKYASESIS GIPSRFSGSGSGTDFTLSINSVESEDIADYYCQQNNNWPTTFGAGTKLELKRT VAAPSVFIFPPSDEQLKSGTASVVCLLNNFYPREAKVQWKVDNALQSGNSQE SVTEQDSKDSTYSLSSTLTLSKADYEKHKVYACEVTHQGLSSPVTKSFNRGEC |

TABLE 6-continued

| SEQ ID NO. | Description | Sequence |
|---|---|---|
| 5 | anti-EGFR VHH (7D12)- Cys-Myc- His10 | QVKLEESGGGSVQTGGSLRLTCAASGRTSRSYGMGWFRQAPGKEREFVSGI SWRGDSTGYADSVKGRFTISRDNAKNTVDLQMNSLKPEDTAIYCAAAAGS AWYGTLYEYDYWGQGTQVTVSSCSGSSEQKLISEEDLASHHHHHHHHHH |
| 6 | GE11 peptide | AC-YHWYGYTPQNVIGGGK |

The embodiments described above are intended to be merely exemplary, and those skilled in the art will recognize, or will be able to ascertain using no more than routine experimentation, numerous equivalents of specific compounds, materials and procedures. All such equivalents are considered to be within the scope of the claimed subject matter and are encompassed by the appended claims. Since modifications will be apparent to those of skill in the art, it is intended that the claimed subject matter be limited only by the scope of the appended claims.

We claim:

1. A phthalocyanine dye having the Formula (I):

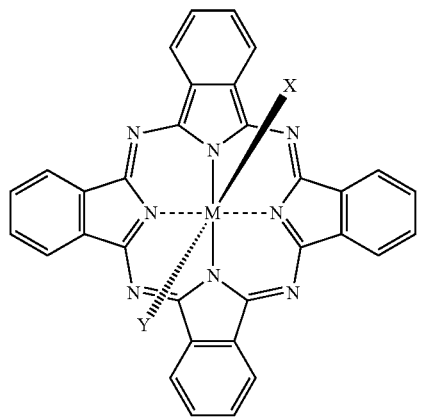

(I)

or a salt, stereoisomer, or tautomer thereof, wherein,
M is Si;
X is

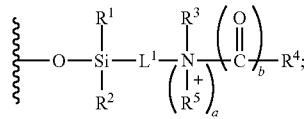

Y is

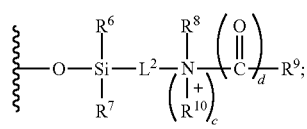

$R^1$ and $R^2$ are each independently alkyl;
$R^3$, $R^4$ or $R^5$ are selected from substituent group (a) substituent group (b) wherein, (a) $R^3$ is hydrogen, -$L^3$-H, -$L^3$-A, or -$L^3$-Z;
$R^4$ is -$L^4$-H, —(NH)$_m$-$L^4$-A, —(NH)$_m$-$L^4$-Z, —(O)$_m$-$L^4$-A, or —(O)$_m$-$L^4$-Z;
$R^5$ is -$L^4$-H or -$L^5$-A; and (b) $R^3$ is -$L^3$-H, or -$L^3$-A;
$R^4$ is -$L^4$-H, —(NH)$_m$-$L^4$-A; wherein $R^3$ and $R^4$ are connected with a bond to form a heterocyclyl substituted with -$L^4$-A; and
$R^5$ is -$L^4$-H or -$L^5$-A;
provided at least one of $R^3$, $R^4$ and $R^5$ is a group containing A;
A is a group selected from —C(O)O$R^{11}$ or —N$R^{12}R^{13}$, wherein each $R^{11}$ is independently hydrogen, alkyl, haloalkyl, alkenyl, heterocyclyl, aryl or heteroaryl, and each $R^{11}$ is independently optionally substituted with one to five groups each independently selected from halo, —SO$_3$H and —SO$_2$F; each $R^{12}$ is independently hydrogen, alkyl or haloalkyl;
each $R^{13}$ is aryl or heteroaryl, and each $R^{13}$ is independently optionally substituted with one to five groups each independently selected from halo, —SO$_3$H and —SO$_2$F; or optionally $R^{12}$ and $R^{13}$, together with the nitrogen to which they are attached, form a cyclic imide;
$R^6$ and $R^7$ are each independently alkyl;
$R^8$, $R^9$ or $R^{10}$ are selected from substituent group (a) or substituent group (b) wherein, (a) $R^8$ is hydrogen, -$L^8$-H or -$L^8$-Z;
$R^9$ is -$L^9$-H, —(NH)$_n$-$L^9$-Z or —(O)$_n$-$L^9$-Z;
$R^{10}$ is -$L^{10}$-Z; and (b) $R^8$ and $R^9$ are connected with a bond to form a heterocyclyl substituted with -$L^9$-Z and $R^{10}$ is -$L^{10}$-H or -$L^{10}$-Z;
provided at least one of $R^8$, $R^9$ and $R^{10}$ is a group containing Z;
Z is selected from:
—(CH$_2$)$_q$(OCH$_2$CH$_2$)$_v$O$R^{22}$,
—(CH$_2$)$_q$O(CH$_2$)$_x$N[(CH$_2$CH$_2$O)$_w$CH$_2$CH$_2$O$R^{22}$]$_t$,
—(CH$_2$)$_q$N[(CH$_2$)$_p$(OCH$_2$CH$_2$)$_v$O$R^{22}$]$_t$,
—(CH$_2$)$_q$N[(CH$_2$)$_p$SO$_3$H]$_t$,
—(CH$_2$)$_q$N$R^b$[(CH$_2$)$_p$SO$_3$H]$_u$,
—(CH$_2$)$_q$N$R^b$[(CH$_2$)$_p$CH(SO$_3$H)$_2$]$_u$,
—SO$_3$H,
—CH(SO$_3$H)$_2$,
—PO$_3$H, —$(CH_2)_qN[(CH_2)_pPO_3H]_t$,
—$(CH_2)_qNR^b[(CH_2)_pPO_3H]_u$, or
—$(CH_2)_qNR^b(CH_2)_pCH(PO_3H)_2$, each $R^{22}$ is independently alkyl, haloalkyl, cycloalkyl or aryl;
each $R^b$ is independently hydrogen, alkyl, haloalkyl or cycloalkyl;
each v, w and p are independently an integer from 1 to 10;
each q is independently an integer from 0 to 10;
t is 2 or 3; and
u is 1 or 2,
$L^1$ and $L^2$ are each independently optionally substituted $C_{2-4}$ alkylene;
$L^3$, $L^4$, $L^5$, $L^8$, $L^9$ and $L^{10}$ are each independently optionally substituted alkylene, or optionally substituted heteroalkylene, where the carbon atom of the alkylene, or heteroalkylene is further optionally substituted with Z and each nitrogen atom of the heteroalkylene or heteroalkenylene is optionally substituted with one or two L'-Z;
L' is each independently optionally substituted alkylene, or optionally substituted heteroalkylene;
a is 0 or 1;
b is 0 or 1;
c is 0 or 1;
d is 0 or 1;
m is 0 or 1;
n is 0 or 1;
provided that if b is 1, then a is 0;
if d is 1, then c is 0;
if m is 1, b is 1; and
if n is 1, c is 1; and
provided that when $R^6$ and $R^7$ are both methyl, and $L^2$ is propylene, c is 1 and d is 0, then
$L^8$, $L^9$ and $L^{10}$ are each not propylene.

2. The compound of claim 1, or a salt, stereoisomer, or tautomer thereof, wherein $R^3$ is H, and $L^4$ is optionally substituted alkylene.

3. The compound of claim 1, or a salt, stereoisomer, or tautomer thereof, wherein $R^3$ is H, and $L^4$ is optionally substituted heteroalkylene.

4. The compound of claim 1, or a salt, stereoisomer, or tautomer thereof, wherein $L^3$ and $L^4$ are each independently optionally substituted alkylene; and $L^5$ is optionally substituted heteroalkylene.

5. The compound of claim 1, or a salt, stereoisomer, or tautomer thereof, wherein $L^3$, $L^4$, and $L^5$ are each independently optionally substituted alkylene.

6. The compound of claim 1, or a salt, stereoisomer, or tautomer thereof, wherein $R^8$ is H, and $L^9$ is optionally substituted alkylene.

7. The compound of claim 1, or a salt, stereoisomer, or tautomer thereof, wherein $L^8$, $L^9$, and $L^{10}$ are each independently optionally substituted alkylene.

8. The compound of claim 1, or a salt, stereoisomer, or tautomer thereof, wherein the group A is selected from the group consisting of:

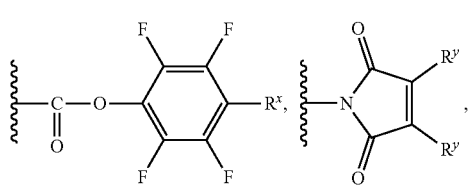

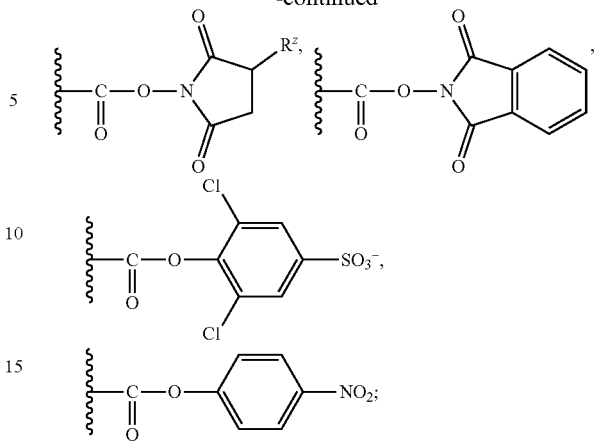

wherein each $R^x$ and $R^y$ are independently hydrogen or halo, and $R^z$ is hydrogen or —$SO_3H$.

9. The compound of claim 1, or a salt, stereoisomer, or tautomer thereof, wherein the group A is —$CO_2H$.

10. The compound of claim 1, or a salt, stereoisomer, or tautomer thereof, wherein the group A is

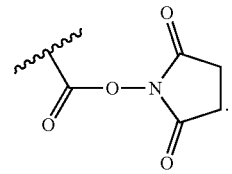 [SMILES: *C(=O)ON1C(=O)CCC1=O]

11. The compound of claim 1, or a salt, stereoisomer, or tautomer thereof, wherein the group Z is —$SO_3H$.

12. The compound of claim 1, or a salt, stereoisomer, or tautomer thereof, wherein the group Z is —$CH(SO_3H)_2$.

13. The compound of claim 1, or a salt, stereoisomer, or tautomer thereof, wherein the group Z is —$(CH_2)_qN[(CH_2)_pSO_3H]_t$.

14. The compound of claim 1, or a salt, stereoisomer, or tautomer thereof, wherein the group Z is —$(CH_2)_qN[(CH_2)_p(OCH_2CH_2)_vOR^{22}]_t$.

15. The compound of claim 1, or a salt, stereoisomer, or tautomer thereof, wherein the group Z is —$(CH_2)_qN[(CH_2)_pSO_3H]_t$.

16. The compound of claim 1, or a salt, stereoisomer, or tautomer thereof, wherein the group Z is —$(CH_2)_q(OCH_2CH_2)_vOR^{22}$.

17. The compound of claim 1, or a salt, stereoisomer, or tautomer thereof, wherein a and c are 0, and b and d are 1.

18. The compound of claim 1, or a salt, stereoisomer, or tautomer thereof, wherein a and c are 1, and b and d are 0.

19. The compound of claim 1, or a salt, stereoisomer, or tautomer thereof, wherein X is:

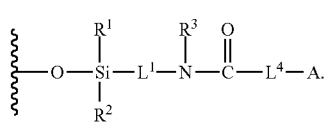

20. The compound of claim 1, or a salt, stereoisomer, or tautomer thereof, wherein X is:
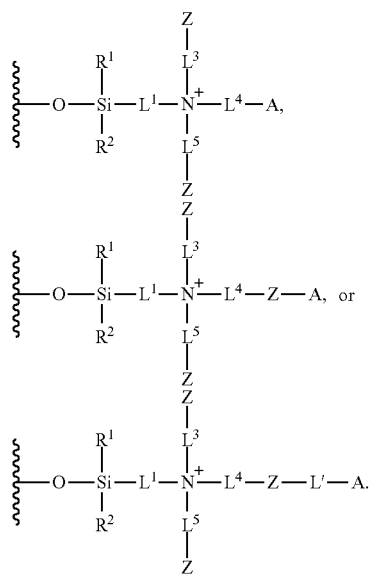
21. The compound of any claim 1, or a salt, stereoisomer, or tautomer thereof, wherein Y is:
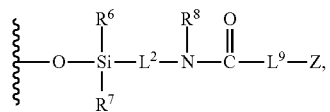
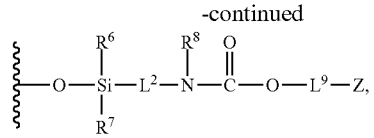
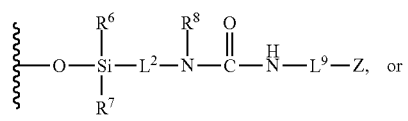
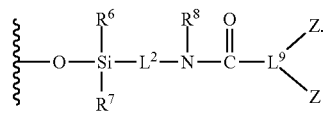
22. The compound of any claim 1, or a salt, stereoisomer, or tautomer thereof, wherein Y is:
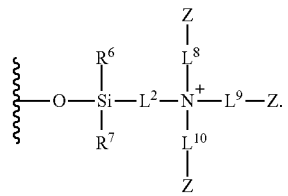
23. The compound of claim 1, or a salt, stereoisomer, or tautomer thereof, selected from the group consisting of:
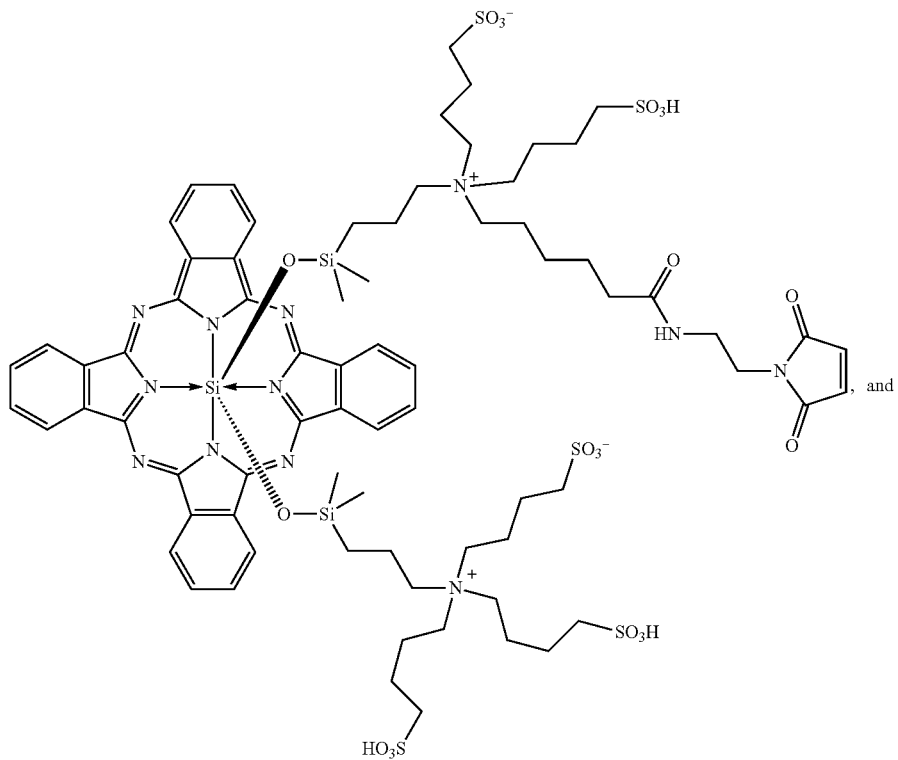
, and

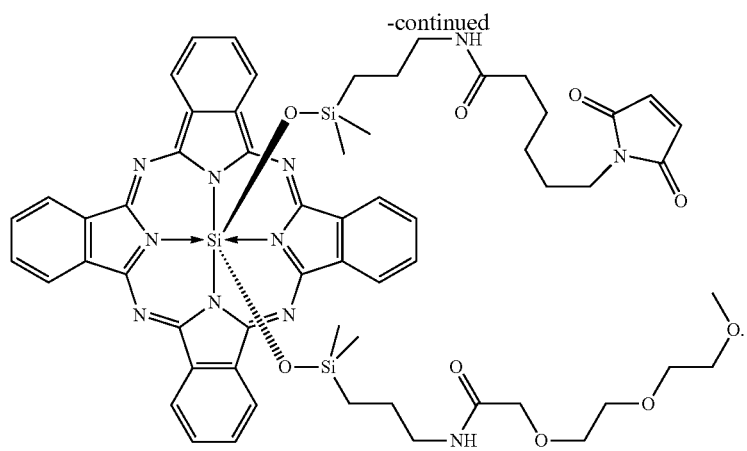
24. The compound of claim 1, or a salt, stereoisomer, or tautomer thereof, selected from the group consisting of:
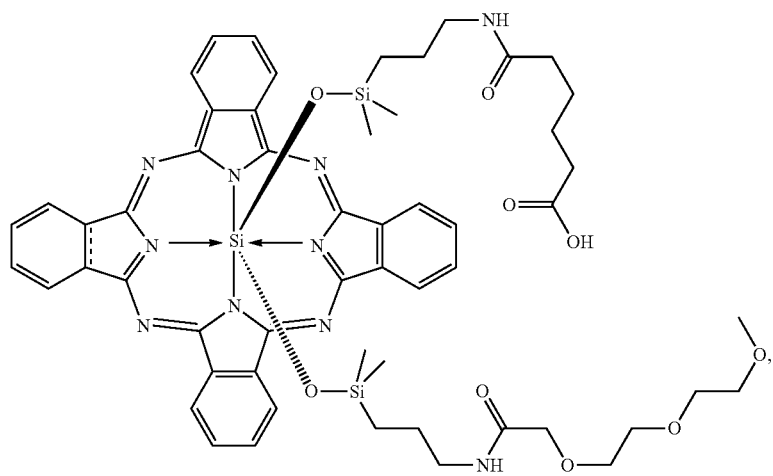
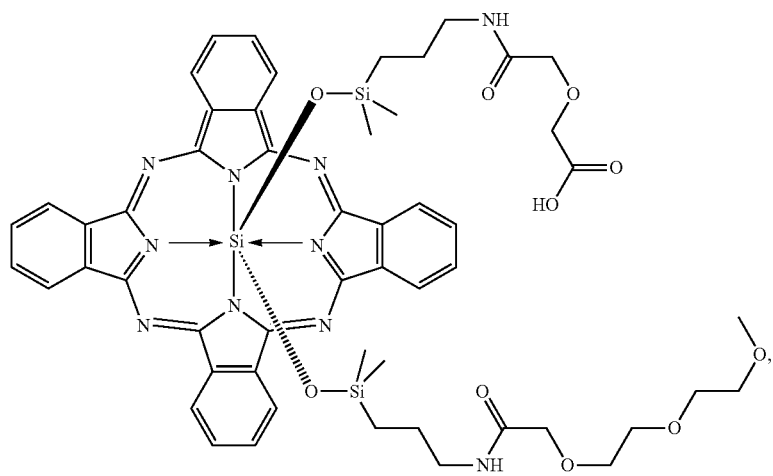

-continued
293
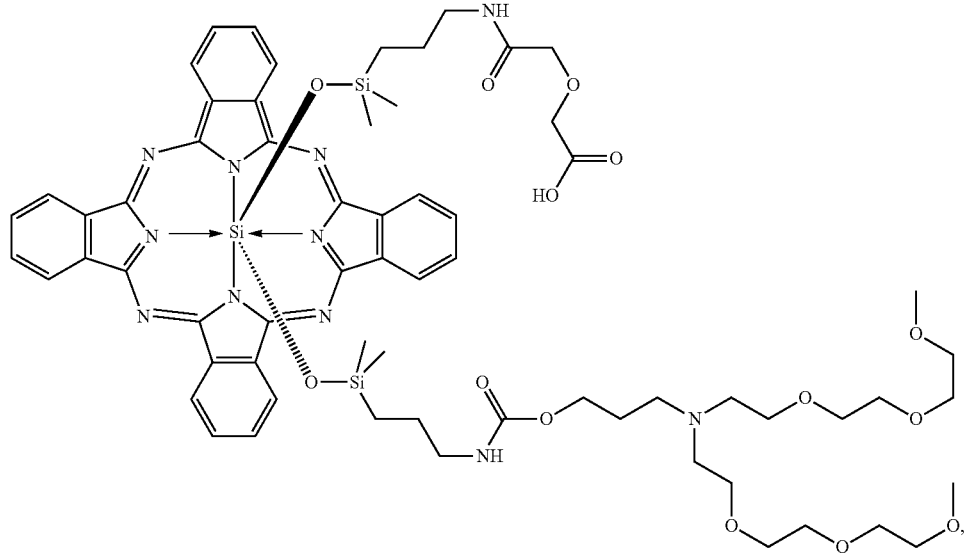
294
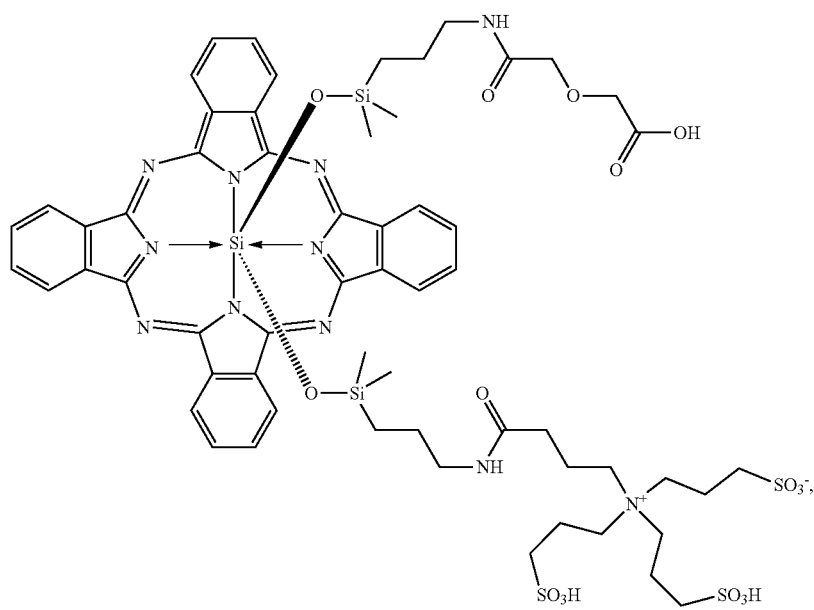

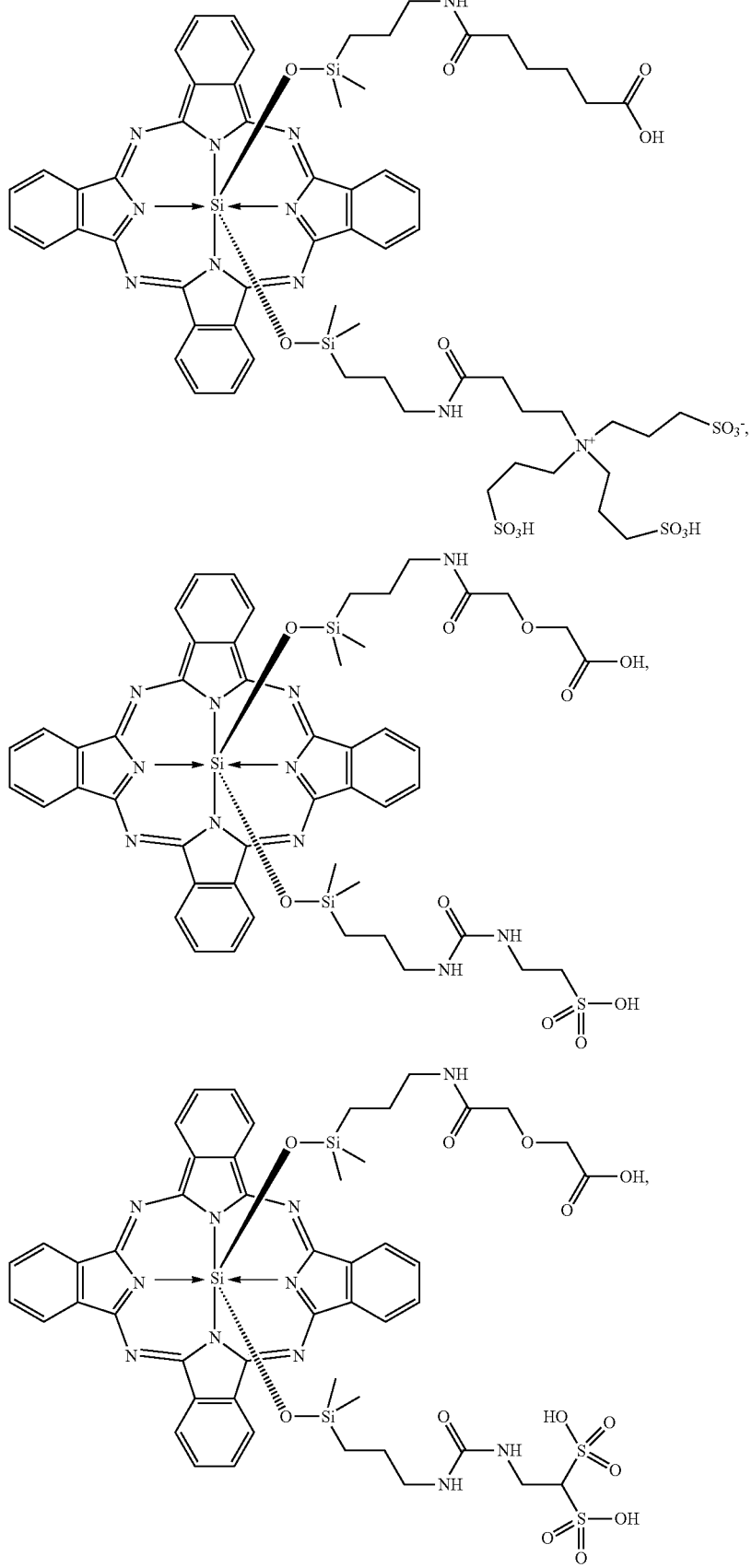

-continued
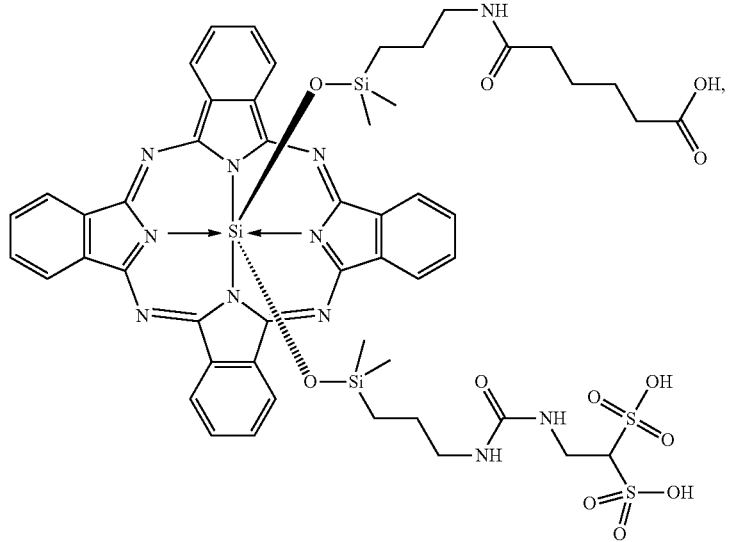
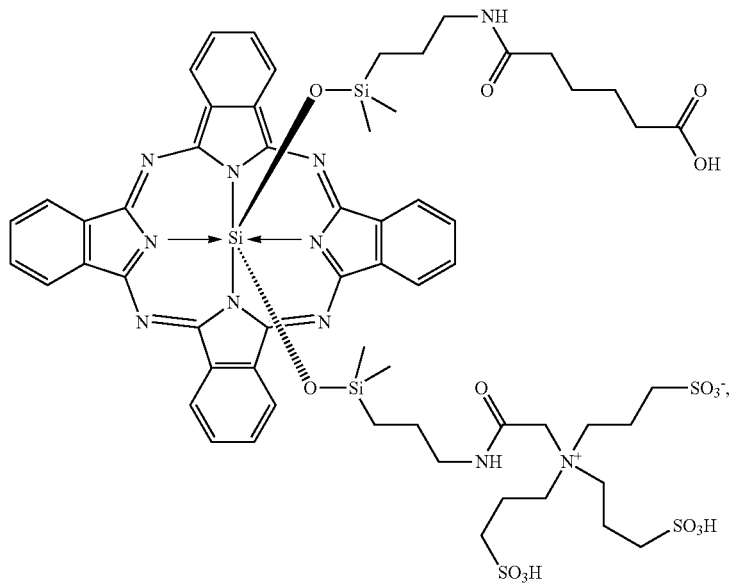
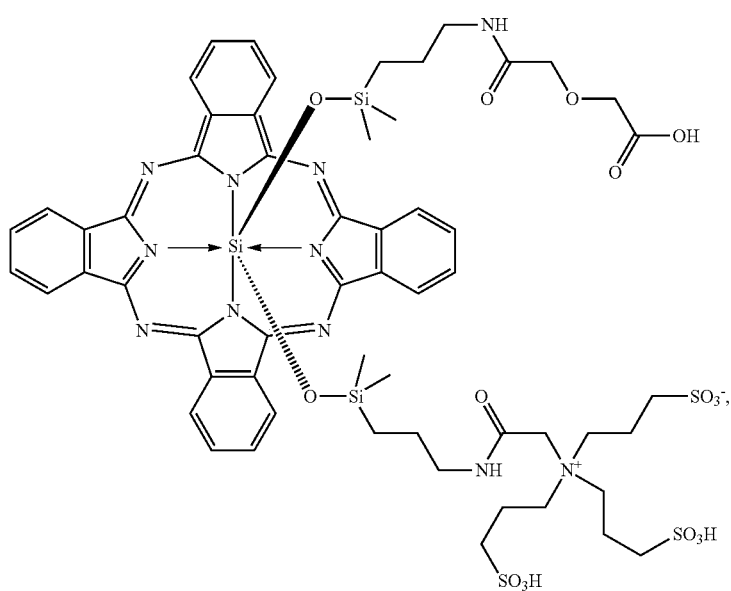

-continued
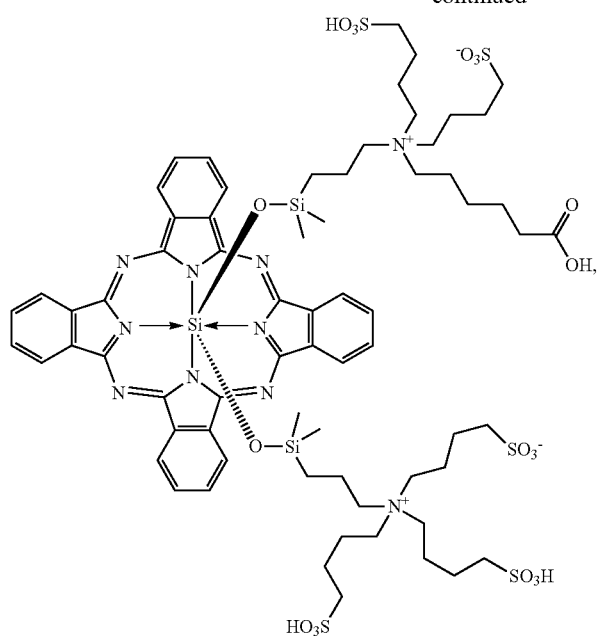
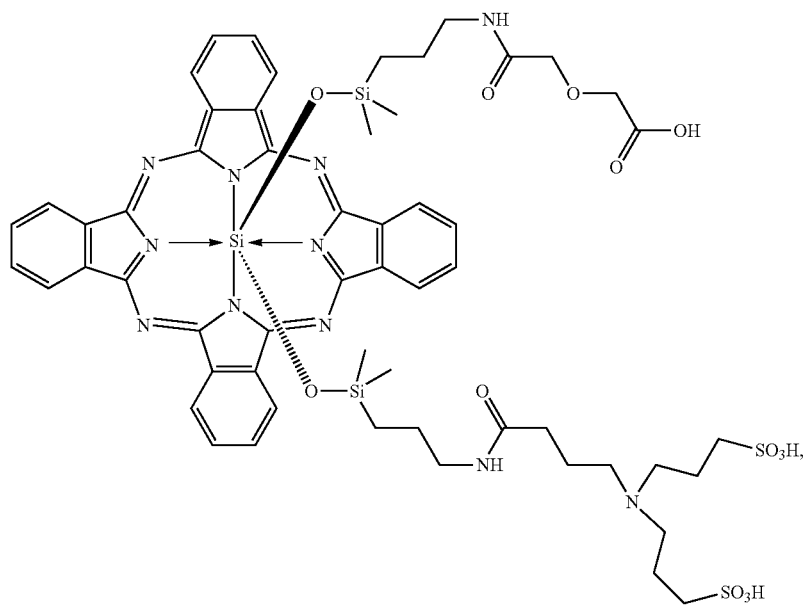

-continued
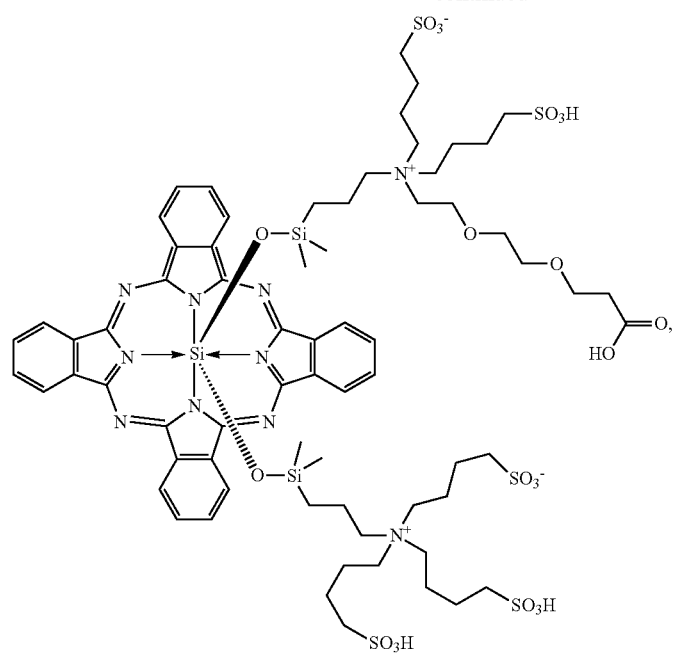
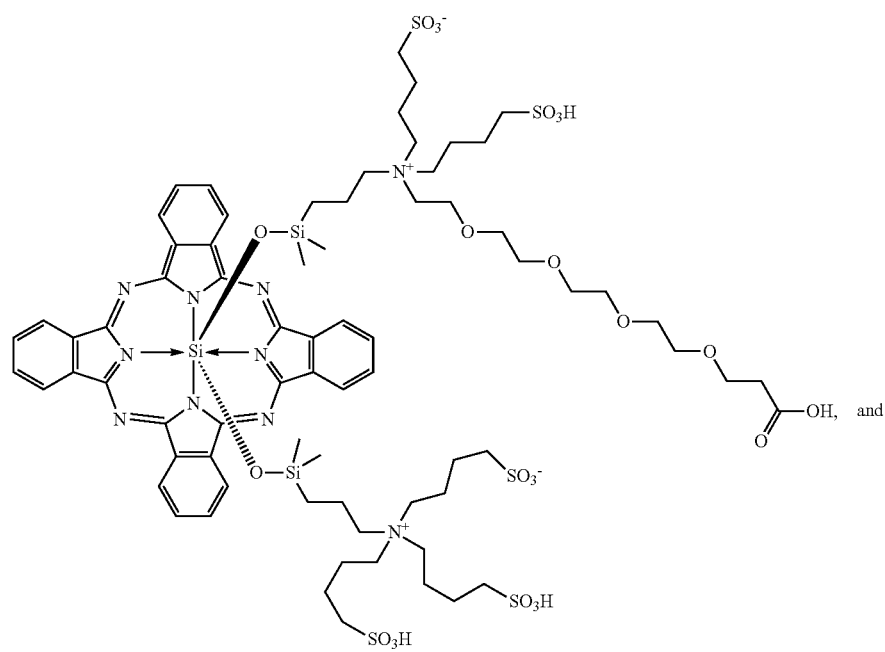

-continued
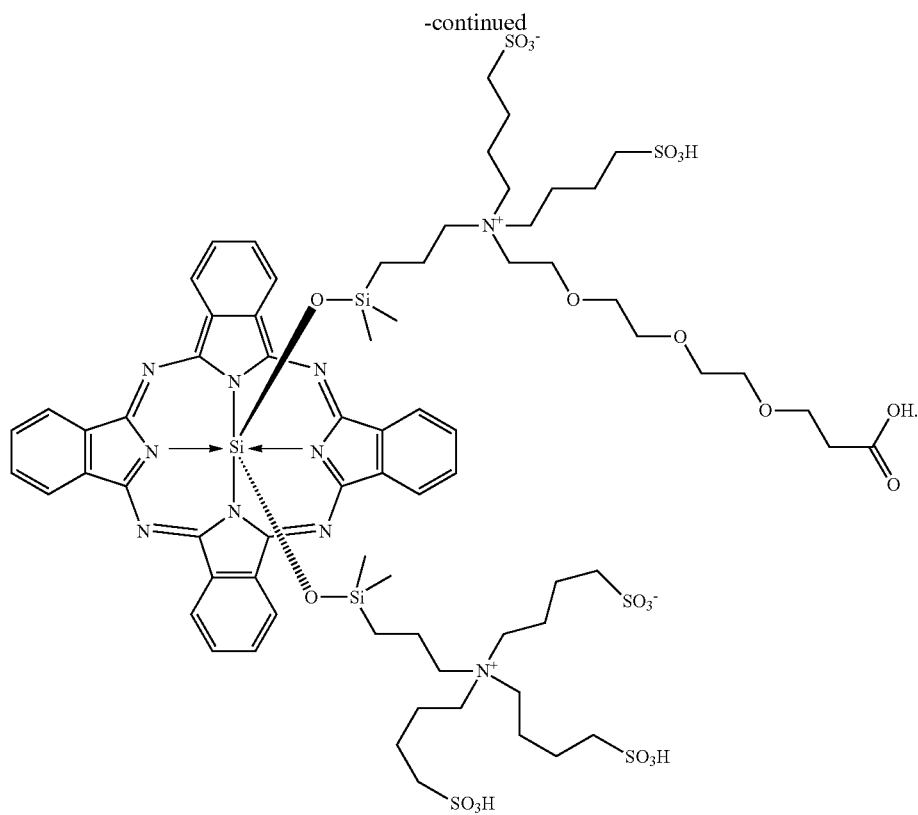
25. The compound of claim 1, or a salt, stereoisomer, or tautomer thereof, selected from the group consisting of:
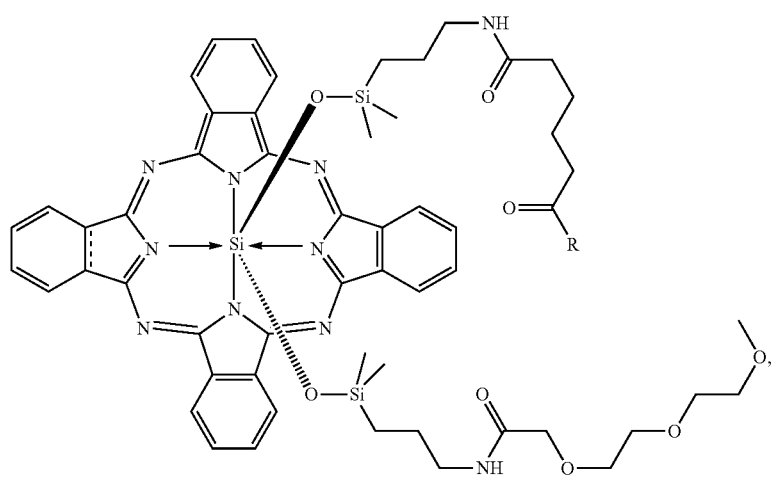

-continued
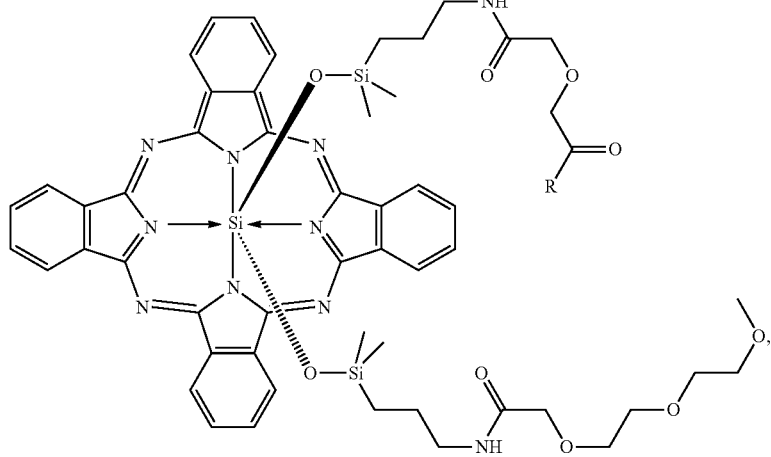
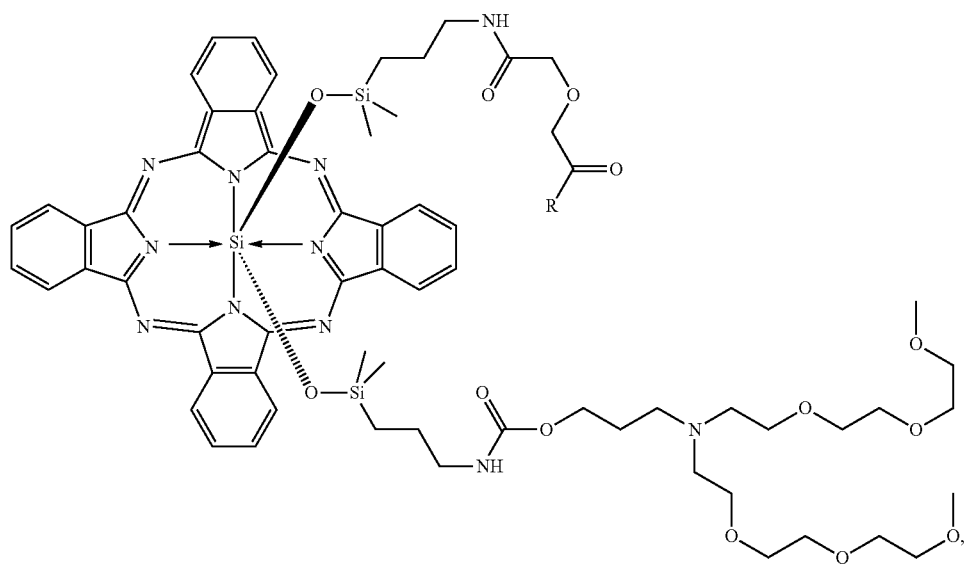
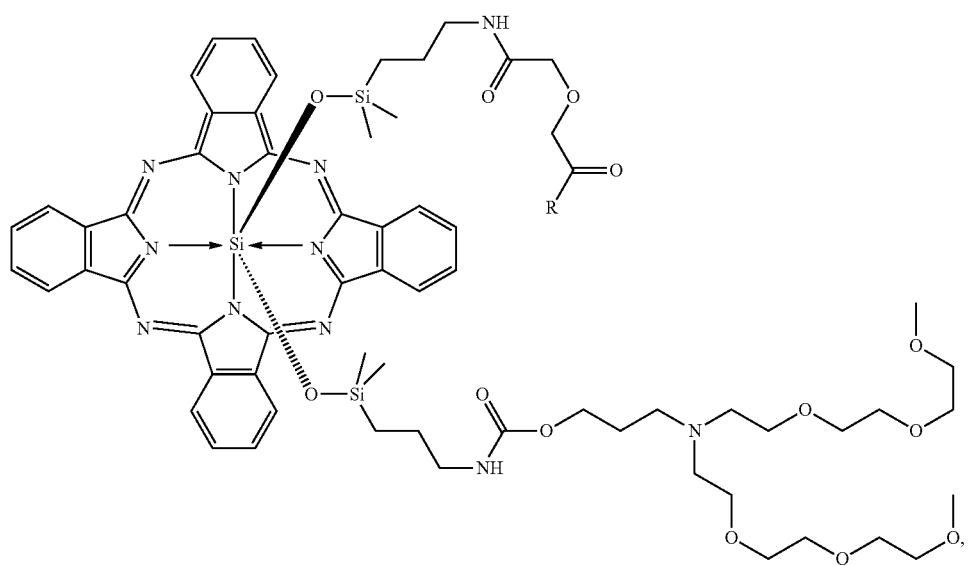

-continued
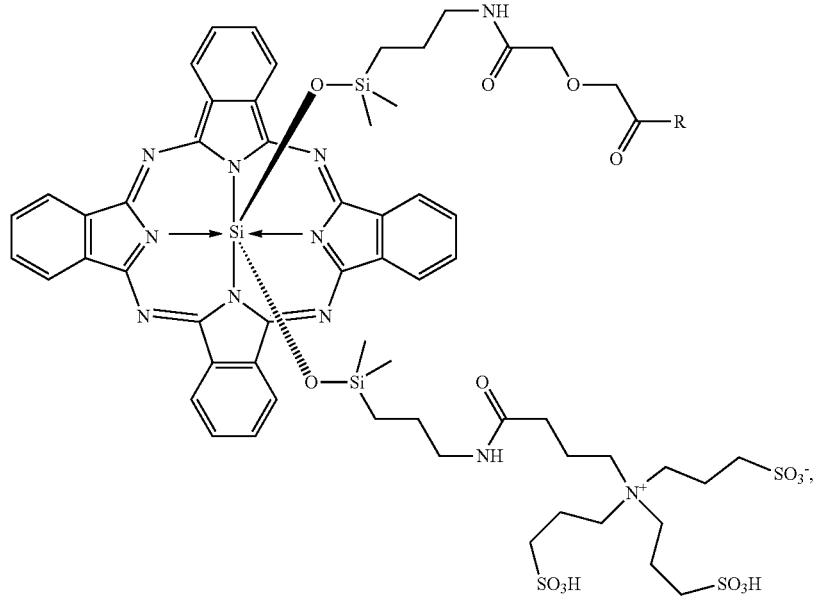
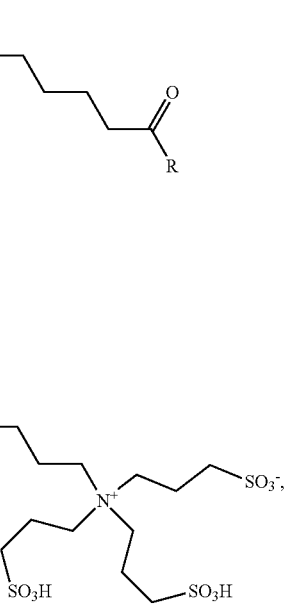

-continued
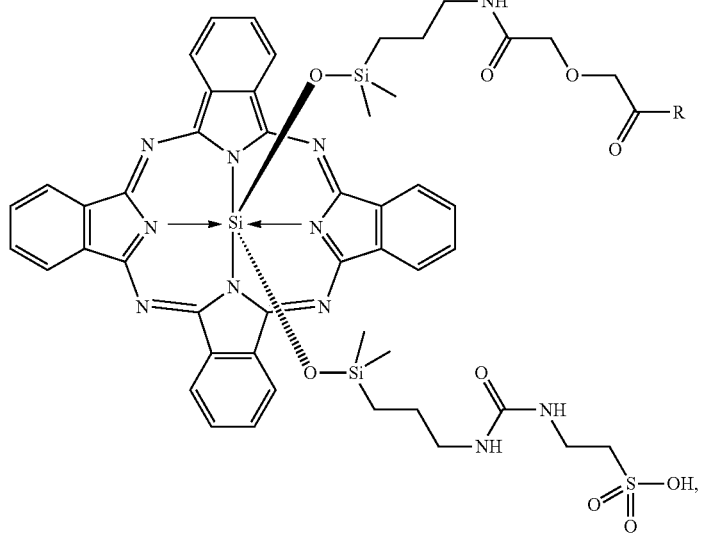
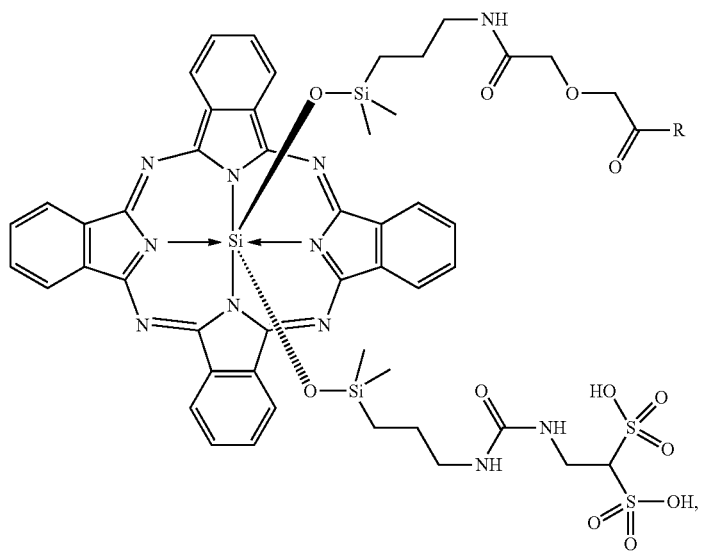
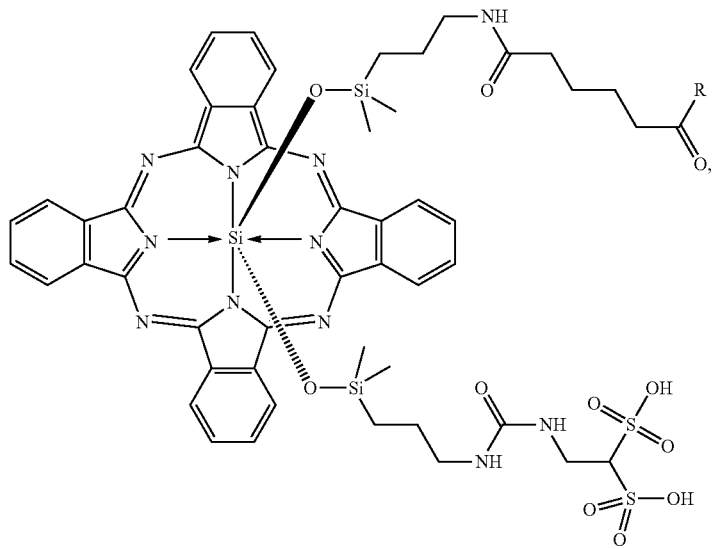

311
-continued
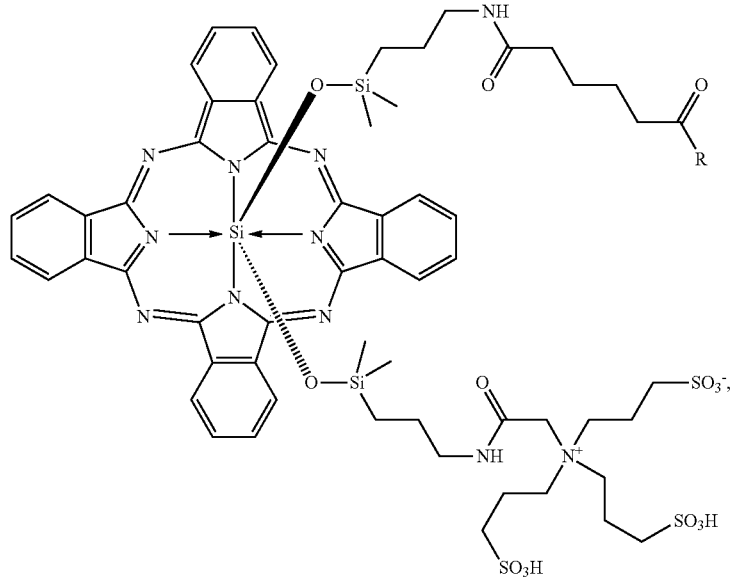
312
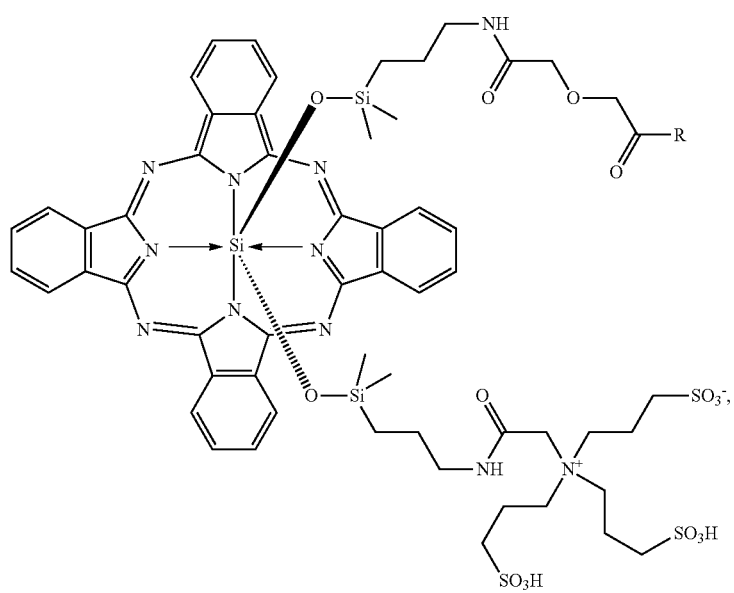

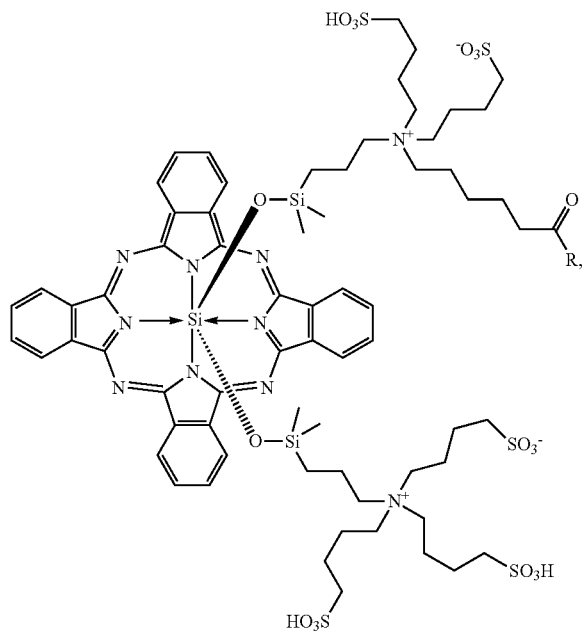
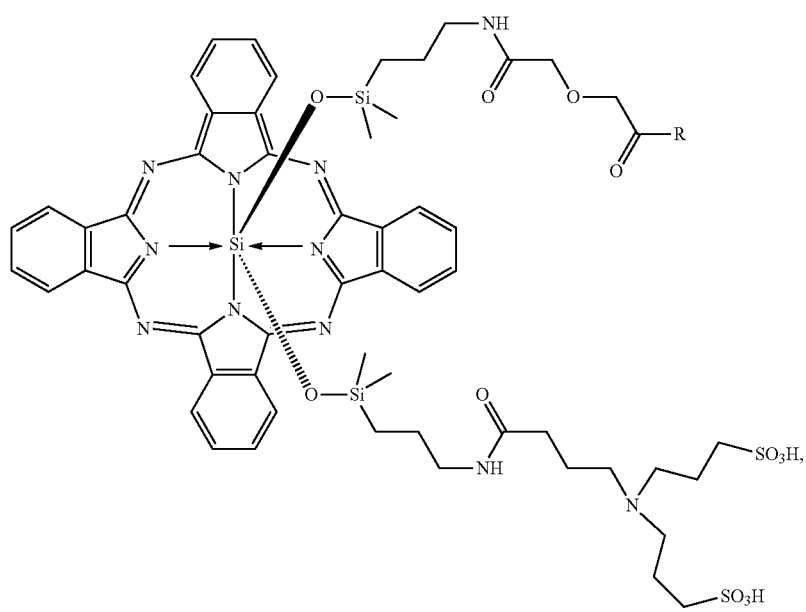

-continued
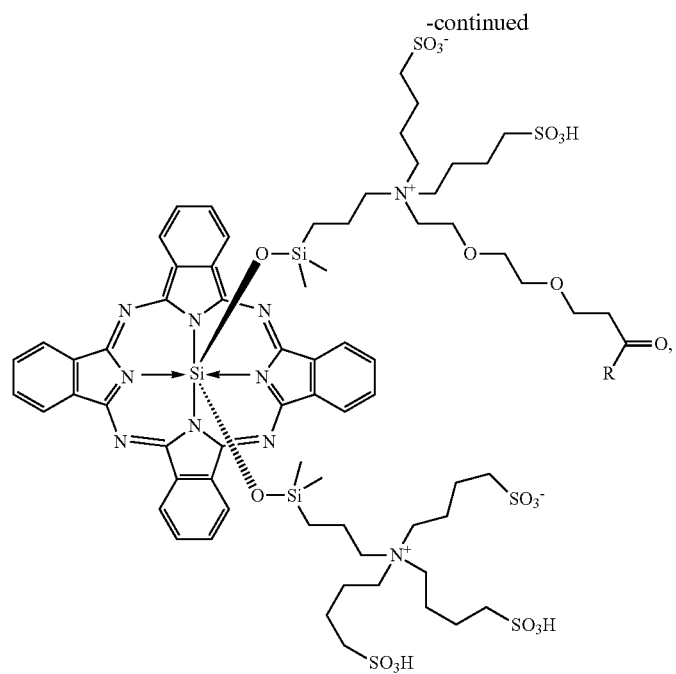
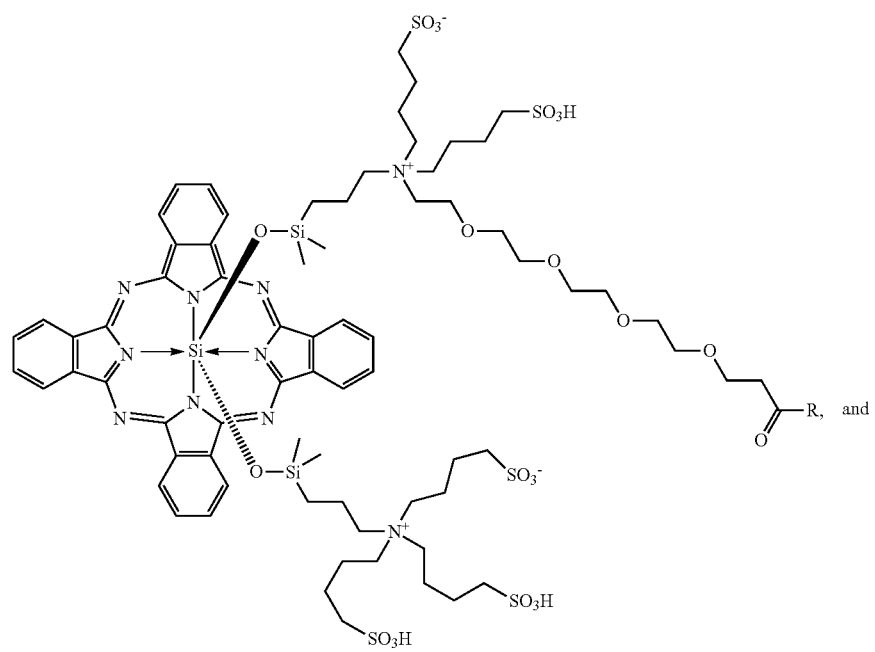

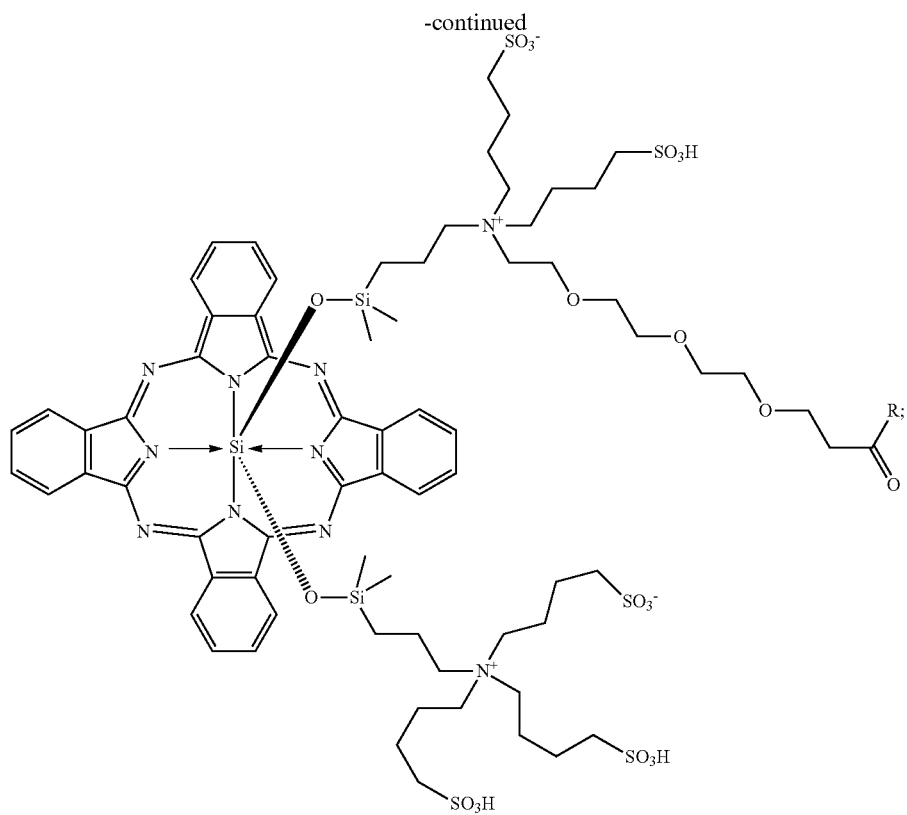
wherein R is selected from
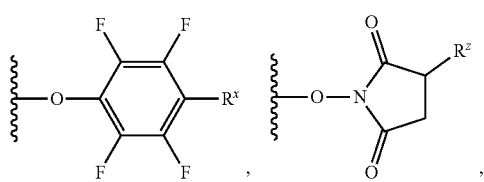
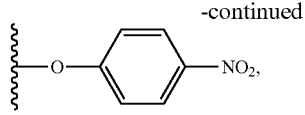
$R^x$ is hydrogen or halo; and $R^z$ is hydrogen or —SO₃H.
26. The compound of claim 25, or a salt, stereoisomer, or tautomer thereof, wherein R is
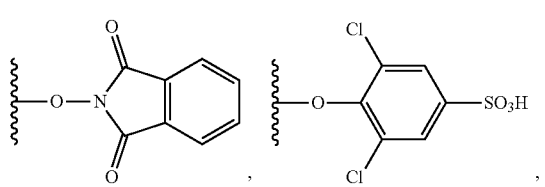
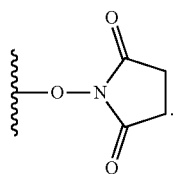 [SMILES: *ON1C(=O)CCC1=O]

27. The compound of claim 1, or a salt, stereoisomer, or tautomer thereof, selected from the group consisting of:
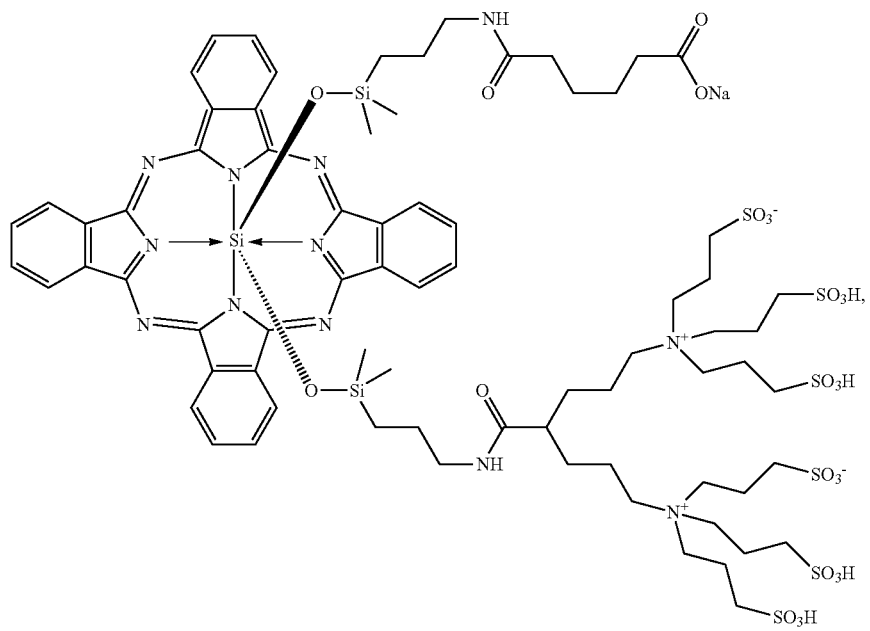
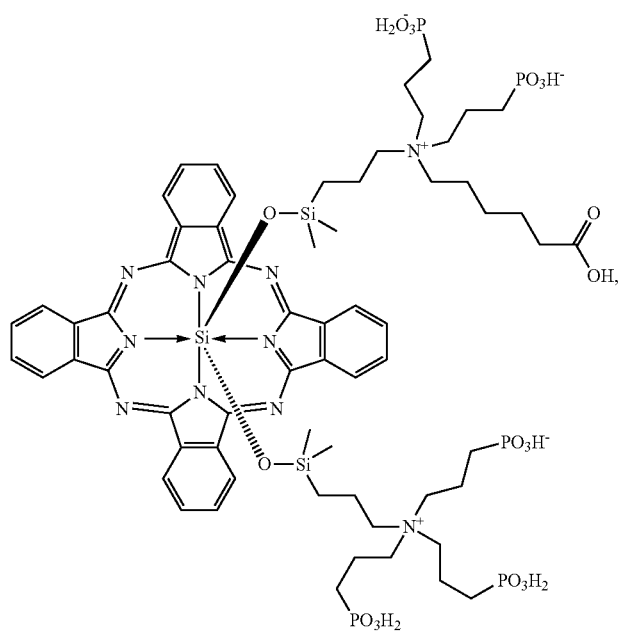

-continued
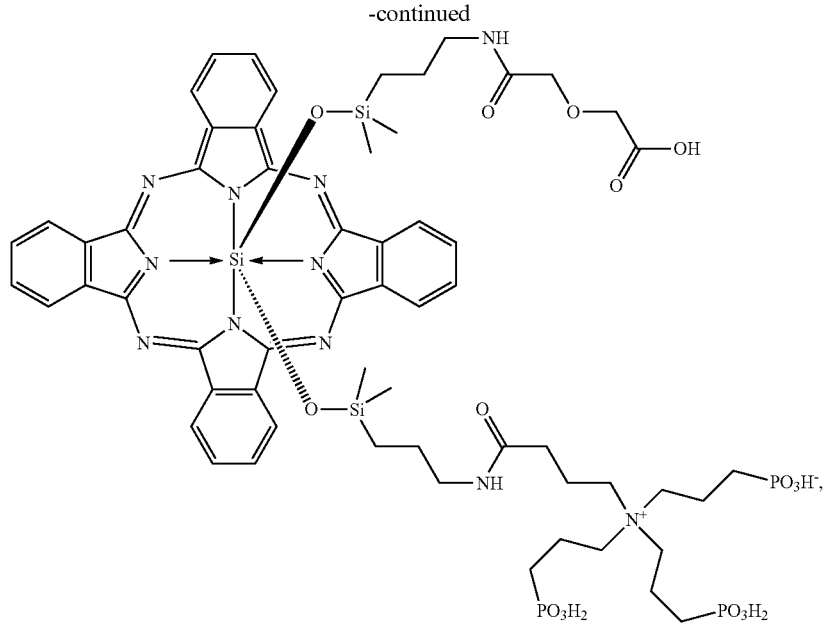
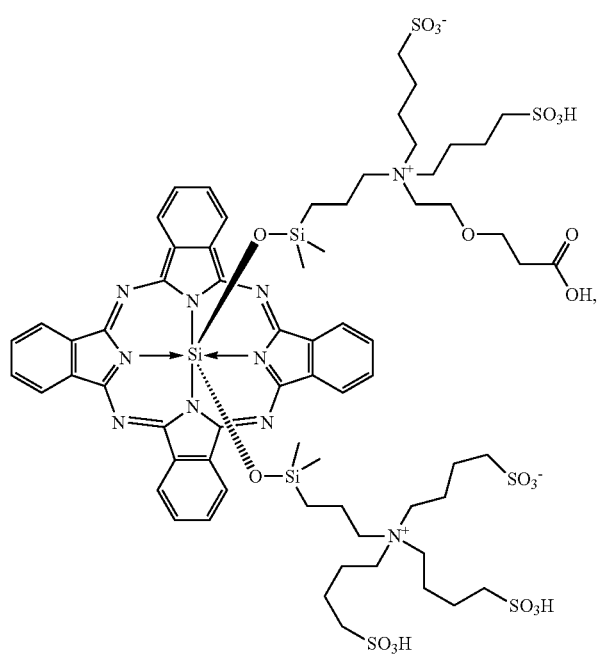

-continued
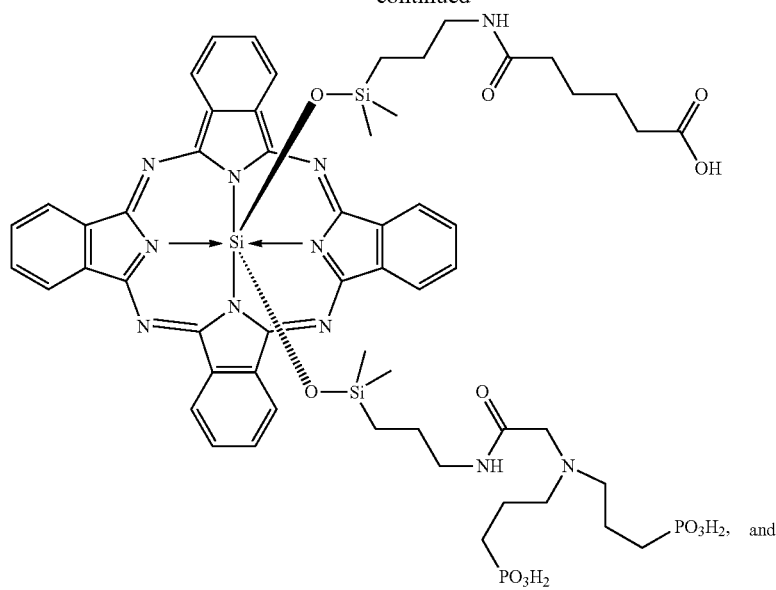
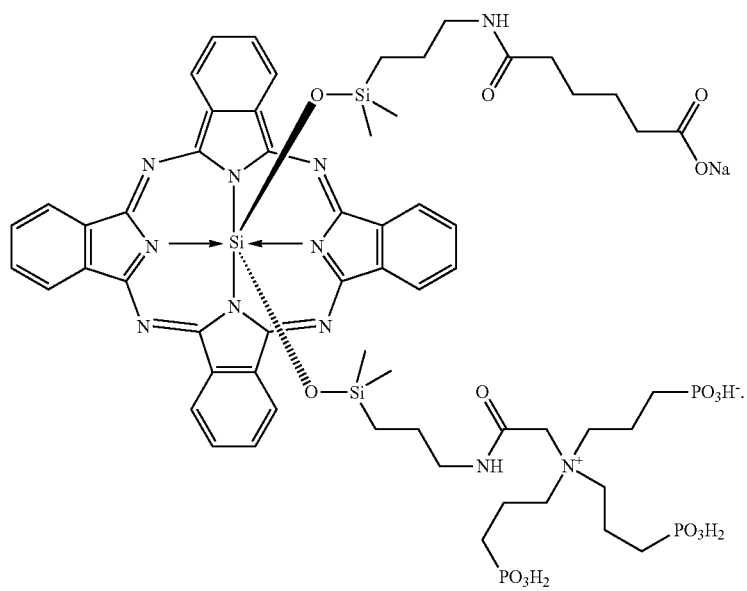

28. The compound of claim 1, or a salt, stereoisomer, or tautomer thereof, selected from the group consisting of:
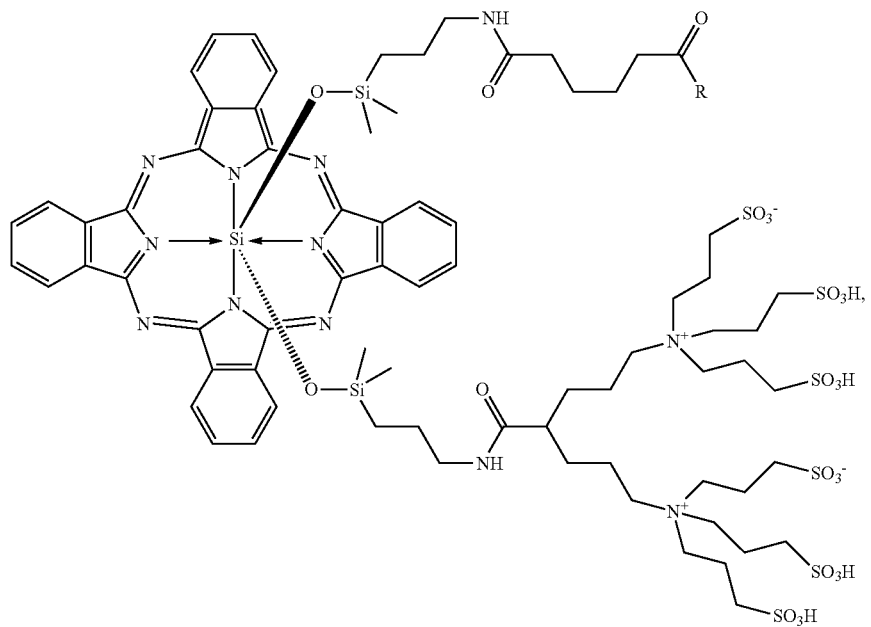
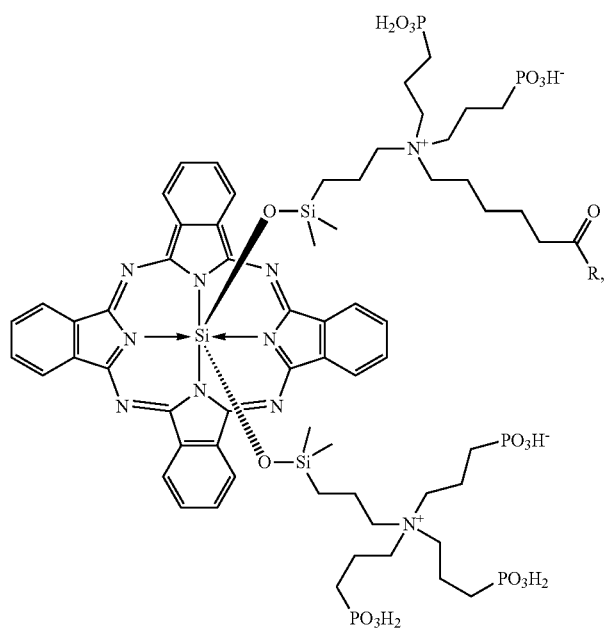

-continued
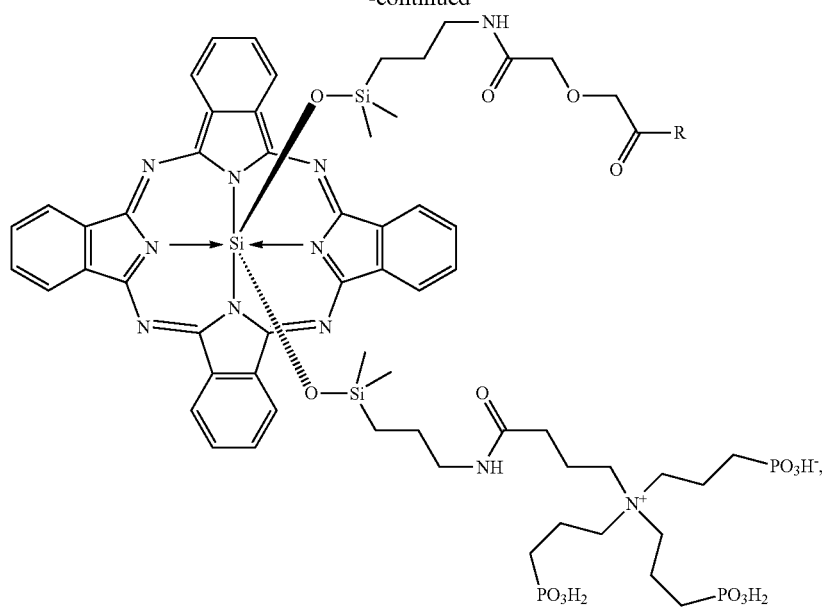
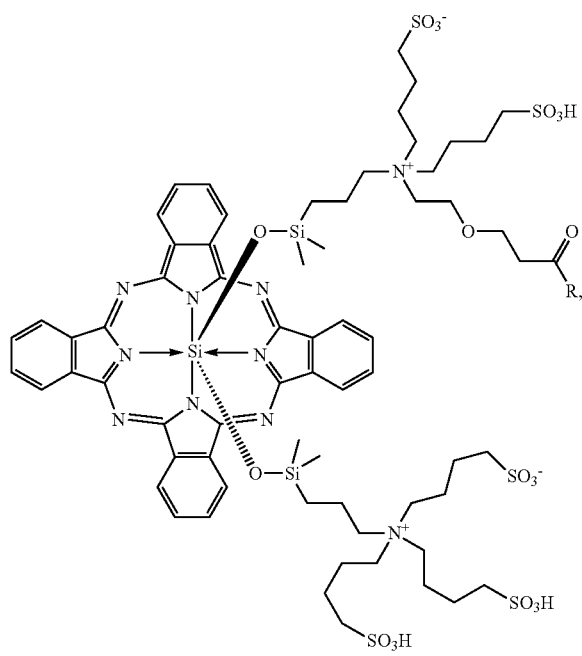

-continued
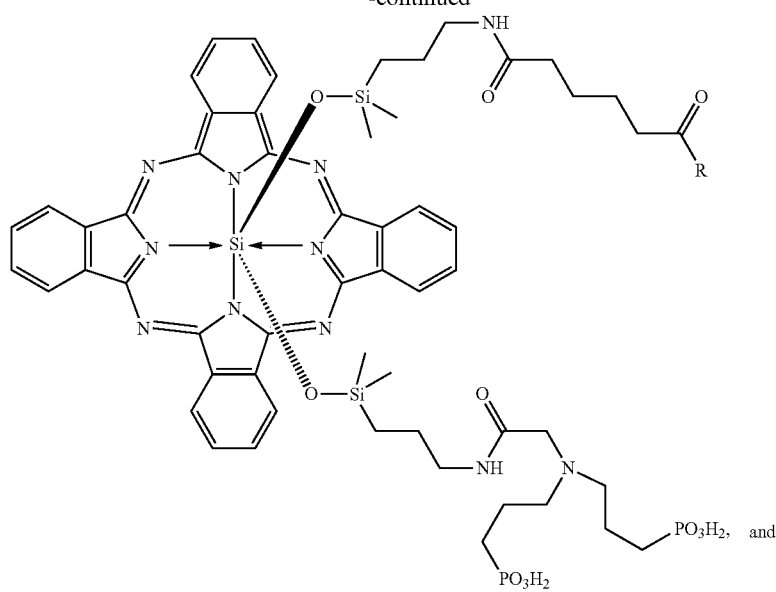
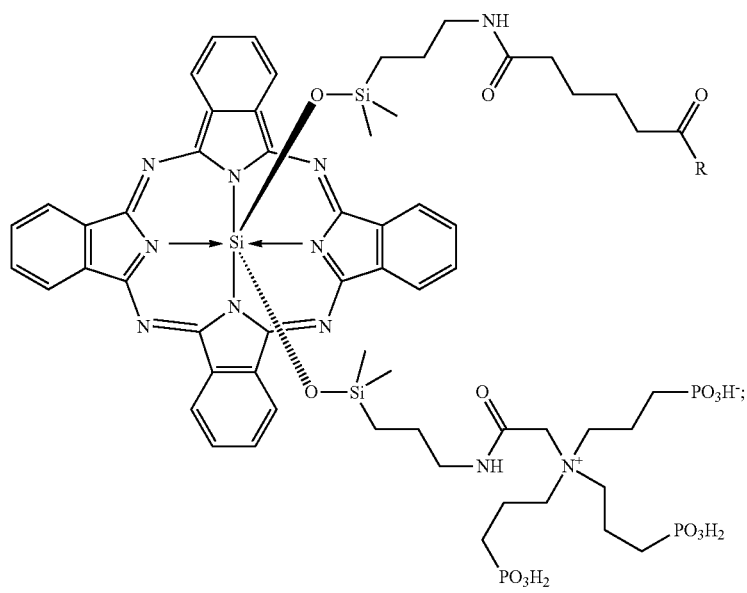

wherein R is selected from
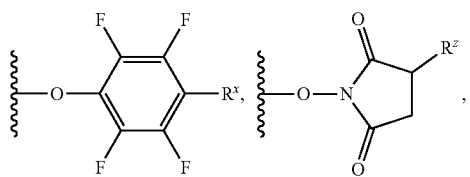
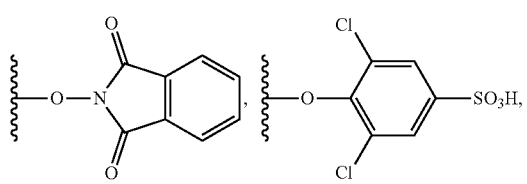
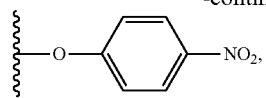
where $R^x$ is hydrogen or halo; and $R^z$ is hydrogen or —SO₃H.
29. The compound of claim 28, or a salt, stereoisomer, or tautomer thereof, wherein R is
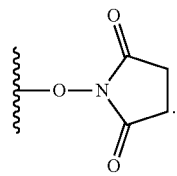 [SMILES: *ON1C(=O)CCC1=O]
* * * * *

UNITED STATES PATENT AND TRADEMARK OFFICE
CERTIFICATE OF CORRECTION

PATENT NO. : 11,466,158 B2  
APPLICATION NO. : 17/482239  
DATED : October 11, 2022  
INVENTOR(S) : Juan Betancort et al.

Page 1 of 1

It is certified that error appears in the above-identified patent and that said Letters Patent is hereby corrected as shown below:

In the Claims

Column 286, Line 26, Claim 1:  
Replace "$R^5$ is -$L^4$-H or -$L^5$-A; and" with -- $R^5$ is -$L^5$-H or -$L^5$-A; and --

Column 286, Line 31, Claim 1:  
Please replace "$R^5$ is -$L^4$-H or -$L^5$-A;" with -- $R^5$ is -$L^5$-H or -$L^5$-A; --

Column 305, Claim 24, 3rd Chemical Structure:

Please replace " 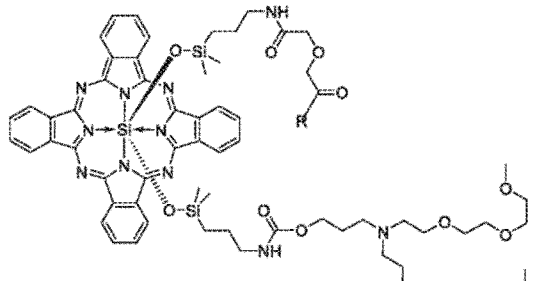 " with

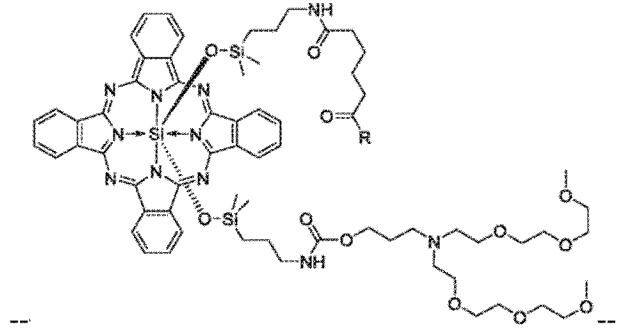

--

Signed and Sealed this  
Eighteenth Day of November, 2025

John A. Squires  
*Director of the United States Patent and Trademark Office*